US011433139B2

(12) United States Patent
Bammert et al.

(10) Patent No.: US 11,433,139 B2
(45) Date of Patent: Sep. 6, 2022

(54) PEPTIDE VACCINES AGAINST INTERLEUKIN-31

(71) Applicant: Zoetis Services LLC, Parsippany, NJ (US)

(72) Inventors: Gary Francis Bammert, Portage, MI (US); Steven Alan Dunham, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 16/356,505

(22) Filed: Mar. 18, 2019

(65) Prior Publication Data

US 2019/0282704 A1 Sep. 19, 2019

Related U.S. Application Data

(60) Provisional application No. 62/643,921, filed on Mar. 16, 2018.

(51) Int. Cl.

| | |
|---|---|
| ***A61K 39/00*** | (2006.01) |
| ***A61K 38/12*** | (2006.01) |
| ***A61K 47/64*** | (2017.01) |
| ***A61K 39/385*** | (2006.01) |
| ***G01N 33/68*** | (2006.01) |

(52) U.S. Cl.

CPC ............ *A61K 47/646* (2017.08); *A61K 38/12* (2013.01); *A61K 39/0008* (2013.01); *A61K 39/00114* (2018.08); *A61K 39/385* (2013.01); *A61K 47/642* (2017.08); *A61K 47/6415* (2017.08); *G01N 33/6854* (2013.01); *G01N 33/6869* (2013.01); *A61K 2039/552* (2013.01); *A61K 2039/55505* (2013.01); *A61K 2039/577* (2013.01); *A61K 2039/6037* (2013.01)

(58) Field of Classification Search

None

See application file for complete search history.

(56) References Cited

U.S. PATENT DOCUMENTS 6,713,301 B1 3/2004 Wang
6,989,145 B2 1/2006 Shitara et al.
(Continued)

FOREIGN PATENT DOCUMENTS

EP 17200091.1 5/2019
WO WO 03/060080 A2 7/2003
(Continued)

OTHER PUBLICATIONS

Le Saux et al. (2010, J. Biol. Chem. 285(5):3470-3477).*
(Continued)

*Primary Examiner* — Elizabeth C. Kemmerer
(74) *Attorney, Agent, or Firm* — Gloria K. Szakiel

(57) ABSTRACT

A vaccine composition for immunizing and/or protecting a mammal against an IL-31 mediated disorder is provided, wherein the composition includes: the combination of a carrier polypeptide and at least one mimotope selected from a feline IL-31 mimotope, a canine IL-31 mimotope, a horse IL-31 mimotope, and a human IL-31 mimotope; and an adjuvant. Such vaccines can be in the form of pharmaceutical compositions useful for treating or protecting mammals such as cats, dogs, horses, or humans against IL-31-mediated disorders.

20 Claims, 25 Drawing Sheets

Specification includes a Sequence Listing.

(56) References Cited

U.S. PATENT DOCUMENTS

| | | | | |
|---|---|---|---|---|
| 7,531,637 | B2 | 5/2009 | Siadak et al. | |
| 7,534,585 | B2 | 5/2009 | Paul | |
| 7,608,267 | B2 | 10/2009 | Paul | |
| 7,615,213 | B2 | 11/2009 | Kasaian et al. | |
| 7,939,068 | B2 | 5/2011 | Yao et al. | |
| 7,947,288 | B2 | 5/2011 | Paul | |
| 8,133,899 | B2 | 3/2012 | Mitton-Fry et al. | |
| 8,481,271 | B2 | 7/2013 | Galon et al. | |
| 8,546,550 | B2 * | 10/2013 | Lipford | A61P 43/00 536/23.1 |
| 8,790,651 | B2 | 6/2014 | Bammert et al. | |
| 9,206,253 | B2 | 12/2015 | Bammert et al. | |
| 9,623,095 | B2 | 4/2017 | Kallen et al. | |
| 9,669,090 | B2 | 6/2017 | Mannie | |
| 9,670,279 | B2 | 6/2017 | Ab et al. | |
| 10,093,731 | B2 | 10/2018 | Li et al. | |
| 10,150,810 | B2 | 12/2018 | Li et al. | |
| 10,172,935 | B2 | 1/2019 | Kallen et al. | |
| 10,191,059 | B2 | 1/2019 | Galon et al. | |
| 10,363,306 | B2 | 7/2019 | Mannie | |
| 10,369,204 | B2 | 8/2019 | Schøller et al. | |
| 10,532,107 | B2 | 1/2020 | Bachmann et al. | |
| 10,556,003 | B2 | 2/2020 | Fettelschoss et al. | |
| 10,588,959 | B2 | 3/2020 | Kallen et al. | |
| 10,596,252 | B2 | 3/2020 | Kallen et al. | |
| 10,729,761 | B2 | 8/2020 | Kallen et al. | |
| 2002/0052030 | A1 | 5/2002 | Wonderling et al. | |
| 2004/0176283 | A1 * | 9/2004 | Robinson | C07K 16/20 424/185.1 |
| 2004/0208870 | A1 | 10/2004 | Allan | |
| 2005/0063945 | A1 | 3/2005 | Paul | |
| 2006/0063228 | A1 | 3/2006 | Wyeth | |
| 2006/0228329 | A1 | 10/2006 | Brady et al. | |
| 2007/0110713 | A1 | 5/2007 | Paul | |
| 2009/0208494 | A1 | 8/2009 | Bondensgaard et al. | |
| 2009/0215053 | A1 | 8/2009 | Galon et al. | |
| 2009/0252732 | A1 | 10/2009 | Siadak et al. | |
| 2010/0074869 | A1 | 3/2010 | Paul | |
| 2010/0196324 | A1 | 8/2010 | Paul | |
| 2010/0221244 | A1 | 9/2010 | Yao et al. | |
| 2011/0154514 | A1 | 6/2011 | Saito et al. | |
| 2011/0318380 | A1 | 12/2011 | Brix et al. | |
| 2012/0082644 | A1 | 4/2012 | Mannie | |
| 2012/0258126 | A1 | 10/2012 | Scholler et al. | |
| 2013/0216542 | A1 | 8/2013 | Siadak et al. | |
| 2013/0295043 | A1 | 11/2013 | Kallen et al. | |
| 2013/0336998 | A1 | 12/2013 | Kallen et al. | |
| 2014/0057257 | A1 | 2/2014 | Galon et al. | |
| 2014/0286958 | A1 | 9/2014 | Bammert et al. | |
| 2015/0104414 | A1 | 4/2015 | Mannie | |
| 2015/0268245 | A1 | 9/2015 | Galon et al. | |
| 2016/0102127 | A1 | 4/2016 | Thepen et al. | |
| 2016/0151474 | A1 | 6/2016 | Kallen et al. | |
| 2016/0166678 | A1 | 6/2016 | Kallen et al. | |
| 2017/0072019 | A1 | 3/2017 | Fremder et al. | |
| 2017/0182150 | A1 | 6/2017 | Kallen et al. | |
| 2017/0196969 | A1 | 7/2017 | Kallen et al. | |
| 2017/0239338 | A1 | 8/2017 | Szalay et al. | |
| 2017/0266268 | A1 | 9/2017 | Kallen et al. | |
| 2017/0312358 | A1 | 11/2017 | Mannie | |
| 2017/0312371 | A1 | 11/2017 | Bachmann et al. | |
| 2018/0000912 | A1 | 1/2018 | Meruelo et al. | |
| 2018/0244766 | A1 | 8/2018 | Li et al. | |
| 2018/0244767 | A1 | 8/2018 | Li et al. | |
| 2018/0250388 | A1 | 9/2018 | Fettelschoss et al. | |
| 2018/0280498 | A1 | 10/2018 | Mannie | |
| 2018/0296644 | A1 | 10/2018 | Fremder et al. | |
| 2019/0054164 | A1 | 2/2019 | Kallen et al. | |
| 2019/0151438 | A1 | 5/2019 | Kallen et al. | |
| 2019/0167782 | A1 | 6/2019 | Kallen et al. | |
| 2019/0169285 | A1 | 6/2019 | Li et al. | |
| 2019/0178892 | A1 | 6/2019 | Galon et al. | |
| 2019/0209668 | A1 | 7/2019 | Tars | |
| 2019/0240263 | A1 | 8/2019 | Goodman et al. | |
| 2019/0284272 | A1 | 9/2019 | Bammert et al. | |
| 2019/0314427 | A1 | 10/2019 | Goodman et al. | |
| 2019/0314471 | A1 | 10/2019 | Schøller et al. | |
| 2020/0016248 | A1 | 1/2020 | Fettelschoss et al. | |
| 2020/0062816 | A1 | 2/2020 | Laster | |
| 2020/0062840 | A1 | 2/2020 | Li et al. | |
| 2020/0155668 | A1 | 5/2020 | Kallen et al. | |
| 2020/0155699 | A1 | 5/2020 | Bachmann et al. | |
| 2020/0230231 | A1 | 7/2020 | Fettelschoss et al. | |
| 2020/0254028 | A1 | 8/2020 | Goodman et al. | |

FOREIGN PATENT DOCUMENTS

| | | | |
|---|---|---|---|
| WO | WO 05014642 | A2 | 2/2005 |
| WO | WO 05014642 | A3 | 2/2005 |
| WO | WO 2006/081573 | A2 | 8/2006 |
| WO | WO 2006/088855 | A1 | 8/2006 |
| WO | WO 2006/088955 | A2 | 8/2006 |
| WO | WO 2006/104978 | A2 | 10/2006 |
| WO | WO 07045996 | A1 | 4/2007 |
| WO | WO 2007/133816 | A2 | 11/2007 |
| WO | WO 2007/143231 | A2 | 12/2007 |
| WO | WO 2008/021976 | A2 | 2/2008 |
| WO | WO 2008/028192 | A2 | 3/2008 |
| WO | WO 09106073 | A2 | 9/2009 |
| WO | WO 09106073 | A3 | 9/2009 |
| WO | WO 09148194 | A1 | 12/2009 |
| WO | WO 10037395 | A2 | 4/2010 |
| WO | WO 10037395 | A3 | 4/2010 |
| WO | WO 10037402 | A1 | 4/2010 |
| WO | WO 2010/117448 | A2 | 10/2010 |
| WO | WO 2011/047262 | A2 | 4/2011 |
| WO | WO 2011/065935 | A1 | 6/2011 |
| WO | WO 12116714 | A1 | 9/2012 |
| WO | WO 12116715 | A1 | 9/2012 |
| WO | WO 12116810 | A1 | 9/2012 |
| WO | WO 12116811 | A1 | 9/2012 |
| WO | WO 14191391 | A1 | 12/2014 |
| WO | WO 15024669 | A1 | 2/2015 |
| WO | WO 15173812 | A1 | 11/2015 |
| WO | WO 16062720 | A1 | 4/2016 |
| WO | WO 16065330 | A1 | 4/2016 |
| WO | WO 2017/042212 | A1 * | 3/2017 |
| WO | WO 17058923 | A1 | 4/2017 |
| WO | WO 17152042 | A2 | 9/2017 |
| WO | WO 17152042 | A3 | 9/2017 |
| WO | WO 2017/186813 | A1 | 11/2017 |
| WO | WO 18112363 | A1 | 6/2018 |
| WO | WO 18156180 | A1 | 8/2018 |
| WO | WO 18156367 | A1 | 8/2018 |
| WO | WO 2018/162577 | A1 | 9/2018 |
| WO | WO 19051380 | A1 | 3/2019 |
| WO | WO 19051381 | A1 | 3/2019 |
| WO | WO 19075452 | A1 | 4/2019 |
| WO | WO 2019086694 | | 5/2019 |
| WO | WO 2019/118512 | A2 | 6/2019 |
| WO | WO 19177697 | A9 | 9/2019 |
| WO | WO 19228990 | A1 | 12/2019 |
| WO | WO 20016897 | A1 | 1/2020 |
| WO | WO 20128037 | A1 | 6/2020 |
| WO | WO 20132275 | A1 | 6/2020 |
| WO | WO 10117848 | A1 | 10/2020 |

OTHER PUBLICATIONS

Almagro et al., "Antibody modeling assessment," Proteins: Structure, Function, Bioinformatics 79 (2011) pp. 3050-3066.

Aaronson, D.S. et al., "A Road Map for Those Who Don't know JAK-STAT," Science, vol. 296, May 31, 2002, pp. 1653-1655.

Bachmann, M.F. et al., "Vaccination against IL-31 for the treatment of atopic dermatitis in dogs," Letters to the Editor, J Allergy Clin. Immunol. Jul. 2018, vol. 142, No. 1, pp. 279-281.

Bieber, T., "Mechanisms of Disease, Atopic Dermatitis," The New England Journal of Medicine, 2008, 358, pp. 1483-1494.

Bilsborough, J. et al. "IL-31 is Associated with Cutaneous Lymphocyte Antigen-Positive Skin Homing T Cells in Patients with Atopic Dermatitis" J Allergy Clin. Immunol. 2006 117(2): pp. 418-425.

(56) References Cited

OTHER PUBLICATIONS

Buckley, L., "Treatment of presumed allergic skin disease in cats," In Practice, Jun. 2017, vol. 39, pp. 242-254.
Buddenkotte, J. et al. "Pathophysiology and therapy of pruritus in allergic and atopic diseases," Allergy 65, 2010; 65: pp. 805-821.
Carr, M.N. et al., "Investigation of the pruritogenic effects of histamine, serotonin, tryptase, substance P and interleukin-2 in healthy dogs," 2009 The Authors, Journal compilation, pp. 105-110.
Casset, F. et al., "A peptide mimetic of an anti-CD4 monoclonal antibody by rational design," Biochemical and Biophysical Research Communications, 307 (2003), pp. 198-205.
Cevikbas, F. et al., Interleukin-31 directly regulates neuronal function in inflammation and itch, Journal of Investigative Dermatology (2010), Abstract, vol. 130, p. S117.
Chattopadhyay, S. et al. "Interleukin-31 and Oncostatin-M Mediate Distince Signaling Reactions and Response Patterns in Lung Epithelial Cells" Journal of Biological Chemistry 2007; 282, pp. 3014-3026.
Chen, Y. et al., "Selection and Analysis of an Optimized Anti-VEGF Antibody: Crystal Structure of an Affinity-matured Fab in Complex with Antigen," J. Mol. Biol. 1999; 293, pp. 865-881.
Chin, R. et al., Transcript of Q1 2017 Earnings, Conference Call of May 3, 2017 of Dr. Richard Chin.
Dambucher, J. et al., "Interleukin 31 mediates MAP kinase and STAT⅓ activation in intestinal epithelial cells and its expression is upregulated in inflammatory bowel disease," Gut 2007; 56: pp. 1257-1265.
De Bellis, F., "Latest Thinking On Atopic Dermatitis In Cats And Dogs," Vet Times, https://www.vettimes.co.uk, pp. 1-23, 2014.
Dillon, S. R. et al., "Interleukin31, a Cytokine Produced by Activated T Cells, Induces Dermatitis in Mice," Nature Immunology 2004; 5, pp. 752-760.
Diveu, C. et al., "Predominant expression of the long isoform of GP130-like (GPL) receptor is required for interleukin-31 signaling," Eur. Cytokine Netw., vol. 15, No. 4, Dec. 2004, pp. 291-302.
European Medicines Agency, EPAR summary for the public of Cytopoint, 2017.
Excerpt from the UniProt database, Interleukin 31, Oct. 13, 2009.
Fadok, V.A., "Update on Equine Allergies," Vet. Clin. Equine, 29, 2013, pp. 541-550.
Favrot, C., "Feline allergic dermatitis: clinical aspects and diagnosis" Update on feline hypersensitivity dermatoses Dermatology Service, Vetsuisse Faculty, University of Zurich, Zurich, Switzerland, 2013.
Felsburg, P.J., "Overview of immune system development in the dog: comparison with humans," Human & Experimental Toxicology (2002) 21, pp. 487-492.
Gonzales, A.J., et al., "Abstracts of the 26th Annual Congress of the ECVD-ESVD, Sep. 19-21, 2013, Valencia, Spain," Veterinary Dermatology, 2013; 24: pp. 377-397.
Gonzales, A.J. et al., "Oclacitinib (APOQUEL®) is a novel Janus kinase inhibitor with activity against cytokines involved in allergy," Journal of Veterinary Pharmacology and Therapeutics, 2014, pp. 1-8.
Gonzales, A.J. et al., "Interleukin-31: its role in canine pruritus and naturally occurring canine atopic dermatitis," Veterinary Dermatology, 2013; 24: pp. 48-53.
Gonzales, A.J. et al., "Plenary Session Abstracts from the Seventh World Congress of Veterinary Dermatology Meeting held Jul. 24-28, 2012, Vancouver, Canada," Veterinary Dermatology, 23 (Suppl. 1), pp. 2-104.
Grimstad, O. et al., "The Effect of Anti-interleukin-31-Antibodies on Scratching Behaviour and Development of Dermatitis on NC/Nga Mice" Inflammation Research Supplement Jun. 3, 2007, pp. S 396-397.
Grimstad, O. et al., "Anti-interleukin-31 Antibodies Ameliorate Scratching Behaviour in NC/Nga Mice: a Model of Atopic Dermatitis" Experimental Dermatology 2009;18: pp. 35-43.
Halliwell, R.E.W., "The immunopathogenesis of allergic skin diseases in dogs and cats," Dermatology, EJCAP—vol. 19—Issue 3 Dec. 2009, pp. 213-218.
Hobi, S. et al., "Clinical characteristics and causes of pruritus in cats: a multicentre study on feline hypersensitivity-associated dermatoses," Veterinary Dermatology, 22, pp. 406-413, 2011.
Hill, P.B., et al., "Pilot study of the effect of individualized homeopathy on the pruritus associated with atopic dermatitis in dogs," Veterinary Record, 2009 vol. 164, Issue 12, pp. 364-370.
Hillier, A. et al. "The ACVD Task Force on Canine Atopic Dermatitis (I): Incidence and Prevalence" Veterinary Immunology and Immunopathology 2001; 81: pp. 147-151.
Holm, P. et al., "Functional mapping and single chain construction of the anti-cytokeratin 8 monoclonal antibody TS1," Molecular Immunology 2007, 44(6), pp. 1075-1084.
Hvid, M. et al., "IL-25 in Atopic Dermatitis: A Possible Link between Inflammation and Skin Barrier Dysfunction?" Journal of Investigative Dermatology (2011) 131, pp. 150-157.
Javens, C. et al., Abstract, "Oclacitinib inhibits canine IL-4 and IL-13-activated JAK-STAT pathways in canine DH82 cells," Veterinary Dermatology, Annual Conference of the North American Veterinary Dermatology Forum, 2018, pp. 1-2.
Le Saux, S. et al. "Molecular Dissection of Human Interleukin-31-mediated Signal Transduction Through Site-directed Mutagenesis" The Journal of Biological Chemistry Jan. 29, 2010;285(5), pp. 3470-3477.
Maeda, S. et al. "Expression of CC Chemokine Receptor 4 (CCR4) mRNA in Canine Atopic Skin Lesion" Veterinary Immunology Immunopathology 2002b; 90, pp. 145-154.
Maeda, S. et al., "Lesional expression of thymus and activation-regulated chemokine in canine atopic dermatitis," Veterinary Immunology and Immunopathology 88 (2002), pp. 79-87.
Maeda, S. et al. "Production of a Monoclonal Antibody to Canine Thymus and Activation-regulated Chemokine (TARC) and Detection of TARC in Lesional Skin from Dogs with Atopic Dermatitis" Veterinary Immunology Immunopathology 2005; 103, pp. 83-92.
Maeda, S. et al. "Expression Analysis of CCL27 and CCL28 mRNA in Lesional and Non-Lesional Skin of Dogs with Atopic Dermatitis" Journal Veterinary Medical Science 2008; 70, pp. 51-55.
Marsella, R. et al., "Canine Models of Atopic Dermatitis: A Useful Tool with Untapped Potential," Journal of Investigative Dermatology (2009) 129, pp. 2351-2357.
Marsella, R. et al., "Current understanding of the pathophysiologic mechanisms of canine atopic dermatitis," Vet Med Today: Reference Point, JAVMA, vol. 241, No. 2, Jul. 15, 2012, pp. 194-207.
Marsella, R., "Equine Allergy Therapy, Update on the Treatment of Environmental, Insect Bite Hypersensitivity, and Food Allergies," Vet Clin. Equine, 29 (2013), pp. 551-557.
Mac Callum, R. M. et al., "Antibody-antigen Interactions: Contact Analysis and Binding Site Topography," J. Mol. Biol. 1996; 262, pp. 732-745.
Michels, G.M. et al., "A blinded, randomized, placebo-controlled, dose determination trial of lokivetmab (ZTS-00103289), a caninized, anti-canine IL-31 monoclonal antibody in client owned dogs with atopic dermatitis," Vet. Dermatol. 2016; 27, pp. 478-e129.
Mizuno, T. et al., "Molecular Cloning of Canine Interleukin-31 and its Expression in Various Tissues" Veterinary Immunology and Immunopathology 2009; 131, pp. 140-143.
Neis, M. M. et al., "Enhanced Expression Levels of IL-31 Correlate with IL-4 and IL-13 in Atopic and Allergic Contact Dermatitis" Journal Allergy Clinical Immunology 2006; 118, pp. 930-937.
Nuttall, T.J. et al., "T-helper 1, T-helper 2 and Immunosuppressive Cytokines in Canine Atopic Dermatitis" Veterinary Immunology Immunopathology 2002; 87, pp. 379-384.
O'Kennedy, R. et al., "A Review of Enzyme-Immunoassay and a Description of a Competitive Enzyme-Linked Immunosorbent Assay for the Detection of Immunoglobulin Concentrations," Biochemical Education 18(3) 1990, pp. 136-140.
Olivry, T. et al., "The ACVD Task Force on Canine Atopic Dermatitis: Forewords and Lexicon" Veterinary Immunology and Immunopathology 2001; 81: pp. 143-146.
Olivry, T. et al., "Animal Models of Atopic Dermatitis" 2001 supra; Marsella & Olivry Clinics in Dermatology 2003; 21: pp. 122-133.

(56) References Cited

OTHER PUBLICATIONS

Olivry, T. et al., "Treatment of canine atopic dermatitis: 2010 clinical practice guidelines from the International Task Force on Canine Atopic Dermatitis," Veterinary Dermatology, 21, pp. 233-248.
Pakula, A. et al, "Genetic Analysis of Protein Stability and Function," Annu. Rev. Genet, 1989; 23, pp. 289-310.
Paul, W., Fundamental Immunology, 3rd edition, 1993, Raven Press, New York, pp. 292-295.
Paul, William E., "Diversity and Constraints on the Sequence and Structure of CDR-H3," Fundamental Immunology, Sixth Edition Philadelphia: Lippincott Williams & Wilkins, 2008, pp. 135-136.
PCT International Search Report PCT/IP2012/053450 dated Jan. 30, 2014.
"Predicted: Felis catus interleukin 31 (IL31), mRNA", GenBank, Feb. 10, 2015 (Feb. 10, 2015), XP002770325, Retrieved from the Internet: URL:https://www.ncbi.nlm.nih.gov/nuccor.
Picco, F. et al., "A Prospective Study on Canine Atopic Dermatitis and Food-Induced Allergic Dermatitis in Switzerland," Veterinary Dermatology 2008; 19: pp. 150-155.
Product Information from ImmunoGlobe Antikorpertechnik GmbH, last modified Jan. 29, 2018.
Prost, C., "Feline atopic dermatitis: Clinical signs and diagnosis" Dermatology, EJCAP—vol. 19—Issue 3 Dec. 2009, pp. 223-229.
Raap, U. et al., "Correlation of IL-31 Serum Levels with Severity of Atopic Dermatitis" Journal Allergy Clinical Immunology 2008;122(2), pp. 421-423.
Raap, U. et al., "Increased Levels of Serum IL-31 in Chronic Spontaneous Urticaria" Experimental Dermatology 2010;19(5), pp. 464-466.
Ravens, P. A. et al., "Feline atopic dermatitis: a retrospective study of 45 cases (2001-2012)," Veterinary Dermatology, 2014; 25, 95-e28.
Riechmann, L. et al., "Reshaping human antibodies for therapy," 1988, Nature, vol. 332, pp. 323-327.
Roitt, I. et al., Immunology, Seventh Edition, Mosby, 2006, p. 67.
Scott, D.W. et al., "Treatment of Canine Atopic Dermatitis with a Commercial Homeopathic Remedy: A Single-Blinded, Placebo-Controlled Study," Canadian Veterinary Journal 2002; 43, pp. 601-603.
Jean-Pierre Y. Scheerlinck, "Functional and structural comparison of cytokines in different species," Veterinary Immunology and Immunopathology 72 (1999) pp. 39-44.
Schwartzman, et al. "Canine Reaginic Antibody" "Characterization of the Spontaneous Anti-Ragweed and Induced Anti-Dinitrophenyl Reaginic Antibodies of the Atopic Dog" Clin. Exp. Immunol. 1971; 9, pp. 549-569.
Singer, M. et al., Genes & Genomes, a Changing Perspective, University of Science Books, Mill Valley, California, 1991, pp. 31, 67 and 70.
Sonkoly, E. et al., "IL-31: A New Link Between T Cells and Pruritus in Atopic Skin Inflammation," Journal Allergy Clinical Immunology 2006; 117, pp. 411-417.
Soumelis, V. et al., "Human epithelial cells trigger dendritic cell-mediated allergic inflammation by producing TSLP," Nature Immunology, vol. 3, No. 7, Jul. 2002, pp. 673-680.
Sousa & Marsella "The ACVD Task Force on Canine Atopic Dermatitis (II): Genetic Factors" Veterinary Immunology and Immunopathology 2001; 81, pp. 153-157.
Spencer, G. "Analysis Sheds Light on Human Disease; Differences Among Canine Breeds," Researchers Publish Dog Genome Sequence—National Human Genome Research Institute, Dec. 7, 2005, pp. 1-2.
Strachan, D. P., "Family size, infection and atopy: the first decade of the "hygiene hypothesis"," Thorax 2000; 55 (Suppl 1): pp. S2-S10.
Tang, Liang "Molecular cloning of canine IL-13 receptor $\alpha$ chain ($\alpha$1 and $\alpha$2) cDNAs and detection of corresponding mRNAs in canine tissues", Veterinary Immunology and Immunopathology, 79 (2001), pp. 181-195.
Takaoka, A. et al., "Expression of IL-31 Gene Transcripts in NC/Nga Mice with Atopic Dermatitis" European Journal of Pharmacology 2005; 516, pp. 180-181.
Takaoka, A. et al., "Involvement of IL-31 on Scratching Behavior in NC/Nga Mice with Atopic-Like Dermatitis" Experimental Dermatology 2006; 15, pp. 161-167.
Terada, Y. et al., "Clinical comparison of human and canine atopic dermatitis using human diagnostic criteria (Japanese Dermatological Association, 2009): Proposal of provisional diagnostic criteria for canine atopic dermatitis," Journal of Dermatology 2011; 38: pp. 784-790.
TGR BioSciences, "AlphaScreen® SureFire® STAT3 (p-Tyr705) Assay Kits," Manual, pp. 1-8, Mar. 27, 2018.
Torres, S.M.F., editor, Advances in Veterinary Dermatology, vol. 7, Proceedings of the Seventh World Congress of Veterinary Dermatology Vancouver, Canada, Jul. 24-28, 2012.
Vajdos, F. F. et al., "Comprehensive Functional Maps of the Antigen-binding Site of an Anti-Erb82 Antibody Obtained with Shotgun Scanning Mutagenesis," J. Mol. Biol. 2002, 320(2), pp. 415-428.
Wai K. IP et al., "Interleukin-31 Induces Cytokine and Chemokine Production from Human Bronchial Epithelial Cells Through Activation of Mitogen-activated Protein Kinase Signalling Pathways: Implications for the Allergic Response" Immunology, 2007; 122, pp. 532-541.
White, S.D., "Advances in Equine Atopic Dermatitis, Serologic and Intradermal Allergy Testing," Clin. Tech. Equine Practice, 4, 2005, pp. 311-313.
Yagi, Y. et al., "Interleukin-31 Stimulates Production of Inflammatory Mediators from Human Colonic Subepithelial Myofibroblasts" International Journal of Molecular Medicine 2007; 19(6), pp. 941-946.
Zhang, Q. et al., "Structures and biological functions of IL-31 and IL-31 receptors," Cytokine Growth Factor Rev. 2008; 19(5-6): pp. 347-356.
Zoetis Press Release, Dec. 21, 2016—Zoetis Receives USDA License for CYTOPOINT™.
Zoetis Press Release, Apr. 26, 2017—Zoetis Received European Commission Marketing Authorization for Cytopoint® (lokivetmab).
Zucker, K. et al., "Cloning of the cDNA for Canine Interferon-$\gamma$," Journal of Interferon Research, 12, pp. 191-194 (1992).
PCT Search Report—PCT/US2019/022774—dated Mar. 18, 2019.
Sergeyev O.V. et al., "Synthetic peptide vaccines," Questions of virology, vol. 61, N 1, 2016, pp. 5-8 (English translation of the relevant portions).
Sequence listing for PCT/EP2016/071078, corresponding to WO 170422212.
An English translation of the relevant parts of O.Sergeyev O.V. et al., Synthetic peptide Vaccines, Questions of virology, vol. 61, N 1, 2016, pp. 5-8.

* cited by examiner

```
SEQ_ID_NO_155_Canine_IL31             1 MLSHTGPSRFALFLLCSMETLLSSHMAPTHQLPP-SDVRKIILELQPLSRGLLEDYQ 56
SEQ_ID_NO_157_Feline_IL31_wildtype    1 MLSHAGPARFALFLLCCMETLLPSHMAPAHRLQP-SDIRKIILELRPMSKGLLQDYL 56
SEQ_ID_NO_165_Equine_IL31             1 -------MGWSCIILFLVATATGVHSGPIYQLQP-KEIQAIIVELQNLSKKLLDDYL 49
SEQ_ID_NO_181_Human_IL31              1 MASHSGPSTSVLFLFCCLGGWLASHTLPVRLLRPSDDVQKIVEELQSLSKMLLKDVE 57

SEQ_ID_NO_155_Canine_IL31            57 KKETGVPESNRTLLLCLTSDSQPP-RLNSSAILPYFRAIRPLSDKNIIDKIIEQLDK 112
SEQ_ID_NO_157_Feline_IL31_wildtype   57 KKEIGLPESNHSSLPCLSSDSQLP-HINGSAILPYFRAIRPLSDKNTIDKIIEQLDK 112
SEQ_ID_NO_165_Equine_IL31            50 NKEKGVQKFDSDLPSCFTSDSQAPGNINSSAILPYFKAISPSLNNDKSLYIIEQLDK 106
SEQ_ID_NO_181_Human_IL31             58 -EEKGVLVSQNYTLPCLSPDAQPPNNIHSPAIRAYLKTIRQLDNKSVIDEIIEHLDK 113

SEQ_ID_NO_155_Canine_IL31           113 LKFQHEPETEISVPADTFECKSFILTILQQFSACLESVFKSLNSGPQ------ 159
SEQ_ID_NO_157_Feline_IL31_wildtype  113 LKFQREPEAKVSMPADNFERKNFILAVLQQFSACLEHVLQSLNSGPQHHHHHH 165
SEQ_ID_NO_165_Equine_IL31           107 LNFQNAPETEVSMPTDNFERKRFILTILRWFSNCLEHRAQHHHHHH------- 152
SEQ_ID_NO_181_Human_IL31            114 LIFQDAPETNISVPTDTHECKRFILTISQQFSECMDLALKSLTSGAQQATT-- 164
```

FIG. 1A

| | Percent Identity | | |
|---|---|---|---|
| | Feline_IL31 | Horse_IL31 | Human_IL31 |
| Canine_IL31 | 74 | 57 | 56 |
| Feline_IL31 | | 56 | 49 |
| Horse_IL31 | | | 48 |

FIG. 1B

Antibodies with CDRs of Mouse Origin

| | | | | Affinity to Feline IL-31 | | | Affinity to Canine IL-31 | | |
|---|---|---|---|---|---|---|---|---|---|
| | Antibody | VH | VL | ka ($M^{-1}s^{-1}$) | kd ($s^{-1}$) | KD (M) | ka ($M^{-1}s^{-1}$) | kd ($s^{-1}$) | KD (M) |
| A | HBS-EP | | | no binding | | | no binding | | |
| | MU-15H05 | MU-15H05-VH | MU-15H05-VL | 4.84E+04 | 1.69E-05 | 3.48E-10 | 1.35E+05 | 6.56E-07 | 4.87E-12 |
| | MU-11E12 | MU-11E12-VH | MU-11E12-VL | 1.67E+05 | 1.23E-04 | 7.38E-10 | 6.29E+05 | 4.80E-07 | 7.63E-13 |
| | Mouse:Canine 15H05 Chimera | MU-15E05-VH | MU-15H05-VL | | | | | | |
| | Mouse:Feline 15H05 Chimera | MU-15E05-VH | MU-15H05-VL | 1.65E+05 | 7.29E-05 | 6.99E-09 | 1.26E+04 | 1.62E-07 | 1.29E-11 |
| | Mouse:Canine 11E12 Chimera | MU-11E12-VH | MU-11E12-VL | 4.37E+05 | 1.08E-04 | 2.48E-10 | 7.93E+05 | 6.55E-07 | 8.26E-13 |
| | Mouse:Feline 11E12 Chimera | MU-11E12-VH | MU-11E12-VL | 3.88E+05 | 5.06E-05 | 1.30E-10 | 6.84E+05 | 8.70E-08 | 1.27E-13 |
| B | Feline 11E12 1.1 | FEL-11E12-VH1 | FEL-11E12-VL1 | 2.00E+04 | 4.44E-04 | 2.22E-08 | 1.85E+05 | 1.41E-04 | 7.64E-10 |
| | Feline 11E12 1.2 | FEL-11E12-VH1 | FEL-11E12-VL2 | no binding | | | no binding | | |
| | Feline_11E12 1.1_FW2 | FEL-11E12-VH1 | FEL-11E12-VL1_FW2 | 8.52E+05 | 6.39E-04 | 7.50E-10 | 4.52E+04 | 3.18E-04 | 7.02E-09 |
| | Feline_11E12 1.1_K46Q | FEL-11E12-VH1 | FEL-11E12-VL1_K46Q | 1.15E+04 | 1.45E-04 | 1.26E-08 | 4.64E+04 | 8.85E-05 | 1.91E-09 |
| C | Feline 15H05 1.1 | FEL-15H05-VH1 | FEL-15H05-VL1 | 9.71E+04 | 1.31E-03 | 1.35E-08 | 2.70E+04 | 1.36E-07 | 5.04E-12 |
| | Feline 15H05 1.2 | FEL-15H05-VH1 | FEL-15H05-VL2 | 1.41E+04 | 1.47E-03 | 1.04E-07 | 3.30E+04 | 1.15E-04 | 3.48E-09 |
| | Feline 15H05 1.3 | FEL-15H05-VH1 | FEL-15H05-VL3 | 3.80E+04 | 3.28E-03 | 8.64E-08 | 2.97E+04 | 1.90E-04 | 6.38E-09 |
| | Feline 15H05 2.1 | FEL-15H05-VH2 | FEL-15H05-VL1 | 2.08E+05 | 4.65E-03 | 2.23E-08 | 5.25E+05 | 8.66E-04 | 1.65E-09 |
| | Feline 15H05 2.2 | FEL-15H05-VH2 | FEL-15H05-VL2 | 9.05E+05 | 1.95E-03 | 2.15E-09 | 2.77E+04 | 1.09E-05 | 3.93E-10 |
| | Feline 15H05 2.3 | FEL-15H05-VH2 | FEL-15H05-VL3 | 3.41E+05 | 5.35E-04 | 1.57E-09 | no binding | | |
| | Feline 15H05 3.1 | FEL-15H05-VH3 | FEL-15H05-VL1 | 4.47E+04 | 1.66E-03 | 3.71E-08 | 2.65E+04 | 2.11E-05 | 7.95E-10 |
| | Feline 15H05 3.2 | FEL-15H05-VH3 | FEL-15H05-VL2 | 1.32E+05 | 1.66E-03 | 1.26E-08 | 2.97E+04 | 6.04E-06 | 2.04E-10 |
| | Feline 15H05 3.3 | FEL-15H05-VH3 | FEL-15H05-VL3 | 7.63E+04 | 8.86E-04 | 1.16E-08 | no binding | | |
| | Feline 15H05 VH1 mouse VL | FEL-15H05-VH1 | MU-15H05-VL | 1.31E+05 | 2.20E-05 | 1.68E-10 | 1.08E+05 | 2.66E-07 | 2.46E-12 |
| | Feline 15H05 VH2 mouse VL | FEL-15H05-VH2 | MU-15H05-VL | 3.40E+04 | 5.47E-05 | 1.61E-09 | 1.71E+05 | 3.79E-04 | 2.22E-09 |
| | Feline 15H05 VH3 mouse VL | FEL-15H05-VH3 | MU-15H05-VL | 8.89E+04 | 1.57E-05 | 1.77E-10 | 1.00E+05 | 2.64E-07 | 2.64E-12 |
| | Feline 15H05 1.1 FW1 | FEL-15H05-VH1 | FEL-15H05-VL1_FW1 | 5.06E+03 | 2.86E-03 | 5.64E-07 | 1.92E+04 | 1.56E-02 | 8.13E-07 |
| | Feline 15H05 1.1 FW2 | FEL-15H05-VH1 | FEL-15H05-VL1_FW2 | 3.83E+05 | 2.49E-05 | 6.50E-11 | 3.84E+05 | 1.66E-07 | 4.31E-13 |
| | Feline 15H05 1.1 FW3 | FEL-15H05-VH1 | FEL-15H05-VL1_FW3 | 2.14E+05 | 1.21E-05 | 5.64E-11 | 3.00E+03 | 3.91E-07 | 1.30E-10 |
| | Feline 15H05 1.1 FW1_2 | FEL-15H05-VH1 | FEL-15H05-VL1_FW1_FW2 | 7.56E+03 | 6.70E-06 | 8.87E-10 | 6.91E+03 | 3.82E-06 | 2.63E-10 |
| | Feline 15H05 1.1 FW2_3 | FEL-15H05-VH1 | FEL-15H05-VL1_FW2_FW3 | 9.49E+03 | 1.16E-03 | 1.23E-07 | 9.05E+03 | 1.93E-03 | 2.14E-07 |
| | Feline 15H05 1.1 FW1_3 | FEL-15H05-VH1 | FEL-15H05-VL1_FW1_FW3 | 4.48E+05 | 3.02E-05 | 6.74E-11 | 6.59E+03 | 2.88E-08 | 4.36E-12 |
| | Feline 15H05 1.1 K42N | FEL-15H05-VH1 | FEL-15H05-VL1_FW2_K42N | 1.63E+03 | 1.10E-02 | 6.77E-06 | | | |
| | Feline 15H05 1.1 V43I | FEL-15H05-VH1 | FEL-15H05-VL1_FW2_V43I | 2.94E+04 | 4.01E-04 | 1.36E-08 | | | |
| | Feline 15H05 1.1 L46V | FEL-15H05-VH1 | FEL-15H05-VL1_FW2_L46V | 3.55E+04 | 8.11E-04 | 2.28E-08 | | | |
| | Feline 15H05 1.1 Y49N | FEL-15H05-VH1 | FEL-15H05-VL1_FW2_Y49N | 2.40E+04 | 9.50E-04 | 3.95E-08 | | | |
| | Feline 15H05 1.1 K42N_V43I | FEL-15H05-VH1 | FEL-15H05-VL1_FW2_K42N_V43I | 2.34E+05 | 2.20E-03 | 9.42E-09 | | | |
| D | ZTS-927 | FEL-15H05-VH1 | FEL-15H05-VL1_FW2 | 3.74E+04 | 2.30E-05 | 6.14E-10 | | | |
| | ZTS-361 | FEL-15H05-VH1 | FEL-15H05-VL1_FW2 | 4.60E+04 | 2.18E-05 | 4.74E-10 | | | |

FIG. 2

Potency of Antibodies with CDRs of Mouse Origin

| | $IC_{50}$ (μg/ml) | | | |
|---|---|---|---|---|
| | Canine DH82 cells | | Feline FCWF4 cells | |
| Antibody | Canine IL-31 | Feline IL-31 | Canine IL-31 | Feline IL-31 |
| **Mouse** | | | | |
| 11E12 | | 2.47 | | 2.01 |
| 15H05 | 11.17 | 2.7 | 25.68 | 4.26 |
| **Chimera** | | | | |
| Mouse:Feline 11E12 | | 4.4 | | 3.45 |
| Mouse:Canine 11E12 | | | | 1.15 |
| Mouse:Feline 15H05 | 28.61 | 5.59 | | 3.25 |
| Mouse:Canine 15H05 | 12.69 | 0.71 | | 3.11 |
| **Felinized** | | | | |
| 11E12 1.1 | | 28.98 | | 4.47 |
| 11E12 1.2 | | > 100 | | > 100 |
| 11E12 1.1 FW2 | | 5.66 | | 4.38 |
| ZTS-927 | 23.18 | 1.57 | 39.57 | 5.26 |
| ZTS-361 | 22.99 | 2.01 | 38.80 | 4.89 |

Not Tested

FIG. 3

Binding of Antibodies with CDRs of Dog Origin

| | | | Binding (ELISA OD) | | Binding (Biacore) | | | | | |
|---|---|---|---|---|---|---|---|---|---|---|
| | SEQ ID NO: | | 157 | 163 | 155 | 157 | 165 | 181 | 163 | 161 |
| Antibody | VH | VL | Feline IL-31 wiltype | Feline IL-31 15H05 Mutant | Canine | Feline IL-31 wiltype | Equine | Human | Feline IL-31 15H05 Mutant | Feline IL-31 11E12 Mutant |
| ZIL1 | 75 | 77 | 1.89 | 0.92 | - | + | + | - | - | + / - |
| ZIL8 | 79 | 81 | 0.57 | 0.08 | - | + | - | - | - | - |
| ZIL9 | 83 | 85 | 1.80 | 0.73 | - | + | + | - | - | + |
| ZIL11 | 87 | 89 | 1.32 | 0.33 | - | + | - | - | - | + |
| ZIL69 | 91 | 93 | 1.48 | 0.92 | + / - | + | - | - | - | + |
| ZIL94 | 95 | 97 | 1.67 | 1.30 | + | + | - | - | + | + |
| ZIL154 | 99 | 101 | 1.62 | 1.38 | - | + | - | - | + | + |
| ZIL159 | 103 | 105 | 1.60 | 1.31 | + | + | - | - | - | - |
| ZIL171 | 107 | 109 | 1.42 | 0.93 | - | + | - | - | + / - | + |
| Controls | | | | | | | | | | |
| Mouse 11E12 | 71 | 73 | 1.15 | 1.33 | + | + | - | - | + | - |
| Mouse 15H05 | 67 | 69 | 1.94 | 0.05 | + | + | + | - | - | + |

FIG. 4

```
SEQ_ID_NO_157_Feline_IL31_wildtype        1 MLSHAGPARFALFLLCCMETLLPSHMAPAHRLQPSDIRKIILELR 45
SEQ_ID_NO_161_Feline_IL31_11E12_mutant    1 MLSHAGPARFALFLLCCMETLLPSHMAPAHRLQPSDIRKIILELR 45
SEQ_ID_NO_163_Feline_IL31_15H05_mutant    1 MLSHAGPARFALFLLCCMETLLPSHMAPAHRLQPSDIRKIILELR 45

SEQ_ID_NO_157_Feline_IL31_wildtype       46 PMSKGLLQDYLKKEIGLPESNHSSLPCLSSDSQLPHINGSAILPY 90
SEQ_ID_NO_161_Feline_IL31_11E12_mutant   46 PMSKGLLQDYLKKEIGLPESNHSSLPCLSSDSQLPHINGSAILPY 90
SEQ_ID_NO_163_Feline_IL31_15H05_mutant   46 PMSKGLLQDYLKKEIGLPESNHSSLPCLSSDSQLPHINGSAILPY 90

SEQ_ID_NO_157_Feline_IL31_wildtype       91 FRAIRPLSDKNTIDKIIEQLDKLKFQREPEAKVSMPADNFERKNF 135
SEQ_ID_NO_161_Feline_IL31_11E12_mutant   91 FRAIRPLSDKNTIAKIAEQLDKLKFQREPEAKVSMPADNFERKNF 135
SEQ_ID_NO_163_Feline_IL31_15H05_mutant   91 FRAIRPLSDKNTIDKIIEQLDKLKFQREPEAKVSMAAANFERKNF 135

SEQ_ID_NO_157_Feline_IL31_wildtype      136 ILAVLQQFSACLEHVLQSLNSGPQHHHHHH 165
SEQ_ID_NO_161_Feline_IL31_11E12_mutant  136 ILAVLQQFSACLEHVLQSLNSGPQHHHHHH 165
SEQ_ID_NO_163_Feline_IL31_15H05_mutant  136 ILAVLQQFSACLEHVLQSLNSGPQHHHHHH 165
```

FIG. 6A

| | Laboratory Beagle Dogs | Atopic Dermatitis Dogs | Allergic Dermatitis Dogs |
|---|---|---|---|
| Number of values | 55 | 243 | 61 |
| | | | |
| Minimum | 20 | 25 | 379 |
| 25% Percentile | 61 | 284 | 2768 |
| Median | 154 | 871 | 8042 |
| 75% Percentile | 396 | 3566 | 16054 |
| Maximum | 4145 | 1280345 | 240387 |
| | | | |
| Mean | 465.7 | 13152 | 19976 |
| Std. Deviation | 788 | 86273 | 39240 |
| Std. Error of Mean | 106.3 | 5534 | 5024 |
| | | | |
| Lower 95% CI of mean | 252.7 | 2250 | 9926 |
| Upper 95% CI of mean | 678.7 | 24053 | 30026 |

ALLOWED AMINO ACID SUBSTITUTIONS ON CANINE IL-31 TO RETAIN ANTIBODY 15H05 BINDING

| IL-31 SPECIES | TAR | ALL EXCEPT GIED | NONE | NONE | NONE | ALL EXCEPT LWNCQMDEG | NONE | NONE | ALL EXCEPT IEDP | KRMQ | K | ALL EXCEPT DP |
|---|---|---|---|---|---|---|---|---|---|---|---|---|
| CANINE | S | V | P | A | D | T | F | E | C | K | S | F |
| FELINE | S | M | P | A | D | N | F | E | R | K | N | F |
| EQUINE | S | M | P | T | D | N | F | E | R | K | R | F |
| HUMAN | S | V | P | T | D | T | H | E | C | K | R | F |
| CANINE REF. POSITION FROM SEQ ID NO 155 | 124 | 125 | 126 | 127 | 128 | 129 | 130 | 131 | 132 | 133 | 134 | 135 |

FIG. 12

| ZTS PEPTIDE NUMBER | MOL WT | DESCRIPTION | TYPE | PEPTIDE SEQUENCE (N TO C TERMINUS) |
|---|---|---|---|---|
| ZTS-561 | 2449.9 | IL31 15H05 MIMOTOPE - CANINE | CONSTRAINED | C(mT2a)TEISVPADTFERKSFILT C(mT2a) |
| ZTS-562 | 2021.3 | IL31 15H05 MIMOTOPE - CANINE SHORT | CONSTRAINED | C(mT2a)EISVPADTFERKSF C(mT2a) |
| ZTS-563 | 2477 | IL31 15H05 MIMOTOPE - FELINE | CONSTRAINED | C(mT2a)AKVSMPADNFERKNFILT C(mT2a) |
| ZTS-564 | 2350.7 | IL31 15H05 MIMOTOPE - CANINE ALTERNATE LINKAGE | CONSTRAINED | C(mT2b)TEISVPADTFECKSFILT C(mT2b) |

* TERMINAL CYSTEINES (C) UNDERLINED ABOVE WERE ADDED TO FACILITATE CONJUGATION CHEMISTRY USING THE FREE THIOL GROUPS

FIG. 13A

LINKER mT2a

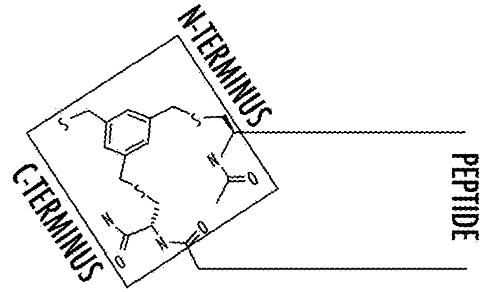

LINKER mT2b

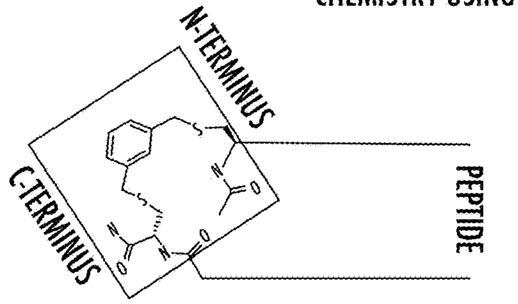

FIG. 13B

| PEPTIDE | KD (M) BIACORE ZTS-927 | INHIBITION OF ZTS-361 IL-31 BINDING USING PEPTIDES FELINE FCWF4 CELLS IC50 (µg/ml) CRM-197 CONJUGATED | UNCONJUGATED |
|---|---|---|---|
| ZTS-561 | 1.02E-09 | 7 | ND |
| ZTS-562 | 2.78E-09 | 3.02 | 1.05 |
| ZTS-563 | 1.48E-09 | 3.38 | 1.74 |
| ZTS-564 | 4.13E-09 | 9.44 | ND |

ND DUE TO POOR SOLUBILITY

TREATMENT GROUPS FOR SECOND DOG SEROLOGY STUDY

| TREATMENT GROUP | ZTS PEPTIDE NUMBER | DESCRIPTION | TYPE | PEPTIDE SEQUENCE (N TO C TERMINUS) | CONJUGATED TO |
|---|---|---|---|---|---|
| T01 | | FULL LENGTH CANINE IL-31 | PROTEIN | SEQ ID NO 155 | CRM-197 |
| T02 | ZTS-420 | CANINE 15H05 MIMOTOPE | CONSTRAINED | Ac-CTEISVPADTFERKSFILTC | CRM-197 |
| T03 | ZTS-421 | HUMAN 15H05 MIMOTOPE | CONSTRAINED | C(mT2b) TNISVPTDTHECKRFILTC(mT2b) | CRM-197 |
| T04 | ZTS-766 | CANINE BC HELIX MIMOTOPE | LINEAR | Ac-CGSGNSSAILPYFRAIRPLSDKNIIDKEQLDKLKF-Am | CRM-197 |

FIG. 16A

SEQUENCE ALIGNMENT OF IL-31 BC HELIX REGION FROM MULTIPLE SPECIES

| IL-31 SPECIES | PEPTIDE SEQUENCE (N TO C TERMINUS) | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| CANINE | N | S | S | A | I | L | P | Y | F | R | A | I | R | P | L | S | D | K | N | I | I | D | K | I | I | E | Q | L | D | K | L | K | F |
| FELINE | N | G | S | A | I | L | P | Y | F | R | A | I | R | P | L | S | D | K | N | T | I | D | K | I | I | E | Q | L | D | K | L | K | F |
| EQUINE | N | S | S | A | I | L | P | Y | F | K | A | I | S | P | S | L | N | N | D | K | S | L | Y | I | I | E | Q | L | D | K | L | N | F |
| HUMAN | H | S | P | A | I | R | A | Y | L | K | T | I | R | Q | L | D | N | K | S | V | I | D | E | I | I | E | H | L | D | K | L | I | F |

| SEQ ID NO | | AMINO ACID NUMBER IN REFERENCE SEQUENCE | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| 155 | CANINE | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
| 157 | FELINE | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
| 165 | EQUINE | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
| 181 | HUMAN | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 |

FIG. 16B

DOG TITERS TO CANINE AND HUMAN IL-31 FOLLOWING VACCINATION WITH CANINE IL-31 PROTEIN OR MIMOTOPES WITH CANINE OR HUMAN AMINO ACID SEQUENCES

TREATMENT GROUPS FOR FELINE SEROLOGY STUDY

| TREATMENT GROUP | ZTS PEPTIDE NUMBER | DESCRIPTION | TYPE | PEPTIDE SEQUENCE IN (N TO C TERMINUS) | CONJUGATED TO |
|---|---|---|---|---|---|
| T01 | | FULL LENGTH FELINE IL-31 | PROTEIN | SEQ ID NO 157 | CRM-197 |
| T02 | ZTS-563 | FELINE 15H05 MIMOTOPE LINKER mT2a | CONSTRAINED | C(mT2a) AKVSMPADNFERKNFILTC(mT2a) | CRM-197 |
| T03 | ZTS-418 | EQUINE 15H05 MIMOTOPE | CONSTRAINED | Ac-CTEVSMPTDNFERKRFILTC | CRM-197 |
| T04 | ZTS-423 | FELINE BC HELIX MIMOTOPE | LINEAR | Ac-CGSGNGSAILPYFRAIRPLSDKNTIDKIIEQLDKLKF-Am | CRM-197 |
| T05 | ZTS-422 | FELINE 15H05 MIMOTOPE LINKER mT2b | CONSTRAINED | C{Ahx}C(mT2b)AKVSMPADNFERKNFILT C(mT2b) | CRM-197 |

FIG. 18A

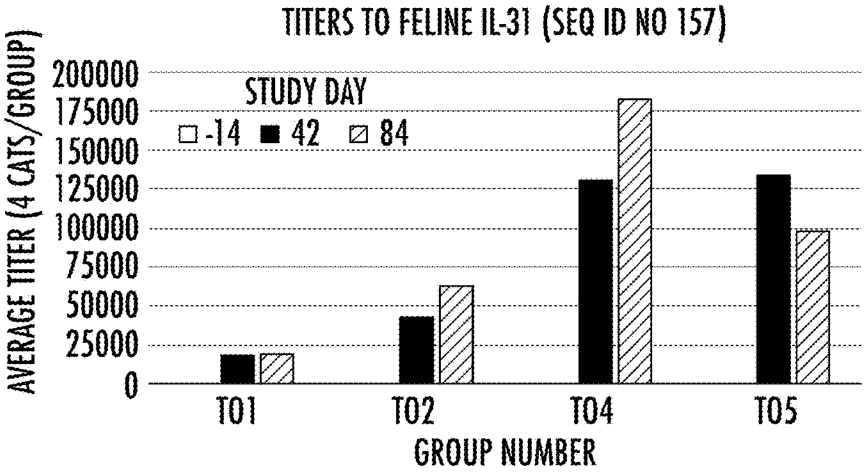

SEQUENCE ALIGNMENT OF IL-31 HELIX A REGION FROM MULTIPLE SPECIES

| SEQ ID NO | IL-31 SPECIES | PEPTIDE SEQUENCE (N TO C TERMINUS) | | | | | | | |
|---|---|---|---|---|---|---|---|---|---|
| 155 | CANINE | P | S | D | V | R | K | I | |
| 157 | FELINE | P | S | D | I | R | K | I | |
| 165 | EQUINE | P | K | E | I | Q | A | I | |
| 181 | HUMAN | P | S | D | D | V | Q | K | I |
| | | AMINO ACID NUMBER IN REFERENCE SEQUENCE | | | | | | | |
| | CANINE | 34 | 35 | 36 | 37 | 38 | 39 | 40 | |
| | FELINE | 34 | 35 | 36 | 37 | 38 | 39 | 40 | |
| | EQUINE | 27 | 28 | 29 | 30 | 31 | 32 | 33 | |
| | HUMAN | 34 | 35 | 36 | 37 | 38 | 39 | 40 | 41 |

FIG. 19B

SEQUENCE ALIGNMENT OF IL-31 EXTENDED HELIX A REGION FROM MULTIPLE SPECIES

| SEQ ID NO | IL-31 SPECIES | PEPTIDE SEQUENCE (N TO C TERMINUS) | | | | | | | | | | | | | | | | | | | | | | | | |
|---|---|---|---|---|---|---|---|---|---|---|---|---|---|---|---|---|---|---|---|---|---|---|---|---|---|---|
| 155 | CANINE | A | P | T | H | Q | L | P | P | S | D | V | R | K | I | I | L | E | L | Q | P | L | S | R | G | |
| 157 | FELINE | A | P | A | H | R | L | Q | P | S | D | I | R | K | I | I | L | E | L | R | P | M | S | K | G | |
| 165 | EQUINE | G | P | I | Y | Q | L | Q | P | K | E | I | Q | A | I | I | V | E | L | Q | N | L | S | K | K | |
| 181 | HUMAN | L | P | V | R | L | L | R | P | S | D | D | V | Q | K | I | V | E | E | L | Q | S | L | S | K | M |
| | | AMINO ACID NUMBER IN REFERENCE SEQUENCE | | | | | | | | | | | | | | | | | | | | | | | | |
| | CANINE | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | |
| | FELINE | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | |
| | EQUINE | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | |
| | HUMAN | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 |

SEQUENCE ALIGNMENT OF IL-31 AB LOOP REGION FROM MULTIPLE SPECIES

| SEQ ID NO | IL-31 SPECIES | PEPTIDE SEQUENCE (N TO C TERMINUS) | | | | | |
|---|---|---|---|---|---|---|---|
| 155 | CANINE | T | G | V | P | E | S |
| 157 | FELINE | I | G | L | P | E | S |
| 165 | EQUINE | K | G | V | Q | K | F |
| 181 | HUMAN | K | G | V | L | V | S |
| | | AMINO ACID NUMBER IN REFERENCE SEQUENCE | | | | | |
| | CANINE | 60 | 61 | 62 | 63 | 64 | 65 |
| | FELINE | 60 | 61 | 62 | 63 | 64 | 65 |
| | EQUINE | 53 | 54 | 55 | 56 | 57 | 58 |
| | HUMAN | 60 | 61 | 62 | 63 | 64 | 65 |

FIG. 20

EQUINE MIMOTOPES USED TO THE PROBE MOUSE ANTI EQUINE IL-31 RESPONSE

| SEQ ID NO | IL-31 SPECIES | MIMOTOPE | PEPTIDE SEQUENCE (N TO C TERMINUS) |
|---|---|---|---|
| 165 | EQUINE | 15H05 | BIOTIN G S G C T E V S M P T D N F E R K R F I L T C |
| 165 | EQUINE | BC HELIX | BIOTIN G S G N S S A I L P Y F K A I S P S L N N D K S L Y I I E Q L D K L N F |
| 165 | EQUINE | A HELIX | BIOTIN G S G G P I Y Q L Q P K E I Q A I I V E L Q N L S K K |

| IL-31 SPECIES | MIMOTOPE | AMINO ACID NUMBER IN REFERENCE SEQUENCE |
|---|---|---|
| EQUINE | 15H05 | 115 116 117 118 119 120 121 122 123 124 125 126 127 128 129 130 131 132 |
| EQUINE | BC HELIX | 77 78 79 80 81 82 83 84 85 86 87 88 89 90 91 92 93 94 95 96 97 98 99 100 101 102 103 104 105 106 107 108 109 |
| EQUINE | A HELIX | 20 21 22 23 24 25 26 27 28 29 30 31 32 33 34 35 36 37 38 39 40 41 42 43 |

FIG. 21A

BINDING OF SERUM, FROM EQUINE IL-31 VACCINATED VERSUS CONTROL MICE, TO EQUINE IL-31 MIMOTOPUS USING BIO-LAYER INTERFEROMETRY

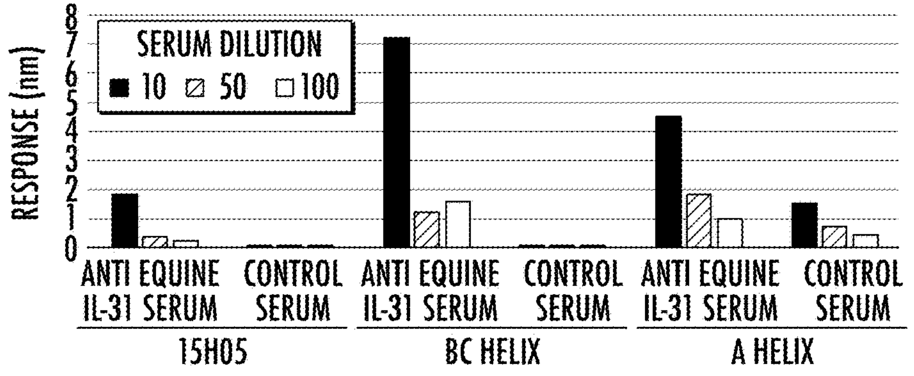

FIG. 21B

SEQUENCE LISTING

<160> NUMBER OF SEQ ID NOS: 203

<210> SEQ ID NO 1
<211> LENGTH: 5
<212> TYPE: PRT
<213> ORGANISM: Mus musculus

<400> SEQUENCE: 1

Ser Tyr Thr Ile His
1               5

<210> SEQ ID NO 2
<211> LENGTH: 17
<212> TYPE: PRT
<213> ORGANISM: Mus musculus

<400> SEQUENCE: 2

Asn Ile Asn Pro Thr Ser Gly Tyr Thr Glu Asn Asn Gln Arg Phe Lys
1               5                   10                  15

Asp

<210> SEQ ID NO 3
<211> LENGTH: 13
<212> TYPE: PRT
<213> ORGANISM: Mus musculus

<400> SEQUENCE: 3

Trp Gly Phe Lys Tyr Asp Gly Glu Trp Ser Phe Asp Val
1               5                   10

<210> SEQ ID NO 4
<211> LENGTH: 11
<212> TYPE: PRT
<213> ORGANISM: Mus musculus

<400> SEQUENCE: 4

Arg Ala Ser Gln Gly Ile Ser Ile Trp Leu Ser
1               5                   10

<210> SEQ ID NO 5
<211> LENGTH: 7
<212> TYPE: PRT
<213> ORGANISM: Mus musculus

<400> SEQUENCE: 5

Lys Ala Ser Asn Leu His Ile
1               5

<210> SEQ ID NO 6
<211> LENGTH: 9
<212> TYPE: PRT
<213> ORGANISM: Mus musculus

<400> SEQUENCE: 6

Leu Gln Ser Gln Thr Tyr Pro Leu Thr
1               5

<210> SEQ ID NO 7
<211> LENGTH: 5
<212> TYPE: PRT
<213> ORGANISM: Mus musculus

<400> SEQUENCE: 7

Tyr Tyr Asp Ile Asn 1 5

<210> SEQ ID NO 8
<211> LENGTH: 17
<212> TYPE: PRT
<213> ORGANISM: Mus musculus

<400> SEQUENCE: 8

Trp Ile Phe Pro Gly Asp Gly Gly Thr Lys Tyr Asn Glu Thr Phe Lys
1 5 10 15

Gly

<210> SEQ ID NO 9
<211> LENGTH: 14
<212> TYPE: PRT
<213> ORGANISM: Mus musculus

<400> SEQUENCE: 9

Ala Arg Gly Gly Thr Ser Val Ile Arg Asp Ala Met Asp Tyr
1 5 10

<210> SEQ ID NO 10
<211> LENGTH: 15
<212> TYPE: PRT
<213> ORGANISM: Mus musculus

<400> SEQUENCE: 10

Arg Ala Ser Glu Ser Val Asp Asn Tyr Gly Ile Ser Phe Met His
1 5 10 15

<210> SEQ ID NO 11
<211> LENGTH: 7
<212> TYPE: PRT
<213> ORGANISM: Mus musculus

<400> SEQUENCE: 11

Arg Ala Ser Asn Leu Glu Ser
1 5

<210> SEQ ID NO 12
<211> LENGTH: 9
<212> TYPE: PRT
<213> ORGANISM: Mus musculus

<400> SEQUENCE: 12

Gln Gln Ser Asn Lys Asp Pro Leu Thr
1 5

<210> SEQ ID NO 13
<211> LENGTH: 5
<212> TYPE: PRT
<213> ORGANISM: Canis familiaris

<400> SEQUENCE: 13

Ser Tyr Gly Met Ser
1 5

<210> SEQ ID NO 14
<211> LENGTH: 17
<212> TYPE: PRT
<213> ORGANISM: Canis familiaris

<400> SEQUENCE: 14

His Ile Asn Ser Gly Gly Ser Ser Thr Tyr Tyr Ala Asp Ala Val Lys

-continued 1 5 10 15

Gly

<210> SEQ ID NO 15
<211> LENGTH: 15
<212> TYPE: PRT
<213> ORGANISM: Canis familiaris

<400> SEQUENCE: 15

Val Tyr Thr Thr Leu Ala Ala Phe Trp Thr Asp Asn Phe Asp Tyr
1 5 10 15

<210> SEQ ID NO 16
<211> LENGTH: 13
<212> TYPE: PRT
<213> ORGANISM: Canis familiaris

<400> SEQUENCE: 16

Ser Gly Ser Thr Asn Asn Ile Gly Ile Leu Ala Ala Thr
1 5 10

<210> SEQ ID NO 17
<211> LENGTH: 7
<212> TYPE: PRT
<213> ORGANISM: Canis familiaris

<400> SEQUENCE: 17

Ser Asp Gly Asn Arg Pro Ser
1 5

<210> SEQ ID NO 18
<211> LENGTH: 11
<212> TYPE: PRT
<213> ORGANISM: Canis familiaris

<400> SEQUENCE: 18

Gln Ser Phe Asp Thr Thr Leu Asp Ala Tyr Val
1 5 10

<210> SEQ ID NO 19
<211> LENGTH: 5
<212> TYPE: PRT
<213> ORGANISM: Canis familiaris

<400> SEQUENCE: 19

Asp Tyr Ala Met Ser
1 5

<210> SEQ ID NO 20
<211> LENGTH: 17
<212> TYPE: PRT
<213> ORGANISM: Canis familiaris

<400> SEQUENCE: 20

Gly Ile Asp Ser Val Gly Ser Gly Thr Ser Tyr Ala Asp Ala Val Lys
1 5 10 15

Gly

<210> SEQ ID NO 21
<211> LENGTH: 8
<212> TYPE: PRT
<213> ORGANISM: Canis familiaris

<400> SEQUENCE: 21

Gly Phe Pro Gly Ser Phe Glu His
1 5

<210> SEQ ID NO 22
<211> LENGTH: 13
<212> TYPE: PRT
<213> ORGANISM: Canis familiaris

<400> SEQUENCE: 22

Thr Gly Ser Ser Ser Asn Ile Gly Ser Gly Tyr Val Gly
1 5 10

<210> SEQ ID NO 23
<211> LENGTH: 7
<212> TYPE: PRT
<213> ORGANISM: Canis familiaris

<400> SEQUENCE: 23

Tyr Asn Ser Asp Arg Pro Ser
1 5

<210> SEQ ID NO 24
<211> LENGTH: 10
<212> TYPE: PRT
<213> ORGANISM: Canis familiaris

<400> SEQUENCE: 24

Ser Val Tyr Asp Arg Thr Phe Asn Ala Val
1 5 10

<210> SEQ ID NO 25
<211> LENGTH: 5
<212> TYPE: PRT
<213> ORGANISM: Canis familiaris

<400> SEQUENCE: 25

Ser Tyr Asp Met Thr
1 5

<210> SEQ ID NO 26
<211> LENGTH: 17
<212> TYPE: PRT
<213> ORGANISM: Canis familiaris

<400> SEQUENCE: 26

Asp Val Asn Ser Gly Gly Thr Gly Thr Ala Tyr Ala Val Ala Val Lys
1 5 10 15

Gly

<210> SEQ ID NO 27
<211> LENGTH: 9
<212> TYPE: PRT
<213> ORGANISM: Canis familiaris

<400> SEQUENCE: 27

Leu Gly Val Arg Asp Gly Leu Ser Val
1 5

<210> SEQ ID NO 28
<211> LENGTH: 11
<212> TYPE: PRT
<213> ORGANISM: Canis familiaris

<400> SEQUENCE: 28

Ser Gly Glu Ser Leu Asn Glu Tyr Tyr Thr Gln
1 5 10

<210> SEQ ID NO 29
<211> LENGTH: 7
<212> TYPE: PRT
<213> ORGANISM: Canis familiaris

<400> SEQUENCE: 29

Arg Asp Thr Glu Arg Pro Ser
1 5

<210> SEQ ID NO 30
<211> LENGTH: 10
<212> TYPE: PRT
<213> ORGANISM: Canis familiaris

<400> SEQUENCE: 30

Glu Ser Ala Val Asp Thr Gly Thr Leu Val
1 5 10

<210> SEQ ID NO 31
<211> LENGTH: 5
<212> TYPE: PRT
<213> ORGANISM: Canis familiaris

<400> SEQUENCE: 31

Thr Tyr Val Met Asn
1 5

<210> SEQ ID NO 32
<211> LENGTH: 17
<212> TYPE: PRT
<213> ORGANISM: Canis familiaris

<400> SEQUENCE: 32

Ser Ile Asn Gly Gly Gly Ser Ser Pro Thr Tyr Ala Asp Ala Val Arg
1 5 10 15

Gly

<210> SEQ ID NO 33
<211> LENGTH: 8
<212> TYPE: PRT
<213> ORGANISM: Canis familiaris

<400> SEQUENCE: 33

Ser Met Val Gly Pro Phe Asp Tyr
1 5

<210> SEQ ID NO 34
<211> LENGTH: 11
<212> TYPE: PRT
<213> ORGANISM: Canis familiaris

<400> SEQUENCE: 34

Ser Gly Glu Ser Leu Ser Asn Tyr Tyr Ala Gln
1 5 10

<210> SEQ ID NO 35
<211> LENGTH: 7
<212> TYPE: PRT
<213> ORGANISM: Canis familiaris

<400> SEQUENCE: 35

-continued

Lys Asp Thr Glu Arg Pro Ser
1 5

<210> SEQ ID NO 36
<211> LENGTH: 10
<212> TYPE: PRT
<213> ORGANISM: Canis familiaris

<400> SEQUENCE: 36

Glu Ser Ala Val Ser Ser Asp Thr Ile Val
1 5 10

<210> SEQ ID NO 37
<211> LENGTH: 5
<212> TYPE: PRT
<213> ORGANISM: Canis familiaris

<400> SEQUENCE: 37

Ser Tyr Ala Met Lys
1 5

<210> SEQ ID NO 38
<211> LENGTH: 17
<212> TYPE: PRT
<213> ORGANISM: Canis familiaris

<400> SEQUENCE: 38

Thr Ile Asn Asn Asp Gly Thr Arg Thr Gly Tyr Ala Asp Ala Val Arg
1 5 10 15

Gly

<210> SEQ ID NO 39
<211> LENGTH: 15
<212> TYPE: PRT
<213> ORGANISM: Canis familiaris

<400> SEQUENCE: 39

Gly Asn Ala Glu Ser Gly Cys Thr Gly Asp His Cys Pro Pro Tyr
1 5 10 15

<210> SEQ ID NO 40
<211> LENGTH: 11
<212> TYPE: PRT
<213> ORGANISM: Canis familiaris

<400> SEQUENCE: 40

Ser Gly Glu Ser Leu Asn Lys Tyr Tyr Ala Gln
1 5 10

<210> SEQ ID NO 41
<211> LENGTH: 7
<212> TYPE: PRT
<213> ORGANISM: Canis familiaris

<400> SEQUENCE: 41

Lys Asp Thr Glu Arg Pro Ser
1 5

<210> SEQ ID NO 42
<211> LENGTH: 10
<212> TYPE: PRT
<213> ORGANISM: Canis familiaris

<400> SEQUENCE: 42

Glu Ser Ala Val Ser Ser Glu Thr Asn Val
1 5 10

<210> SEQ ID NO 43
<211> LENGTH: 5
<212> TYPE: PRT
<213> ORGANISM: Canis familiaris

<400> SEQUENCE: 43

Thr Tyr Phe Met Ser
1 5

<210> SEQ ID NO 44
<211> LENGTH: 17
<212> TYPE: PRT
<213> ORGANISM: Canis familiaris

<400> SEQUENCE: 44

Leu Ile Ser Ser Asp Gly Ser Gly Thr Tyr Tyr Ala Asp Ala Val Lys
1 5 10 15

Gly

<210> SEQ ID NO 45
<211> LENGTH: 7
<212> TYPE: PRT
<213> ORGANISM: Canis familiaris

<400> SEQUENCE: 45

Phe Trp Arg Ala Phe Asn Asp
1 5

<210> SEQ ID NO 46
<211> LENGTH: 14
<212> TYPE: PRT
<213> ORGANISM: Canis familiaris

<400> SEQUENCE: 46

Gly Leu Asn Ser Gly Ser Val Ser Thr Ser Asn Tyr Pro Gly
1 5 10

<210> SEQ ID NO 47
<211> LENGTH: 7
<212> TYPE: PRT
<213> ORGANISM: Canis familiaris

<400> SEQUENCE: 47

Asp Thr Gly Ser Arg Pro Ser
1 5

<210> SEQ ID NO 48
<211> LENGTH: 10
<212> TYPE: PRT
<213> ORGANISM: Canis familiaris

<400> SEQUENCE: 48

Ser Leu Tyr Thr Asp Ser Asp Ile Leu Val
1 5 10

<210> SEQ ID NO 49
<211> LENGTH: 5
<212> TYPE: PRT
<213> ORGANISM: Canis familiaris

<400> SEQUENCE: 49

Asp Arg Gly Met Ser
1 5

<210> SEQ ID NO 50
<211> LENGTH: 17
<212> TYPE: PRT
<213> ORGANISM: Canis familiaris

<400> SEQUENCE: 50

Tyr Ile Arg Tyr Asp Gly Ser Arg Thr Asp Tyr Ala Asp Ala Val Glu
1 5 10 15

Gly

<210> SEQ ID NO 51
<211> LENGTH: 8
<212> TYPE: PRT
<213> ORGANISM: Canis familiaris

<400> SEQUENCE: 51

Trp Asp Gly Ser Ser Phe Asp Tyr
1 5

<210> SEQ ID NO 52
<211> LENGTH: 16
<212> TYPE: PRT
<213> ORGANISM: Canis familiaris

<400> SEQUENCE: 52

Lys Ala Ser Gln Ser Leu Leu His Ser Asp Gly Asn Thr Tyr Leu Asp
1 5 10 15

<210> SEQ ID NO 53
<211> LENGTH: 7
<212> TYPE: PRT
<213> ORGANISM: Canis familiaris

<400> SEQUENCE: 53

Lys Val Ser Asn Arg Asp Pro
1 5

<210> SEQ ID NO 54
<211> LENGTH: 9
<212> TYPE: PRT
<213> ORGANISM: Canis familiaris

<400> SEQUENCE: 54

Met Gln Ala Ile His Phe Pro Leu Thr
1 5

<210> SEQ ID NO 55
<211> LENGTH: 5
<212> TYPE: PRT
<213> ORGANISM: Canis familiaris

<400> SEQUENCE: 55

Ser Tyr Val Met Thr
1 5

<210> SEQ ID NO 56
<211> LENGTH: 17
<212> TYPE: PRT
<213> ORGANISM: Canis familiaris

<400> SEQUENCE: 56

Gly Ile Asn Ser Glu Gly Ser Arg Thr Ala Tyr Ala Asp Ala Val Lys
1 5 10 15

Gly

<210> SEQ ID NO 57
<211> LENGTH: 10
<212> TYPE: PRT
<213> ORGANISM: Canis familiaris

<400> SEQUENCE: 57

Gly Asp Ile Val Ala Thr Gly Thr Ser Tyr
1 5 10

<210> SEQ ID NO 58
<211> LENGTH: 11
<212> TYPE: PRT
<213> ORGANISM: Canis familiaris

<400> SEQUENCE: 58

Ser Gly Glu Thr Leu Asn Arg Phe Tyr Thr Gln
1 5 10

<210> SEQ ID NO 59
<211> LENGTH: 7
<212> TYPE: PRT
<213> ORGANISM: Canis familiaris

<400> SEQUENCE: 59

Lys Asp Thr Glu Arg Pro Ser
1 5

<210> SEQ ID NO 60
<211> LENGTH: 10
<212> TYPE: PRT
<213> ORGANISM: Canis familiaris

<400> SEQUENCE: 60

Lys Ser Ala Val Ser Ile Asp Val Gly Val
1 5 10

<210> SEQ ID NO 61
<211> LENGTH: 5
<212> TYPE: PRT
<213> ORGANISM: Canis familiaris

<400> SEQUENCE: 61

Thr Tyr Val Met Asn
1 5

<210> SEQ ID NO 62
<211> LENGTH: 17
<212> TYPE: PRT
<213> ORGANISM: Canis familiaris

<400> SEQUENCE: 62

Ser Ile Asn Gly Gly Gly Ser Ser Pro Thr Tyr Ala Asp Ala Val Arg
1 5 10 15

Gly

<210> SEQ ID NO 63
<211> LENGTH: 8
<212> TYPE: PRT
<213> ORGANISM: Canis familiaris

```
<400> SEQUENCE: 63

Ser Met Val Gly Pro Phe Asp Tyr
1               5


<210> SEQ ID NO 64
<211> LENGTH: 11
<212> TYPE: PRT
<213> ORGANISM: Canis familiaris

<400> SEQUENCE: 64

Ser Gly Lys Ser Leu Ser Tyr Tyr Tyr Ala Gln
1               5                   10


<210> SEQ ID NO 65
<211> LENGTH: 7
<212> TYPE: PRT
<213> ORGANISM: Canis familiaris

<400> SEQUENCE: 65

Lys Asp Thr Glu Arg Pro Ser
1               5


<210> SEQ ID NO 66
<211> LENGTH: 10
<212> TYPE: PRT
<213> ORGANISM: Canis familiaris

<400> SEQUENCE: 66

Glu Ser Ala Val Ser Ser Asp Thr Ile Val
1               5                   10


<210> SEQ ID NO 67
<211> LENGTH: 122
<212> TYPE: PRT
<213> ORGANISM: Mus musculus

<400> SEQUENCE: 67

Gln Val Gln Leu Gln Gln Ser Ala Ala Glu Leu Ala Arg Pro Gly Ala
1               5                   10                  15

Ser Val Lys Met Ser Cys Lys Thr Ser Gly Tyr Thr Phe Thr Ser Tyr
            20                  25                  30

Thr Ile His Trp Ile Lys Gln Arg Pro Gly Gln Gly Leu Glu Trp Ile
        35                  40                  45

Gly Asn Ile Asn Pro Thr Ser Gly Tyr Thr Glu Asn Asn Gln Arg Phe
    50                  55                  60

Lys Asp Lys Thr Thr Leu Thr Val Asp Arg Ser Ser Asn Thr Ala Tyr
65                  70                  75                  80

Leu Gln Leu His Ser Leu Thr Ser Glu Asp Ser Ala Val Tyr Phe Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
        115                 120


<210> SEQ ID NO 68
<211> LENGTH: 366
<212> TYPE: DNA
<213> ORGANISM: Mus musculus

<400> SEQUENCE: 68
```

```
caggtccagc tgcagcagtc tgcagctgaa ctggcaagac ctggggcctc agtgaagatg     60

tcctgcaaga cttctggcta cacatttact tcctacacga tacactggat aaaacagagg    120

cctggacagg gtctggaatg gattggaaac attaatccca ccagtggata cactgagaac    180

aatcagaggt tcaaggacaa gaccacattg actgtagaca gatcctccaa cacagcctat    240

ttgcaactgc acagcctgac atctgaggac tctgcggtct atttctgtgc aagatggggc    300

tttaaatatg acggagaatg gtccttcgat gtctggggcg cagggaccac ggtcaccgtc    360

tcctca                                                               366


<210> SEQ ID NO 69
<211> LENGTH: 107
<212> TYPE: PRT
<213> ORGANISM: Mus musculus

<400> SEQUENCE: 69

Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Asn Ile Pro Lys Val Leu Ile
        35                  40                  45

Asn Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Asn
            100                 105


<210> SEQ ID NO 70
<211> LENGTH: 321
<212> TYPE: DNA
<213> ORGANISM: Mus musculus

<400> SEQUENCE: 70

gacatccaaa tgaaccagtc tccatccagt ctgtctgcat ccctcggaga cacaatcacc     60

gtcacttgcc gtgccagtca gggcatcagt atttggttaa gctggtacca gcagaaacca    120

ggaaatattc ctaaagtatt gatcaataag gcttccaact tgcacatagg agtcccacca    180

aggtttagtg gcagtggatc tggaacacat ttcacattaa ctatcaccag cctacagcct    240

gaagacattg ccacttacta ctgtctacag agtcaaactt atcctctcac gttcggaggg    300

gggaccaagc tggaaataaa c                                              321


<210> SEQ ID NO 71
<211> LENGTH: 121
<212> TYPE: PRT
<213> ORGANISM: Mus musculus

<400> SEQUENCE: 71

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Lys Tyr Tyr
            20                  25                  30

Asp Ile Asn Trp Val Arg Gln Arg Pro Glu Gln Gly Leu Glu Trp Ile
        35                  40                  45
```

-continued

Gly Trp Ile Phe Pro Gly Asp Gly Gly Thr Lys Tyr Asn Glu Thr Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gly Gly Thr Ser Val Ile Arg Asp Ala Met Asp Tyr Trp Gly
            100                 105                 110

Gln Gly Thr Ser Val Thr Val Ser Ser
        115                 120

<210> SEQ ID NO 72
<211> LENGTH: 363
<212> TYPE: DNA
<213> ORGANISM: Mus musculus

<400> SEQUENCE: 72
caggttcagc tgcagcagtc tggagctgaa ctggtaaagc ctggggcttc agtgaagttg 60
tcctgcaagg cttctggcta caccttcaaa tactatgata taaactgggt gaggcagagg 120
cctgaacagg gacttgagtg gattggatgg atttttcctg gagatggtgg tactaagtac 180
aatgagacgt tcaagggcaa ggccacactg actacagaca aatcctccag cacagcctac 240
atgcagctca gcaggctgac atctgaggac tctgctgtct atttctgtgc aagagggggg 300
acttcggtga taagggatgc tatggactac tggggtcaag gaacctcagt caccgtctcc 360
tca 363

<210> SEQ ID NO 73
<211> LENGTH: 111
<212> TYPE: PRT
<213> ORGANISM: Mus musculus

<400> SEQUENCE: 73

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
            100                 105                 110

<210> SEQ ID NO 74
<211> LENGTH: 333
<212> TYPE: DNA
<213> ORGANISM: Mus musculus

<400> SEQUENCE: 74
gacattgtgc tgacccaatc tccagcttct ttggctgtgt ctctagggca gagggccacc 60
atctcctgca gagccagcga aagtgttgat aattatggca ttagttttat gcactggtac 120

```
cagcagaaac caggacagcc acccaaactc ctcatctatc gtgcatccaa cctagaatct    180

gggatccctg ccaggttcag tggcagtggg tctaggacag acttcaccct caccattaat    240

cctgtggaga ctgatgatgt tgcaacctat tactgtcagc aaagtaataa ggatccgctc    300

acgttcggtg ctgggaccaa gctggagctg aaa                                333
```

<210> SEQ ID NO 75
<211> LENGTH: 124
<212> TYPE: PRT
<213> ORGANISM: Canis familiaris

<400> SEQUENCE: 75

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met Ser Trp Val Arg Gln Ala Pro Gly Lys Gly Leu Gln Trp Val
        35                  40                  45

Ala His Ile Asn Ser Gly Gly Ser Ser Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Glu Val Tyr Thr Thr Leu Ala Ala Phe Trp Thr Asp Asn Phe Asp
            100                 105                 110

Tyr Trp Gly Gln Gly Thr Leu Val Thr Val Ser Ser
        115                 120
```

<210> SEQ ID NO 76
<211> LENGTH: 372
<212> TYPE: DNA
<213> ORGANISM: Canis familiaris

<400> SEQUENCE: 76

```
gaggtgcagc tggtggagtc tgggggagac ctggtgaagc ctggggggtc cctgagactc    60

tcctgtgtgg cttctggatt caccttcagt agttatggca tgagctgggt ccgccaggct    120

ccagggaagg gactgcagtg ggtcgcacac attaacagtg gtggaagtag cacatactac    180

gcagacgctg tgaagggacg attcaccatc tccagagaca acgccaagaa cacgctctat    240

ctgcagatga acagcctgag agctgaggac acggccgtct attactgtgt ggaggtttac    300

actacgttag ctgcattctg gacagacaat tttgactact ggggccaggg aaccctggtc    360

accgtctcct ca                                                        372
```

<210> SEQ ID NO 77
<211> LENGTH: 110
<212> TYPE: PRT
<213> ORGANISM: Canis familiaris

<400> SEQUENCE: 77

```
Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
            20                  25                  30

Ala Ala Thr Trp Tyr Gln Gln Leu Pro Gly Lys Ala Pro Lys Val Leu
        35                  40                  45
```

```
Val Tyr Ser Asp Gly Asn Arg Pro Ser Gly Val Pro Asp Arg Phe Ser
    50                  55                  60

Gly Ser Lys Ser Gly Asn Ser Ala Thr Leu Thr Ile Thr Gly Leu Gln
65                  70                  75                  80

Ala Glu Asp Glu Ala Asp Tyr Tyr Cys Gln Ser Phe Asp Thr Thr Leu
                85                  90                  95

Asp Ala Tyr Val Phe Gly Ser Gly Thr Gln Leu Thr Val Leu
            100                 105                 110


<210> SEQ ID NO 78
<211> LENGTH: 330
<212> TYPE: DNA
<213> ORGANISM: Canis familiaris

<400> SEQUENCE: 78

cagtctgtgc tgactcagcc gacctcagtg tcggggtccc ttggccagag ggtcaccatc     60

tcctgctctg gaagcacgaa caacatcggt attcttgctg cgacctggta ccaacaactc    120

ccaggaaagg cccctaaagt cctcgtgtac agtgatggga atcgaccgtc aggggtccct    180

gaccggtttt ccggctccaa gtctggcaac tcagccaccc tgaccatcac tgggcttcag    240

gctgaggacg aggctgatta ttactgccag tcctttgata ccacgcttga tgcttacgtg    300

ttcggctcag gaacccaact gaccgtcctt                                     330


<210> SEQ ID NO 79
<211> LENGTH: 117
<212> TYPE: PRT
<213> ORGANISM: Canis familiaris

<400> SEQUENCE: 79

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Asp Tyr
            20                  25                  30

Ala Met Ser Trp Val Arg Gln Ala Pro Gly Arg Gly Leu Gln Trp Val
        35                  40                  45

Ala Gly Ile Asp Ser Val Gly Ser Gly Thr Ser Tyr Ala Asp Ala Val
    50                  55                  60

Lys Gly Arg Phe Thr Ile Ser Arg Asp Asp Ala Lys Asn Thr Leu Tyr
65                  70                  75                  80

Leu Gln Met Phe Asn Leu Arg Ala Glu Asp Thr Ala Ile Tyr Tyr Cys
                85                  90                  95

Ala Ser Gly Phe Pro Gly Ser Phe Glu His Trp Gly Gln Gly Thr Leu
            100                 105                 110

Val Thr Val Ser Ser
        115


<210> SEQ ID NO 80
<211> LENGTH: 351
<212> TYPE: DNA
<213> ORGANISM: Canis familiaris

<400> SEQUENCE: 80

gaggtgcagc tggtggagtc tgggggagac ctggtgaagc ctgcagggtc cctgagactg     60

tcctgtgtgg cctctggatt caccttcagt gactatgcca tgagctgggt ccgccaggct    120

cctgggaggg gactgcagtg ggtcgcaggt attgacagtg ttggaagtgg cacaagctac    180

gcagacgctg tgaagggccg attcacaatc tccagagacg acgccaagaa cacactgtat    240
```

ctgcagatgt tcaacctgag agccgaggac acggccatat attactgtgc gagcgggttc 300
cctgggtcct ttgagcactg gggccagggc accctggtca ccgtctcctc a 351

<210> SEQ ID NO 81
<211> LENGTH: 104
<212> TYPE: PRT
<213> ORGANISM: Canis familiaris

<400> SEQUENCE: 81

Gln Ser Val Leu Thr Gln Pro Ala Ser Val Ser Gly Ser Leu Gly Gln
1 5 10 15

Lys Val Thr Ile Ser Cys Thr Gly Ser Ser Ser Asn Ile Gly Ser Gly
20 25 30

Tyr Val Gly Trp Tyr Gln Gln Leu Pro Gly Thr Gly Pro Arg Thr Leu
35 40 45

Ile Tyr Tyr Asn Ser Asp Arg Pro Ser Gly Val Pro Asp Arg Phe Ser
50 55 60

Gly Ser Arg Ser Gly Thr Thr Ala Thr Leu Thr Ile Ser Gly Leu Gln
65 70 75 80

Ala Glu Asp Glu Ala Asp Tyr Tyr Cys Ser Val Tyr Asp Arg Thr Phe
85 90 95

Asn Ala Val Phe Gly Gly Gly Thr
100

<210> SEQ ID NO 82
<211> LENGTH: 327
<212> TYPE: DNA
<213> ORGANISM: Canis familiaris

<400> SEQUENCE: 82
cagtctgtac tgactcagcc ggcctcagtg tctgggtccc tgggccagaa ggtcaccatc 60
tcctgcactg gaagtagttc caacattggt agtggttatg tgggctggta ccagcagctc 120
ccaggaacag gccccagaac cctcatctat tataacagtg accgaccttc gggggtcccc 180
gatcgattct ctggctccag gtcaggcacc acagcaaccc tgaccatctc tggactccag 240
gctgaggacg aggctgatta ttactgctca gtatatgaca ggactttcaa tgctgtgttc 300
ggcggaggca cccacctgac cgtcctc 327

<210> SEQ ID NO 83
<211> LENGTH: 118
<212> TYPE: PRT
<213> ORGANISM: Canis familiaris

<400> SEQUENCE: 83

Glu Val Gln Leu Val Glu Ser Gly Gly Asp Leu Val Lys Pro Pro Gly
1 5 10 15

Ser Leu Arg Leu Ser Cys Val Ala Ser Gly Phe Thr Phe Ser Ser Tyr
20 25 30

Asp Met Thr Trp Val Arg Gln Ala Pro Gly Lys Gly Leu Gln Trp Val
35 40 45

Ala Asp Val Asn Ser Gly Gly Thr Gly Thr Ala Tyr Ala Val Ala Val
50 55 60

Lys Gly Arg Phe Thr Ile Ser Arg Asp Asn Ala Lys Lys Thr Leu Tyr
65 70 75 80

Leu Gln Met Asn Ser Leu Arg Ala Glu Asp Thr Ala Val Tyr Tyr Cys
85 90 95

Ala Lys Leu Gly Val Arg Asp Gly Leu Ser Val Trp Gly Gln Gly Thr
100 105 110

Leu Val Thr Val Ser Ser
115

<210> SEQ ID NO 84
<211> LENGTH: 354
<212> TYPE: DNA
<213> ORGANISM: Canis familiaris

<400> SEQUENCE: 84
gaggtgcagc tggtggagtc tggggggagac ctggtgaagc ctccagggtc cctgagactg 60
tcctgtgtgg cctctggatt caccttcagc agttatgaca tgacctgggt ccgccaggct 120
cctgggaagg gactgcagtg ggtcgcagat gttaacagtg gtggaactgg cacggcctac 180
gcagtcgctg tgaagggccg attcaccatc tccagagaca acgccaagaa aacactctat 240
ttacagatga acagcctgag agccgaagac acggccgttt attattgtgc gaaactaggt 300
gtgagagatg gtctttctgt ctggggccag ggcaccctgg tcaccgtctc ctcg 354

<210> SEQ ID NO 85
<211> LENGTH: 107
<212> TYPE: PRT
<213> ORGANISM: Canis familiaris

<400> SEQUENCE: 85

Ser Ser Val Leu Thr Gln Pro Pro Ser Val Ser Val Ser Leu Gly Gln
1 5 10 15

Thr Ala Thr Ile Ser Cys Ser Gly Glu Ser Leu Asn Glu Tyr Tyr Thr
20 25 30

Gln Trp Phe Gln Gln Lys Ala Gly Gln Ala Pro Val Leu Val Ile Tyr
35 40 45

Arg Asp Thr Glu Arg Pro Ser Gly Ile Pro Asp Arg Phe Ser Gly Ser
50 55 60

Ser Ser Gly Asn Thr His Thr Leu Thr Ile Ser Gly Ala Arg Ala Glu
65 70 75 80

Asp Glu Ala Asp Tyr Tyr Cys Glu Ser Ala Val Asp Thr Gly Thr Leu
85 90 95

Val Phe Gly Gly Gly Thr His Leu Ala Val Leu
100 105

<210> SEQ ID NO 86
<211> LENGTH: 321
<212> TYPE: DNA
<213> ORGANISM: Canis familiaris

<400> SEQUENCE: 86
tccagtgtgc tgactcagcc tccctcggta tcagtgtctc tgggacagac agcaaccatc 60
tcctgctctg gagagagtct gaatgaatat tatacacaat ggttccagca gaaggcaggc 120
caagcccctg tcttggtcat atatagggac actgagcggc cctctgggat ccctgaccga 180
ttctctggct ccagttcagg gaacacacac accctaacca tcagcggggc tcgggccgag 240
gacgaggctg actattactg cgagtcagcg gtcgacactg gaacccttgt ctttggcgga 300
ggcacccacc tggccgtcct c 321

<210> SEQ ID NO 87
<211> LENGTH: 117

<212> TYPE: PRT
<213> ORGANISM: Canis familiaris

<400> SEQUENCE: 87

```
Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Arg Thr Tyr
            20                  25                  30

Val Met Asn Trp Val Arg Gln Ala Pro Gly Lys Gly Leu Gln Trp Val
        35                  40                  45

Ala Ser Ile Asn Gly Gly Gly Ser Ser Pro Thr Tyr Ala Asp Ala Val
    50                  55                  60

Arg Gly Arg Phe Thr Val Ser Arg Asp Asn Ala Gln Asn Ser Leu Phe
65                  70                  75                  80

Leu Gln Met Asn Ser Leu Arg Ala Glu Asp Thr Ala Val Tyr Phe Cys
                85                  90                  95

Val Val Ser Met Val Gly Pro Phe Asp Tyr Trp Gly Gln Gly Thr Leu
            100                 105                 110

Val Thr Val Ser Ser
        115
```

<210> SEQ ID NO 88
<211> LENGTH: 351
<212> TYPE: DNA
<213> ORGANISM: Canis familiaris

<400> SEQUENCE: 88

```
gaggtgcagc tggtggagtc tggggggagac ctggtgaagc ctgcagggtc cctgagactg      60

tcctgtgtgg cctctggatt caccttcagg acctatgtca tgaactgggt ccgccaggct     120

cctgggaagg ggctgcaatg ggtcgcaagt attaacggtg gtggaagtag cccaacctac     180

gcagacgctg tgaggggccg attcaccgtc tccagggaca acgcccagaa ctcactgttt     240

ctgcagatga acagcctgag agccgaggac acagccgtgt atttttgtgt cgtgtcgatg     300

gttgggccct tcgactactg gggccaaggg accctggtca ccgtgtcctc a              351
```

<210> SEQ ID NO 89
<211> LENGTH: 102
<212> TYPE: PRT
<213> ORGANISM: Canis familiaris

<400> SEQUENCE: 89

```
Ser Ser Val Leu Thr Gln Pro Pro Ser Val Ser Val Ser Leu Gly Gln
1               5                   10                  15

Thr Ala Thr Ile Ser Cys Ser Gly Glu Ser Leu Ser Asn Tyr Tyr Ala
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60

Ser Ser Gly Asn Thr His Thr Leu Thr Ile Ser Gly Ala Arg Ala Glu
65                  70                  75                  80

Asp Glu Ala Asp Tyr Tyr Cys Glu Ser Ala Val Ser Ser Asp Thr Ile
                85                  90                  95

Val Phe Gly Gly Gly Thr
            100
```

<210> SEQ ID NO 90
<211> LENGTH: 321
<212> TYPE: DNA
<213> ORGANISM: Canis familiaris

<400> SEQUENCE: 90
tccagtgtgc tgactcagcc tccctcggta tcagtgtctc tggggcagac agcaaccatc 60
tcctgctctg gagagagtct gagtaactat tatgcacaat ggttccagca gaaggcaggc 120
caagcccctg tgttggtcat atataaggac actgagcggc cctctgggat ccctgaccga 180
ttctctggct ccagttcagg gaacacacac accctgacca tcagcggggc tcgggccgag 240
gacgaggctg actattactg tgagtcagca gtcagttctg atactattgt gttcggcgga 300
ggcacccacc tgaccgtcct c 321

<210> SEQ ID NO 91
<211> LENGTH: 124
<212> TYPE: PRT
<213> ORGANISM: Canis familiaris

<400> SEQUENCE: 91

Glu Val Gln Leu Val Glu Ser Gly Gly Asp Leu Val Lys Pro Ala Gly
1 5 10 15

Ser Leu Arg Leu Ser Cys Val Ala Ser Gly Phe Thr Phe Ser Ser Tyr
20 25 30

Ala Met Lys Trp Val Arg Gln Ala Pro Gly Lys Gly Leu Gln Trp Val
35 40 45

Ala Thr Ile Asn Asn Asp Gly Thr Arg Thr Gly Tyr Ala Asp Ala Val
50 55 60

Arg Gly Arg Phe Thr Ile Ser Lys Asp Asn Ala Lys Asn Thr Leu Tyr
65 70 75 80

Leu Gln Met Asp Ser Leu Arg Ala Asp Asp Thr Ala Val Tyr Tyr Cys
85 90 95

Thr Lys Gly Asn Ala Glu Ser Gly Cys Thr Gly Asp His Cys Pro Pro
100 105 110

Tyr Trp Gly Gln Gly Thr Leu Val Thr Val Ser Ser
115 120

<210> SEQ ID NO 92
<211> LENGTH: 372
<212> TYPE: DNA
<213> ORGANISM: Canis familiaris

<400> SEQUENCE: 92
gaggtgcagc tggtggagtc tgggggagac ctggtgaagc ctgcggggtc cctgagactg 60
tcctgtgtgg cctctggatt caccttcagt agttatgcca tgaaatgggt ccgccaggct 120
cctgggaagg ggctgcagtg ggtcgcgact attaacaatg atggaaccag aacaggctac 180
gcagacgctg tgaggggccg attcaccatc tccaaagaca acgccaaaaa cacactgtat 240
ctgcagatgg acagcctgag agccgacgac acggccgtct attactgtac aaagggcaat 300
gccgaatccg gctgtactgg tgatcactgt cctccctact ggggccaggg aaccctggtc 360
accgtctcct ca 372

<210> SEQ ID NO 93
<211> LENGTH: 107
<212> TYPE: PRT
<213> ORGANISM: Canis familiaris

<400> SEQUENCE: 93

Ser Ser Val Leu Thr Gln Pro Pro Ser Val Ser Val Ser Leu Gly Gln
1               5                   10                  15

Thr Ala Thr Ile Ser Cys Ser Gly Glu Ser Leu Asn Lys Tyr Tyr Ala
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60

Ser Ala Gly Asn Thr His Thr Leu Thr Ile Ser Gly Ala Arg Ala Glu
65                  70                  75                  80

Asp Glu Ala Asp Tyr Tyr Cys Glu Ser Ala Val Ser Ser Glu Thr Asn
                85                  90                  95

Val Phe Gly Ser Gly Thr Gln Leu Thr Val Leu
            100                 105

<210> SEQ ID NO 94
<211> LENGTH: 321
<212> TYPE: DNA
<213> ORGANISM: Canis familiaris

<400> SEQUENCE: 94
tccagtgtgc tgactcagcc tccctcggta tcagtgtctc tgggacagac agcaaccatc      60
tcctgctctg gagagagtct gaataaatat tatgcacaat ggttccaaca gaaggcaggc     120
caagcccctg tgttggtcat atataaggac actgagcggc cctctgggat ccctgaccga     180
ttctccggct ccagtgcagg caacacacac accctgacca tcagcggggc tcgggccgag     240
gacgaggctg actattactg cgagtcagca gtcagttctg aaactaacgt gttcggctca     300
ggaacccaac tgaccgtcct t                                               321

<210> SEQ ID NO 95
<211> LENGTH: 116
<212> TYPE: PRT
<213> ORGANISM: Canis familiaris

<400> SEQUENCE: 95

Glu Val Gln Leu Val Asp Ser Gly Gly Asp Leu Val Lys Pro Gly Gly
1               5                   10                  15

Ser Leu Arg Leu Ser Cys Val Ala Ser Gly Phe Thr Phe Ser Thr Tyr
            20                  25                  30

Phe Met Ser Trp Val Arg Gln Ala Pro Gly Arg Gly Leu Gln Trp Val
        35                  40                  45

Ala Leu Ile Ser Ser Asp Gly Ser Gly Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ile Phe Trp Arg Ala Phe Asn Asp Trp Gly Gln Gly Thr Leu Val
            100                 105                 110

Thr Val Ser Ser
        115

<210> SEQ ID NO 96
<211> LENGTH: 348
<212> TYPE: DNA

<213> ORGANISM: Canis familiaris

<400> SEQUENCE: 96
gaggtacaac tggtggactc tgggggagac ctggtgaagc ctggggggtc cctgagactc 60
tcctgtgtgg cctctggatt caccttcagt acctacttca tgtcctgggt ccgccaggct 120
ccagggaggg ggcttcagtg ggtcgcactt attagcagtg atggaagtgg cacatactac 180
gcagacgctg tgaagggccg attcaccatc tccagagaca atgccaagaa cacgctgtat 240
ctgcagatga acagcctgag agccgaggac acggctatgt attactgtgc gatattctgg 300
cgggccttta acgactgggg ccagggcacc ctggtcaccg tctcctca 348

<210> SEQ ID NO 97
<211> LENGTH: 110
<212> TYPE: PRT
<213> ORGANISM: Canis familiaris

<400> SEQUENCE: 97

Gln Thr Val Val Ile Gln Glu Pro Ser Leu Ser Val Ser Pro Gly Gly
1               5                   10                  15

Thr Val Thr Leu Thr Cys Gly Leu Asn Ser Gly Ser Val Ser Thr Ser
            20                  25                  30

Asn Tyr Pro Gly Trp Tyr Gln Gln Thr Arg Gly Arg Thr Pro Arg Thr
        35                  40                  45

Ile Ile Tyr Asp Thr Gly Ser Arg Pro Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Thr Asp Ser
                85                  90                  95

Asp Ile Leu Val Phe Gly Gly Gly Thr His Leu Thr Val Leu
            100                 105                 110

<210> SEQ ID NO 98
<211> LENGTH: 330
<212> TYPE: DNA
<213> ORGANISM: Canis familiaris

<400> SEQUENCE: 98
cagactgtgg taatccagga gccatcactc tcagtgtctc caggagggac agtcacactc 60
acatgtggcc tcaactctgg gtcagtctcc acaagtaatt accctggctg gtaccagcag 120
acccgaggcc ggactcctcg cacgattatc tacgacacag gcagtcgccc ctctggggtc 180
cctaatcgct tctccggatc catctctgga aacaaagccg ccctcaccat cacaggagcc 240
cagcccgagg atgaggctga ctattactgt tccttatata cggatagtga cattcttgtt 300
ttcggcggag gcacccacct gaccgtcctc 330

<210> SEQ ID NO 99
<211> LENGTH: 117
<212> TYPE: PRT
<213> ORGANISM: Canis familiaris

<400> SEQUENCE: 99

Glu Val His Leu Val Glu Ser Gly Gly Asp Leu Val Lys Pro Trp Gly
1               5                   10                  15

Ser Leu Arg Leu Ser Cys Val Ala Ser Gly Phe Thr Phe Ser Asp Arg
            20                  25                  30

```
Gly Met Ser Trp Val Arg Gln Ser Pro Gly Lys Gly Leu Gln Trp Val
        35                  40                  45

Ala Tyr Ile Arg Tyr Asp Gly Ser Arg Thr Asp Tyr Ala Asp Ala Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Ser Ser Phe Asp Tyr Trp Gly Gln Gly Thr Leu
            100                 105                 110

Val Thr Val Ser Ser
        115


<210> SEQ ID NO 100
<211> LENGTH: 351
<212> TYPE: DNA
<213> ORGANISM: Canis familiaris

<400> SEQUENCE: 100

gaggtgcatt tggtggagtc tgggggagac ctggtgaagc cttgggggtc cttgagactg      60

tcctgtgtgg cctctggatt cacctttagt gatcgtggca tgagctgggt ccgtcagtct     120

ccagggaagg ggctgcagtg ggtcgcatat attaggtatg atgggagtag gacagactac     180

gcagacgctg tggagggccg attcaccatc tccagagaca acgccaagaa cacgctctac     240

ctgcagatga acagcctgag agccgaggac acggccgtgt attactgtgc gagatgggac     300

ggtagttctt ttgactattg gggccagggc accctggtca ccgtctcctc a              351


<210> SEQ ID NO 101
<211> LENGTH: 112
<212> TYPE: PRT
<213> ORGANISM: Canis familiaris

<400> SEQUENCE: 101

Asp Ile Val Val Thr Gln Thr Pro Leu Ser Leu Ser Val Ser Pro Gly
1               5                   10                  15

Glu Thr Ala Ser Phe Ser Cys Lys Ala Ser Gln Ser Leu Leu His Ser
            20                  25                  30

Asp Gly Asn Thr Tyr Leu Asp Trp Phe Arg Gln Lys Pro Gly Gln Ser
        35                  40                  45

Pro Gln Arg Leu Ile Tyr Lys Val Ser Asn Arg Asp Pro Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Ala Asp Asp Ala Gly Leu Tyr Tyr Cys Met Gln Ala
                85                  90                  95

Ile His Phe Pro Leu Thr Phe Gly Ala Gly Thr Lys Val Glu Leu Lys
            100                 105                 110


<210> SEQ ID NO 102
<211> LENGTH: 336
<212> TYPE: DNA
<213> ORGANISM: Canis familiaris

<400> SEQUENCE: 102

gatattgtcg tgacacagac cccgctgtcc ctgtccgtca gccctggaga gactgcctcc      60

ttctcctgca aggccagtca gagcctcctg cacagtgatg gaaacacgta tttggattgg     120
```

-continued

```
ttccgacaga agccaggcca gtctccacag cgtttgatct acaaggtctc caacagagac    180

cctggggtcc cagacaggtt cagtggcagc gggtcaggga cagatttcac cctgagaatc    240

agcggagtgg aggctgacga tgctggactt tattactgca tgcaagcaat acactttcct    300

ctgacgttcg gagcaggaac caaggtggag ctcaaa                              336


<210> SEQ ID NO 103
<211> LENGTH: 119
<212> TYPE: PRT
<213> ORGANISM: Canis familiaris

<400> SEQUENCE: 103

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Val Met Thr Trp Val Arg Gln Ala Pro Gly Lys Gly Leu Gln Trp Val
        35                  40                  45

Ala Gly Ile Asn Ser Glu Gly Ser Arg Thr Ala Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Arg Ala Glu Asp Thr Ala Ile Tyr Tyr Cys
                85                  90                  95

Ala Thr Gly Asp Ile Val Ala Thr Gly Thr Ser Tyr Trp Gly Gln Gly
            100                 105                 110

Thr Leu Val Thr Val Ser Ser
        115


<210> SEQ ID NO 104
<211> LENGTH: 357
<212> TYPE: DNA
<213> ORGANISM: Canis familiaris

<400> SEQUENCE: 104

gaggtgcagc tggtggagtc tgggggagac ctggtgaagc ctgcagggtc cctgagactg     60

tcctgtgtgg cctctggatt caccttcagt agttatgtca tgacctgggt ccgccaggct    120

cctgggaagg gactgcagtg ggtcgcaggc attaatagtg aggggagtag gacagcctac    180

gcagacgctg tgaagggccg attcaccatc tccagagaca acgccaagaa tacactttat    240

ctacaaatag acagcctgag agccgaggac acggccatat attactgtgc gacaggcgat    300

atagtagcga ctggtacttc gtattggggc cagggcaccc tggtcaccgt ctcctca       357


<210> SEQ ID NO 105
<211> LENGTH: 107
<212> TYPE: PRT
<213> ORGANISM: Canis familiaris

<400> SEQUENCE: 105

Ser Asn Val Leu Thr Gln Pro Pro Ser Val Ser Val Ser Leu Gly Gln
1               5                   10                  15

Thr Ala Thr Ile Ser Cys Ser Gly Glu Thr Leu Asn Arg Phe Tyr Thr
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60
```

-continued

```
Ser Ser Gly Asn Ile His Thr Leu Thr Ile Ser Gly Ala Arg Ala Glu
65                  70                  75                  80

Asp Glu Ala Ala Tyr Tyr Cys Lys Ser Ala Val Ser Ile Asp Val Gly
                85                  90                  95

Val Phe Gly Gly Gly Thr His Leu Thr Val Phe
            100                 105


<210> SEQ ID NO 106
<211> LENGTH: 321
<212> TYPE: DNA
<213> ORGANISM: Canis familiaris

<400> SEQUENCE: 106

tccaatgtac tgactcagcc tccctcggta tcagtgtctc tgggacagac agcaaccatc      60

tcctgctctg gagagactct gaatagattt tatacacaat ggttccagca gaaggcaggc     120

caagcccctg tgttggtcat atataaggac actgagcggc cctctgggat ccctgaccga     180

ttctccggct ccagttcagg gaacatacac accctgacca tcagcggggc tcgggccgag     240

gacgaggctg cctattactg caagtcagca gtcagtattg atgttggtgt gttcggcgga     300

ggcacccacc tgaccgtctt c                                               321


<210> SEQ ID NO 107
<211> LENGTH: 117
<212> TYPE: PRT
<213> ORGANISM: Canis familiaris

<400> SEQUENCE: 107

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Arg Thr Tyr
            20                  25                  30

Val Met Asn Trp Val Arg Gln Ala Pro Gly Lys Gly Leu Gln Trp Val
        35                  40                  45

Ala Ser Ile Asn Gly Gly Gly Ser Ser Pro Thr Tyr Ala Asp Ala Val
    50                  55                  60

Arg Gly Arg Phe Thr Val Ser Arg Asp Asn Ala Gln Asn Ser Leu Phe
65                  70                  75                  80

Leu Gln Met Asn Ser Leu Arg Ala Glu Asp Thr Ala Ile Tyr Phe Cys
                85                  90                  95

Val Val Ser Met Val Gly Pro Phe Asp Tyr Trp Gly His Gly Thr Leu
            100                 105                 110

Val Thr Val Ser Ser
        115


<210> SEQ ID NO 108
<211> LENGTH: 351
<212> TYPE: DNA
<213> ORGANISM: Canis familiaris

<400> SEQUENCE: 108

gaggtgcagc tggtggagtc tgggggagac ctggtgaagc ctgcagggtc cctgagactg      60

tcctgtgtgg cctctggatt caccttcagg acctatgtca tgaactgggt ccgccaggct     120

cctgggaagg ggctgcaatg ggtcgcaagt attaacggtg gtggaagtag cccaacctac     180

gcagacgctg tgaggggccg attcaccgtc tccagggaca acgcccagaa ctcactgttt     240

ctgcagatga acagcctgag agccgaggac acagccatat atttttgtgt cgtgtcgatg     300
```

gttgggccct tcgactactg gggccatggg accctggtca ccgtgtcctc a 351

<210> SEQ ID NO 109
<211> LENGTH: 107
<212> TYPE: PRT
<213> ORGANISM: Canis familiaris

<400> SEQUENCE: 109

Ser Ser Val Leu Thr Gln Pro Pro Ser Val Ser Val Ser Leu Gly Gln
1 5 10 15

Thr Ala Thr Ile Ser Cys Ser Gly Lys Ser Leu Ser Tyr Tyr Tyr Ala
20 25 30

Gln Trp Phe Gln Gln Lys Ala Gly Gln Ala Pro Val Leu Val Ile Tyr
35 40 45

Lys Asp Thr Glu Arg Pro Ser Gly Ile Pro Asp Arg Phe Ser Gly Ser
50 55 60

Ser Ser Gly Asn Thr His Thr Leu Thr Ile Ser Gly Ala Arg Ala Glu
65 70 75 80

Asp Glu Ala Asp Tyr Tyr Cys Glu Ser Ala Val Ser Ser Asp Thr Ile
85 90 95

Val Phe Gly Gly Gly Thr His Leu Thr Val Leu
100 105

<210> SEQ ID NO 110
<211> LENGTH: 321
<212> TYPE: DNA
<213> ORGANISM: Canis familiaris

<400> SEQUENCE: 110
tccagtgtgc tgactcagcc tccctcggta tcagtgtctc tggggcagac agcaaccatc 60
tcctgctctg gaaagagtct gagttactat tatgcacaat ggttccagca gaaggcaggc 120
caagcccctg tgttggtcat atataaggac actgagcggc cctctgggat ccctgaccga 180
ttctctggct ccagttcagg gaacacacac accctgacca tcagcggggc tcgggccgag 240
gacgaggctg actattactg tgagtcagca gtcagttctg atactattgt gttcggcgga 300
ggcacccacc tgaccgtcct c 321

<210> SEQ ID NO 111
<211> LENGTH: 121
<212> TYPE: PRT
<213> ORGANISM: Artificial Sequence
<220> FEATURE:
<223> OTHER INFORMATION: Felinized variable heavy mAb sequence, from Mus musculus and Felis catus

<400> SEQUENCE: 111

Gln Val Leu Leu Val Gln Ser Gly Ala Glu Val Lys Lys Pro Gly Ala
1 5 10 15

Ser Val Lys Ile Phe Cys Lys Ala Ser Gly Tyr Ser Phe Thr Tyr Tyr
20 25 30

Asp Ile Asn Trp Leu Arg Gln Ala Pro Glu Gln Gly Leu Glu Trp Met
35 40 45

Gly Trp Ile Phe Pro Gly Asp Gly Gly Thr Lys Tyr Asn Glu Thr Phe
50 55 60

Lys Gly Arg Leu Thr Leu Thr Ala Asp Thr Ser Thr Asn Thr Val Tyr
65 70 75 80

Met Glu Leu Ser Ser Leu Arg Ser Ala Asp Thr Ala Met Tyr Tyr Cys

```
                85                  90                  95

Ala Arg Gly Gly Thr Ser Val Ile Arg Asp Ala Met Asp Tyr Trp Gly
            100                 105                 110

Gln Gly Ala Leu Val Thr Val Ser Ser
        115                 120


<210> SEQ ID NO 112
<211> LENGTH: 363
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 112

caggtgctgc tggtccagtc aggagcagag gtaaaaaagc ccggggcgag tgtcaagatt      60

ttctgtaagg cctccggata ctcttttacg tattacgata ttaactggct tcgccaggcc     120

cctgagcagg ggctcgaatg gatgggttgg atattccccg gagatggggg aaccaagtac     180

aacgaaacct tcaaggggag gctgaccctg actgcagata ccagcacgaa cacagtgtat     240

atggagttgt cctcactgcg atctgctgat actgccatgt actactgcgc tcgcggcggc     300

acttcagtta tcagggatgc catggactat tgggggcagg gcgcactcgt cactgtctcg     360

agc                                                                   363


<210> SEQ ID NO 113
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 113

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
            20                  25                  30

Gly Ile Ser Phe Met His Trp Tyr Gln Gln Lys Pro Gly Lys Val Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105


<210> SEQ ID NO 114
<211> LENGTH: 333
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 114

gaaatccaga tgacacaatc tcccagctcc ctcagcgcat ctcctggcga cagggtaacc      60

atcacctgcc gcgccagcga gtcagtagac aactatggca tatccttcat gcactggtat     120
```

```
caacaaaagc ccgggaaagt ccccaaactg ttgatttaca gagcaagcaa tctcgagtca    180

ggagtcccat ctcgcttctc tggttccggt tccggaaccg acttcactct gacaatttct    240

tctctggagc ccgaggatgc cgctacatat tactgtcagc aaagcaataa agatccactg    300

accttcggac agggtaccaa gctggagatc aaa                                 333


<210> SEQ ID NO 115
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 115

Glu Val Val Leu Thr Gln Ser Ser Ala Phe Leu Ser Arg Thr Leu Lys
1               5                   10                  15

Glu Lys Ala Thr Ile Thr Cys Arg Ala Ser Glu Ser Val Asp Asn Tyr
            20                  25                  30

Gly Ile Ser Phe Met His Trp Tyr Gln Gln Lys Pro Asn Gln Ala Pro
        35                  40                  45

Lys Leu Leu Val Lys Arg Ala Ser Asn Leu Glu Ser Gly Ala Pro Ser
    50                  55                  60

Arg Phe Ser Gly Ser Gly Ser Gly Thr Asp Phe Thr Leu Thr Ile Ser
65                  70                  75                  80

Ser Pro Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105


<210> SEQ ID NO 116
<211> LENGTH: 318
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 116

gaggtggtgc tgactcagag tagcgcgttt ctgtctcgga ccctgaaaga gaaagctacc     60

atcacgtgca gggcaagcga gagcgtggac aactatggta tcagcttcat gcattggtat    120

cagcagaaac ctaatcaggc gcctaagctg ctcgtgaaaa gagcctccaa ccttgagagc    180

ggcgcaccat caaggttttc aggaagtggc agcgggacag acttcaccct tacaatctct    240

agtccagagc cggaggacgc agctacctac tattgccagc aatccaataa agacccgttg    300

acattcggcc aaggtacc                                                  318


<210> SEQ ID NO 117
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 117

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
```

```
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105


<210> SEQ ID NO 118
<211> LENGTH: 318
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 118

gagatccaga tgacccagtc tccatcctca ctgagtgcta gcccggggga tcgagtgact      60

ataacatgtc gggccagtga atcagtggac aactatggaa tcagttttat gcactggtat     120

cagcagaagc ccggccagcc accgaagctg ttgatttatc gcgcaagcaa tctggagtca     180

ggagtgccct ctagattttc tgggagcggt tctggcacag atttcacact cacaatatca     240

tccttggaac cggaagacgc agccacatac tattgccagc agagtaacaa ggaccctttg     300

acttttggcc agggtacc                                                   318


<210> SEQ ID NO 119
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 119

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
            20                  25                  30

Gly Ile Ser Phe Met His Trp Tyr Gln Gln Lys Pro Gly Gln Val Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105


<210> SEQ ID NO 120
<211> LENGTH: 318
<212> TYPE: DNA
<213> ORGANISM: Artificial Sequence
<220> FEATURE:
<223> OTHER INFORMATION: Nucleotide sequence encoding felinized variable
```

-continued light mAb sequence, from Mus musculus and Felis catus

<400> SEQUENCE: 120
gagatccaga tgacccagtc tccatcctca ctgagtgcta gcccggggga tcgagtgact 60
ataacatgtc gggccagtga atcagtggac aactatggaa tcagttttat gcactggtat 120
cagcagaagc ccggccaggt cccgaagctg ttgatttatc gcgcaagcaa tctggagtca 180
ggagtgccct ctagattttc tgggagcggt tctggcacag atttcacact cacaatatca 240
tccttggaac cggaagacgc agccacatac tattgccagc agagtaacaa ggaccctttg 300
acttttggcc agggtacc 318

<210> SEQ ID NO 121
<211> LENGTH: 122
<212> TYPE: PRT
<213> ORGANISM: Artificial Sequence
<220> FEATURE:
<223> OTHER INFORMATION: Felinized variable heavy mAb sequence, from Mus musculus and Felis catus

<400> SEQUENCE: 121

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ser Phe Thr Ser Tyr
            20                  25                  30

Thr Ile His Trp Leu Arg Gln Ala Pro Ala Gln Gly Leu Glu Trp Met
        35                  40                  45

Gly Asn Ile Asn Pro Thr Ser Gly Tyr Thr Glu Asn Asn Gln Arg Phe
    50                  55                  60

Lys Asp Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
        115                 120

<210> SEQ ID NO 122
<211> LENGTH: 366
<212> TYPE: DNA
<213> ORGANISM: Artificial Sequence
<220> FEATURE:
<223> OTHER INFORMATION: Nucleotide sequence encoding felinized variable heavy mAb sequence, from Mus musculus and Felis catus

<400> SEQUENCE: 122
caagtgcttc tggtgcaaag cggggcggaa gttaggaccc caggagcctc agtaaaaatt 60
ttttgtaagg catccggcta cagtttcacc agctacacta ttcactggct gaggcaggcc 120
ccggcccaag ggctggagtg gatgggaaat atcaatccca cgtctggcta tacagagaat 180
aaccaaaggt ttaaggatag gctgactctg acagctgaca catcaaccaa tacggcatac 240
atggagctct cctctctccg gagtgccgac accgccatgt actactgtgc tcggtggggg 300
tttaaatacg atggcgagtg gagcttcgac gtgtggggcg cgggcacaac cgtgaccgtc 360
tcgagc 366

<210> SEQ ID NO 123
<211> LENGTH: 122

-continued

<212> TYPE: PRT
<213> ORGANISM: Artificial Sequence
<220> FEATURE:
<223> OTHER INFORMATION: Felinized variable heavy mAb sequence, from Mus musculus and Felis catus

<400> SEQUENCE: 123

```
Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Gly Phe Thr Ser Tyr
            20                  25                  30

Thr Ile His Trp Val Arg Gln Ser Pro Ala Gln Gly Leu Glu Trp Met
        35                  40                  45

Gly Asn Ile Asn Pro Thr Ser Gly Tyr Thr Glu Asn Asn Gln Arg Phe
    50                  55                  60

Lys Asp Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
        115                 120
```

<210> SEQ ID NO 124
<211> LENGTH: 366
<212> TYPE: DNA
<213> ORGANISM: Artificial Sequence
<220> FEATURE:
<223> OTHER INFORMATION: Nucleotide sequence encoding felinized variable heavy mAb sequence, from Mus musculus and Felis catus

<400> SEQUENCE: 124

```
caggtgctgc tcgtgcagag cggagccgaa gtgaggacac ccggtgcgag tgtaaaaatt      60

ttttgcaagg caagcggcta cgggtttaca tcctatacca tccactgggt gaggcagtcc     120

ccagcgcagg gacttgaatg gatgggaaat attaatccaa caagcgggta tactgaaaac     180

aaccaaagat ttaaggacag actgacactc accgcagata catctacaaa tacagcctac     240

atggagttgt cttccctgcg gagtgccgac acggctatgt actactgtgc tcggtggggg     300

tttaagtatg atggcgaatg gtccttcgac gtctggggag ctggaaccac cgtgaccgtc     360

tcgagc                                                                366
```

<210> SEQ ID NO 125
<211> LENGTH: 122
<212> TYPE: PRT
<213> ORGANISM: Artificial Sequence
<220> FEATURE:
<223> OTHER INFORMATION: Felinized variable heavy mAb sequence, from Mus musculus and Felis catus

<400> SEQUENCE: 125

```
Gln Val Leu Leu Val Gln Ser Gly Ala Glu Val Arg Lys Pro Gly Ala
1               5                   10                  15

Ser Val Lys Ile Phe Cys Lys Ala Ser Gly Tyr Ser Phe Thr Ser Tyr
            20                  25                  30

Thr Ile His Trp Leu Arg Gln Ala Pro Glu Gln Gly Leu Glu Trp Met
        35                  40                  45

Gly Asn Ile Asn Pro Thr Ser Gly Tyr Thr Glu Asn Asn Gln Arg Phe
    50                  55                  60
```

```
Lys Asp Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
        115                 120


<210> SEQ ID NO 126
<211> LENGTH: 366
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 126

caggtcctct tggttcaaag cggagccgaa gtccgaaaac cgggtgcctc agtgaaaatc      60

ttctgtaagg cctccggcta tagtttcacg agttacacaa tccactggct gcgacaggca     120

ccagagcagg gactggagtg gatgggaaat ataaatccga cgtctgggta cacagaaaac     180

aaccagagat tcaaggatag attgacactg accgcggata ctagtacaaa tacggcttac     240

atggaactgt cctcactccg gtcagccgac accgccatgt attactgtgc tcgctggggg     300

ttcaagtatg atggagagtg gagcttcgac gtatggggag ccggaaccac tgtgaccgtc     360

tcgagc                                                                366


<210> SEQ ID NO 127
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 127

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105


<210> SEQ ID NO 128
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus
```

<400> SEQUENCE: 128

```
gaaattcaga tgactcaatc accttcatct ttgagtgcat cacccggaga tagagttaca     60

atcacctgca gggcgagtca agggatctcc atatggttgt catggtatca gcagaaaccc    120

ggaaaggtcc cgaaactctt gatctacaag gcctctaacc tgcacattgg cgtgccaagc    180

cgattcagcg ggagcggaag tggcaccgac tttactctga cgatcagttc actggagccc    240

gaggacgctg caacatacta ttgtctgcaa tctcagacct accctctcac ctttggagga    300

ggtaccaagc tggagatcaa a                                              321
```

<210> SEQ ID NO 129
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 129

```
Glu Ile Thr Met Thr Gln Ser Pro Gly Ser Leu Ala Gly Ser Pro Gly
1               5                   10                  15

Gln Gln Val Thr Met Asn Cys Arg Ala Ser Gln Gly Ile Ser Ile Trp
            20                  25                  30

Leu Ser Trp Tyr Gln Gln Lys Pro Gly Gln His Pro Lys Leu Leu Ile
        35                  40                  45

Tyr Lys Ala Ser Asn Leu His Ile Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 130
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 130

```
gaaattacca tgacacaaag ccccggctcc ctggccggct cccccggaca gcaagtgacc     60

atgaattgtc gggccagcca gggaatttct atatggctct cttggtatca gcaaaaaccc    120

ggacagcacc ctaaacttct gatctacaaa gcaagtaact tgcacatcgg cgtccctgat    180

cgattcagtg gctcaggttc cggtacagat tttactctta ccatcagcaa tctgcaggct    240

gaggatgtgg caagctatta ctgtctccaa agtcagactt accctctgac atttgggggc    300

ggtaccaagc tggagatcaa a                                              321
```

<210> SEQ ID NO 131
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 131

```
Glu Val Val Leu Thr Gln Ser Ser Ala Phe Leu Ser Arg Thr Leu Lys
1               5                   10                  15

Glu Lys Ala Thr Ile Thr Cys Arg Ala Ser Gln Gly Ile Ser Ile Trp
            20                  25                  30

Leu Ser Trp Tyr Gln Gln Lys Pro Asn Gln Ala Pro Lys Leu Leu Val
        35                  40                  45

Lys Lys Ala Ser Asn Leu His Ile Gly Ala Pro Ser Arg Phe Ser Gly
    50                  55                  60

Ser Gly Ser Gly Thr Asp Phe Thr Leu Thr Ile Ser Ser Pro Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Gly Asp Gln
            100                 105


<210> SEQ ID NO 132
<211> LENGTH: 322
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 132

gaggtagtgc tgactcagtc ctccgccttc ttgtcaagaa ctctcaaaga gaaagcaaca      60

atcacttgtc gggcgtctca agggatatca atttggctga gctggtatca gcagaaacca     120

aatcaagcgc cgaaactgct ggtgaagaag gcctccaatc tccacattgg cgcacccagc     180

aggttttccg gcagtggctc tggcacagat ttcactctga ccatcagctc acccgagccc     240

gaagacgccg ctacatacta ttgcttgcaa tcccagacat accccctgac ttttggggga     300

ggtaccaagc tgggagatca aa                                              322


<210> SEQ ID NO 133
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 133

Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105


<210> SEQ ID NO 134
```

<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 134
gacattcaga tgaatcagtc tcctagctca ctgtcagcca gccttggaga caccattaca 60
gtcacttgca gggcgagtca agggatctcc atatggttgt catggtatca gcagaaaccc 120
ggaaaggtcc cgaaactctt gatctacaag gcctctaacc tgcacattgg cgtgccaagc 180
cgattcagcg ggagcggaag tggcaccgac tttactctga cgatcagttc actggagccc 240
gaggacgctg caacatacta ttgtctgcaa tctcagacct accctctcac ctttggagga 300
ggtaccaagc tggagatcaa a 321

<210> SEQ ID NO 135
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 135

Glu Ile Gln Met Thr Gln Ser Pro Ser Ser Leu Ser Ala Ser Pro Gly
1 5 10 15

Asp Arg Val Thr Ile Thr Cys Arg Ala Ser Gln Gly Ile Ser Ile Trp
20 25 30

Leu Ser Trp Tyr Gln Gln Lys Pro Gly Asn Ile Pro Lys Val Leu Ile
35 40 45

Asn Lys Ala Ser Asn Leu His Ile Gly Val Pro Ser Arg Phe Ser Gly
50 55 60

Ser Gly Ser Gly Thr Asp Phe Thr Leu Thr Ile Ser Ser Leu Glu Pro
65 70 75 80

Glu Asp Ala Ala Thr Tyr Tyr Cys Leu Gln Ser Gln Thr Tyr Pro Leu
85 90 95

Thr Phe Gly Gly Gly Thr Lys Leu Glu Ile Lys
100 105

<210> SEQ ID NO 136
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 136
gaaattcaga tgactcaatc accttcatct ttgagtgcat cacccggaga tagagttaca 60
atcacctgca gggcgagtca agggatctcc atatggttgt catggtatca gcagaaaccg 120
ggcaatatcc caaaggtgct gattaacaag gcctctaacc tgcacattgg cgtgccaagc 180
cgattcagcg ggagcggaag tggcaccgac tttactctga cgatcagttc actggagccc 240
gaggacgctg caacatacta ttgtctgcaa tctcagacct accctctcac ctttggagga 300
ggtaccaagc tggagatcaa a 321

<210> SEQ ID NO 137
<211> LENGTH: 107

```
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 137

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105


<210> SEQ ID NO 138
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 138

gaaattcaga tgactcaatc accttcatct ttgagtgcat cacccggaga tagagttaca      60

atcacctgca gggcgagtca agggatctcc atatggttgt catggtatca gcagaaaccc     120

ggaaaggtcc cgaaactctt gatctacaag gcctctaacc tgcacattgg ggtcccccca     180

aggttcagcg gatctggatc cgggacccac tttactctga ccataacaag cctgcagcct     240

gaagacattg ctacctatta ctgcctgcaa tctcagacct accctctcac ctttggagga     300

ggtaccaagc tggagatcaa a                                               321


<210> SEQ ID NO 139
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 139

Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Asn Ile Pro Lys Val Leu Ile
        35                  40                  45

Asn Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
```

```
                85                  90                  95

Thr Phe Gly Gly Gly Thr Lys Leu Glu Ile Lys
            100                 105
```

<210> SEQ ID NO 140
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 140

```
gacattcaga tgaatcagtc tcctagctca ctgtcagcca gccttggaga caccattaca     60

gtcacttgca gggcgagtca agggatctcc atatggttgt catggtatca gcagaaaccg    120

ggcaatatcc caaaggtgct gattaacaag gcctctaacc tgcacattgg cgtgccaagc    180

cgattcagcg ggagcggaag tggcaccgac tttactctga cgatcagttc actggagccc    240

gaggacgctg caacatacta ttgtctgcaa tctcagacct accctctcac ctttggagga    300

ggtaccaagc tggagatcaa a                                              321
```

<210> SEQ ID NO 141
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 141

```
Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 142
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 142

```
gacattcaga tgaatcagtc tcctagctca ctgtcagcca gccttggaga caccattaca     60

gtcacttgca gggcgagtca agggatctcc atatggttgt catggtatca gcagaaaccc    120

ggaaaggtcc cgaaactctt gatctacaag gcctctaacc tgcacattgg ggtcccccca    180

aggttcagcg gatctggatc cgggacccac tttactctga ccataacaag cctgcagcct    240
```

gaagacattg ctacctatta ctgcctgcaa tctcagacct accctctcac ctttggagga 300
ggtaccaagc tggagatcaa a 321

<210> SEQ ID NO 143
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 143

Glu Ile Gln Met Thr Gln Ser Pro Ser Ser Leu Ser Ala Ser Pro Gly
1 5 10 15

Asp Arg Val Thr Ile Thr Cys Arg Ala Ser Gln Gly Ile Ser Ile Trp
20 25 30

Leu Ser Trp Tyr Gln Gln Lys Pro Gly Asn Ile Pro Lys Val Leu Ile
35 40 45

Asn Lys Ala Ser Asn Leu His Ile Gly Val Pro Pro Arg Phe Ser Gly
50 55 60

Ser Gly Ser Gly Thr His Phe Thr Leu Thr Ile Thr Ser Leu Gln Pro
65 70 75 80

Glu Asp Ile Ala Thr Tyr Tyr Cys Leu Gln Ser Gln Thr Tyr Pro Leu
85 90 95

Thr Phe Gly Gly Gly Thr Lys Leu Glu Ile Lys
100 105

<210> SEQ ID NO 144
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 144
gaaattcaga tgactcaatc accttcatct ttgagtgcat cacccggaga tagagttaca 60
atcacctgca gggcgagtca agggatctcc atatggttgt catggtatca gcagaaaccg 120
ggcaatatcc caaaggtgct gattaacaag gcctctaacc tgcacattgg ggtcccccca 180
aggttcagcg gatctggatc cgggacccac tttactctga ccataacaag cctgcagcct 240
gaagacattg ctacctatta ctgcctgcaa tctcagacct accctctcac ctttggagga 300
ggtaccaagc tggagatcaa a 321

<210> SEQ ID NO 145
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 145

Glu Ile Gln Met Thr Gln Ser Pro Ser Ser Leu Ser Ala Ser Pro Gly
1 5 10 15

Asp Arg Val Thr Ile Thr Cys Arg Ala Ser Gln Gly Ile Ser Ile Trp
20 25 30

Leu Ser Trp Tyr Gln Gln Lys Pro Gly Asn Val Pro Lys Leu Leu Ile
35 40 45

```
Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 146
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 146

```
gaaatccaga tgacacagtc ccccagtagc ctttccgctt caccgggcga tagagtcact      60

attacgtgca gggcctccca gggtatttct atctggctga gctggtatca gcagaagccc     120

ggtaatgtgc caaagctctt gatctacaag gcatctaacc ttcatatcgg agtgccctca     180

agatttagtg ggtcaggcag cggaaccgat ttcacattga ccattagttc tctggaacca     240

gaggacgctg ccacttacta ctgcctgcag tcccaaacat accctttgac ttttgggggg     300

ggtaccaagc tggagatcaa a                                               321
```

<210> SEQ ID NO 147
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 147

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 148
<211> LENGTH: 321
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 148

```
gagattcaga tgacccagag cccatcaagc ctctccgctt cccccggaga ccgggtgacc      60
```

atcacatgca gagcttcaca gggaatctca atctggctca gctggtatca gcagaagcca 120
ggcaagattc cgaagttgct tatctataag gccagtaacc tgcatatcgg agttccatca 180
agattcagtg gtagcggaag tgggacagat ttcactctca ccatcagctc cctcgaacca 240
gaggacgctg caacttacta ctgcctgcag tcccagacat atccacttac tttcggcggg 300
ggtaccaagc tggagatcaa a 321

<210> SEQ ID NO 149
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 149

Glu Ile Gln Met Thr Gln Ser Pro Ser Ser Leu Ser Ala Ser Pro Gly
1 5 10 15

Asp Arg Val Thr Ile Thr Cys Arg Ala Ser Gln Gly Ile Ser Ile Trp
20 25 30

Leu Ser Trp Tyr Gln Gln Lys Pro Gly Lys Val Pro Lys Val Leu Ile
35 40 45

Tyr Lys Ala Ser Asn Leu His Ile Gly Val Pro Ser Arg Phe Ser Gly
50 55 60

Ser Gly Ser Gly Thr Asp Phe Thr Leu Thr Ile Ser Ser Leu Glu Pro
65 70 75 80

Glu Asp Ala Ala Thr Tyr Tyr Cys Leu Gln Ser Gln Thr Tyr Pro Leu
85 90 95

Thr Phe Gly Gly Gly Thr Lys Leu Glu Ile Lys
100 105

<210> SEQ ID NO 150
<211> LENGTH: 322
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 150
gagattcaga tgactcagag cccatctagt ctctctgcat ctcccggaga cagagttacg 60
atcacctgca gggctagcca agggatatca atttggctgt cctggtatca gcaaaaacct 120
ggcaaagtgc caaaggtctt gatttacaaa gcatccaatt tgcacatcgg cgtccctagt 180
cgcttttccg ggtctggtag cggcaccgac ttcaccctca ccataagctc actcgagccg 240
gaagatgccg ctacttacta ttgcctgcag tctcagactt accccctgac tttcggcgga 300
ggtaccaagc tggagatcaa ac 322

<210> SEQ ID NO 151
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 151

Glu Ile Gln Met Thr Gln Ser Pro Ser Ser Leu Ser Ala Ser Pro Gly
1 5 10 15

```
Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Asn Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105


<210> SEQ ID NO 152
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 152

gagatccaga tgacgcagag ccctagcagc ctctctgcat ccccaggaga cagagtaaca      60

attacctgtc gcgccagcca gggaatatct atatggctgt catggtatca acagaaaccg     120

ggaaaggttc caaagctctt gatcaataag gctagcaatc tgcatattgg agtgccctcc     180

cgcttctctg gtagcggaag tggcacagat ttcaccctga ccattagtag tctggagcct     240

gaggatgcgg ccacctacta ctgcctccag tcccaaacct atcccctgac cttcggagga     300

ggtaccaagc tggagatcaa a                                               321


<210> SEQ ID NO 153
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 153

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105


<210> SEQ ID NO 154
<211> LENGTH: 321
<212> TYPE: DNA
<213> ORGANISM: Artificial Sequence
```

<220> FEATURE:
<223> OTHER INFORMATION: Nucleotide sequence encoding felinized variable light mAb sequence, from Mus musculus and Felis catus

<400> SEQUENCE: 154
gaaattcaga tgactcagag tcctagcagc ctgtccgcaa gcccaggtga ccgagtcacc 60
ataacctgca gggccagtca ggggatctcc atatggctct cttggtatca acagaaaccc 120
ggcaatatcc ctaagctcct gatttataaa gcgtcaaatc tgcatatcgg ggtgccatca 180
agattctctg ggtccggctc aggaaccgac tttaccctga ccatttcttc tctcgaaccc 240
gaggatgccg ccacctatta ttgccttcaa agccagacat acccattgac cttcggcggc 300
ggtaccaagc tggagatcaa a 321

<210> SEQ ID NO 155
<211> LENGTH: 159
<212> TYPE: PRT
<213> ORGANISM: Canis familiaris

<400> SEQUENCE: 155

Met Leu Ser His Thr Gly Pro Ser Arg Phe Ala Leu Phe Leu Leu Cys
1 5 10 15

Ser Met Glu Thr Leu Leu Ser Ser His Met Ala Pro Thr His Gln Leu
20 25 30

Pro Pro Ser Asp Val Arg Lys Ile Ile Leu Glu Leu Gln Pro Leu Ser
35 40 45

Arg Gly Leu Leu Glu Asp Tyr Gln Lys Lys Glu Thr Gly Val Pro Glu
50 55 60

Ser Asn Arg Thr Leu Leu Leu Cys Leu Thr Ser Asp Ser Gln Pro Pro
65 70 75 80

Arg Leu Asn Ser Ser Ala Ile Leu Pro Tyr Phe Arg Ala Ile Arg Pro
85 90 95

Leu Ser Asp Lys Asn Ile Ile Asp Lys Ile Ile Glu Gln Leu Asp Lys
100 105 110

Leu Lys Phe Gln His Glu Pro Glu Thr Glu Ile Ser Val Pro Ala Asp
115 120 125

Thr Phe Glu Cys Lys Ser Phe Ile Leu Thr Ile Leu Gln Gln Phe Ser
130 135 140

Ala Cys Leu Glu Ser Val Phe Lys Ser Leu Asn Ser Gly Pro Gln
145 150 155

<210> SEQ ID NO 156
<211> LENGTH: 477
<212> TYPE: DNA
<213> ORGANISM: Canis familiaris

<400> SEQUENCE: 156
atgctctccc acacaggacc atccaggttt gccctgttcc tgctctgctc tatggaaacc 60
ttgctgtcct cccatatggc acccacccat cagctaccac caagtgatgt acgaaaaatc 120
atcttggaat tacagccctt gtcgagggga cttttggaag actatcagaa gaaagagaca 180
ggggtgccag aatccaaccg taccttgctg ctgtgtctca cctctgattc ccaaccacca 240
cgcctcaaca gctcagccat cttgccttat ttcagggcaa tcagaccatt atcagataag 300
aacattattg ataaaatcat agaacagctt gacaaactca aatttcaaca tgaaccagaa 360
acagaaattt ctgtgcctgc agatactttt gaatgtaaaa gcttcatctt gacgatttta 420
cagcagttct cggcgtgcct ggaaagtgtg tttaagtcac taaactctgg acctcag 477

<210> SEQ ID NO 157
<211> LENGTH: 165
<212> TYPE: PRT
<213> ORGANISM: Artificial Sequence
<220> FEATURE:
<223> OTHER INFORMATION: Amino acid sequence representing wild-type
      feline IL-31 with C-terminal His tag

<400> SEQUENCE: 157

```
Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Pro Ala Asp
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln His
145                 150                 155                 160

His His His His His
                165
```

<210> SEQ ID NO 158
<211> LENGTH: 495
<212> TYPE: DNA
<213> ORGANISM: Artificial Sequence
<220> FEATURE:
<223> OTHER INFORMATION: Nucleotide sequence representing wild-type
      feline IL-31 gene with encoded C-terminal His tag

<400> SEQUENCE: 158

```
atgctttcac acgctggacc agcccgattc gccctcttcc tcctctgctg tatggagact     60

ctgttgccgt cccacatggc cccggcacat aggctgcagc cgtctgacat ccggaagatc    120

attctcgaac ttcgccccat gtcgaagggg ttgctgcaag actacctgaa gaaggagatc    180

ggcctgcccg aaagcaacca ctcctcgctg ccttgcctgt caagcgattc ccagctgccc    240

cacattaacg gttccgccat cctcccgtac ttccgggcca tcagaccact gtcggacaag    300

aacaccatcg acaagatcat tgaacagctg gacaagctga agtttcagcg cgagcctgaa    360

gccaaagtgt ccatgcccgc cgataacttc gagcggaaga atttcattct cgcggtgctg    420

cagcagttct ccgcgtgcct ggagcacgtc ctgcaatccc tgaacagcgg acctcagcac    480

caccatcacc accat                                                     495
```

<210> SEQ ID NO 159
<211> LENGTH: 148
<212> TYPE: PRT
<213> ORGANISM: Artificial Sequence
<220> FEATURE:
<223> OTHER INFORMATION: Amino acid sequence representing feline IL-31 protein with N-terminal His tag

<400> SEQUENCE: 159

Met Arg Gly Ser His His His His His His Gly Ser Ser His Met Ala
1               5                   10                  15

Pro Ala His Arg Leu Gln Pro Ser Asp Ile Arg Lys Ile Ile Leu Glu
            20                  25                  30

Leu Arg Pro Met Ser Lys Gly Leu Leu Gln Asp Tyr Leu Lys Lys Glu
        35                  40                  45

Ile Gly Leu Pro Glu Ser Asn His Ser Ser Leu Pro Cys Leu Ser Ser
    50                  55                  60

Asp Ser Gln Leu Pro His Ile Asn Gly Ser Ala Ile Leu Pro Tyr Phe
65                  70                  75                  80

Arg Ala Ile Arg Pro Leu Ser Asp Lys Asn Thr Ile Asp Lys Ile Ile
                85                  90                  95

Glu Gln Leu Asp Lys Leu Lys Phe Gln Arg Glu Pro Glu Ala Lys Val
            100                 105                 110

Ser Met Pro Ala Asp Asn Phe Glu Arg Lys Asn Phe Ile Leu Ala Val
        115                 120                 125

Leu Gln Gln Phe Ser Ala Cys Leu Glu His Val Leu Gln Ser Leu Asn
    130                 135                 140

Ser Gly Pro Gln
145

<210> SEQ ID NO 160
<211> LENGTH: 444
<212> TYPE: DNA
<213> ORGANISM: Artificial Sequence
<220> FEATURE:
<223> OTHER INFORMATION: Nucleotide sequence representing feline IL-31 gene with encoded N-terminal His tag

<400> SEQUENCE: 160
atgagaggat cccatcacca tcaccaccac ggctcatctc atatggcccc cgcacatcgc     60
ctgcagccga gtgacattcg taaaattatc ttggagctgc gcccgatgtc caagggctta    120
ctgcaggatt atctgaagaa agagatcggg ctgcctgaaa gcaaccatag tagcctgccg    180
tgtttatcgt ctgatagcca gttaccacac atcaatggct ctgcgatttt gccctacttt    240
cgcgccatcc gtccgctgtc cgataaaaat accatcgaca aaattatcga acaactggat    300
aaattgaagt ttcagcgcga gcctgaagcg aaagtttcga tgccagcmga taacttcgaa    360
cgcaaaaact ttattttagc ggtgttgcag cagttttctg cctgtctgga acacgtgctc    420
cagtcactca atagtgggcc acaa                                           444

<210> SEQ ID NO 161
<211> LENGTH: 165
<212> TYPE: PRT
<213> ORGANISM: Artificial Sequence
<220> FEATURE:
<223> OTHER INFORMATION: Amino acid sequence representing mutant Feline IL-31 11E12 protein with C-terminal His tag

<400> SEQUENCE: 161

Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

```
Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Ala Lys Ile Ala Glu Gln Leu Asp Lys
            100                 105                 110

Leu Lys Phe Gln Arg Glu Pro Glu Ala Lys Val Ser Met Pro Ala Asp
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln His
145                 150                 155                 160

His His His His His
                165
```

<210> SEQ ID NO 162
<211> LENGTH: 495
<212> TYPE: DNA
<213> ORGANISM: Artificial Sequence
<220> FEATURE:
<223> OTHER INFORMATION: Nucleotide sequence representing mutant feline IL-31 11E12 gene with encoded C-terminal His tag

<400> SEQUENCE: 162

```
atgctctctc acgccggtcc tgcccggttc gcactgttcc tcctctgttg catggagact      60

ctgcttccct cccacatggc accggcccat agactgcagc cgtccgacat cagaaagatc     120

atccttgaat tgcgccctat gagcaagggg ctgctgcagg attacctgaa aaaggagatc     180

ggcctgccgg aatcgaacca cagctcactg ccatgcctgt cctccgactc gcaactgccc     240

cacatcaatg gatccgccat tctgccgtac ttccgcgcta ttcggcctct ctccgacaag     300

aacaccatcg ccaagattgc cgagcagctg gataagctga agttccagag ggagccagaa     360

gccaaggtgt ccatgcccgc tgacaacttc gagcggaaga actttatcct cgcggtgctg     420

cagcagttct cagcgtgcct cgaacacgtc ttgcaaagcc tgaactcggg accccagcac     480

caccaccatc atcac                                                      495
```

<210> SEQ ID NO 163
<211> LENGTH: 165
<212> TYPE: PRT
<213> ORGANISM: Artificial Sequence
<220> FEATURE:
<223> OTHER INFORMATION: Amino acid sequence representing mutant feline IL-31 15H05 protein with C-terminal His tag

<400> SEQUENCE: 163

```
Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60
```

```
Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Ala Ala Ala
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln His
145                 150                 155                 160

His His His His His
                165


<210> SEQ ID NO 164
<211> LENGTH: 495
<212> TYPE: DNA
<213> ORGANISM: Artificial Sequence
<220> FEATURE:
<223> OTHER INFORMATION: Nucleotide sequence representing mutant feline
      IL-31 15H05 gene with encoded C-terminal His tag

<400> SEQUENCE: 164

atgctctctc acgccggtcc tgcccggttc gcactgttcc tcctctgttg catggagact      60

ctgcttccct cccacatggc accggcccat agactgcagc cgtccgacat cagaaagatc     120

atccttgaat tgcgccctat gagcaagggg ctgctgcagg attacctgaa aaaggagatc     180

ggcctgccgg aatcgaacca cagctcactg ccatgcctgt cctccgactc gcaactgccc     240

cacatcaatg gatccgccat tctgccgtac ttccgcgcta ttcggcctct ctccgacaag     300

aacaccatcg acaagattat tgagcagctg gataagctga agttccagag ggagccagaa     360

gccaaggtgt ccatggccgc tgccaacttc gagcggaaga actttatcct cgcggtgctg     420

cagcagttct cagcgtgcct cgaacacgtc ttgcaaagcc tgaactcggg accccagcac     480

caccaccatc atcac                                                      495


<210> SEQ ID NO 165
<211> LENGTH: 152
<212> TYPE: PRT
<213> ORGANISM: Artificial Sequence
<220> FEATURE:
<223> OTHER INFORMATION: Amino acid sequence of Equine IL-31 protein
      with C-terminal His tag

<400> SEQUENCE: 165

Met Gly Trp Ser Cys Ile Ile Leu Phe Leu Val Ala Thr Ala Thr Gly
1               5                   10                  15

Val His Ser Gly Pro Ile Tyr Gln Leu Gln Pro Lys Glu Ile Gln Ala
            20                  25                  30

Ile Ile Val Glu Leu Gln Asn Leu Ser Lys Lys Leu Leu Asp Asp Tyr
        35                  40                  45

Leu Asn Lys Glu Lys Gly Val Gln Lys Phe Asp Ser Asp Leu Pro Ser
    50                  55                  60

Cys Phe Thr Ser Asp Ser Gln Ala Pro Gly Asn Ile Asn Ser Ser Ala
65                  70                  75                  80

Ile Leu Pro Tyr Phe Lys Ala Ile Ser Pro Ser Leu Asn Asn Asp Lys
                85                  90                  95
```

```
Ser Leu Tyr Ile Ile Glu Gln Leu Asp Lys Leu Asn Phe Gln Asn Ala
            100                 105                 110

Pro Glu Thr Glu Val Ser Met Pro Thr Asp Asn Phe Glu Arg Lys Arg
        115                 120                 125

Phe Ile Leu Thr Ile Leu Arg Trp Phe Ser Asn Cys Leu Glu His Arg
    130                 135                 140

Ala Gln His His His His His His
145                 150
```

```
<210> SEQ ID NO 166
<211> LENGTH: 456
<212> TYPE: DNA
<213> ORGANISM: Artificial Sequence
<220> FEATURE:
<223> OTHER INFORMATION: Nucleotide sequence of Equine IL-31 gene with
      encoded C-terminal His tag

<400> SEQUENCE: 166

atgggctggt cctgcatcat tctgtttctg gtggccacag ccaccggcgt gcactctgga      60

cctatctatc agctgcagcc caaagagatc caggccatca tcgtggaact gcagaacctg     120

agcaagaagc tgctggacga ctacctgaac aaagaaaagg gcgtgcagaa gttcgacagc     180

gacctgccta gctgcttcac cagcgattct caggcccctg gcaacatcaa cagcagcgcc     240

atcctgcctt acttcaaggc catctctccc agcctgaaca acgacaagag cctgtacatc     300

atcgagcagc tggacaagct gaacttccag aacgcccctg aaaccgaggt gtccatgcct     360

accgacaact tcgagcggaa gcggttcatc ctgaccatcc tgcggtggtt cagcaactgc     420

ctggaacaca gagcccagca ccaccaccat caccat                               456
```

```
<210> SEQ ID NO 167
<211> LENGTH: 652
<212> TYPE: PRT
<213> ORGANISM: Artificial Sequence
<220> FEATURE:
<223> OTHER INFORMATION: Amino acid sequence of extracellular domain of
      feline OSMR fused to human IgG1 Fc

<400> SEQUENCE: 167

Met Ala Leu Phe Ser Ala Phe Gln Thr Thr Phe Leu Leu Ala Leu Leu
1               5                   10                  15

Ser Leu Lys Thr Tyr Gln Ser Glu Val Leu Ser Glu Pro Leu Ser Leu
            20                  25                  30

Ala Pro Glu Ser Leu Glu Val Ser Ile Asp Ser Ala Arg Gln Cys Leu
        35                  40                  45

His Leu Lys Trp Ser Val His Asn Leu Ala Tyr His Gln Glu Leu Lys
    50                  55                  60

Met Val Phe Gln Ile Glu Ile Ser Arg Ile Lys Thr Ser Asn Val Ile
65                  70                  75                  80

Trp Val Glu Asn Tyr Ser Thr Thr Val Lys Arg Asn Gln Val Leu Arg
                85                  90                  95

Trp Ser Trp Glu Ser Lys Leu Pro Leu Glu Cys Ala Lys His Ser Val
            100                 105                 110

Arg Met Arg Gly Ala Val Asp Asp Ala Gln Val Pro Glu Leu Arg Phe
        115                 120                 125

Trp Ser Asn Trp Thr Ser Trp Glu Glu Val Asp Val Gln Ser Ser Leu
    130                 135                 140

Gly His Asp Pro Leu Phe Val Phe Pro Lys Asp Lys Leu Val Glu Glu
```

-continued

```
145                 150                 155                 160

Gly Ser Asn Val Thr Ile Cys Tyr Val Ser Arg Ser His Gln Asn Asn
                165                 170                 175

Ile Ser Cys Tyr Leu Glu Gly Val Arg Met His Gly Glu Gln Leu Asp
            180                 185                 190

Pro Asn Val Cys Val Phe His Leu Lys Asn Val Pro Phe Ile Arg Glu
        195                 200                 205

Thr Gly Thr Asn Ile Tyr Cys Lys Ala Asp Gln Gly Asp Val Ile Lys
    210                 215                 220

Gly Ile Val Leu Phe Val Ser Lys Val Phe Glu Glu Pro Lys Asp Phe
225                 230                 235                 240

Ser Cys Glu Thr Arg Asp Leu Lys Thr Leu Asn Cys Thr Trp Ala Pro
                245                 250                 255

Gly Ser Asp Ala Gly Leu Leu Thr Gln Leu Ser Gln Ser Tyr Thr Leu
            260                 265                 270

Phe Glu Ser Phe Ser Gly Lys Lys Thr Leu Cys Lys His Lys Ser Trp
        275                 280                 285

Cys Asn Trp Gln Val Ser Pro Asp Ser Gln Glu Met Tyr Asn Phe Thr
    290                 295                 300

Leu Thr Ala Glu Asn Tyr Leu Arg Lys Arg Ser Val His Leu Leu Phe
305                 310                 315                 320

Asn Leu Thr His Arg Val His Pro Met Ala Pro Phe Asn Val Phe Val
                325                 330                 335

Lys Asn Val Ser Ala Thr Asn Ala Thr Met Thr Trp Lys Val His Ser
            340                 345                 350

Ile Gly Asn Tyr Ser Thr Leu Leu Cys Gln Ile Glu Leu Asp Gly Glu
        355                 360                 365

Gly Lys Val Ile Gln Lys Gln Asn Val Ser Val Lys Val Asn Gly Lys
    370                 375                 380

His Leu Met Lys Lys Leu Glu Pro Ser Thr Glu Tyr Ala Ala Gln Val
385                 390                 395                 400

Arg Cys Ala Asn Ala Asn His Phe Trp Lys Trp Ser Glu Trp Thr Arg
                405                 410                 415

Arg Asn Phe Thr Thr Ala Glu Ala Ala Asp Lys Thr His Thr Cys Pro
            420                 425                 430

Pro Cys Pro Ala Pro Glu Leu Leu Gly Gly Pro Ser Val Phe Leu Phe
        435                 440                 445

Pro Pro Lys Pro Lys Asp Thr Leu Met Ile Ser Arg Thr Pro Glu Val
    450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Ala Leu Pro Ala Pro Ile Glu Lys Thr Ile Ser Lys Ala
    530                 535                 540

Lys Gly Gln Pro Arg Glu Pro Gln Val Tyr Thr Leu Pro Pro Ser Arg
545                 550                 555                 560

Glu Glu Met Thr Lys Asn Gln Val Ser Leu Thr Cys Leu Val Lys Gly
                565                 570                 575
```

```
Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650


<210> SEQ ID NO 168
<211> LENGTH: 2076
<212> TYPE: DNA
<213> ORGANISM: Artificial Sequence
<220> FEATURE:
<223> OTHER INFORMATION: Nucleotide sequence encoding extracellular
      domain of feline OSMR fused to human IgG1 Fc

<400> SEQUENCE: 168

atggccctgt tcagcgcctt ccagaccacc ttcctgctgg ccctgctgag cctgaaaacc     60

taccagagcg aggtgctgag cgagcccctg tctctggccc ctgagagcct ggaagtgtcc    120

atcgacagcg ccagacagtg cctgcacctg aagtggagcg tgcacaacct ggcctaccac    180

caggaactga agatggtgtt ccagatcgag atcagccgga tcaagaccag caacgtgatc    240

tgggtggaaa actacagcac caccgtgaag cggaaccagg tgctgcggtg gtcctgggag    300

tctaagctgc ctctggaatg cgccaagcac agcgtgcgga tgagaggcgc cgtggatgat    360

gcccaggtgc ccgagctgag attctggtcc aactggacct cctgggaaga ggtggacgtg    420

cagtctagcc tgggccacga ccccctgttc gtgttcccca aggacaagct ggtggaagag    480

ggctccaacg tgaccatctg ctacgtgtcc agaagccacc agaacaacat cagctgctac    540

ctggaaggcg tgcgcatgca cggcgagcag ctggacccta acgtgtgcgt gttccacctg    600

aagaacgtgc ccttcatcag agagacaggc accaacatct actgcaaggc cgaccagggc    660

gacgtgatca agggcatcgt gctgtttgtg tccaaggtgt tcgaggaacc caaggacttc    720

agctgcgaga cacgggatct gaaaaccctg aactgtacct gggcccctgg ctccgatgcc    780

ggactgctga ctcagctgtc ccagagctac accctgttcg agagcttcag cggcaaaaag    840

accctgtgca agcacaagag ctggtgcaac tggcaagtgt cccccgatag ccaggaaatg    900

tacaacttca ccctgaccgc cgagaactac ctgcggaaga gatccgtgca tctgctgttc    960

aacctgaccc acagagtgca ccccatggcc cccttcaacg tgttcgtgaa gaatgtgtcc   1020

gccaccaacg ccaccatgac atggaaggtg cacagcatcg gcaactactc caccctgctg   1080

tgtcagatcg agctggacgg cgagggcaaa gtgatccaga aacagaacgt gtcagtgaaa   1140

gtgaacggca agcacctgat gaagaagctg gaacccagca ccgagtacgc cgcccaggtg   1200

cgctgtgcca acgccaacca cttctggaag tggagtgaat ggacccggcg gaacttcacc   1260

acagccgaag ccgccgctga gaacgaggtg tccacaccta tgcaggccct gaccaccaac   1320

aaggacgacg acaacatcct gttccgggac tccgccaatg ccaccagcct gcctgtgcag   1380

gatagcagct ctgtgctgcc cgccaagccc gagaacatct cctgcgtgtt ctactacgag   1440

gaaaacttca cttgcacctg gtcccccgag aaagaggcca gctacacctg gtacaaagtg   1500

aagagaacct acagctacgg ctacaagagc gacatctgcc ccagcgacaa cagcaccaga   1560
```

```
ggcaaccaca ccttctgcag ctttctgccc cccaccatca ccaaccccga caactacacc   1620

atccaggtgg aagcccagaa cgccgacggc atcatcaagt ccgacatcac ccactggtcc   1680

ctggacgcca tcacaaagat cgagcccccc gagatcttct ccgtgaagcc tgtgctgggc   1740

gtgaagagga tggtgcagat caagtggatc cggcccgtgc tggccccagt gtctagcacc   1800

ctgaagtaca ccctgcggtt caagaccgtg aacagcgcct actggatgga agtgaatttc   1860

accaaagagg acatcgaccg ggacgagaca tacaatctga ccggactgca ggccttcaca   1920

gagtacgtgc tggctctgag atgcgccacc aaagaatcca tgttttggag cggctggtcc   1980

caggaaaaga tgggcaccac cgaagagggt aagcctatcc ctaaccctct cctcggtctc   2040

gattctacgc gtaccggtca tcatcaccat caccat                             2076
```

```
<210> SEQ ID NO 169
<211> LENGTH: 474
<212> TYPE: PRT
<213> ORGANISM: Artificial Sequence
<220> FEATURE:
<223> OTHER INFORMATION: Amino acid sequence of feline IL-31-Ra fused to
      human IgG1 Fc

<400> SEQUENCE: 169

Met Met Trp Pro Gln Val Trp Gly Leu Glu Ile Gln Phe Ser Pro Gln
1               5                   10                  15

Pro Ala Cys Ile Asp Leu Gly Met Met Trp Ala His Ala Leu Trp Thr
            20                  25                  30

Leu Leu Leu Leu Cys Lys Phe Ser Leu Ala Val Leu Pro Ala Lys Pro
        35                  40                  45

Glu Asn Ile Ser Cys Val Phe Tyr Tyr Glu Glu Asn Phe Thr Cys Thr
    50                  55                  60

Trp Ser Pro Glu Lys Glu Ala Ser Tyr Thr Trp Tyr Lys Val Lys Arg
65                  70                  75                  80

Thr Tyr Ser Tyr Gly Tyr Lys Ser Asp Ile Cys Pro Ser Asp Asn Ser
                85                  90                  95

Thr Arg Gly Asn His Thr Phe Cys Ser Phe Leu Pro Pro Thr Ile Thr
            100                 105                 110

Asn Pro Asp Asn Tyr Thr Ile Gln Val Glu Ala Gln Asn Ala Asp Gly
        115                 120                 125

Ile Ile Lys Ser Asp Ile Thr His Trp Ser Leu Asp Ala Ile Thr Lys
    130                 135                 140

Ile Glu Pro Pro Glu Ile Phe Ser Val Lys Pro Val Leu Gly Val Lys
145                 150                 155                 160

Arg Met Val Gln Ile Lys Trp Ile Arg Pro Val Leu Ala Pro Val Ser
                165                 170                 175

Ser Thr Leu Lys Tyr Thr Leu Arg Phe Lys Thr Val Asn Ser Ala Tyr
            180                 185                 190

Trp Met Glu Val Asn Phe Thr Lys Glu Asp Ile Asp Arg Asp Glu Thr
        195                 200                 205

Tyr Asn Leu Thr Gly Leu Gln Ala Phe Thr Glu Tyr Val Leu Ala Leu
    210                 215                 220

Arg Cys Ala Thr Lys Glu Ser Met Phe Trp Ser Gly Trp Ser Gln Glu
225                 230                 235                 240

Lys Met Gly Thr Thr Glu Glu Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270
```

```
Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 170
<211> LENGTH: 1422
<212> TYPE: DNA
<213> ORGANISM: Artificial Sequence
<220> FEATURE:
<223> OTHER INFORMATION: Nucleotide sequence encoding feline IL-31 Ra fused to human IgG1 Fc

<400> SEQUENCE: 170

```
atgatgtggc cacaagtgtg gggcctggag atccagttca gcccccagcc tgcctgcatc      60

gatctgggca tgatgtgggc tcacgctctg tggaccctgc tgctgctgtg caagttttcc     120

ctggccgtgc tgcccgctaa gcctgagaac atcagctgcg tgttctacta tgaggagaac     180

ttcacctgta catggtcccc cgagaaggag gctagctata cctggtacaa ggtgaagaga     240

acatacagct atggctacaa gtctgatatc tgccccagcg acaactctac ccgcggcaat     300

cacacattct gttcttttct gccccctacc atcacaaacc ctgataatta taccatccag     360

gtggaggccc agaacgctga tggcatcatc aagtctgaca tcacccattg gtccctggac     420

gccatcacaa agatcgagcc acccgagatt ttctccgtga agcccgtgct gggcgtgaag     480

aggatggtgc agatcaagtg gatcaggcct gtgctggctc cagtgtccag caccctgaag     540

tatacactga gattcaagac cgtgaactcc gcttactgga tggaggtgaa cttcaccaag     600

gaggacatcg atagggacga gacctataat ctgacaggcc tgcaggcctt caccgagtac     660

gtgctggccc tgaggtgcgc tacaaaggag tccatgtttt ggtccggctg gagccaggag     720

aagatgggca ccacagagga ggataagacc cacacatgcc ctccatgtcc agctccagag     780

ctgctgggag gaccaagcgt gttcctgttt ccacctaagc ctaaggacac cctgatgatc     840
```

```
tctcgcaccc ctgaggtgac atgcgtggtg gtggacgtgt cccacgagga cccagaggtg    900

aagtttaact ggtatgtgga tggcgtggag gtgcataatg ccaagaccaa gcctagagag    960

gagcagtata acagcaccta ccgcgtggtg tctgtgctga cagtgctgca tcaggactgg   1020

ctgaacggca aggagtacaa gtgcaaggtg agcaataagg ccctgcctgc tccaatcgag   1080

aagaccatct ctaaggctaa gggacagcca agggagccac aggtgtatac actgccaccc   1140

agccgggagg agatgaccaa gaaccaggtg tctctgacat gtctggtgaa gggcttctac   1200

ccatctgata tcgctgtgga gtgggagtcc aatggccagc ccgagaacaa ttataagacc   1260

acacctccag tgctggattc tgacggctcc ttctttctgt actccaagct gaccgtggac   1320

aagagcaggt ggcagcaggg caacgtgttt tcttgctccg tgatgcatga ggctctgcac   1380

aatcattaca cacagaagag cctgtctctg tccccaggca ag                      1422


<210> SEQ ID NO 171
<211> LENGTH: 335
<212> TYPE: PRT
<213> ORGANISM: Felis catus

<400> SEQUENCE: 171

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270
```

```
Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335


<210> SEQ ID NO 172
<211> LENGTH: 1005
<212> TYPE: DNA
<213> ORGANISM: Felis catus

<400> SEQUENCE: 172

gcctccacca cggccccatc ggtgttccca ctggccccca gctgcgggac cacatctggc      60

gccaccgtgg ccctggcctg cctggtgtta ggctacttcc ctgagccggt gaccgtgtcc     120

tggaactccg gcgccctgac cagcggtgtg cacaccttcc cggccgtcct gcaggcctcg     180

gggctgtact ctctcagcag catggtgaca gtgccctcca gcaggtggct cagtgacacc     240

ttcacctgca acgtggccca cccgcccagc aacaccaagg tggacaagac cgtgcgcaaa     300

acagaccacc caccgggacc caaaccctgc gactgtccca aatgcccacc ccctgagatg     360

cttggaggac cgtccatctt catcttcccc ccaaaaccca aggacaccct ctcgatttcc     420

cggacgcccg aggtcacatg cttggtggtg gacttgggcc cagatgactc cgatgtccag     480

atcacatggt ttgtggataa cacccaggtg tacacagcca agacgagtcc gcgtgaggag     540

cagttcaaca gcacctaccg tgtggtcagt gtcctcccca tcctacacca ggactggctc     600

aaggggaagg agttcaagtg caaggtcaac agcaaatccc tcccctcccc catcgagagg     660

accatctcca aggccaaagg acagccccac gagccccagg tgtacgtcct gcctccagcc     720

caggaggagc tcagcaggaa caaagtcagt gtgacctgcc tgatcaaatc cttccacccg     780

cctgacattg ccgtcgagtg ggagatcacc ggacagccgg agccagagaa caactaccgg     840

acgaccccgc cccagctgga cagcgacggg acctacttcg tgtacagcaa gctctcggtg     900

gacaggtccc actggcagag gggaaacacc tacacctgct cggtgtcaca cgaagctctg     960

cacagccacc acacacagaa atccctcacc cagtctccgg gtaaa                    1005


<210> SEQ ID NO 173
<211> LENGTH: 335
<212> TYPE: PRT
<213> ORGANISM: Artificial Sequence
<220> FEATURE:
<223> OTHER INFORMATION: Amino acid sequence of feline heavy chain
      engineered with modifications to modulate antibody effector
      function

<400> SEQUENCE: 173

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
```

-continued 65 70 75 80

Phe Thr Cys Asn Val Ala His Pro Pro Ser Asn Thr Lys Val Asp Lys
85 90 95

Thr Val Arg Lys Thr Asp His Pro Pro Gly Pro Lys Pro Cys Asp Cys
100 105 110

Pro Lys Cys Pro Pro Pro Glu Ala Ala Gly Ala Pro Ser Ile Phe Ile
115 120 125

Phe Pro Pro Lys Pro Lys Asp Thr Leu Ser Ile Ser Arg Thr Pro Glu
130 135 140

Val Thr Cys Leu Val Val Asp Leu Gly Pro Asp Asp Ser Asp Val Gln
145 150 155 160

Ile Thr Trp Phe Val Asp Asn Thr Gln Val Tyr Thr Ala Lys Thr Ser
165 170 175

Pro Arg Glu Glu Gln Phe Asn Ser Thr Tyr Arg Val Val Ser Val Leu
180 185 190

Pro Ile Leu His Gln Asp Trp Leu Lys Gly Lys Glu Phe Lys Cys Lys
195 200 205

Val Asn Ser Lys Ser Leu Pro Ser Pro Ile Glu Arg Thr Ile Ser Lys
210 215 220

Ala Lys Gly Gln Pro His Glu Pro Gln Val Tyr Val Leu Pro Pro Ala
225 230 235 240

Gln Glu Glu Leu Ser Arg Asn Lys Val Ser Val Thr Cys Leu Ile Lys
245 250 255

Ser Phe His Pro Pro Asp Ile Ala Val Glu Trp Glu Ile Thr Gly Gln
260 265 270

Pro Glu Pro Glu Asn Asn Tyr Arg Thr Thr Pro Pro Gln Leu Asp Ser
275 280 285

Asp Gly Thr Tyr Phe Val Tyr Ser Lys Leu Ser Val Asp Arg Ser His
290 295 300

Trp Gln Arg Gly Asn Thr Tyr Thr Cys Ser Val Ser His Glu Ala Leu
305 310 315 320

His Ser His His Thr Gln Lys Ser Leu Thr Gln Ser Pro Gly Lys
325 330 335

<210> SEQ ID NO 174
<211> LENGTH: 1005
<212> TYPE: DNA
<213> ORGANISM: Artificial Sequence
<220> FEATURE:
<223> OTHER INFORMATION: Nucleotide sequence encoding feline heavy chain engineered with modifications to modulate antibody effector function

<400> SEQUENCE: 174
gcctccacca cggccccatc ggtgttccca ctggccccca gctgcgggac cacatctggc 60
gccaccgtgg ccctggcctg cctggtgtta ggctacttcc ctgagccggt gaccgtgtcc 120
tggaactccg gcgccctgac cagcggtgtg cacaccttcc cggccgtcct gcaggcctcg 180
gggctgtact ctctcagcag catggtgaca gtgccctcca gcaggtggct cagtgacacc 240
ttcacctgca acgtggccca cccgcccagc aacaccaagg tggacaagac cgtgcgcaaa 300
acagaccacc caccgggacc caaaccctgc gactgtccca aatgcccacc ccctgaggcg 360
gctggagcac cgtccatctt catcttcccc ccaaaaccca aggacaccct ctcgatttcc 420
cggacgcccg aggtcacatg cttggtggtg gacttgggcc cagatgactc cgatgtccag 480
atcacatggt ttgtggataa cacccaggtg tacacagcca agacgagtcc gcgtgaggag 540

```
cagttcaaca gcacctaccg tgtggtcagt gtcctcccca tcctacacca ggactggctc    600

aaggggaagg agttcaagtg caaggtcaac agcaaatccc tcccctcccc catcgagagg    660

accatctcca aggccaaagg acagccccac gagccccagg tgtacgtcct gcctccagcc    720

caggaggagc tcagcaggaa caaagtcagt gtgacctgcc tgatcaaatc cttccacccg    780

cctgacattg ccgtcgagtg ggagatcacc ggacagccgg agccagagaa caactaccgg    840

acgaccccgc cccagctgga cagcgacggg acctacttcg tgtacagcaa gctctcggtg    900

gacaggtccc actggcagag ggaaacacc tacacctgct cggtgtcaca cgaagctctg     960

cacagccacc acacacagaa atccctcacc cagtctccgg gtaaa                   1005


<210> SEQ ID NO 175
<211> LENGTH: 110
<212> TYPE: PRT
<213> ORGANISM: Artificial Sequence
<220> FEATURE:
<223> OTHER INFORMATION: Amino acid sequence of feline Kappa light chain
      engineered with glycosylation knockout (G-) at position 103

<400> SEQUENCE: 175

Arg Ser Asp Ala Gln Pro Ser Val Phe Leu Phe Gln Pro Ser Leu Asp
1               5                   10                  15

Glu Leu His Thr Gly Ser Ala Ser Ile Val Cys Ile Leu Asn Asp Phe
            20                  25                  30

Tyr Pro Lys Glu Val Asn Val Lys Trp Lys Val Asp Gly Val Val Gln
        35                  40                  45

Asn Lys Gly Ile Gln Glu Ser Thr Thr Glu Gln Asn Ser Lys Asp Ser
    50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                85                  90                  95

Thr Leu Val Lys Ser Phe Gln Arg Ser Glu Cys Gln Arg Glu
            100                 105                 110


<210> SEQ ID NO 176
<211> LENGTH: 330
<212> TYPE: DNA
<213> ORGANISM: Artificial Sequence
<220> FEATURE:
<223> OTHER INFORMATION: Nucleotide sequence encoding feline Kappa light
      chain engineered with glyosylation knockout (G-)

<400> SEQUENCE: 176

cggagtgatg ctcagccatc tgtctttctc ttccaaccat ctctggacga gttacataca     60

ggaagtgcct ctatcgtgtg catattgaat gacttctacc ccaaagaggt caatgtcaag    120

tggaaagtgg atggcgtagt ccaaaacaaa ggcatccagg agagcaccac agagcagaac    180

agcaaggaca gcacctacag cctcagcagc accctgacga tgtccagtac ggagtaccaa    240

agtcatgaaa agttctcctg cgaggtcact cacaagagcc tggcctccac cctcgtcaag    300

agcttccaga ggagcgagtg tcagagagag                                     330


<210> SEQ ID NO 177
<211> LENGTH: 335
<212> TYPE: PRT
<213> ORGANISM: Canis familiaris

<400> SEQUENCE: 177
```

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

<210> SEQ ID NO 178
<211> LENGTH: 1005
<212> TYPE: DNA
<213> ORGANISM: Canis familiaris

<400> SEQUENCE: 178

```
gcctcaacaa ctgctcctag cgtgtttccc ctggccccta gctgcggaag tacctcaggc      60

agcacagtgg ccctggcttg tctggtgtct ggatatttcc ctgagccagt gaccgtgagt     120

tggaacagcg gctctctgac ctccggggtg cacacatttc catctgtgct gcagtctagt     180

ggcctgtact ccctgtcaag catggtgact gtgccttcct ctaggtggcc atcagaaact     240
```

-continued

```
ttcacctgca acgtggccca tcccgccagc aagaccaaag tggacaagcc cgtgcctaaa    300

agggagaatg gaagggtgcc aagaccacct gattgcccta agtgtccagc tccagaagcg    360

gcgggagcac caagcgtgtt catctttcca cccaagccca aagacacact gctgattgct    420

agaactcccg aggtgacctg cgtggtggtg gacctggatc cagaggaccc cgaagtgcag    480

atctcctggt tcgtggatgg gaagcagatg cagacagcca aaactcagcc tcgggaggaa    540

cagtttaacg gaacctatag agtggtgtct gtgctgccaa ttggacacca ggactggctg    600

aagggcaaac agtttacatg caaggtgaac aacaaggccc tgcctagtcc aatcgagagg    660

actatttcaa aagctagggg acaggctcat cagccttccg tgtatgtgct gcctccatcc    720

cgggaggaac tgtctaagaa cacagtgagt ctgacttgtc tgatcaaaga tttctttccc    780

cctgacattg atgtggagtg gcagagcaat gggcagcagg agccagaatc caagtacaga    840

accacaccac cccagctgga cgaagatggc tcctatttcc tgtacagtaa gctgtcagtg    900

gacaaatcta ggtggcagcg cggggatacc tttatctgcg ccgtgatgca cgaggctctg    960

cacaatcatt acacacaaga aagtctgtca catagccccg gcaag                   1005
```

<210> SEQ ID NO 179
<211> LENGTH: 106
<212> TYPE: PRT
<213> ORGANISM: Canis familiaris

<400> SEQUENCE: 179

```
Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105
```

<210> SEQ ID NO 180
<211> LENGTH: 318
<212> TYPE: DNA
<213> ORGANISM: Canis familiaris

<400> SEQUENCE: 180

```
aggaacgacg cccagcctgc tgtgtatctg tttcagccct cccctgatca gctgcacact     60

ggctctgcta gtgtggtgtg tctgctgaac agcttctacc caaaggatat caatgtgaag    120

tggaaagtgg acggcgtgat ccaggatact gggattcagg agtccgtgac cgaacaggac    180

aaagattcaa catatagcct gagctccact ctgaccatgt ctagtaccga gtacctgagc    240

cacgaactgt attcctgcga gatcactcat aagtccctgc cctctaccct gatcaagagc    300

ttccagagat cagagtgt                                                  318
```

<210> SEQ ID NO 181
<211> LENGTH: 164

<212> TYPE: PRT
<213> ORGANISM: Homo sapiens

<400> SEQUENCE: 181

```
Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Glu Lys Gly Val Leu Val
    50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr
```

<210> SEQ ID NO 182
<211> LENGTH: 111
<212> TYPE: PRT
<213> ORGANISM: Artificial Sequence
<220> FEATURE:
<223> OTHER INFORMATION: Caninized variable light chain mAb sequence, from Mus musculus and Canis

<400> SEQUENCE: 182

```
Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Phe Gln Gln Lys Pro Gly Gln Ser Pro
        35                  40                  45

Gln Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110
```

<210> SEQ ID NO 183
<211> LENGTH: 333
<212> TYPE: DNA
<213> ORGANISM: Artificial Sequence
<220> FEATURE:
<223> OTHER INFORMATION: Nucleotide sequence encoding caninized variable light chain mAb sequence from Mus musculus and Canis

<400> SEQUENCE: 183

-continued gacatcgtga tgacccagac ccccctgagc ctgagcgtgt cccctggcga gcctgccagc 60
atcagctgca gagccagcga gagcgtggac aactacggca tcagcttcat gcactggttc 120
cagcagaagc ccggccagag cccccagcgg ctgatctaca gagccagcaa cctggaaagc 180
ggcgtgcccg atcggtttag cggctctggc agcggcaccg acttcaccct gcggatctct 240
cgggtggaag ccgatgacgc cggagtgtac tactgccagc agagcaacaa ggacccccctg 300 acctttggcg ccggtaccaa gctggagatc aag 333

<210> SEQ ID NO 184
<211> LENGTH: 111
<212> TYPE: PRT
<213> ORGANISM: Artificial Sequence
<220> FEATURE:
<223> OTHER INFORMATION: Caninized variable light chain mAb sequence
from Mus musculus and Canis

<400> SEQUENCE: 184

Asp Ile Val Met Thr Gln Thr Pro Leu Ser Leu Ser Val Ser Pro Gly
1 5 10 15

Glu Pro Ala Ser Ile Ser Cys Arg Ala Ser Glu Ser Val Asp Asn Tyr
20 25 30

Gly Ile Ser Phe Met His Trp Tyr Gln Gln Lys Pro Gly Gln Pro Pro
35 40 45

Lys Leu Leu Ile Tyr Arg Ala Ser Asn Leu Glu Ser Gly Val Pro Asp
50 55 60

Arg Phe Ser Gly Ser Gly Ser Gly Thr Asp Phe Thr Leu Arg Ile Ser
65 70 75 80

Arg Val Glu Ala Asp Asp Ala Gly Val Tyr Tyr Cys Gln Gln Ser Asn
85 90 95

Lys Asp Pro Leu Thr Phe Gly Ala Gly Thr Lys Leu Glu Ile Lys
100 105 110

<210> SEQ ID NO 185
<211> LENGTH: 333
<212> TYPE: DNA
<213> ORGANISM: Artificial Sequence
<220> FEATURE:
<223> OTHER INFORMATION: Nucleotide sequence encoding caninized variable
light chain mAb sequence from Mus musculus and Canis

<400> SEQUENCE: 185
gatatagtga tgacacaaac tcctctcagt ctttccgtat caccgggaga accggcttcc 60
atttcctgtc gggcctcaga gtctgtggac aactacggga tatccttcat gcactggtat 120
cagcagaaac ccggccagcc ccctaaactc cttatttaca gggccagtaa tctggaaagc 180
ggtgtgcccg atcgatttag cggttccggg agcggcacag atttcaccct gcgaatctct 240
agagttgaag cggatgatgc aggagtatat tactgccagc aatccaataa ggatcccctt 300
acattcggcg cgggtaccaa gctggagatc aag 333

<210> SEQ ID NO 186
<211> LENGTH: 12
<212> TYPE: PRT
<213> ORGANISM: Artificial Sequence
<220> FEATURE:
<223> OTHER INFORMATION: Canine IL-31 15H05 mimotope sequence

<400> SEQUENCE: 186

Ser Val Pro Ala Asp Thr Phe Glu Cys Lys Ser Phe 1 5 10

<210> SEQ ID NO 187
<211> LENGTH: 12
<212> TYPE: PRT
<213> ORGANISM: Artificial Sequence
<220> FEATURE:
<223> OTHER INFORMATION: Canine IL-31 15H05 mimotope sequence

<400> SEQUENCE: 187

Ser Val Pro Ala Asp Thr Phe Glu Arg Lys Ser Phe
1 5 10

<210> SEQ ID NO 188
<211> LENGTH: 12
<212> TYPE: PRT
<213> ORGANISM: Artificial Sequence
<220> FEATURE:
<223> OTHER INFORMATION: Feline IL-31 15H05 mimotope sequence

<400> SEQUENCE: 188

Ser Met Pro Ala Asp Asn Phe Glu Arg Lys Asn Phe
1 5 10

<210> SEQ ID NO 189
<211> LENGTH: 12
<212> TYPE: PRT
<213> ORGANISM: Artificial Sequence
<220> FEATURE:
<223> OTHER INFORMATION: Equine IL-31 15H05 mimotope sequence

<400> SEQUENCE: 189

Ser Met Pro Thr Asp Asn Phe Glu Arg Lys Arg Phe
1 5 10

<210> SEQ ID NO 190
<211> LENGTH: 12
<212> TYPE: PRT
<213> ORGANISM: Artificial Sequence
<220> FEATURE:
<223> OTHER INFORMATION: Human IL-31 15H05 mimotope sequence

<400> SEQUENCE: 190

Ser Val Pro Thr Asp Thr His Glu Cys Lys Arg Phe
1 5 10

<210> SEQ ID NO 191
<211> LENGTH: 12
<212> TYPE: PRT
<213> ORGANISM: Artificial Sequence
<220> FEATURE:
<223> OTHER INFORMATION: Human IL-31 15H05 mimotope sequence

<400> SEQUENCE: 191

Ser Val Pro Thr Asp Thr His Glu Arg Lys Arg Phe
1 5 10

<210> SEQ ID NO 192
<211> LENGTH: 33
<212> TYPE: PRT
<213> ORGANISM: Artificial Sequence
<220> FEATURE:
<223> OTHER INFORMATION: Canine IL-31 helix BC region mimotope sequence

<400> SEQUENCE: 192

Asn Ser Ser Ala Ile Leu Pro Tyr Phe Arg Ala Ile Arg Pro Leu Ser
1 5 10 15

```
Asp Lys Asn Ile Ile Asp Lys Ile Ile Glu Gln Leu Asp Lys Leu Lys
            20                  25                  30

Phe


<210> SEQ ID NO 193
<211> LENGTH: 33
<212> TYPE: PRT
<213> ORGANISM: Artificial Sequence
<220> FEATURE:
<223> OTHER INFORMATION: Feline IL-31 helix BC region mimotope sequence

<400> SEQUENCE: 193

Asn Gly Ser Ala Ile Leu Pro Tyr Phe Arg Ala Ile Arg Pro Leu Ser
1               5                   10                  15

Asp Lys Asn Thr Ile Asp Lys Ile Ile Glu Gln Leu Asp Lys Leu Lys
            20                  25                  30

Phe


<210> SEQ ID NO 194
<211> LENGTH: 33
<212> TYPE: PRT
<213> ORGANISM: Artificial Sequence
<220> FEATURE:
<223> OTHER INFORMATION: Equine IL-31 helix BC region mimotope sequence

<400> SEQUENCE: 194

Asn Ser Ser Ala Ile Leu Pro Tyr Phe Lys Ala Ile Ser Pro Ser Leu
1               5                   10                  15

Asn Asn Asp Lys Ser Leu Tyr Ile Ile Glu Gln Leu Asp Lys Leu Asn
            20                  25                  30

Phe


<210> SEQ ID NO 195
<211> LENGTH: 33
<212> TYPE: PRT
<213> ORGANISM: Artificial Sequence
<220> FEATURE:
<223> OTHER INFORMATION: Human IL-31 helix BC region mimotope sequence

<400> SEQUENCE: 195

His Ser Pro Ala Ile Arg Ala Tyr Leu Lys Thr Ile Arg Gln Leu Asp
1               5                   10                  15

Asn Lys Ser Val Ile Asp Glu Ile Ile Glu His Leu Asp Lys Leu Ile
            20                  25                  30

Phe


<210> SEQ ID NO 196
<211> LENGTH: 24
<212> TYPE: PRT
<213> ORGANISM: Artificial Sequence
<220> FEATURE:
<223> OTHER INFORMATION: Canine IL-31 helix A region mimotope sequence

<400> SEQUENCE: 196

Ala Pro Thr His Gln Leu Pro Pro Ser Asp Val Arg Lys Ile Ile Leu
1               5                   10                  15

Glu Leu Gln Pro Leu Ser Arg Gly
            20


<210> SEQ ID NO 197
<211> LENGTH: 24
```

-continued

<212> TYPE: PRT
<213> ORGANISM: Artificial Sequence
<220> FEATURE:
<223> OTHER INFORMATION: Feline IL-31 helix A region mimotope sequence

<400> SEQUENCE: 197

Ala Pro Ala His Arg Leu Gln Pro Ser Asp Ile Arg Lys Ile Ile Leu
1               5                   10                  15

Glu Leu Arg Pro Met Ser Lys Gly
            20

<210> SEQ ID NO 198
<211> LENGTH: 24
<212> TYPE: PRT
<213> ORGANISM: Artificial Sequence
<220> FEATURE:
<223> OTHER INFORMATION: Equine IL-31 helix A region mimotope sequence

<400> SEQUENCE: 198

Gly Pro Ile Tyr Gln Leu Gln Pro Lys Glu Ile Gln Ala Ile Ile Val
1               5                   10                  15

Glu Leu Gln Asn Leu Ser Lys Lys
            20

<210> SEQ ID NO 199
<211> LENGTH: 25
<212> TYPE: PRT
<213> ORGANISM: Artificial Sequence
<220> FEATURE:
<223> OTHER INFORMATION: Human IL-31 helix A region mimotope sequence

<400> SEQUENCE: 199

Leu Pro Val Arg Leu Leu Arg Pro Ser Asp Asp Val Gln Lys Ile Val
1               5                   10                  15

Glu Glu Leu Gln Ser Leu Ser Lys Met
            20                  25

<210> SEQ ID NO 200
<211> LENGTH: 6
<212> TYPE: PRT
<213> ORGANISM: Artificial Sequence
<220> FEATURE:
<223> OTHER INFORMATION: Canine IL-31 AB loop region mimotope sequence

<400> SEQUENCE: 200

Thr Gly Val Pro Glu Ser
1               5

<210> SEQ ID NO 201
<211> LENGTH: 6
<212> TYPE: PRT
<213> ORGANISM: Artificial Sequence
<220> FEATURE:
<223> OTHER INFORMATION: Feline IL-31 AB loop region mimotope sequence

<400> SEQUENCE: 201

Ile Gly Leu Pro Glu Ser
1               5

<210> SEQ ID NO 202
<211> LENGTH: 6
<212> TYPE: PRT
<213> ORGANISM: Artificial Sequence
<220> FEATURE:
<223> OTHER INFORMATION: Equine IL-31 AB loop region mimotope sequence -continued

```
<400> SEQUENCE: 202

Lys Gly Val Gln Lys Phe
1               5


<210> SEQ ID NO 203
<211> LENGTH: 6
<212> TYPE: PRT
<213> ORGANISM: Artificial Sequence
<220> FEATURE:
<223> OTHER INFORMATION: Human IL-31 AB loop region mimotope sequence

<400> SEQUENCE: 203

Lys Gly Val Leu Val Ser
1               5
```

PEPTIDE VACCINES AGAINST INTERLEUKIN-31

CROSS-REFERENCE TO RELATED APPLICATIONS

This application claims the benefit of U.S. Provisional Application No. 62/643,921, filed Mar. 16, 2018, the entire contents of which are incorporated herein by reference in their entirety.

FIELD OF THE INVENTION

The present invention relates to the field of peptide vaccines and their uses in clinical and scientific procedures, including diagnostic procedures. The peptide vaccines of the present invention are useful to immunize and/or protect a mammal, such as a cat, dog, horse, or human, against an IL-31-mediated disorder.

BACKGROUND OF THE INVENTION

Atopic dermatitis has been defined by the American College of Veterinary Dermatology task force as “a genetically-predisposed inflammatory and pruritic allergic skin disease with characteristic clinical features” (Olivry, et al. Veterinary Immunology and Immunopathology 2001; 81: 143-146). The task force also recognized that the disease in canines has been associated with allergen-specific IgE (Olivry, et al. 2001 supra; Marsella & Olivry Clinics in Dermatology 2003; 21: 122-133). Severe pruritus, along with secondary alopecia and erythema, are the most noticeable and concerning symptoms to pet owners.

The potential factors involved in allergic dermatitis are numerous and poorly understood. Components in food may trigger atopic dermatitis (Picco, et al. Vet Dermatol. 2008; 19: 150-155), as well as environmental allergens such as fleas, dust mites, ragweed, plant extracts, etc. Genetic factors also play an important role. Although there is no confirmed breed predilection, some mode of inheritance is thought to increase predisposition to atopic dermatitis (Sousa & Marsella Veterinary Immunology and Immunopathology 2001; 81: 153-157; Schwartzman, et al. Clin. Exp. Immunol. 1971; 9: 549-569).

The prevalence of atopic dermatitis is estimated to be 10% of the total canine population (Marsella & Olivry 2003 supra; Scott, et al. Canadian Veterinary Journal 2002; 43: 601-603; Hillier Veterinary Immunology and Immunopathology 2001; 81: 147-151). Globally, about 4.5 million dogs are affected with this chronic and lifelong condition. Incidence appears to be increasing. Canine breed and sex predilections have been suspected, but may vary greatly depending on geographical region (Hillier, 2001 supra; Picco, et al. 2008 supra).

Feline allergic dermatitis is an inflammatory and pruritic skin condition thought to be caused by an abnormal response of the immune system to substances that do not induce a reaction in healthy cats. The most consistent feature of feline allergic dermatitis is chronic recurrent pruritus. Common clinical presentations of allergic dermatitis in cats include self-induced alopecia, miliary dermatitis, eosinophilic granuloma complex lesions (including plaques, granulomas, and indolent ulcer), and focused head and neck pruritus characterized by excoriations, erosions, and/or ulcers. Breed and sex predilections have not been demonstrated and young cats seem more prone to the disease (Hobi et al. Vet Dermatol 2011 22: 406-413; Ravens et al. Vet Dermatol 2014; 25: 95-102; Buckely In Practice 2017; 39: 242-254).

Current treatments for cats diagnosed with allergic dermatitis depend on the severity of the clinical signs, duration, and owner preferences and include allergen-specific immunotherapy and antipruritic drugs such as glucocorticoids and cyclosporines (Buckley, supra). Immunotherapy treatment is effective for some patients but requires frequent injections, and clinical improvement may not be seen for 6-9 months (Buckley, supra). Immunosuppressive drugs like glucocorticoids and cyclosporines are generally effective however long term use often results in undesirable adverse effects.

Atopic dermatitis in horses is recognized as a potential cause of pruritus. The role of environmental allergens in equine atopic dermatitis is becoming better appreciated. The disease may be seasonal or non-seasonal, depending on the allergen(s) involved. Age, breed, and sex predilections have not been extensively reported. In preliminary work at the School of Veterinary Medicine, University of California, Davis (SVM-UCD), the median age at onset was 6.5 years, Thoroughbreds were the most common breed, accounting for 25% of the horses, and males (usually geldings) were almost twice as prevalent as mares; however, these data are from only 24 horses, and have not yet been compared with the hospital population at large. Pruritus, often directed against the face, distal legs, or trunk, is the most common clinical sign of equine atopic dermatitis. Alopecia, erythema, urticaria, and papules may all be present. Urticarial lesions may be quite severe, yet nonpruritic. There may be a familial predisposition for urticarial atopic dermatitis in the horse. Horses may have a secondary pyoderma, typified by excess scaling, small epidermal collarettes, or encrusted papules (“miliary dermatitis”). Diagnosis of atopic dermatitis is based on clinical signs and the exclusion of other diagnoses, especially insect (Culicoides) hypersensitivity (White Clin Tech Equine Pract 2005; 4: 311-313; Fadok Vet Clin Equine 2013; 29 541-550). Currently, management of atopic dermatitis in horses is done both symptomatically, by suppressing the inflammation and the pruritus triggered by the allergic response, and by addressing the specific cause (i.e., by identifying the responsible allergens and by formulating an allergen-specific vaccine). The symptomatic approach is typically needed in the short term to make the patient comfortable and minimize self-trauma. This approach relies on the use of a combination of topical and systemic therapies including antihistamines, essential fatty acids, pentoxifylline, and glucocorticoids. The primary approach to environmental allergy control involves the identification of allergens that trigger the hypersensitivity reaction. It is commonly accepted by dermatologists that allergen-specific immunotherapy can be of help to atopic horses. However, as a general rule, most horses show improvement only after the first 6 months of immunotherapy (Marsella Vet Clin Equine 2013; 29: 551-557). Also, long term use of immunosuppressive drugs in horses can result in undesirable adverse effects.

Interleukin-31 (IL-31), a cytokine produced by T helper type 2 cells, has been shown to induce pruritus in humans, mice, and dogs (Bieber N Engl J Med 2008; 358: 1483-1494; Dillon et al. Nat Immunol 2004; 5:752-60; U.S. Pat. No. 8,790,651 to Bammert et al.; Gonzalez et al. Vet Dermatl. 2013; 24(1): 48-53). IL-31 binds a co-receptor composed of IL-31 receptor A (IL-31 RA) and the oncostatin M receptor (OSMR) (Dillon et al. 2004 supra and Bilsborough et al. J Allergy Clin Immunol. 2006 117(2):418-25). Receptor activation results in phosphorylation of STAT through JAK receptor(s). Expression of the co-receptor has been shown in macrophages, keratinocytes and in dorsal root ganglia.

Recently, it has been found that IL-31 is involved in dermatitis, pruritic skin lesions, allergy, and airway hypersensitivity. Cytopoint®, a canine anti-IL-31 monoclonal antibody produced by Zoetis Inc., Parsippany, N.J., has been shown to reduce pruritus and skin lesions in dogs with atopic dermatitis (Gonzalez et al. 2013 supra, Michels et al. Vet Dermatol. 2016; December; 27(6): 478-e129). It would be desirable to provide for alternative approaches to prevent and treat IL-31-mediated disorders in mammals. It would be especially desirable to provide vaccines to reduce pruritus and skin lesions in dogs, cats, horses, and humans with atopic dermatitis.

SUMMARY OF THE INVENTION

In one embodiment, the present invention provides a vaccine composition for immunizing and/or protecting a mammal against an IL-31 mediated disorder, wherein the composition includes: the combination of a carrier polypeptide and at least one mimotope selected from a feline IL-31 mimotope, a canine IL-31 mimotope, a horse IL-31 mimotope, or a human IL-31 mimotope; and an adjuvant.

In one embodiment of the vaccine composition, the canine IL-31 mimotope is and/or comprises as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment of the vaccine composition, the feline IL-31 mimotope is and/or comprises as part thereof the amino acid sequence SMPADNFERKNF (SEQ ID NO: 188), NG SAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In a still further embodiment of the vaccine composition, the equine IL-31 mimotope is and/or comprises as part thereof the amino acid sequence SMPTDNFERKRF (SEQ ID NO: 189), NS SAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In yet another embodiment of the vaccine composition, the human IL-31 mimotope is and/or comprises as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In one embodiment, the mimotope contained in the vaccine composition binds to an anti-IL31 antibody or antigen-binding portion thereof that specifically binds to a region on a mammalian IL-31 protein involved with interaction of the IL-31 protein with its co-receptor. In one embodiment, the binding of said antibody to said region is impacted by mutations in a 15H05 epitopebinding region selected from the group consisting of:

a) a region between about amino acid residues 124 and 135 of a feline IL-31 sequence represented by SEQ ID NO: 157 (Feline_IL31_wildtype);

b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31).

In a specific embodiment, the mimotope binds to an anti-IL-31 antibody or antigen-binding portion thereof comprising at least one of the following combinations of complementary determining region (CDR) sequences:

1) antibody 15H05: variable heavy (VH)-CDR1 of SYTIH (SEQ ID NO: 1), VH-CDR2 of NINPTSGYTENNQRFKD (SEQ ID NO: 2), VH-CDR3 of WGFKYDGEWSFDV (SEQ ID NO: 3), variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);

2) antibody ZIL1: variable heavy (VH)-CDR1 of SYGMS (SEQ ID NO: 13), VH-CDR2 of HINSGGSSTYYADAVKG (SEQ ID NO:14), VH-CDR3 of VYTTLAAFWTDNFDY (SEQ ID NO: 15), variable light (VL)-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);

3) antibody ZIL8: VH-CDR1 of DYAMS (SEQ ID NO: 19), VH-CDR2 of GIDSVGSGTSYADAVKG (SEQ ID NO: 20), VH-CDR3 of GFPGSFEH (SEQ ID NO: 21), VL-CDR1 of TGSSSNIGSGYVG (SEQ ID NO: 22), VL-CDR2 of YNSDRPS (SEQ ID NO: 23), VL-CDR3 of SVYDRTFNAV (SEQ ID NO: 24);

4) antibody ZIL9: VH-CDR1 of SYDMT (SEQ ID NO: 25), VH-CDR2 of DVNSGGTGTAYAVAVKG (SEQ ID NO: 26), VH-CDR3 of LGVRDGLSV (SEQ ID NO: 27), VL-CDR1 of SGESLNEYYTQ (SEQ ID NO: 28), VL-CDR2 of RDTERPS (SEQ ID NO: 29), VL-CDR3 of ESAVDTGTLV (SEQ ID NO: 30);

5) antibody ZIL11: VH-CDR1 of TYVMN (SEQ ID NO: 31), VH-CDR2 of SINGGGSSPTYADAVRG (SEQ ID NO: 32), VH-CDR3 of SMVGPFDY (SEQ ID NO: 33), VL-CDR1 of SGESLSNYYAQ (SEQ ID NO: 34), VL-CDR2 of KDTERPS (SEQ ID NO: 35), VL-CDR3 of ESAVSSDTIV (SEQ ID NO: 36);

6) antibody ZIL69: VH-CDR1 of SYAMK (SEQ ID NO: 37), VH-CDR2 of TINNDGTRTGYADAVRG (SEQ ID NO: 38), VH-CDR3 of GNAESGCTGDHCPPY (SEQ ID NO: 39), VL-CDR1 of SGESLNKYYAQ (SEQ ID NO: 40), VL-CDR2 of KDTERPS (SEQ ID NO: 41), VL-CDR3 of ESAVSSETNV (SEQ ID NO: 42);

7) antibody ZIL94: VH-CDR1 of TYFMS (SEQ ID NO: 43), VH-CDR2 of LISSDGSGTYYADAVKG (SEQ ID NO: 44), VH-CDR3 of FWRAFND (SEQ ID NO: 45), VL-CDR1 of GLNSGSVSTSNYPG (SEQ ID NO: 46), VL-CDR2 of DTGSRPS (SEQ ID NO: 47), VL-CDR3 of SLYTDSDILV (SEQ ID NO: 48);

8) antibody ZIL154: VH-CDR1 of DRGMS (SEQ ID NO: 49), VH-CDR2 of YIRYDGSRTDYADAVEG (SEQ ID NO: 50), VH-CDR3 of WDGSSFDY (SEQ ID NO: 51), VL-CDR1 of KASQSLLHSDGNTYLD (SEQ ID NO: 52), VL-CDR2 of KVSNRDP (SEQ ID NO: 53), VL-CDR3 of MQAIHFPLT (SEQ ID NO: 54);

9) antibody ZIL159: VH-CDR1 of SYVMT (SEQ ID NO: 55), VH-CDR2 of GINSEGSRTAYADAVKG (SEQ ID NO: 56), VH-CDR3 of GDIVATGTSY (SEQ ID NO: 57), VL-CDR1 of SGETLNRFYTQ (SEQ ID NO: 58), VL-CDR2 of KDTERPS (SEQ ID NO: 59), VL-CDR3 of KSAVSIDVGV (SEQ ID NO: 60);

10) antibody ZIL171: VH-CDR1 of TYVMN (SEQ ID NO: 61), VH-CDR2 of SINGGGSSPTYADAVRG (SEQ ID NO: 62), VH-CDR3 of SMVGPFDY (SEQ ID NO: 63), VL-CDR1 of SGKSLSYYYAQ (SEQ ID NO: 64), VL-CDR2 of KDTERPS (SEQ ID NO: 65), VL-CDR3 of ESAVSSDTIV (SEQ ID NO: 66); or 11) a variant of 1) to 10) that differs from respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH or VL CDR1, CDR2, or CDR3.

In some embodiments, the mimotope employed in the vaccine compositions of the present invention binds to an anti-IL-31 antibody or antigen-binding portion thereof which binds to feline IL-31, wherein the antibody includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

In one embodiment of the vaccine compositions described above, the mimotope is a constrained mimotope. In a particular embodiment, the constrained mimotope is a chemically-linked cyclic peptide.

In some embodiments of the above-described vaccine compositions, the mimotope is chemically conjugated to the carrier polypeptide. In other embodiments, the carrier polypepide and the mimotope are part of a recombinant fusion protein.

In one embodiment of the vaccine compositions described above, the carrier polypeptide which is combined with the mimotope includes a bacterial toxoid or a derivative thereof, keyhole limpet hemocyanin (KLH), or a virus-like particle. In one embodiment, the mimotope is combined with a bacterial toxoid or derivative selected from tetanus toxoid, a diphtheria toxoid, a tetanus toxoid, the outer membrane protein complex from group B *N. meningitidis, Pseudomonas* exotoxin, or the nontoxic mutant of diphtheria toxin (CRM197). In another embodiment, the mimotope is combined with a virus-like particle selected from HBsAg, HBcAg, *E. coli* bacteriophage Qbeta, Norwalk virus, canine distemper virus (CDV), or influenza HA. In a specific embodiment, the mimotope is combined with a carrier polypeptide which comprises or consists of CRM197.

In one embodiment, the adjuvant contained in the above-described vaccine compositions of the present invention is selected from an oil-in-water adjuvant, a polymer and water adjuvant, a water-in-oil adjuvant, an aluminum hydroxide adjuvant, a vitamin E adjuvant and combinations thereof.

In one embodiment, the adjuvant is a formulation comprising a saponin, a sterol, a quaternary ammonium compound, and a polymer. In a specific embodiment, the saponin is Quil A or a purified fraction thereof, the sterol is cholesterol, the quaternary ammonium compound is dimethyl dioctadecyl ammonium bromide (DDA), and the polymer is polyacrylic acid.

In another embodiment, the adjuvant comprises the combination of one or more isolated immunostimulatory oligonucleotides, a sterol, and a saponin. In a specific embodiment, the one or more isolated immunostimulatory oligonucleotides comprises CpG, the sterol is cholesterol, and the saponin is Quil A or a purified fraction thereof.

The present invention also provides a method of protecting a mammal against an IL-31 mediated disorder. Such a method includes administering to the mammal a vaccine composition according to the present invention. In one embodiment, the mammal to which a vaccine according to instant invention is administered is selected from a dog, a cat, a horse, or a human. In a particular embodiment, the vaccine composition includes an IL-31 peptide mimotope which is administered to the mammal at about 10 μg to about 100 μg per dose or a corresponding dose to elicit an equivalent immune response. In one embodiment, the vaccine composition includes an IL-31 mimotope which is administered to a mammal, such as a cat, at about 10 μg per dose.

In one embodiment, the IL-31-mediated disorder is a pruritic or allergic condition. In some embodiments, the pruritic or allergic condition is a pruritic condition selected from atopic dermatitis, eczema, psoriasis, scleroderma, and pruritus. In other embodiments, the pruritic or allergic condition is an allergic condition selected from allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity. In other embodiments, the IL-31 mediated disorder is tumor progression. In some embodiments, the IL-31 mediated disorder is eosinophilic disease or mastocytomas.

Also provided herein is a method of determining the identity and/or amount of an anti-IL-31 antibody in a sample. Such a method includes incubating a sample comprising an anti-IL-31 antibody with at least one mimotope selected from a feline IL-31 mimotope, a canine IL-31 mimotope, a horse IL-31 mimotope, and a human IL-31 mimotope; and determining the identity and/or quantity of the anti-IL-31 in the sample.

In one embodiment, the canine IL-31 mimotope employed in the method to determine the identity and/or amount of an anti-IL-31 antibody in the sample is and/or comprises as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment, the feline IL-31 mimotope employed in such a method is and/or comprises as part thereof the amino acid sequence SMPADNFERKNF (SEQ ID NO: 188), NGSAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In a further embodiment, the equine IL-31 mimotope employed in such a method is and/or comprises as part thereof the amino acid sequence SMPTDNFERKRF (SEQ ID NO: 189), NSSAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In a still further, the human IL-31 mimotope employed in such a method is and/or comprises as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In one embodiment of the above-described diagnostic method, the mimotope is a capture reagent bound to a solid surface. In one embodiment, the sample is added to the mimotope capture reagent; and secondary detection reagents are then added to quantify the amount of the antibody in the sample.

The present invention also provides a method of determining the amount of IL-31 in a sample from a mammal. Such a method includes incubating a mammalian sample comprising IL-31 with a labeled anti-IL-31 antibody: IL-31 mimotope complex tethered to a solid surface, wherein the mimotope in the complex is selected from the group consisting of a feline IL-31 mimotope, a canine IL-31 mimotope, a horse IL-31 mimotope, and a human IL-31 mimotope; and determining the level of the IL-31 in the sample, wherein the labeled anti-IL-31 antibody in the complex has an affinity to the mimotope in the complex that is lower than its affinity to the IL-31 in the sample. In one embodiment of this method, the determining step comprises measuring the signal coming from labeled antibody which is liberated from the solid surface when the IL-31 in the sample binds to the labeled anti-IL-3 antibody of the complex, the level of IL-31 in the sample being inversely proportional to the signal.

In one embodiment, the canine IL-31 mimotope employed in the method of determining the amount of IL-31 in the sample is and/or comprises as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment, the feline IL-31 mimotope employed in such a method is and/or comprises as part thereof the amino acid sequence SMPADNFERKNF (SEQ ID NO: 188), NGSAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In yet another embodiment, the equine IL-31 mimotope employed in such a method is and/or comprises as part thereof the amino acid sequence SMPTDNFERKRF (SEQ ID NO: 189), NSSAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In a still further embodiment, the human IL-31 mimotope employed in such a method is and/or comprises as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In some embodiments of any of the above-described diagnostic methods of the invention, the mimotope binds to an anti-IL31 antibody or antigen-binding portion thereof that specifically binds to a region on a mammalian IL-31 protein involved with interaction of the IL-31 protein with its co-receptor. In one embodiment of the diagnostic methods of this invention, the binding of said antibody to said region is impacted by mutations in a 15H05 epitope binding region selected from the group consisting of:

a) a region between about amino acid residues 124 and 135 of a feline IL-31 sequence represented by SEQ ID NO: 157 (Feline_IL31_wildtype);
b) a region between about amino acid residues 124 and 135 of a canine IL-31 sequence represented by SEQ ID NO: 155 (Canine_IL31); and
c) a region between about amino acid residues 118 and 129 of an equine IL-31 sequence represented by SEQ ID NO: 165 (Equine_IL31).

In one specific embodiment of any of the diagnostic methods of the instant invention, the mimotope binds to an anti-IL-31 antibody or antigen-binding portion thereof comprising at least one of the following combinations of complementary determining region (CDR) sequences:

1) antibody 15H05: variable heavy (VH)-CDR1 of SYTIH (SEQ ID NO: 1), VH-CDR2 of NINPTSGYTENNQRFKD (SEQ ID NO: 2), VH-CDR3 of WGFKYDGEWSFDV (SEQ ID NO: 3), variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);

2) antibody ZIL1: variable heavy (VH)-CDR1 of SYGMS (SEQ ID NO: 13), VH-CDR2 of HINSGGSSTYYADAVKG (SEQ ID NO:14), VH-CDR3 of VYTTLAAFWTDNFDY (SEQ ID NO: 15), variable light (VL)-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);

3) antibody ZIL8: VH-CDR1 of DYAMS (SEQ ID NO: 19), VH-CDR2 of GIDSVGSGTSYADAVKG (SEQ ID NO: 20), VH-CDR3 of GFPGSFEH (SEQ ID NO: 21), VL-CDR1 of TGSSSNIGSGYVG (SEQ ID NO: 22), VL-CDR2 of YNSDRPS (SEQ ID NO: 23), VL-CDR3 of SVYDRTFNAV (SEQ ID NO: 24);

4) antibody ZIL9: VH-CDR1 of SYDMT (SEQ ID NO: 25), VH-CDR2 of DVNSGGTGTAYAVAVKG (SEQ ID NO: 26), VH-CDR3 of LGVRDGLSV (SEQ ID NO: 27), VL-CDR1 of SGESLNEYYTQ (SEQ ID NO: 28), VL-CDR2 of RDTERPS (SEQ ID NO: 29), VL-CDR3 of ESAVDTGTLV (SEQ ID NO: 30);

5) antibody ZIL11: VH-CDR1 of TYVMN (SEQ ID NO: 31), VH-CDR2 of SINGGGSSPTYADAVRG (SEQ ID NO: 32), VH-CDR3 of SMVGPFDY (SEQ ID NO: 33), VL-CDR1 of SGESLSNYYAQ (SEQ ID NO: 34), VL-CDR2 of KDTERPS (SEQ ID NO: 35), VL-CDR3 of ESAVSSDTIV (SEQ ID NO: 36);

6) antibody ZIL69: VH-CDR1 of SYAMK (SEQ ID NO: 37), VH-CDR2 of TINNDGTRTGYADAVRG (SEQ ID NO: 38), VH-CDR3 of GNAESGCTGDHCPPY (SEQ ID NO: 39), VL-CDR1 of SGESLNKYYAQ (SEQ ID NO: 40), VL-CDR2 of KDTERPS (SEQ ID NO: 41), VL-CDR3 of ESAVSSETNV (SEQ ID NO: 42);

7) antibody ZIL94: VH-CDR1 of TYFMS (SEQ ID NO: 43), VH-CDR2 of LISSDGSGTYYADAVKG (SEQ ID NO: 44), VH-CDR3 of FWRAFND (SEQ ID NO: 45), VL-CDR1 of GLNSGSVSTSNYPG (SEQ ID NO: 46), VL-CDR2 of DTGSRPS (SEQ ID NO: 47), VL-CDR3 of SLYTDSDILV (SEQ ID NO: 48);

8) antibody ZIL154: VH-CDR1 of DRGMS (SEQ ID NO: 49), VH-CDR2 of YIRYDGSRTDYADAVEG (SEQ ID NO: 50), VH-CDR3 of WDGSSFDY (SEQ ID NO: 51), VL-CDR1 of KASQSLLHSDGNTYLD (SEQ ID NO: 52), VL-CDR2 of KVSNRDP (SEQ ID NO: 53), VL-CDR3 of MQAIHFPLT (SEQ ID NO: 54);

9) antibody ZIL159: VH-CDR1 of SYVMT (SEQ ID NO: 55), VH-CDR2 of GINSEGSRTAYADAVKG (SEQ ID NO: 56), VH-CDR3 of GDIVATGTSY (SEQ ID NO: 57), VL-CDR1 of SGETLNRFYTQ (SEQ ID NO: 58), VL-CDR2 of KDTERPS (SEQ ID NO: 59), VL-CDR3 of KSAVSIDVGV (SEQ ID NO: 60);

10) antibody ZIL171: VH-CDR1 of TYVMN (SEQ ID NO: 61), VH-CDR2 of SINGGGSSPTYADAVRG (SEQ ID NO: 62), VH-CDR3 of SMVGPFDY (SEQ ID NO: 63), VL-CDR1 of SGKSLSYYYAQ (SEQ ID NO: 64), VL-CDR2 of KDTERPS (SEQ ID NO: 65), VL-CDR3 of ESAVSSDTIV (SEQ ID NO: 66); or 11) a variant of 1) to 10) that differs from respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH or VL CDR1, CDR2, or CDR3.

In some embodiments, the mimotope employed in the diagnostic methods of the present invention binds to an anti-IL-31 antibody or antigen-binding portion thereof which binds to feline IL-31, wherein the antibody includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

BRIEF DESCRIPTION OF THE DRAWINGS

FIG. 1A is an alignment showing amino acid sequence conservation between IL-31 from different species. In particular, a comparison between SEQ ID NO: 155 (canine IL-31), SEQ ID NO: 157 (feline IL-31), SEQ ID NO: 165 (equine IL-31), and SEQ ID NO: 181 (human IL-31) is shown. In FIG. 1B, the percent amino acid sequence identity between canine, feline, horse and human IL-31 is also indicated.

FIG. 2 details the affinity with which candidate antibodies with CDRs derived from mouse origin bind feline and canine IL-31 using surface plasmon resonance (SPR) on a Biacore system (Biacore Life Sciences (GE Healthcare), Uppsala, Sweden).

FIG. 3 is a table showing potency (IC50 (μg/ml)) of candidate antibodies with CDRs derived from mouse origin as measured by canine and feline cellular assays. In particular, the candidate antibodies were assessed for their ability to inhibit IL-31-mediated STAT phosphorylation in canine DH-82 or feline FCWF4 macrophage-like cells.

FIG. 4 shows the results obtained for binding of candidate monoclonal antibodies with CDRs of dog origin to various proteins using both an indirect ELISA and Biacore methods. For the indirect ELISA, binding (ELISA OD) to wildtype feline IL-31 and a feline IL-31 15H05 mutant which had mutations in the monoclonal antibody 15H05 epitope region was assessed. To confirm binding, biacore analysis was performed using canine, feline, equine, human, the feline 15H05 mutant, and feline 11E12 mutant IL-31 proteins as surfaces and a single test concentration of antibody. The feline IL-31 11E12 mutant had mutations in the monoclonal antibody 11E12 epitope region.

FIG. 6A shows the alignment of wildtype feline IL-31 (SEQ ID NO: 157) with mutants 15H05 (SEQ ID NO: 163) and 11E12 (SEQ ID NO: 161) highlighting the positions where the alanine substitutions occur.

FIG. 7A shows the competition binding data for mouse 15H05 and 11E12 antibodies to canine IL-31. FIG. 7B shows the competition binding data for antibodies 15H05 and 11E12 on a feline IL-31 surface.

FIG. 10A shows the baseline pre-challenge pruritic behavior for the T01 vehicle placebo and T02 antibody ZTS-361 groups from day −7 through day 28 with day zero being the day of antibody administration to group T02. FIG. 10B shows the efficacy of antibody ZTS-361 demonstrating a significant reduction in pruritus observed on days 7 ($p<0.0001$), 21 ($p<0.0027$), and 28 ($p<0.0238$) following IL-31 challenge when compared to vehicle placebo control.

FIG. 110 is of a graph showing the pharmacokinetic profile of canine IL-31 in dogs following administration of a subcutaneous dose of 1.75 μg/kg canine IL-31.

FIG. 12 is of a table showing the results of a full replacement scan of canine IL-31 encompassing the amino acids outlined in FIG. 12. Each position depicted was individually replaced in the full length canine IL-31 protein (SEQ ID NO: 155) with one of the other possible 19 amino acids and binding of antibody 15H05 was assessed using an indirect ELISA. For comparison, the corresponding region on feline (SEQ ID NO: 157), equine (SEQ ID NO: 165), and human IL-31 (SEQ ID NO: 181) are shown.

FIG. 13A is of a table showing the sequences and chemical linkers of various constrained peptides. Peptide ZTS-561 contains the amino acid sequence N-TEISVPADTFERKS-FILT-C which corresponds to positions 121 through 138 of SEQ ID NO: 155 with the substitution of Arginine (R) for Cysteine (C) at position number 132. Peptide ZTS-562 contains the amino acid sequence N-EISVPADTFERKSF-C which corresponds to positions 122 through 135 of SEQ ID NO: 155 with the substitution of Arginine (R) for Cysteine (C) at position number 132. Peptide ZTS-563 contains the amino acid sequence N-AKVSMPADNFERKNFILT-C which corresponds to positions 121 through 138 of SEQ ID NO: 157 with the substitution of Threonine (T) for Alanine (A) at position number 138. Peptide ZTS-564 contains the amino acid sequence N-TEISVPADTFERKSFILT-C which corresponds to positions 121 through 138 of SEQ ID NO: 155. Each of peptides ZTS-561, ZTS-562, ZTS-563, and ZTS-564 also includes N and C terminal Cysteines as depicted to facilitate conjugation chemistry using the free thiol groups.

FIG. 13B shows the results of an affinity assessment for each of peptides ZTS-561, ZTS-562, ZTS-563, and ZTS-564 which had been independently conjugated to a carrier polypeptide (CRM-197). For affinity assessment, each peptide was independently immobilized to a biacore surface and the KD for the felinized anti IL-31 15H05 mAb (ZTS-927) was determined.

FIG. 15A depicts the average canine antibody titers to full length feline IL-31 protein (SEQ ID NO: 159).

FIG. 15B depicts the average canine antibody titers to the full length feline IL-31 15H05 mutant (SEQ ID NO: 163). FIG. 15C depicts the average canine antibody titers to full length canine IL-31 (SEQ ID NO: 155). FIG. 15D depicts the average canine antibody titers to full length equine IL-31 (SEQ ID NO: 165). FIG. 15E depicts the average canine antibody titers to full length human IL-31 (SEQ ID NO: 181).

FIG. 16A depicts the design for an immunogenicity study undertaken to assess the ability of CRM-197-conjugated full-length canine IL-31 protein or mimotopes to elicit an immune response in laboratory beagle dogs. Each mimotope described herein was designed to generate an epitope-specific immune response driven towards the relevant region on the IL-31 protein where antibody 15H05 and other anti-IL-31 antibodies disclosed herein bind. The sequences and chemical linkers of various mimotope peptides are shown as groups 102-104. Peptide ZTS-420 contains the amino acid sequence N-TEISVPADTFERKSFILT-C which corresponds to positions 121 through 138 of SEQ ID NO: 155 with the substitution of Arginine (R) for Cysteine (C) at position number 132. Peptide ZTS-421 contains the amino acid sequence N-TNISVPTDTHECKRFILT-C which corresponds to positions 122 through 139 of SEQ ID NO: 181. Peptide ZTS-766 contains the amino acid sequence N-NS-SAILPYFRAIRPLSDKNIIDKIIEQLDKLKF-C which corresponds to positions 83 through 115 of SEQ ID NO: 155. Each of peptides ZTS-420, ZTS-421, and ZTS-766 also includes N and C terminal Cysteines as depicted to facilitate conjugation chemistry using the free thiol groups. ZTS-766 also contains an additional three amino acid spacer sequence (GSG) next to the N terminal cysteine. FIG. 16B shows homologous sequences allowing comparison of the canine BC helix mimotope (ZTS-766) to the corresponding sequence from feline, equine, and human IL-31 and includes the sequence reference number and amino acid positions for each.

FIG. 17A depicts the average canine antibody titers to full length canine IL-31 protein (SEQ ID NO: 155). FIG. 17B depicts the average canine antibody titers to the full length humanIL-31 (SEQ ID NO: 181) on days 0, 42, and 84 for group T03 only. Dogs in group T03 (human 15H05 mimotope) had no CRAR to canine IL-31 (data not shown).

FIG. 18A depicts the design for an immunogenicity study undertaken to assess the ability of CRM-197-conjugated full-length feline IL-31 protein or mimotopes to elicit an immune response in laboratory cats. All treatment groups were formulated with an adjuvant mixture including the glycolipid adjuvant Bay R1005 (N-(2-Deoxy-2-L-leucylamino-6-D-glucopyranosyl)-N-octadecyldodecanoylamidehydroacetate) as well as CpG oligonucleotides.

Each mimotope described herein was designed to generate an epitope-specific immune response driven towards the relevant region on the IL-31 protein where antibody 15H05 and other anti-IL-31 antibodies disclosed herein bind._The sequences and chemical linkers of various mimotope peptides are shown as groups 102-105. Peptide ZTS-563 contains the amino acid sequence N-AKVSMPADNFERKN-FILT-C which corresponds to positions 121 through 138 of SEQ ID NO: 157 with the substitution of Threonine (T) for Alanine (A) at position number 138. Peptide ZTS-418 contains the amino acid sequence N-TEVSMPTDNFERKR-FILT-C which corresponds to positions 115 through 132 of SEQ ID NO: 165. Peptide ZTS-423 contains the amino acid sequence N-NGSAILPYFRAIRPLSDKNTID-KIIEQLDKLKF-C which corresponds to positions 83 through 115 of SEQ ID NO: 157. Peptide ZTS-422 contains the amino acid sequence N-AKVSMPADNFERKNFILT-C which corresponds to positions 121 through 138 of SEQ ID NO: 157 with the substitution of Threonine (T) for Alanine (A) at position number 138. Each of peptides ZTS-563, ZTS-418, ZTS-423, and ZTS-422 also includes N and C terminal Cysteines as depicted to facilitate conjugation chemistry using the free thiol groups. ZTS-422 also contains an additional aminohexanoic acid linker (Ahx) between the two N terminal cysteines. ZTS-423 also contains an additional three amino acid spacer sequence (GSG) next to the N terminal cysteine. FIG. 18B depicts the average feline antibody titers to the full length feline IL-31 (SEQ ID NO: 157) for all treatment groups except T03. Cats in group T03 (equine 15H05 mimotope) had no CRAR to feline IL-31 (data not shown).

FIG. 19A is the minimum epitope amino acid sequence bound by anti-canine IL-31 antibody M14 according to WO 2018/156367 (Kindred Biosciences, Inc.) The comparison of multiple species, sequence reference IDs, and relative amino acid positions are shown. FIG. 19B shows this minimum amino acid sequence on canine IL-31 highlighted in a black box. This figure also shows the alignment of sequence in the surrounding region of the protein and the relative positions of the corresponding amino acids in the sequence ID indicated.

FIG. 20 shows a fragment of the IL-31 protein from a loop formed by the convergence of helix A with the trailing random coil sequence which shares positional and structural attributes to the 15H05 loop. Comparison of the amino acid sequences from multiple species and reference to the sequence IDs and amino acid positions are shown.

FIG. 21A shows the amino acid sequences of three equine IL-31 mimotope peptides representing different key epitope regions on the protein. Mimotope 15H05 contains the amino acid sequence N-TEVSMPTDNFERKRFILT-C which corresponds to positions 115 through 132 of SEQ ID NO: 165. Mimotope BC helix contains the amino acid sequence N-NSSAILPYFKAISPSLNNDKSLYIIEQLDKLNF-C which corresponds to positions 77 through 109 of SEQ ID NO: 165. Mimotope A helix contains the amino acid sequence N-GPIYQLQPKEIQAIIVELQNLSKK-C which corresponds to positions 20 through 43 of SEQ ID NO: 165. Mimotope 15H05 also includes N and C terminal Cysteines as depicted to facilitate conjugation chemistry using the free thiol groups. All three mimotopes contain an additional three amino acid spacer sequence (GSG) next to the N biotin group shown as bold and underlined in the sequences. The corresponding positions of each amino acid residue in SEQ ID NO: 165 are shown. FIG. 21B shows the results from a binding assay using bio-layer interferometry. The mimotopes indicated were absorbed to streptavidin pins and used to probe multiple dilutions of mouse serum. The serum used was from mice vaccinated with the equine IL-31 protein (SEQ ID NO: 165) or control serum from mice vaccinated with an unrelated protein.

DEFINITIONS

Figure 5A:
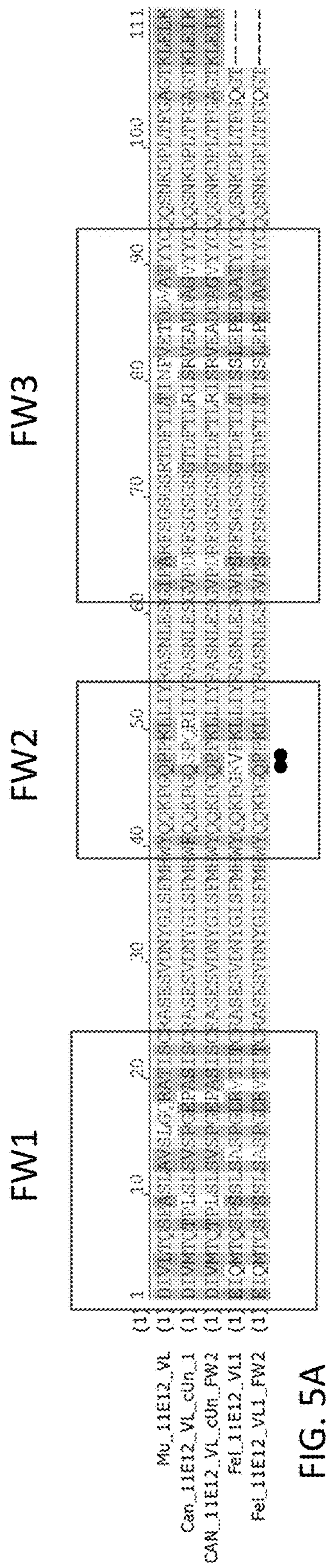
FIG. 5A shows an alignment of mouse antibody 11E12 VL sequence (SEQ ID NO: 73) comparing previously disclosed caninized 11E12 sequences designated as Can_11E12_VL_cUn_1 (SEQ ID NO: 182) and CAN_11E12_VL_cUn_FW2 (SEQ ID NO: 184) to the felinized versions designated as FEL_11E12_VH1 (SEQ ID NO: 111) and FEL_11E12_VL1_FW2 (SEQ ID NO: 117). Noted below the alignment in FIG. 5A are dots showing the positions of relevant changes to Fel_11E12_VL1 that were necessary to restore affinity of this antibody to the IL-31 protein.

Before describing the present invention in detail, several terms used in the context of the present invention will be defined. In addition to these terms, others are defined elsewhere in the specification, as necessary. Unless otherwise expressly defined herein, terms of art used in this specification will have their art-recognized meanings.

As used in the specification and claims, the singular form "a", "an" and "the" include plural references unless the context clearly dictates otherwise. For example, reference to "an antibody" includes a plurality of such antibodies. As another example, reference to "a mimotope", "an IL-31 mimotope" and the like includes a plurality of such mimotopes.

As used herein, the term "comprising" is intended to mean that the compositions and methods include the recited elements, but not excluding others.

As used herein, the term "vaccine composition" includes at least one antigen or immunogen in a pharmaceutically acceptable vehicle useful for inducing an immune response in a host. Vaccine compositions can be administered in dosages, and by techniques well known to those skilled in the medical or veterinary arts, taking into consideration factors such as the age, sex, weight, species and condition of the recipient mammal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray, or mixed in food and/or water, or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences" (1990), may be consulted to prepare suitable preparations, without undue experimentation.

The term "immune response" as used herein refers to a response elicited in an animal or human. An immune response may refer to cellular immunity (CMI), humoral immunity, or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response, such that resistance to the disease or disorder will be enhanced, and/or the clinical severity of the disease reduced. Such protection will be demonstrated by either a reduction or lack of symptoms normally displayed by an affected host, a quicker recovery time, and/or a lowered antigen (e.g., IL-31) titer in the affected host.

The term "protecting" as used herein means conferring a therapeutic immunological response to a host mammal, such that resistance to a disease or disorder will be enhanced, and/or the clinical severity of the disease reduced in the host mammal.

As used herein, the term "immunogenicity" means capable of producing an immune response in a host mammal against an antigen or antigens. This immune response forms the basis of the protective immunity elicited by a vaccine against a specific antigen.

As used herein, immunizing, immunization, and the like is the process whereby a mammal is made immune or resistant to a disease, typically by the administration of a vaccine. Vaccines stimulate the mammal's own immune system to protect the mammal against subsequent disease.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right, and are believed to function synergistically.

Epitope, as used herein, refers to the antigenic determinant recognized by the CDRs of the antibody. In other words, epitope refers to that portion of any molecule capable of being recognized by, and bound by, an antibody. Unless indicated otherwise, the term "epitope" as used herein, refers to the region of IL-31 to which an anti-IL-31 agent is reactive to.

An "antigen" is a molecule or a portion of a molecule capable of being bound by an antibody which is additionally capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics. Epitopes are the antigenic determinant on a protein that is recognized by the immune system. The components of the immune system recognizing epitopes are antibodies, T-cells, and B-cells. T-cell epitopes are displayed on the surface of antigen-presenting cells (APCs) and are typically 8-11 (MHC class I) or 15 plus (MHC class II) amino acids in length. Recognition of the displayed MHC-peptide complex by T-cells is critical to their activation. These mechanisms allow for the appropriate recognition of self versus "non-self" proteins such as bacteria and viruses. Independent amino acid residues that are not necessarily contiguous contribute to interactions with the APC binding cleft and subsequent recognition by the T-Cell receptor (Janeway, Travers, Walport, Immunobiology: The Immune System in Health and Disease. 5th edition New York: Garland Science; 2001). Epitopes that are recognized by soluble antibodies and cell surface associated B-cell receptors vary greatly in length and degree of continuity (Sivalingam and Shepherd, Immunol. 2012 July; 51(3-4):304-309 9). Again even linear epitopes or epitopes found in a continuous stretch of protein sequence will often have discontiguous amino acids that represent the key points of contact with the antibody paratopes or B-cell receptor. Epitopes recognized by antibodies and B-cells can be conformational with amino acids comprising a common area of contact on the protein in three dimensional space and are dependent on tertiary and quaternary structural features of the protein. These residues are often found in spatially distinct areas of the primary amino acid sequence.

A "mimotope" as used herein is a linear or constrained peptide which mimics an antigen's epitope. A mimotope may have a primary amino acid sequence capable of eliciting a T-cell effector response and/or a three dimensional structure necessary to bind B-cells resulting in maturation of an acquired immunological response in an animal. An antibody for a given epitope antigen will recognize a mimotope which mimics that epitope. An IL-31 mimotope may alternatively be referred to herein as an IL-31 peptide mimotope. In some embodiments, a mimotope (linear or constrained) for use in the compositions and/or methods of the present invention is and/or comprises as part thereof a peptide which is from about 5 amino acid residues to about 40 amino acid residues in length.

The term "specifically" in the context of antibody binding, refers to high avidity and/or high affinity binding of an antibody to a specific antigen, i.e., a polypeptide, or epitope. In many embodiments, the specific antigen is an antigen (or a fragment or subfraction of an antigen) used to immunize the animal host from which the antibody-producing cells were isolated.

Antibody specifically binding an antigen is stronger than binding of the same antibody to other antigens. Antibodies which bind specifically to a polypeptide may be capable of binding other polypeptides at a weak, yet detectable level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_D$ of $10^{-7}$M or less, e.g., $10^{-8}$M or less (e.g., $10^{-9}$M or less, $10^{-10}$ or less, $10^{-11}$ or less, $10^{-12}$ or less, or $10^{-13}$ or less, etc.).

As used herein, the term "antibody" refers to an intact immunoglobulin having two light and two heavy chains. Thus a single isolated antibody or fragment may be a polyclonal antibody, a monoclonal antibody, a synthetic antibody, a recombinant antibody, a chimeric antibody, a heterochimeric antibody, a caninized antibody, a felinized antibody, a fully canine antibody, a fully feline antibody, a fully equine antibody, or a fully human antibody. The term "antibody" preferably refers to monoclonal antibodies and fragments thereof (e.g., including but not limited to, antigen-binding portions of the antibody), and immunologic binding equivalents thereof that can bind to the IL-31 protein and fragments or modified fragments thereof. Such fragments and modified fragments of IL-31 can include the IL-31 peptide mimotopes employed in the various embodiments of this invention. For example, an antibody for a given epitope on IL-31 will recognize an IL-31 peptide mimotope which mimics that epitope. The term antibody is used both to refer to a homogeneous molecular, or a mixture such as a serum product made up of a plurality of different molecular entities.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "antibody fragment" refers to less than an intact antibody structure, including, without limitation, an isolated single antibody chain, an Fv construct, a Fab construct, an Fc construct, a light chain variable or complementarity determining region (CDR) sequence, etc. For example, an antibody fragment can comprise the antigen-binding portion of the antibody.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise multiple FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term “hypervariable region” when used herein refers to the amino acid residues of an antibody which are responsible for antigen binding. The hypervariable region comprises amino acid residues from a “complementarity determining region” or “CDR” (Kabat, et al. (1991), above) and/or those residues from a “hypervariable loop” (Chothia and Lesk J. Mol. Biol. 196:901-917 (1987). “Framework” or “FR” residues are those variable domain residues other than the hypervariable region residues as herein defined.

Papain digestion of antibodies produces two identical antigen-binding fragments, called “Fab” fragments, each with a single antigen-binding site, and a residual “Fc” fragment, whose name reflects its ability to crystallize readily. Pepsin treatment yields an F(ab')2 fragment that has two antigen-combining sites and is still capable of cross-linking antigen.

“Fv” is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The “light chains” of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2 (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

“Monoclonal antibody” as defined herein is an antibody produced by a single clone of cells (e.g., a single clone of hybridoma cells) and therefore a single pure homogeneous type of antibody. All monoclonal antibodies produced from the same clone are identical and have the same antigen specificity. The term “monoclonal” pertains to a single clone of cells, a single cell, and the progeny of that cell.

“Fully canine antibody” as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto canine constant domains (heavy chain and light chain kappa or lambda constant) results in the generation of recombinant fully canine antibodies. All fully canine monoclonal antibodies produced from the same clone are identical and have the same antigen specificity. The term “monoclonal” pertains to a single clone of cells, a single cell, and the progeny of that cell.

“Fully feline antibody” as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto feline constant domains (heavy chain and light chain kappa or lambda constant) results in the generation of recombinant fully feline antibodies. All fully feline monoclonal antibodies produced from the same clone are identical and have the same antigen specificity. The term “monoclonal” pertains to a single clone of cells, a single cell, and the progeny of that cell.

“Fully equine antibody” as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto equine constant domains (heavy chain and light chain kappa or lambda constant) results in the generation of recombinant fully equine antibodies. All fully equine monoclonal antibodies produced from the same clone are identical and have the same antigen specificity. The term “monoclonal” pertains to a single clone of cells, a single cell, and the progeny of that cell.

“Fully human antibody” as defined herein is a monoclonal antibody produced by a clone of cells (typically a CHO cell line) and therefore a single pure homogeneous type of antibody.

Antibodies identified from single B cells of immunized mammals, such as dogs are created as recombinant IgG proteins following identification of their variable domain sequences. Grafting of these variable domains onto human constant domains (heavy chain and light chain kappa or lambda constant) results in the generation of recombinant fully human antibodies. All fully human monoclonal antibodies produced from the same clone are identical and have the same antigen specificity. The term “monoclonal” pertains to a single clone of cells, a single cell, and the progeny of that cell.

The monoclonal antibodies herein specifically include “chimeric” antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. In one embodiment of a chimeric mouse: canine IgG, the antigen binding site is derived from mouse while the $F_C$ portion is canine.

"Caninized" forms of non-canine (e.g., murine) antibodies are genetically engineered antibodies that contain minimal sequence derived from non-canine immunoglobulin. Caninized antibodies are canine immunoglobulin sequences (recipient antibody) in which hypervariable region residues of the recipient are replaced by hypervariable region residues from a non-canine species (donor antibody) such as mouse having the desired specificity, affinity, and capacity. In some instances, framework region (FR) residues of the canine immunoglobulin sequences are replaced by corresponding non-canine residues. Furthermore, caninized antibodies may include residues that are not found in the recipient antibody or in the donor antibody. These modifications are made to further refine antibody performance. In general, the caninized antibody will include substantially all of at least one, and typically two, variable domains, in which all or substantially all of the hypervariable regions correspond to those of a non-canine immunoglobulin sequence and all or substantially all of the FRs are those of a canine immunoglobulin sequence. The caninized antibody optionally also will comprise a complete, or at least a portion of an immunoglobulin constant region (Fc), typically that of a canine immunoglobulin sequence. In one embodiment of speciation or caninization of a mouse IgG, mouse CDRs are grafted onto canine frameworks.

"Felinized" forms of non-feline (e.g., murine) antibodies are genetically engineered antibodies that contain minimal sequence derived from non-feline immunoglobulin. Felinized antibodies are feline immunoglobulin sequences (recipient antibody) in which hypervariable region residues of the recipient are replaced by hypervariable region residues from a non-feline species (donor antibody) such as mouse having the desired specificity, affinity, and capacity. In some instances, framework region (FR) residues of the feline immunoglobulin sequences are replaced by corresponding non-feline residues. Furthermore, felinized antibodies may include residues that are not found in the recipient antibody or in the donor antibody. These modifications are made to further refine antibody performance. In general, the felinized antibody will include substantially all of at least one, and typically two, variable domains, in which all or substantially all of the hypervariable regions correspond to those of a non-feline immunoglobulin sequence and all or substantially all of the FRs are those of a feline immunoglobulin sequence. The felinized antibody optionally also will comprise a complete, or at least a portion of an immunoglobulin constant region (Fc), typically that of a feline immunoglobulin sequence.

"Equinized" forms of non-equine (e.g., murine) antibodies are genetically engineered antibodies that contain minimal sequence derived from non-equine immunoglobulin. Equinized antibodies are equine immunoglobulin sequences (recipient antibody) in which hypervariable region residues of the recipient are replaced by hypervariable region residues from a non-equine species (donor antibody) such as mouse having the desired specificity, affinity, and capacity. In some instances, framework region (FR) residues of the equine immunoglobulin sequences are replaced by corresponding non-equine residues. Furthermore, equinized antibodies may include residues that are not found in the recipient antibody or in the donor antibody. These modifications are made to further refine antibody performance. In general, the equinized antibody will include substantially all of at least one, and typically two, variable domains, in which all or substantially all of the hypervariable regions correspond to those of a non-equine immunoglobulin sequence and all or substantially all of the FRs are those of an equine immunoglobulin sequence. The equinized antibody optionally also will comprise a complete, or at least a portion of an immunoglobulin constant region (Fc), typically that of an equine immunoglobulin sequence.

"Humanized" forms of non-human (e.g., murine) antibodies are genetically engineered antibodies that contain minimal sequence derived from non-human immunoglobulin. Humanized antibodies are human immunoglobulin sequences (recipient antibody) in which hypervariable region residues of the recipient are replaced by hypervariable region residues from a non-human species (donor antibody) such as mouse having the desired specificity, affinity, and capacity. In some instances, framework region (FR) residues of the human immunoglobulin sequences are replaced by corresponding non-human residues. Furthermore, humanized antibodies may include residues that are not found in the recipient antibody or in the donor antibody. These modifications are made to further refine antibody performance. In general, the humanized antibody will include substantially all of at least one, and typically two, variable domains, in which all or substantially all of the hypervariable regions correspond to those of a non-human immunoglobulin sequence and all or substantially all of the FRs are those of an human immunoglobulin sequence. The humanized antibody optionally also will comprise a complete, or at least a portion of an immunoglobulin constant region (Fc), typically that of an human immunoglobulin sequence.

"Fully Canine" antibodies are genetically engineered antibodies that contain no sequence derived from non-canine immunoglobulin. Fully canine antibodies are canine immunoglobulin sequences (recipient antibody) in which hypervariable region residues are derived from a naturally occurring canine antibody (donor antibody) having the desired specificity, affinity, and capacity. In some instances, framework region (FR) residues of the canine immunoglobulin sequences are replaced by corresponding non-canine residues. Furthermore, fully canine antibodies may include residues that are not found in the recipient antibody or in the donor antibody, such as including, but not limited to changes in the CDRs to modify affinity. These modifications are made to further refine antibody performance. In general, the fully canine antibody will include substantially all of at least one, and typically two, variable domains, in which all or substantially all of the hypervariable regions correspond to those of a canine immunoglobulin sequence and all or substantially all of the FRs are those of an canine immunoglobulin sequence. The fully canine antibody optionally also will comprise a complete, or at least a portion of an immunoglobulin constant region (Fc), typically that of canine immunoglobulin sequence.

"Fully Feline" antibodies are genetically engineered antibodies that contain no sequence derived from non-feline immunoglobulin. Fully feline antibodies are feline immunoglobulin sequences (recipient antibody) in which hypervariable region residues are derived from a naturally occurring feline antibody (donor antibody) having the desired specificity, affinity, and capacity. In some instances, framework region (FR) residues of the feline immunoglobulin sequences are replaced by corresponding non-feline residues. Furthermore, fully feline antibodies may include residues that are not found in the recipient antibody or in the donor antibody, such as including, but not limited to changes in the CDRs to modify affinity. These modifications are made to further refine antibody performance. In general, the fully feline antibody will include substantially all of at least one, and typically two, variable domains, in which all or substantially all of the hypervariable regions correspond to those of a feline immunoglobulin sequence and all or substantially all of the FRs are those of an feline immunoglobulin sequence. The fully feline antibody optionally also will comprise a complete, or at least a portion of an immunoglobulin constant region (Fc), typically that of feline immunoglobulin sequence.

"Fully Equine" antibodies are genetically engineered antibodies that contain no sequence derived from non-equine immunoglobulin. Fully equine antibodies are equine immunoglobulin sequences (recipient antibody) in which hypervariable region residues are derived from a naturally occurring equine antibody (donor antibody) having the desired specificity, affinity, and capacity. In some instances, framework region (FR) residues of the equine immunoglobulin sequences are replaced by corresponding non-equine residues. Furthermore, fully equine antibodies may include residues that are not found in the recipient antibody or in the donor antibody, such as including, but not limited to changes in the CDRs to modify affinity. These modifications are made to further refine antibody performance. In general, the fully equine antibody will include substantially all of at least one, and typically two, variable domains, in which all or substantially all of the hypervariable regions correspond to those of a equine immunoglobulin sequence and all or substantially all of the FRs are those of an equine immunoglobulin sequence. The fully equine antibody optionally also will comprise a complete, or at least a portion of an immunoglobulin constant region (Fc), typically that of equine immunoglobulin sequence.

"Fully Human" antibodies are genetically engineered antibodies that contain no sequence derived from non-human immunoglobulin. Fully human antibodies are human immunoglobulin sequences (recipient antibody) in which hypervariable region residues are derived from a naturally occurring human antibody (donor antibody) having the desired specificity, affinity, and capacity. In some instances, framework region (FR) residues of the human immunoglobulin sequences are replaced by corresponding non-human residues. Furthermore, fully human antibodies may include residues that are not found in the recipient antibody or in the donor antibody, such as including, but not limited to changes in the CDRs to modify affinity. These modifications are made to further refine antibody performance. In general, the fully human antibody will include substantially all of at least one, and typically two, variable domains, in which all or substantially all of the hypervariable regions correspond to those of a human immunoglobulin sequence and all or substantially all of the FRs are those of a human immunoglobulin sequence. The fully human antibody optionally also will comprise a complete, or at least a portion of an immunoglobulin constant region (Fc), typically that of human immunoglobulin sequence.

The term "heterochimeric" as defined herein, refers to an antibody in which one of the antibody chains (heavy or light) is, for example, caninized, felinized, equinized, or humanized while the other is chimeric. In one embodiment, a felinized variable heavy chain (where all of the CDRs are mouse and all FRs are feline) is paired with a chimeric variable light chain (where all of the CDRs are mouse and all FRs are mouse. In this embodiment, both the variable heavy and variable light chains are fused to a feline constant region.

The term "variant" as used herein refers to a peptide, polypeptide or a nucleic acid sequence encoding a peptide or polypeptide, that has one or more conservative amino acid variations or other minor modifications such that the corresponding peptide or polypeptide has substantially equivalent function when compared to the wild-type peptide or polypeptide. Ordinarily, variant peptide mimotopes for use in the present invention will have at least 30% identity to the parent mimotope, more preferably at least 50%, more preferably at least 75%, more preferably at least 80%, more preferably at least 85%, more preferably at least 90%, and most preferably at least 95% sequence identity to the parent mimotope.

A "variant" anti-IL-31 antibody, refers herein to a molecule which differs in amino acid sequence from a "parent" anti-IL-31 antibody amino acid sequence by virtue of addition, deletion, and/or substitution of one or more amino acid residue(s) in the parent antibody sequence and retains at least one desired activity of the parent anti-IL-31-antibody. Desired activities can include the ability to bind the antigen specifically, the ability to reduce, inhibit or neutralize IL-31 activity in an animal, and the ability to inhibit IL-31-mediated pSTAT signaling in a cell-based assay. In one embodiment, the variant comprises one or more amino acid substitution(s) in one or more hypervariable and/or framework region(s) of the parent antibody. For example, the variant may comprise at least one, e.g. from about one to about ten, and preferably from about two to about five, substitutions in one or more hypervariable and/or framework regions of the parent antibody.

Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind an IL-31 and preferably has desired activities which are superior to those of the parent antibody. For example, the variant may have a stronger binding affinity, enhanced ability to reduce, inhibit or neutralize IL-31 activity in an animal, and/or enhanced ability to inhibit IL-31-mediated pSTAT signaling in a cell-based assay.

A "variant" nucleic acid refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The "parent" antibody herein is one that is encoded by an amino acid sequence used for the preparation of the variant. In one embodiment, the parent antibody has a canine framework region and, if present, has canine antibody constant region(s). For example, the parent antibody may be a caninized or canine antibody. As another example, the parent antibody may be a felinized or feline antibody. As yet another example, the parent antibody may be an equinized or equine antibody. In another example, the parent antibody may be a humanized or human antibody. In a still further example, the parent antibody is a murine monoclonal antibody.

The term "antigen binding region", "antigen-binding portion", and the like as used throughout the specification and claims refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. The antigen-binding portion of an antibody according to the present invention may alternatively be referred to herein as an IL-31-specific peptide or polypeptide or as an anti-IL-31 peptide or polypeptide, for example.

The term "isolated" means that the material (e.g., antibody or nucleic acid) is separated and/or recovered from a component of its natural environment. Contaminant components of its natural environment are materials that would interfere with diagnostic or therapeutic uses for the material, and may include enzymes, hormones, and other proteinaceous or nonproteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

The word "label" when used herein refers to a detectable compound or composition that is conjugated directly or indirectly to the antibody, nucleic acid, or mimotope, for example. The label may itself be detectable by itself (e.g., radioisotope labels or fluorescent labels) or, in the case of an enzymatic label, may catalyze chemical alteration of a substrate compound or composition that is detectable.

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included.

A "subject" or "patient" refers to a mammal in need of treatment that can be affected by molecules of the invention. Mammals that can be treated in accordance with the invention include vertebrates, with mammals such as canine, feline, equine, and human mammals being particularly preferred examples.

A "therapeutically effective amount" (or "effective amount") refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with treatment of an IL-31 mediated disorder, such as a pruritic condition or an allergic condition, or tumor progression, including clinical improvement in symptoms. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

"Treatment", "treating", and the like refers to both therapeutic treatment and prophylactic or preventative measures. Animals in need of treatment include those already with the disorder as well as those in which the disorder is to be prevented. The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "allergic condition" is defined herein as a disorder or disease caused by an interaction between the immune system and a substance foreign to the body. This foreign substance is termed "an allergen". Common allergens include aeroallergens, such as pollens, dust, molds, dust mite proteins, injected saliva from insect bites, etc. Examples of allergic conditions include, but are not limited to, the following: allergic dermatitis, summer eczema, urticaria, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

The term "pruritic condition" is defined herein as a disease or disorder characterized by an intense itching sensation that produces the urge to rub or scratch the skin to obtain relief. Examples of pruritic conditions include, but are not limited to the following: atopic dermatitis, allergic dermatitis, eczema, psoriasis, scleroderma, and pruritus.

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

A "composition" is intended to mean a combination of active agent and another compound or composition which can be inert (e.g., a label), or active, such as an adjuvant.

As used herein, the terms "pharmaceutically acceptable carrier" and "pharmaceutically acceptable vehicle" are interchangeable, and refer to a fluid vehicle for containing vaccine antigens that can be injected into a host without adverse effects. Pharmaceutically acceptable carriers suitable for use in the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-HCl, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be any one that occurs within one of the following six groups 1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gln; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gln (Asn); Glu (Asp); Gly (Pro); His (Asn; Gln); Ile (Leu; Val); Leu (Ile; Val); Lys (Arg; Gln; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

DETAILED DESCRIPTION OF THE INVENTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the vaccine compositions and antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification, See e.g., Sambrook et al. MOLECULAR CLONING: LAB. MANUAL (3rd ed., Cold Spring Harbor Lab. Press, Cold Spring Harbor, N.Y., 2001) and Ausubel et al. Current Protocols in Molecular Biology (New York: Greene Publishing Association/Wiley Interscience), 1993. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

Compositions

The present invention provides for IL-31 mimotopes (peptides) and variants thereof and their uses in clinical and scientific procedures, including diagnostic procedures. As used herein, such an IL-31 mimotope is a linear or constrained peptide which mimics an antigen's epitope. An anti-IL-31 antibody for a given IL-31 epitope antigen will recognize an IL-31 mimotope which mimics that epitope.

IL-31 mimotopes (peptides) are employed in vaccine compositions according to the present invention. Such vaccine compositions are useful for protecting a mammal against an IL-31 mediated disorder, such as a pruritic or allergic condition. In some embodiments, the IL-31-mediated pruritic or allergic condition is a pruritic condition selected from atopic dermatitis, eczema, psoriasis, scleroderma, and pruritus. In other embodiments, the IL-31-mediated pruritic or allergic condition is an allergic condition selected from allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity. In other embodiments, the IL-31 mediated disorder is tumor progression. In some embodiments, the IL-31 mediated disorder is eosinophilic disease or mastocytomas.

In one embodiment, a vaccine composition according to the present invention includes the combination of a carrier polypeptide and at least one mimotope selected from a feline IL-31 mimotope, a canine IL-31 mimotope, a horse IL-31 mimotope, and a human IL-31 mimotope; and an adjuvant. In some embodiments, the vaccine compositions of this invention can include more than one IL-31 mimotope from a given species, or even a combination of IL-31 mimotopes from different species. In some embodiments, a mimotope (linear or constrained) for use in the compositions and/or methods of the present invention is and/or comprises as part thereof a peptide which is from about 5 amino acid residues to about 40 amino acid residues in length.

In one embodiment, the at least one mimotope employed in the compositions and methods of the instant invention is selected from an IL-31 15H05 mimotope, an IL-31 helix BC region mimotope, an IL-31 helix A region mimotope, an IL-31 AB loop region mimotope, or any combination thereof.

In one embodiment, the at least one mimotope for use in the compositions and methods of the instant invention generates antibodies that are neutralizing the bioactivity of IL-31.

In another embodiment, the vaccine compositions of this invention are capable of eliciting a focused immune response to generate antibodies in the mammal directed to at least one neutralizing epitope on IL-31, but not against non-neutralizing epitopes on IL-31.

In one embodiment, the vaccine composition includes a canine IL-31 mimotope which is and/or includes as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment, the vaccine composition includes a feline IL-31 mimotope which is and/or includes as part thereof the amino acid sequence SMPADNFERKNF (SEQ ID NO: 188), NGSAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In yet another embodiment, the vaccine composition includes an equine IL-31 mimotope which is and/or includes as part thereof the amino acid sequence SMPTDNFERKRF (SEQ ID NO: 189), NSSAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In a still further embodiment, the vaccine composition includes a human IL-31 mimotope which is and/or includes as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In one embodiment, the mimotope employed in the vaccine compositions according to the present invention is a constrained mimotope. In one embodiment, such a constrained mimotope is a chemically-linked cyclic peptide.

Linear IL-31 mimotopes can be chemically synthesized or recombinantly produced. Constrained IL-31 mimotopes such as a chemically-linked cyclic peptide can be chemically synthesized or can be made using a combination of chemical synthesis and recombinant technology. In some embodiments, the IL-31 mimetope employed in the vaccine composition is chemically conjugated to a carrier polypeptide. In other embodiments, the carrier polypeptide and the mimotope are part of a recombinant fusion protein.

The carrier polypeptide which is combined with the IL-31 mimotope can be or can include as part thereof a bacterial toxoid or a derivative thereof, keyhole limpet hemocyanin (KLH), or a virus-like particle. By way of non-limiting examples, the bacterial toxoid or derivative can be a tetanus toxoid, a diphtheria toxoid, a tetanus toxoid, the outer membrane protein complex from group B *N. meningitidis, Pseudomonas* exotoxin, or the nontoxic mutant of diphtheria toxin (CRM197). By way of other non-limiting examples, the virus-like particle can be HBsAg, HBcAg, *E. coli* bacteriophage Qbeta, Norwalk virus, canine distemper virus (CDV), or influenza HA. In one preferred embodiment, the IL-31 mimotope is in a combination with a carrier polypeptide which includes or consists of CRM197.

The vaccine compositions according to the present invention include at least one adjuvant or adjuvant formulation, as will be described in further detail below.

Vaccines of the present invention can be formulated following accepted convention to include pharmaceutically acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, *Corynebacterium parvum, Bacillus* Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant (N,N-dioctadecyl-N',N'-bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution.

"Immunomodulators" that can be included in the vaccine include, e.g., immunostimulatory oligonucleotides, one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

In one embodiment, the adjuvant is a formulation comprising a saponin, a sterol, a quaternary ammonium compound, and a polymer. In a specific embodiment, the saponin is Quil A or a purified fraction thereof, the sterol is cholesterol, the quaternary ammonium compound is dimethyl dioctadecyl ammonium bromide (DDA), and the polymer is polyacrylic acid.

In another embodiment, the adjuvant comprises the combination of one or more isolated immunostimulatory oligonucleotides, a sterol, and a saponin. In a specific embodiment, the one or more isolated immunostimulatory oligonucleotides comprises CpG, the sterol is cholesterol, and the saponin is Quil A or a purified fraction thereof. As used herein, the ZA-01 adjuvant referred to in the example section includes Quil A (saponin), cholesterol, CpG, and diluent.

In another embodiment, a useful adjuvant to be employed in the compositions of this invention includes CpG-containing immunostimulatory oligonucleotides. CpG-containing oligonucleotides are described for example in U.S. Pat. No. 8,580,280. In one specific embodiment, an adjuvant for use in the present invention is a mixture including at least one glycolipid adjuvant and CpG-containing oligonucleotides. A specific example of a useful adjuvant is a mixture that includes the glycolipid adjuvant Bay R1005 (N-(2-Deoxy-2-L-leucylamino-β-D-glucopyranosyl)-N-octadecyldodecanoylamidehydroacetate) as well as CpG oligonucleotides.

In one embodiment, the adjuvant or adjuvant mixture is added in an amount of about 100 μg to about 10 mg per dose. In another embodiment, the adjuvant/adjuvant mixture is added in an amount of about 200 μg to about 5 mg per dose. In yet another embodiment, the adjuvant/adjuvant mixture is added in an amount of about 300 μg to about 1 mg/dose.

With the advent of methods of molecular biology and recombinant technology, it is possible to produce the aforementioned peptides and polypeptides by recombinant means and thereby generate gene sequences that code for specific amino acid sequences found in the peptide or polypeptide structure. In one embodiment, the peptide is the IL-31 mimotope or is at least part of the IL-31 mimotope. In another embodiment, the polypeptide is the carrier polypeptide which is present in combination with the IL-31 mimotope. In a still further embodiment, the polypeptide is an antibody, such as that to which the IL-31 mimotope employed in the vaccine composition or diagnostic methods of this invention binds. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, or how they are recombinantly-constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

The "antigen binding region", or "antigen-binding portion" of an antibody refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. The antigen-binding portion of an antibody referred to in the specification and claims may be referred to herein as an IL-31-specific peptide or polypeptide or as an anti-IL-31 peptide or polypeptide, for example.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope).

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies referred to herein are meant to include both intact immunoglobulin molecules as well as portions, fragments, peptides and derivatives thereof such as, for example, Fab, Fab', $F(ab')_2$, Fv, Fse, CDR regions, paratopes, or any portion (e.g., a polypeptide) or peptide sequence of the antibody that is capable of binding an antigen or epitope. An antibody is said to be "capable of binding" a molecule if it is capable of specifically reacting with the molecule to thereby bind the molecule to the antibody.

The antibodies referred to herein also include chimeric antibodies, heterochimeric antibodies, caninized antibodies, felinized antibodies, equinized antibodies, humanized antibodies, fully canine antibodies, fully feline antibodies, fully equine antibodies, fully human antibodies, as well as fragments, portions, regions, peptides or derivatives thereof, provided by any known technique, such as, but not limited to, enzymatic cleavage, peptide synthesis, or recombinant techniques. Such antibodies referred to herein are capable of specifically binding at least one of canine IL-31, feline IL-31, equine IL-31, or human IL-31. Antibody fragments or portions may lack the Fc fragment of intact antibody, clear more rapidly from the circulation, and may have less non-specific tissue binding than an intact antibody. Examples of antibody fragments may be produced from intact antibodies using methods well known in the art, for example by proteolytic cleavage with enzymes such as papain (to produce Fab fragments) or pepsin (to produce $F(ab')_2$ fragments). See, e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

Clones 15H05, ZIL1, ZIL8, ZIL9, ZIL11, ZIL69, ZIL94, ZIL154, ZIL159 and ZIL171 Nucleotide and Amino Acid Sequences In some embodiments, the present invention provides for IL-31 mimotopes which bind to novel monoclonal antibodies that specifically bind to at least one of canine IL-31, feline IL-31, or equine IL-31. Such monoclonal antibodies may be employed in the diagnostic methods of this invention together with the IL-31 mimotope. In one embodiment, a monoclonal antibody referred to in the specification and claims binds to canine IL-31, feline IL-31, or equine IL-31 and prevents its binding to, and activation of, its co-receptor complex comprising IL-31 receptor A (IL-31Ra) and Oncostatin-M-specific receptor (OsmR or IL-31 Rb). Examples of such monoclonal antibodies are identified herein as "15H05", "ZIL1", "ZIL8", "ZIL9", "ZIL11", "ZIL69", "ZIL94", "ZIL154", "ZIL159" and "ZIL171", which refers to the number assigned to its clone. Herein, "15H05", "ZIL1", "ZIL8", "ZIL9", "ZIL11", "ZIL69", "ZIL94", "ZIL154", "ZIL159" and "ZIL171" also refers to the portion of the monoclonal antibody, the paratope or CDRs, that bind specifically with an IL-31 epitope identified as 15H05, ZIL1, ZIL8, ZIL9, ZIL11, ZIL69, ZIL94, ZIL154, ZIL159 and ZIL171 because of its ability to bind the 15H05, ZIL1, ZIL8, ZIL9, ZIL11, ZIL69, ZIL94, ZIL154, ZIL159 and ZIL171 antibodies, respectively. The several recombinant, chimeric, heterochimeric, caninized, felinized, equinized, fully canine, fully feline, and/or fully equine forms of 15H05, ZIL1, ZIL8, ZIL9, ZIL11, ZIL69, ZIL94, ZIL154, ZIL159 and ZIL171 described herein may be referred to by the same name.

In one embodiment, a vaccine composition according to the present invention includes a mimotope which binds to an anti-IL31 antibody or antigen-binding portion thereof that specifically binds to a region on a mammalian IL-31 protein involved with interaction of the IL-31 protein with its co-receptor. In one embodiment, the binding of said antibody to said region is impacted by mutations in a 15H05 epitope binding region selected from: a) a region between about amino acid residues 124 and 135 of a feline IL-31 sequence represented by SEQ ID NO: 157 (Feline_IL31_wildtype); b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31). In one embodiment, the mimotope for use in the compositions of the present invention binds to an anti-IL-31 antibody or antigen-binding portion thereof that specifically binds to the aforementioned 15H05 epitope region.

In one particular embodiment of a vaccine composition according to this invention, the mimotope binds to an anti-IL-31 antibody or antigen-binding portion thereof which includes at least one of the following combinations of complementary determining region (CDR) sequences:

1) antibody 15H05: variable heavy (VH)-CDR1 of SYTIH (SEQ ID NO: 1), VH-CDR2 of NINPTSGYTENNQRFKD (SEQ ID NO: 2), VH-CDR3 of WGFKYDGEWSFDV (SEQ ID NO: 3), variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);

2) antibody ZIL1: variable heavy (VH)-CDR1 of SYGMS (SEQ ID NO: 13), VH-CDR2 of HINSGGSSTYYADAVKG (SEQ ID NO:14), VH-CDR3 of VYTTLAAFWTDNFDY (SEQ ID NO: 15), variable light (VL)-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);

3) antibody ZIL8: VH-CDR1 of DYAMS (SEQ ID NO: 19), VH-CDR2 of GIDSVGSGTSYADAVKG (SEQ ID NO: 20), VH-CDR3 of GFPGSFEH (SEQ ID NO: 21), VL-CDR1 of TGSSSNIGSGYVG (SEQ ID NO: 22), VL-CDR2 of YNSDRPS (SEQ ID NO: 23), VL-CDR3 of SVYDRTFNAV (SEQ ID NO: 24);

4) antibody ZIL9: VH-CDR1 of SYDMT (SEQ ID NO: 25), VH-CDR2 of DVNSGGTGTAYAVAVKG (SEQ ID NO: 26), VH-CDR3 of LGVRDGLSV (SEQ ID NO: 27), VL-CDR1 of SGESLNEYYTQ (SEQ ID NO: 28), VL-CDR2 of RDTERPS (SEQ ID NO: 29), VL-CDR3 of ESAVDTGTLV (SEQ ID NO: 30);

5) antibody ZIL11: VH-CDR1 of TYVMN (SEQ ID NO: 31), VH-CDR2 of SINGGGSSPTYADAVRG (SEQ ID NO: 32), VH-CDR3 of SMVGPFDY (SEQ ID NO: 33), VL-CDR1 of SGESLSNYYAQ (SEQ ID NO: 34), VL-CDR2 of KDTERPS (SEQ ID NO: 35), VL-CDR3 of ESAVSSDTIV (SEQ ID NO: 36);

6) antibody ZIL69: VH-CDR1 of SYAMK (SEQ ID NO: 37), VH-CDR2 of TINNDGTRTGYADAVRG (SEQ ID NO: 38), VH-CDR3 of GNAESGCTGDHCPPY (SEQ ID NO: 39), VL-CDR1 of SGESLNKYYAQ (SEQ ID NO: 40), VL-CDR2 of KDTERPS (SEQ ID NO: 41), VL-CDR3 of ESAVSSETNV (SEQ ID NO: 42);

7) antibody ZIL94: VH-CDR1 of TYFMS (SEQ ID NO: 43), VH-CDR2 of LISSDGSGTYYADAVKG (SEQ ID NO: 44), VH-CDR3 of FWRAFND (SEQ ID NO: 45), VL-CDR1 of GLNSGSVSTSNYPG (SEQ ID NO: 46), VL-CDR2 of DTGSRPS (SEQ ID NO: 47), VL-CDR3 of SLYTDSDILV (SEQ ID NO: 48);

8) antibody ZIL154: VH-CDR1 of DRGMS (SEQ ID NO: 49), VH-CDR2 of YIRYDGSRTDYADAVEG (SEQ ID NO: 50), VH-CDR3 of WDGSSFDY (SEQ ID NO: 51), VL-CDR1 of KASQSLLHSDGNTYLD (SEQ ID NO: 52), VL-CDR2 of KVSNRDP (SEQ ID NO: 53), VL-CDR3 of MQAIHFPLT (SEQ ID NO: 54);

9) antibody ZIL159: VH-CDR1 of SYVMT (SEQ ID NO: 55), VH-CDR2 of GINSEGSRTAYADAVKG (SEQ ID NO: 56), VH-CDR3 of GDIVATGTSY (SEQ ID NO: 57), VL-CDR1 of SGETLNRFYTQ (SEQ ID NO: 58), VL-CDR2 of KDTERPS (SEQ ID NO: 59), VL-CDR3 of KSAVSIDVGV (SEQ ID NO: 60);

10) antibody ZIL171: VH-CDR1 of TYVMN (SEQ ID NO: 61), VH-CDR2 of SINGGGSSPTYADAVRG (SEQ ID NO: 62), VH-CDR3 of SMVGPFDY (SEQ ID NO: 63), VL-CDR1 of SGKSLSYYYAQ (SEQ ID NO: 64), VL-CDR2 of KDTERPS (SEQ ID NO: 65), VL-CDR3 of ESAVSSDTIV (SEQ ID NO: 66); or 11) a variant of 1) to 10) that differs from respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH or VL CDR1, CDR2, or CDR3.

In one embodiment, the IL-31 mimotope used in the vaccine composition binds to an antibody which specifically binds feline IL-31, wherein the antibody binds to a region between about amino acid residues 125 and 134 of a feline IL-31 sequence represented by SEQ ID NO: 157 (Feline_IL31_wildtype). In some embodiments, such an antibody includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

In some embodiments, the mimotope binds to an antibody characterized in that:

1) antibody ZIL1 includes at least one of the following:

a) a variable light chain comprising CAN-ZIL1_VL:

```
                                          (SEQ ID NO: 77)
QSVLTQPTSVSGSLGQRVTISCSGSTNNIGILAATWYQQLPGKAPKVLVY

SDGNRPSGVPDRFSGSKSGNSATLTITGLQAEDEADYYCQSFDTTLDAYV

FGSGTQLTVL,
```

and b) a variable heavy chain comprising CAN-ZIL1_VH:

```
                                          (SEQ ID NO: 75)
EVQLVESGGDLVKPGGSLRLSCVASGFTFSSYGMSWVRQAPGKGLQWVAH

INSGGSSTYYADAVKGRFTISRDNAKNTLYLQMNSLRAEDTAVYYCVEVY

TTLAAFWTDNFDYWGQGTLVTVSS;
```

2) antibody ZIL8 includes at least one of the following:

a) a variable light chain comprising CAN-ZIL8_VL:

(SEQ ID NO: 81)
QSVLTQPASVSGSLGQKVTISCTGSSSNIGSGYVGWYQQLPGTGPRTLIY
YNSDRPSGVPDRFSGSRSGTTATLTISGLQAEDEADYYCSVYDRTFNAVF
GGGT, and b) a variable heavy chain comprising CAN-ZIL8_VH:

(SEQ ID NO: 79)
EVQLVESGGDLVKPAGSLRLSCVASGFTFSDYAMSWVRQAPGRGLQWVAG
IDSVGSGTSYADAVKGRFTISRDDAKNTLYLQMFNLRAEDTAIYYCASGF
PGSFEHWGQGTLVTVSS;

3) antibody ZIL9 includes at least one of the following:

a) a variable light chain comprising CAN-ZIL9_VL:

(SEQ ID NO: 85)
SSVLTQPPSVSVSLGQTATISCSGESLNEYYTQWFQQKAGQAPVLVIYRD
TERPSGIPDRFSGSSSGNTHTLTISGARAEDEADYYCESAVDTGTLVFGG
GTHLAVL, and b) a variable heavy chain comprising CAN-ZIL9_VH:

(SEQ ID NO: 83)
EVQLVESGGDLVKPPGSLRLSCVASGFTFSSYDMTWVRQAPGKGLQWVAD
VNSGGTGTAYAVAVKGRFTISRDNAKKTLYLQMNSLRAEDTAVYYCAKLG
VRDGLSVWGQGTLVTVSS;

4) antibody ZIL11 includes at least one of the following:

a) a variable light chain comprising CAN-ZIL11_VL:

(SEQ ID NO: 89)
SSVLTQPPSVSVSLGQTATISCSGESLSNYYAQWFQQKAGQAPVLVIYKD
TERPSGIPDRFSGSSSGNTHTLTISGARAEDEADYYCESAVSSDTIVFGG
GT, and b) a variable heavy chain comprising CAN-ZIL11_VH:

(SEQ ID NO: 87)
EVQLVESGGDLVKPAGSLRLSCVASGFTFRTYVMNWVRQAPGKGLQWVAS
INGGGSSPTYADAVRGRFTVSRDNAQNSLFLQMNSLRAEDTAVYFCVVSM
VGPFDYWGQGTLVTVSS;

5) antibody ZIL69 includes at least one of the following:

a) a variable light chain comprising CAN-ZIL69_VL:

(SEQ ID NO: 93)
SSVLTQPPSVSVSLGQTATISCSGESLNKYYAQWFQQKAGQAPVLVIYKD
TERPSGIPDRFSGSSAGNTHTLTISGARAEDEADYYCESAVSSETNVFGS
GTQLTVL, and b) a variable heavy chain comprising CAN-ZIL69_VH:

(SEQ ID NO: 91)
EVQLVESGGDLVKPAGSLRLSCVASGFTFSSYAMKWVRQAPGKGLQWVAT
INNDGTRTGYADAVRGRFTISKDNAKNTLYLQMDSLRADDTAVYYCTKGN
AESGCTGDHCPPYWGQGTLVTVSS;

6) antibody ZIL94 includes at least one of the following:

a) a variable light chain comprising CAN-ZIL94_VL:

(SEQ ID NO: 97)
QTVVIQEPSLSVSPGGTVTLTCGLNSGSVSTSNYPGWYQQTRGRTPRTII
YDTGSRPSGVPNRFSGSISGNKAALTITGAQPEDEADYYCSLYTDSDILV
FGGGTHLTVL, and b) a variable heavy chain comprising CAN-ZIL94_VH:

(SEQ ID NO: 95)
EVQLVDSGGDLVKPGGSLRLSCVASGFTFSTYFMSWVRQAPGRGLQWVAL
ISSDGSGTYYADAVKGRFTISRDNAKNTLYLQMNSLRAEDTAMYYCAIFW
RAFNDWGQGTLVTVSS;

7) antibody ZIL154 includes at least one of the following:

a) a variable light chain comprising CAN-ZIL154_VL:

(SEQ ID NO: 101)
DIVVTQTPLSLSVSPGETASFSCKASQSLLHSDGNTYLDWFRQKPGQSPQ
RLIYKVSNRDPGVPDRFSGSGSGTDFTLRISGVEADDAGLYYCMQAIHFP
LTFGAGTKVELK, and b) a variable heavy chain comprising CAN-ZIL154_VH:

(SEQ ID NO: 99)
EVHLVESGGDLVKPWGSLRLSCVASGFTFSDRGMSWVRQSPGKGLQWVAY
IRYDGSRTDYADAVEGRFTISRDNAKNTLYLQMNSLRAEDTAVYYCARWD
GSSFDYWGQGTLVTVSS;

8) antibody ZIL159 includes at least one of the following:

a) a variable light chain comprising CAN-ZIL159_VL:

(SEQ ID NO: 105)
SNVLTQPPSVSVSLGQTATISCSGETLNRFYTQWFQQKAGQAPVLVIYKD
TERPSGIPDRFSGSSSGNIHTLTISGARAEDEAAYYCKSAVSIDVGVFGG
GTHLTVF, and b) a variable heavy chain comprising CAN-ZIL159_VH:

(SEQ ID NO: 103)
EVQLVESGGDLVKPAGSLRLSCVASGFTFSSYVMTWVRQAPGKGLQWVAG
INSEGSRTAYADAVKGRFTISRDNAKNTLYLQIDSLRAEDTAIYYCATGD
IVATGTSYWGQGTLVTVSS;

and 9) antibody ZIL171 includes at least one of the following:

a) a variable light chain comprising CAN-ZIL171_VL:

(SEQ ID NO: 109)
SSVLTQPPSVSVSLGQTATISCSGKSLSYYYAQWFQQKAGQAPVLVIYKD
TERPSGIPDRFSGSSSGNTHTLTISGARAEDEADYYCESAVSSDTIVFGG
GTHLTVL, and b) a variable heavy chain comprising CAN-ZIL171_VH:

(SEQ ID NO: 107)
EVQLVESGGDLVKPAGSLRLSCVASGFTFRTYVMNWVRQAPGKGLQWVAS
INGGGSSPTYADAVRGRFTVSRDNAQNSLFLQMNSLRAEDTAIYFCVVSM
VGPFDYWGHGTLVTVSS.

A host cell can be used to produce an antibody described above. Such antibodies can be used in the diagnostic procedures described as part of this invention, although the diagnostic procedures are not limited to these particular antibodies.

Nucleotide sequences encoding the variable regions of the light and heavy chains of the anti-IL-31 antibody can be employed to make the anti-IL-31 antibodies described herein. Such nucleotide sequences include, but are not limited to, any nucleotide sequence that encodes the amino acid sequence of the 15H05, ZIL1, ZIL8, ZIL9, ZIL11, ZIL69, ZIL94, ZIL154, ZIL159 or ZIL171 antibodies or IL-31-specific polypeptides or peptides thereof. In addition, in one embodiment, nucleotide sequences encoding the IL-31 mimotopes can be used to recombinantly produce the mimotopes alone or as part of a fusion protein together with the carrier polypeptide. Alternatively, or in addition, the mimotopes can be chemically synthesized.

In some embodiments, an isolated nucleic acid can be employed to make a useful antibody (such as that used in one of the diagnostic methods described herein), wherein the nucleic acid sequence encodes at least one of the following combinations of variable heavy complementary determining region (CDR) sequences:

1) 15H05: variable heavy (VH)-CDR1 of SYTIH (SEQ ID NO: 1), VH-CDR2 of NINPTSGYTENNQRFKD (SEQ ID NO: 2), and VH-CDR3 of WGFKYDGEWSFDV (SEQ ID NO: 3);

2) ZIL1: VH-CDR1 of SYGMS (SEQ ID NO: 13), VH-CDR2 of HINSGGSSTYYADAVKG (SEQ ID NO:14), and VH-CDR3 of VYTTLAAFWTDNFDY (SEQ ID NO: 15);

3) ZIL8: VH-CDR1 of DYAMS (SEQ ID NO: 19), VH-CDR2 of GIDSVGSGTSYADAVKG (SEQ ID NO: 20), and VH-CDR3 of GFPGSFEH (SEQ ID NO: 21);

4) ZIL9: VH-CDR1 of SYDMT (SEQ ID NO: 25), VH-CDR2 of DVNSGGTGTAYAVAVKG (SEQ ID NO: 26), and VH-CDR3 of LGVRDGLSV (SEQ ID NO: 27);

5) ZIL11: VH-CDR1 of TYVMN (SEQ ID NO: 31), VH-CDR2 of SINGGGSSPTYADAVRG (SEQ ID NO: 32), and VH-CDR3 of SMVGPFDY (SEQ ID NO: 33);

6) ZIL69: VH-CDR1 of SYAMK (SEQ ID NO: 37), VH-CDR2 of TINNDGTRTGYADAVRG (SEQ ID NO: 38), and VH-CDR3 of GNAESGCTGDHCPPY (SEQ ID NO: 39);

7) ZIL94: VH-CDR1 of TYFMS (SEQ ID NO: 43), VH-CDR2 of LISSDGSGTYYADAVKG (SEQ ID NO: 44), and VH-CDR3 of FWRAFND (SEQ ID NO: 45)

8) ZIL154: VH-CDR1 of DRGMS (SEQ ID NO: 49), VH-CDR2 of YIRYDGSRTDYADAVEG (SEQ ID NO: 50), and VH-CDR3 of WDGSSFDY (SEQ ID NO: 51);

9) ZIL159: VH-CDR1 of SYVMT (SEQ ID NO: 55), VH-CDR2 of GINSEGSRTAYADAVKG (SEQ ID NO: 56), and VH-CDR3 of GDIVATGTSY (SEQ ID NO: 57);

10) ZIL171: VH-CDR1 of TYVMN (SEQ ID NO: 61), VH-CDR2 of SINGGGSSPTYADAVRG (SEQ ID NO: 62), and VH-CDR3 of SMVGPFDY (SEQ ID NO: 63), or 11) a variant of 1) to 10) that differs from the CDRs of respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH CDR1, CDR2, or CDR3.

In another embodiment, the isolated nucleic acid comprises a nucleic acid sequence encoding at least one of the following combinations of variable light complementary determining region (CDR) sequences:

1) 15H05: variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);

2) ZIL1: VL-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);

3) ZIL8: VL-CDR1 of TGSSSNIGSGYVG (SEQ ID NO: 22), VL-CDR2 of YNSDRPS (SEQ ID NO: 23), and VL-CDR3 of SVYDRTFNAV (SEQ ID NO: 24);

4) ZIL9: VL-CDR1 of SGESLNEYYTQ (SEQ ID NO: 28), VL-CDR2 of RDTERPS (SEQ ID NO: 29), and VL-CDR3 of ESAVDTGTLV (SEQ ID NO: 30);

5) ZIL11: VL-CDR1 of SGESLSNYYAQ (SEQ ID NO: 34), VL-CDR2 of KDTERPS (SEQ ID NO: 35), and VL-CDR3 of ESAVSSDTIV (SEQ ID NO: 36);

6) ZIL69: VL-CDR1 of SGESLNKYYAQ (SEQ ID NO: 40), VL-CDR2 of KDTERPS (SEQ ID NO: 41), and VL-CDR3 of ESAVSSETNV (SEQ ID NO: 42);
7) ZIL94: VL-CDR1 of GLNSGSVSTSNYPG (SEQ ID NO: 46), VL-CDR2 of DTGSRPS (SEQ ID NO: 47), and VL-CDR3 of SLYTDSDILV (SEQ ID NO: 48);
8) ZIL154: VL-CDR1 of KASQSLLHSDGNTYLD (SEQ ID NO: 52), VL-CDR2 of KVSNRDP (SEQ ID NO: 53), and VL-CDR3 of MQAIHFPLT (SEQ ID NO: 54);
9) ZIL159: VL-CDR1 of SGETLNRFYTQ (SEQ ID NO: 58), VL-CDR2 of KDTERPS (SEQ ID NO: 59), and VL-CDR3 of KSAVSIDVGV (SEQ ID NO: 60);
10) ZIL171: VL-CDR1 of SGKSLSYYYAQ (SEQ ID NO: 64), VL-CDR2 of KDTERPS (SEQ ID NO: 65), and VL-CDR3 of ESAVSSDTIV (SEQ ID NO: 66); or
11) a variant of 1) to 10) that differs from the CDRs of respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VL CDR1, CDR2, or CDR3.

In yet another embodiment, the isolated nucleic acid used in the manufacture of an antibody described herein comprises a nucleic acid sequence encoding the above-described variable light complementary determining region (CDR) sequences, as well as the above-described variable heavy CDR sequences of respective parent antibody 15H05, ZIL1, ZIL8, ZIL9, ZIL11, ZIL69, ZIL94, ZIL154, ZIL159, or ZIL171 or variants thereof.

A vector including at least one of the nucleic acids described above can be used in the manufacture of these antibodies. As will be described in further detail below, the nucleic acid sequence encoding at least one of the above-described combinations of variable heavy complementary determining region (CDR) sequences may be contained on the same vector together with the nucleic acid sequence encoding at least one of the above-described combinations of variable light CDR sequences. Alternatively, the nucleic acid sequence encoding at least one of the above-described combinations of variable light CDR sequences and the nucleic acid sequence encoding at least one of the above-described combinations of variable heavy CDR sequences may each be contained on separate vectors.

Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-IL-31 antibody or IL-31-specific portion thereof. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding anti-IL-31 sequences can be identified. It is also intended that the antibody coding regions could also be provided by altering existing antibody genes using standard molecular biological techniques that result in variants (agonists) of the antibodies and peptides described herein. Such variants include, but are not limited to deletions, additions and substitutions in the amino acid sequence of the anti-IL-31 antibodies or IL-31-specific polypeptides or peptides (such as antibody portions or fragments). Also, variants of the peptide mimotopes described herein can be made by altering the nucleotide sequence encoding the parent peptide mimotope.

For example, one class of substitutions is conservative amino acid substitutions. Such substitutions are those that substitute a given amino acid in an anti-IL-31 antibody, or IL-31 specific polypeptide or peptide by another amino acid of like characteristics. Likewise, IL-31 mimotopes which bind to such an antibody or an antigen-binding portion thereof can include conservative substitutions or other types of amino acid substitutions. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-IL-31 antibodies or IL-31-specific polypeptides, or peptides may be fully functional or may lack function in one or more activities. Likewise, variant or agonist IL-31 mimotopes may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W.H. Freeman & Co., NY, 1993). Many detailed reviews are available on this subject, such as by Wold, Posttranslational Covalent Modification of proteins, 1-12 (Johnson, ed., Academic Press, N Y, 1983); Seifter et al. 182 Meth. Enzymol. 626-46 (1990); and Rattan et al. 663 Ann. NY Acad. Sci. 48-62 (1992).

Accordingly, the IL-31-specific antibodies, polypeptides, and peptides described herein, as well as the IL-31 peptide mimotopes described herein also encompass derivatives or analogs in which a substituted amino acid residue is not one encoded by the genetic code.

Similarly, the additions and substitutions in the amino acid sequence as well as variations, and modifications just described may be equally applicable to the amino acid sequence of the IL-31 antigen and/or epitope or peptides thereof, and are thus encompassed by the present invention.

Antibody and Mimotope Derivatives

Included within the scope of this invention are antibody and mimotope derivatives. A "derivative" of an antibody or mimotope contains additional chemical moieties not normally a part of the protein or peptide. Covalent modifications of the protein or peptide are included within the scope of this invention. Such modifications may be introduced into the molecule by reacting targeted amino acid residues of the antibody or mimotope with an organic derivatizing agent that is capable of reacting with selected side chains or terminal residues. For example, derivatization with bifunctional agents, well-known in the art, is useful for cross-linking the antibody or fragment or mimotope to a water-insoluble support matrix or to other macromolecular carriers.

Derivatives also include radioactively labeled monoclonal antibodies or mimotopes. For example, with radioactive iodine, ($^{125}I$, $^{131}I$), carbon ($^{14}C$), sulfur ($^{35}S$), indium ($^{111}In$), tritium ($^{3}H$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins). Likewise, the mimotopes can be labeled in some embodiments.

Another derivative bifunctional antibody is a bispecific antibody, generated by combining parts of two separate antibodies that recognize two different antigenic groups. This may be achieved by crosslinking or recombinant techniques.

Additionally, moieties may be added to the antibody or a portion thereof or to the IL-31 mimotopes described herein to increase half-life in vivo (e.g., by lengthening the time to clearance from the blood stream. Such techniques include, for example, adding PEG moieties (also termed PEGylation), and are well-known in the art. See U.S. Patent. Appl. Pub. No. 20030031671.

Recombinant Expression of Antibodies, Mimotopes, and Carrier Polypeptides

In some embodiments, the nucleic acids encoding a subject monoclonal antibody or a fusion protein containing both the mimotope and the carrier polypeptide are introduced directly into a host cell, and the cell is incubated under conditions sufficient to induce expression of the encoded antibody or fusion protein. After the subject nucleic acids have been introduced into a cell, the cell is typically incubated, normally at 37° C., sometimes under selection, for a period of about 1-24 hours in order to allow for the expression of the antibody or fusion protein carrying the peptide mimotope and carrier polypeptide. In one embodiment, the antibody or fusion protein secreted into the supernatant of the media in which the cell is growing.

Traditionally, monoclonal antibodies have been produced as native molecules in murine hybridoma lines. In addition to that technology, the present invention provides for recombinant DNA expression of monoclonal antibodies. This allows the production of caninized, felinized, equinized, humanized, fully canine, fully feline, fully equine, and fully human antibodies, as well as a spectrum of antibody derivatives and fusion proteins in a host species of choice.

A nucleic acid sequence encoding at least one anti-IL-31 antibody, portion or IL-31-specific polypeptide thereof or a nucleic acid sequence encoding as part thereof at least one IL-31 peptide mimotope which binds to such an antibody or portion thereof may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, N Y, 1982 and 1989), and Ausubel et al. 1993 supra, may be used to construct nucleic acid sequences which encode a monoclonal antibody molecule or antigen binding region thereof, or IL-31 peptide mimotope.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-IL-31 peptides or antibody portions, or as fusion proteins carrying IL-31 mimotopes in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an anti-IL-31 antibody or IL-31-specific polypeptide or peptide, or fusion protein including an IL-31 mimotope, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host;

and whether it is desirable to be able to "shuttle" the vector between host cells of different species.

Example prokaryotic vectors known in the art include plasmids such as those capable of replication in *E. coli* (such as, for example, pBR322, ColE1, pSC101, pACYC 184, .pi.VX). Such plasmids are, for example, disclosed by Maniatis et al., 1989 supra; Ausubel et al, 1993 supra. *Bacillus* plasmids include pC194, pC221, pT127, etc. Such plasmids are disclosed by Gryczan, in THE MOLEC. BIO. OF THE BACILLI 307-329 (Academic Press, N Y, 1982). Suitable *Streptomyces* plasmids include pIJ101 (Kendall et al., 169 J. Bacteriol. 4177-83 (1987)), and *Streptomyces* bacteriophages such as .phi.C31 (Chater et al., in SIXTH INT'L SYMPOSIUM ON ACTINOMYCETALES BIO. 45-54 (Akademiai Kaido, Budapest, Hungary 1986). *Pseudomonas* plasmids are reviewed in John et al., 8 Rev. Infect. Dis. 693-704 (1986); Izaki, 33 Jpn. J. Bacteriol. 729-42 (1978); and Ausubel et al., 1993 supra.

Alternatively, gene expression elements useful for the expression of cDNA encoding anti-IL-31 antibodies or peptides, or fusion proteins as described herein include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 Proc. Natl. Acad. Sci., USA 6777 (1982)), and Moloney murine leukemia virus LTR (Grosschedl et al., 41 Cell 885 (1985)); (b) splice regions and polyadenylation sites such as those derived from the SV40 late region (Okayarea et al., MCB, 3: 280 (1983), and (c) polyadenylation sites such as in SV40 (Okayama et al., 1983, supra).

Immunoglobulin cDNA genes can be expressed as described by Weidle et al., 51(1) Gene 21-29 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499-505 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with an anti-IL-31 peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-IL-31 peptide or chimeric H and L chains, or portions thereof are assembled in separate expression vectors that are then used to co-transfect a recipient cell. Alternatively the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a nucleotide sequence encoding chimeric, caninized, felinized, equinized, humanized, fully canine, fully feline, fully equine, or fully human anti-IL-31 antibody construct sequences or an IL-31-specific polypeptide or peptide (e.g., antigen-binding portion of the antibodies described herein), or an expression vector carrying a nucleotide sequence encoding a fusion protein as described herein, can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538-1541 (1988).

Yeast can provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl Conference on Yeast, Genetics & Molec. Biol. (Montpelier, France, 1982).

Yeast gene expression systems can be routinely evaluated for the levels of production, secretion and the stability of anti-IL-31 peptides, antibody and assembled murine and chimeric, heterochimeric, caninized, felinized, equinized, humanized, fully canine, fully feline, fully equine, or fully human antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.) IRL Press, Oxford, UK 1985).

Bacterial strains can also be utilized as hosts for the production of antibody molecules or peptides, or fusion proteins described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized, felinized, equinized, humanized, fully canine, fully feline, fully equine, or fully human antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, NY (1994-2001); Colligan et al., eds. Current Protocols in Protein Science, John Wiley & Sons, NY, NY (1997-2001).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells.

Many vector systems are available for the expression of cloned anti-IL-31 peptides H and L chain genes in mammalian cells (see Glover, 1985 supra). Different approaches can be followed to obtain complete $H_2L_2$ antibodies. It is possible to co-express H and L chains in the same cells to achieve intracellular association and linkage of H and L chains into complete tetrameric $H_2L_2$ antibodies and/or anti-IL-31 peptides. The co-expression can occur by using either the same or different plasmids in the same host. Genes for both H and L chains and/or anti-IL-31 peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-IL-31 peptides and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical Applications

The vaccine compositions of the present invention can be used for example in the treatment of and/or protection against IL-31-mediated disorders, such as pruritic and/or allergic conditions in mammals, such as dogs, cats, horses, and humans. The pharmaceutical compositions of this invention are useful for parenteral administration, e.g., subcutaneously, intramuscularly or intravenously. Other suitable modes of administration are described herein.

The vaccines of the present invention can be administered either as individual therapeutic agents or in combination with other therapeutic agents. They can be administered alone, but are generally administered with a pharmaceutical carrier selected on the basis of the chosen route of administration and standard pharmaceutical practice.

Administration of the vaccine compositions disclosed herein may be carried out by any suitable means, including parenteral injection (such as intraperitoneal, subcutaneous, or intramuscular injection), orally, or by topical administration of the vaccines to an airway surface. Topical administration to an airway surface can be carried out by intranasal administration (e.g., by use of dropper, swab, or inhaler). Topical administration of the vaccines to an airway surface can also be carried out by inhalation administration, such as by creating respirable particles of a pharmaceutical formulation (including both solid and liquid particles) containing the vaccines as an aerosol suspension, and then causing the subject to inhale the respirable particles. Methods and apparatus for administering respirable particles of pharmaceutical formulations are well known, and any conventional technique can be employed. Oral administration may be, for example, in the form of an ingestable liquid or solid formulation.

In some desired embodiments, the vaccines are administered by parenteral injection. For parenteral administration, the vaccines can be formulated as a solution, suspension, emulsion or lyophilized powder in association with a pharmaceutically acceptable parenteral vehicle. For example the vehicle may be a solution of the combination of the mimotope and the carrier polypeptide (e.g., mimotope conjugate) or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. Also, as described herein, the vaccine compositions of this invention include an adjuvant or adjuvant formulation. The concentration of mimotope conjugate in these vaccine compositions can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The vaccines of this invention can be lyophilized for storage and reconstituted in a suitable carrier prior to use. Any suitable lyophilization and reconstitution techniques can be employed. It will be appreciated by those skilled in the art that lyophilization and reconstitution can lead to varying degrees of activity loss and that use levels may have to be adjusted to compensate.

The compositions containing the present IL-31 mimotopes (e.g., IL-31 mimotope conjugates) or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art.

In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system. A therapeutically effective amount of a vaccine composition according to the invention may be readily determined by one of ordinary skill in the art.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of IL-31-related pathologies in dogs, cats, horses, or humans can be provided as a biweekly or monthly dosage of vaccines of the present invention in the dosage range described above.

Single or multiple administrations of the vaccine compositions can be carried out with dose levels and pattern being selected by the treating veterinarian or physician. In any event, the pharmaceutical formulations should provide a quantity of the vaccine compositions of this invention sufficient to effectively treat the subject.

Diagnostic Applications

The present invention also provides the IL-31 mimotopes and anti-IL-31 antibodies for use in diagnostic methods for detecting IL-31 or anti-IL-31 antibodies in mammalian samples, including, but not limited to, samples from mammals known to be or suspected of having a puritic and/or allergic condition.

For example, the present invention provides a method of determining the identity and/or amount of an anti-IL-31 antibody in a sample. This method includes incubating a sample including an anti-IL-31 antibody with at least one IL-31 mimotope such as a feline IL-31 mimotope, a canine IL-31 mimotope, a horse IL-31 mimotope, or a human IL-31 mimotope; and determining the identity and/or quantity of the anti-IL-31 in the sample.

In one embodiment, the canine IL-31 mimotope employed in the method to determine the identity and/or amount of an anti-IL-31 antibody in the sample is and/or comprises as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment, the feline IL-31 mimotope employed in such a method is and/or comprises as part thereof the amino acid sequence SMPADNFERKNF (SEQ ID NO: 188), NGSAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In a further embodiment, the equine IL-31 mimotope employed in such a method is and/or comprises as part thereof the amino acid sequence SMPTDNFERKRF (SEQ ID NO: 189), NSSAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In a still further, the human IL-31 mimotope employed in such a method is and/or comprises as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In one embodiment of the above-described diagnostic method, the mimotope is a capture reagent bound to a solid surface. In one embodiment, the sample is added to the mimotope capture reagent; and secondary detection reagents are then added to quantify the amount of the antibody in the sample.

The present invention also provides a method of determining the amount of IL-31 in a sample from a mammal. Such a method will have utility for detecting IL-31 from multiple species. Such a method includes incubating a mammalian sample comprising IL-31 with a labeled anti-IL-31 antibody: IL-31 mimotope complex tethered to a solid surface, wherein the mimotope in the complex is selected from the group consisting of a feline IL-31 mimotope, a canine IL-31 mimotope, a horse IL-31 mimotope, and a human IL-31 mimotope; and determining the level of the IL-31 in the sample, wherein the labeled anti-IL-31 antibody in the complex has an affinity to the mimotope in the complex that is lower than its affinity to the IL-31 in the sample. In one embodiment of this method, the determining step comprises measuring the signal coming from labeled antibody which is liberated from the solid surface when the IL-31 in the sample binds to the labeled anti-IL-3 antibody of the complex, the level of IL-31 in the sample being inversely proportional to the signal.

In one embodiment, the canine IL-31 mimotope employed in the method of determining the amount of IL-31 in the sample is and/or comprises as part thereof the amino acid sequence SVPADTFECKSF (SEQ ID NO: 186), SVPADTFERKSF (SEQ ID NO: 187), NSSAILPYFRAIRPLSDKNIIDKIIEQLDKLKF (SEQ ID NO: 192), APTHQLPPSDVRKIILELQPLSRG (SEQ ID NO: 196), TGVPES (SEQ ID NO: 200) or variants thereof that retain anti-IL-31 binding.

In another embodiment, the feline IL-31 mimotope employed in such a method is and/or comprises as part thereof the amino acid sequence SMPADNFERKNF (SEQ ID NO: 188), NGSAILPYFRAIRPLSDKNTIDKIIEQLDKLKF (SEQ ID NO: 193), APAHRLQPSDIRKIILELRPM SKG (SEQ ID NO: 197), IGLPES (SEQ ID NO: 201) or variants thereof that retain anti-IL-31 binding.

In yet another embodiment, the equine IL-31 mimotope employed in such a method is and/or comprises as part thereof the amino acid sequence SMPTDNFERKRF (SEQ ID NO: 189), NSSAILPYFKAISPSLNNDKSLYIIEQLDKLNF (SEQ ID NO: 194), GPIYQLQPKEIQAIIVELQNLS KK (SEQ ID NO: 198), KGVQKF (SEQ ID NO: 202) or variants thereof that retain anti-IL-31 binding.

In a still further embodiment, the human IL-31 mimotope employed in such a method is and/or comprises as part thereof the amino acid sequence SVPTDTHECKRF (SEQ ID NO: 190), SVPTDTHERKRF (SEQ ID NO: 191), HSPAIRAYLKTIRQLDNKSVIDEIIEHLDKLIF (SEQ ID NO: 195), LPVRLLRPSDDVQKIVEELQSLSKM (SEQ ID NO: 199), KGVLVS (SEQ ID NO: 203) or variants thereof that retain anti-IL-31 binding.

In some embodiments of any of the diagnostic methods of the invention, the mimotope binds to an anti-IL31 antibody or antigen-binding portion thereof that specifically binds to a region on a mammalian IL-31 protein involved with interaction of the IL-31 protein with its co-receptor. In one embodiment of the diagnostic methods of this invention, the binding of said antibody to said region is impacted by mutations in a 15H05 epitope binding region selected from the group consisting of:

a) a region between about amino acid residues 124 and 135 of a feline IL-31 sequence represented by SEQ ID NO: 157 (Feline_IL31_wildtype);
b) a region between about amino acid residues 124 and 135 of a canine IL-31 sequence represented by SEQ ID NO: 155 (Canine_IL31); and
c) a region between about amino acid residues 118 and 129 of an equine IL-31 sequence represented by SEQ ID NO: 165 (Equine_IL31).

In one embodiment of the diagnostic methods of the present invention the mimotope binds to an anti-IL31 antibody or antigen-binding portion thereof that specifically binds to the aforementioned 15H05 epitope region. In one specific embodiment of any of the diagnostic methods of the instant invention, the mimotope binds to an anti-IL-31 antibody or antigen-binding portion thereof comprising at least one of the following combinations of complementary determining region (CDR) sequences:

1) antibody 15H05: variable heavy (VH)-CDR1 of SYTIH (SEQ ID NO: 1), VH-CDR2 of NINPTSGYTENNQRFKD (SEQ ID NO: 2), VH-CDR3 of WGFKYDGEWSFDV (SEQ ID NO: 3), variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);
2) antibody ZIL1: variable heavy (VH)-CDR1 of SYGMS (SEQ ID NO: 13), VH-CDR2 of HINSGGSSTYYADAVKG (SEQ ID NO:14), VH-CDR3 of VYTTLAAFWTDNFDY (SEQ ID NO: 15), variable light (VL)-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);
3) antibody ZIL8: VH-CDR1 of DYAMS (SEQ ID NO: 19), VH-CDR2 of GIDSVGSGTSYADAVKG (SEQ ID NO: 20), VH-CDR3 of GFPGSFEH (SEQ ID NO: 21), VL-CDR1 of TGSSSNIGSGYVG (SEQ ID NO: 22), VL-CDR2 of YNSDRPS (SEQ ID NO: 23), VL-CDR3 of SVYDRTFNAV (SEQ ID NO: 24);
4) antibody ZIL9: VH-CDR1 of SYDMT (SEQ ID NO: 25), VH-CDR2 of DVNSGGTGTAYAVAVKG (SEQ ID NO: 26), VH-CDR3 of LGVRDGLSV (SEQ ID NO: 27), VL-CDR1 of SGESLNEYYTQ (SEQ ID NO: 28), VL-CDR2 of RDTERPS (SEQ ID NO: 29), VL-CDR3 of ESAVDTGTLV (SEQ ID NO: 30);
5) antibody ZIL11: VH-CDR1 of TYVMN (SEQ ID NO: 31), VH-CDR2 of SINGGGSSPTYADAVRG (SEQ ID NO: 32), VH-CDR3 of SMVGPFDY (SEQ ID NO: 33), VL-CDR1 of SGESLSNYYAQ (SEQ ID NO: 34), VL-CDR2 of KDTERPS (SEQ ID NO: 35), VL-CDR3 of ESAVSSDTIV (SEQ ID NO: 36);
6) antibody ZIL69: VH-CDR1 of SYAMK (SEQ ID NO: 37), VH-CDR2 of TINNDGTRTGYADAVRG (SEQ ID NO: 38), VH-CDR3 of GNAESGCTGDHCPPY (SEQ ID NO: 39), VL-CDR1 of SGESLNKYYAQ (SEQ ID NO: 40), VL-CDR2 of KDTERPS (SEQ ID NO: 41), VL-CDR3 of ESAVSSETNV (SEQ ID NO: 42);
7) antibody ZIL94: VH-CDR1 of TYFMS (SEQ ID NO: 43), VH-CDR2 of LISSDGSGTYYADAVKG (SEQ ID NO: 44), VH-CDR3 of FWRAFND (SEQ ID NO: 45), VL-CDR1 of GLNSGSVSTSNYPG (SEQ ID NO: 46), VL-CDR2 of DTGSRPS (SEQ ID NO: 47), VL-CDR3 of SLYTDSDILV (SEQ ID NO: 48);
8) antibody ZIL154: VH-CDR1 of DRGMS (SEQ ID NO: 49), VH-CDR2 of YIRYDGSRTDYADAVEG (SEQ ID NO: 50), VH-CDR3 of WDGSSFDY (SEQ ID NO: 51), VL-CDR1 of KASQSLLHSDGNTYLD (SEQ ID NO: 52), VL-CDR2 of KVSNRDP (SEQ ID NO: 53), VL-CDR3 of MQAIHFPLT (SEQ ID NO: 54);
9) antibody ZIL159: VH-CDR1 of SYVMT (SEQ ID NO: 55), VH-CDR2 of GINSEGSRTAYADAVKG (SEQ ID NO: 56), VH-CDR3 of GDIVATGTSY (SEQ ID NO: 57), VL-CDR1 of SGETLNRFYTQ (SEQ ID NO: 58), VL-CDR2 of KDTERPS (SEQ ID NO: 59), VL-CDR3 of KSAVSIDVGV (SEQ ID NO: 60);
10) antibody ZIL171: VH-CDR1 of TYVMN (SEQ ID NO: 61), VH-CDR2 of SINGGGSSPTYADAVRG (SEQ ID NO: 62), VH-CDR3 of SMVGPFDY (SEQ ID NO: 63), VL-CDR1 of SGKSLSYYYAQ (SEQ ID NO: 64), VL-CDR2 of KDTERPS (SEQ ID NO: 65), VL-CDR3 of ESAVSSDTIV (SEQ ID NO: 66); or
11) a variant of 1) to 10) that differs from respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH or VL CDR1, CDR2, or CDR3.

In some embodiments, the mimotope employed in the diagnostic methods of the present invention binds to an anti-IL-31 antibody or antigen-binding portion thereof which binds to feline IL-31, wherein the antibody includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

Anti-IL-31 antibodies, polypeptides, and/or peptides of the present invention, and IL-31 peptide mimotopes are useful for immunoassays which detect or quantitate IL-31, or anti-IL-31 antibodies, in a sample. An immunoassay for IL-31 typically comprises incubating a clinical or biological sample in the presence of a detectably labeled high affinity (or high avidity) anti-IL-31 antibody, polypeptide, or peptide of the present invention capable of selectively binding to IL-31, and detecting the labeled polypeptide, peptide or antibody which is bound in a sample. In a preferred embodiment, an IL-31 mimotope is bound to a solid surface and is used to capture a labeled anti-IL-31 antibody, such that a labeled anti-IL-31 antibody:IL-31 mimotope complex becomes tethered to the solid surface. The labeled anti-IL-31 antibody in the complex has an affinity to the mimotope in the complex that is lower than its affinity to the IL-31 in the sample. The level of IL-31 in the sample can therefore be determined by measuring the signal coming from labeled antibody which is liberated from the solid surface when the IL-31 in the sample binding to the labeled anti-IL-31 antibody of the anti-IL-31 antibody:IL-31 mimotope complex. In this instance, the level of IL-31 in the sample is inversely proportional to the signal. Various clinical assay procedures are well known in the art. See, e.g., IMMUNOASSAYS FOR THE 80'S (Voller et al., eds., Univ. Park, 1981). Such samples include tissue biopsy, blood, serum, and fecal samples, or liquids collected from animal subjects and subjected to ELISA analysis as described below.

In some embodiments, the binding of antigen to antibody is detected without the use of a solid support. For example, the binding of antigen to antibody can be detected in a liquid format.

In other embodiments, an IL-31 peptide mimotope, or an anti-IL-31 antibody, polypeptide, or peptide can, for example, be fixed to nitrocellulose, or another solid support which is capable of immobilizing cells, cell particles or soluble proteins. The support can then be washed with suitable buffers followed by treatment with the detectably labeled IL-31-specific polypeptide, peptide or antibody. The solid phase support can then be washed with the buffer a second time to remove unbound polypeptide, peptide or antibody. The amount of bound label on the solid support can then be detected by known method steps.

"Solid phase support" or "carrier" refers to any support capable of binding polypeptide, peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to the IL-31 peptide mimotope, IL-31 or an anti-IL-31 antibody. It is envisioned that the IL-31 mimotope bound to the support may itself be conjugated to a carrier polypeptide, if desired. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, polypeptide, peptide or antigen, or can ascertain the same by routine experimentation.

Well known method steps can determine binding activity of a given lot of mimotope or anti-IL-31 polypeptide, peptide and/or antibody. Those skilled in the art can determine operative and optimal assay conditions by routine experimentation.

Detectably labeling an IL-31-specific polypeptide, peptide and/or antibody as well as labeling of an IL-31 peptide mimotope (or conjugate thereof) can be accomplished by several different methods, including linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the IL-31-specific antibodies or mimotopes described herein include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the IL-31-specific antibodies or mimotopes, it is possible to detect IL-31 through the use of a radioimmunoassay (RIA). See Work et al., LAB. TECHNIQUES & BIOCHEM. 1N MOLEC. Bio. (No. Holland Pub. Co., NY, 1978). The radioactive isotope can be detected by such means as the use of a gamma counter or a scintillation counter or by autoradiography. Isotopes which are particularly useful for the purpose of the present invention include: $^{3}H$, $^{125}I$, $^{131}I$, $^{35}S$, $^{14}O$, and $^{125}I$.

It is also possible to label the IL-31-specific antibodies or mimotopes with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The IL-31-specific antibodies or mimotopes can also be detectably labeled using fluorescence-emitting metals such a $^{125}Eu$, or others of the lanthanide series. These metals can be attached to the IL-31-specific antibody or mimotope using such metal chelating groups as diethylenetriaminepentaacetic acid (DTPA) or ethylenediamine-tetraacetic acid (EDTA).

The IL-31-specific antibodies also can be detectably labeled by coupling to a chemiluminescent compound. The presence of the chemiluminescently labeled antibody or mimotope is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the mimotope, or IL-31-specific antibody, portion, fragment, polypeptide, or derivative thereof. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the mimotope, IL-31-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the IL-31 which is detected by the above assays can be present in a biological sample. Any sample containing IL-31 may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and adding a labeled antibody (alone or in a complex with an IL-31 mimotope described herein) to such a specimen. It is also envisioned that the antibody in the complex may comprise only a portion of the antibody. The antibody (or portion thereof) may be provided by applying or by overlaying the labeled antibody (or portion) to a biological sample. Through the use of such a procedure, it is possible to determine not only the presence of IL-31 but also the distribution of IL-31 in the examined tissue. Using the present invention, those of ordinary skill will readily perceive that any of a wide variety of histological methods (such as staining procedures) can be modified in order to achieve such in situ detection.

The mimotope, antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid-phase antibody, antigen, and labeled antibody.

The antibodies or antibody:mimotope complexes may be used to quantitatively or qualitatively detect the IL-31 in a sample or to detect presence of cells that express the IL-31. This can be accomplished by immunofluorescence techniques employing a fluorescently labeled antibody or antibody:mimotope complex (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine or feline immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

In one embodiment, the diagnostic method for detecting IL-31 is a lateral flow immunoassay test. This is also known as the immunochromatographic assay, Rapid ImmunoMigration (RIM™) or strip test. Lateral flow immunoassays are essentially immunoassays adapted to operate along a single axis to suit the test strip format. A number of variations of the technology have been developed into commercial products, but they all operate according to the same basic principle. A typical test strip consists of the following components: (1) sample pad—an absorbent pad onto which the test sample is applied; (2) conjugate or reagent pad—this contains antibodies specific to the target analyte conjugated to colored particles (usually colloidal gold particles, or latex microspheres); (3) reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and (4) wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones.

There are two main types of lateral flow immunoassay used in microbiological testing: double antibody sandwich assays and competitive assays. In the double antibody sandwich format, the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Competitive assays differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed.

Importantly, the mimotopes and antibodies described herein may be helpful in diagnosing a pruritic and/or allergic in dogs, cats, or horses. More specifically, the antibody in the antibody:mimotope complex may bind to IL-31 in the sample and help identify the overexpression of IL-31 in mammals, including companion animals. Thus, the antibodies described herein, which can be used in conjunction with the mimotope, may provide an important immunohistochemistry tool. In one embodiment, an assay design is conceived here whereby an IL-31 mimotope (peptide) is used to capture an antibody of the present invention that is labeled for detection in an assay. This captured antibody would have an affinity to the attached mimotope that is lower that the affinity of native circulating IL-31 in a host species. In this embodiment, incubation of the fluid derived from the host species is incubated with the labeled antibody: mimotope complex that is tethered to a solid surface. The presence of IL-31 in the test fluid derived from the host species will have a higher affinity to the antibody, thus liberating the labeled antibody from the solid surface where it can be removed during wash steps. The level of IL-31 in the test fluid can thus be correlated to the lack of signal that appears on the mimotope-bound surface. It is conceived that such an assay would have utility to measure IL-31 in a research or clinical setting for use as a diagnostic test.

The antibodies and mimotopes described herein may be used on arrays, highly suitable for measuring gene expression profiles.

Kits

Also included within the scope of the present invention are kits for practicing the subject therapeutic methods and diagnostic methods. In one embodiment, a kit according to the present invention at least includes a vaccine composition of the present invention. In one embodiment, a vaccine of the present invention may be provided, usually in a lyophilized form, in a container. In another embodiment, a kit according to the present invention can include the components necessary to carry out the diagnostic methods of this invention. For example, a kit of this invention may include as one of its components an IL-31 mimotope as described herein, such as a feline IL-31 mimotope, a canine IL-31 mimotope, a horse IL-31 mimotope, or a human IL-31 mimotope. Such a mimotope may already be bound to a solid surface. A kit according to the present invention can also include antibodies. The antibodies, which may be conjugated to a label or toxin, or unconjugated, are typically included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kits will generally also include a set of instructions for use.

In one embodiment, a kit according to the present invention is a test strip kit (lateral flow immunoassay kit) useful for detecting IL-31, such as canine, feline, equine, or human IL-31 protein in a sample. Such a test strip will typically include a sample pad onto which the test sample is applied; a conjugate or reagent pad containing an antibody or antibody:mimotope specific to canine, feline, equine, or human IL-31, wherein the antibody or antibody:mimotope complex is conjugated to colored particles (usually colloidal gold particles); a reaction membrane onto which anti-IL-31 antibodies or an antibody:mimotope complex are immobilized in a line across the membrane as a capture zone or test line (a control zone may also be present, containing antibodies or an antibody:mimotope complex specific for the conjugate antibodies); and a further absorbent pad designed to draw the sample across the reaction membrane by capillary action and collect it. The test strip kit will generally also include directions for use.

The invention will now be described further by the non-limiting examples below. In the example section below and in the figures, any data presented for antibodies containing "11E12" in their designation is for purposes of comparison with the antibodies of the present invention.

EXAMPLES

1. Example 1

1.1. Production of Canine Interleukin 31 (cIL-31) from Chinese Hamster Ovary (CHO) Cells The Interleukin 31 protein varies in amino acid sequence conservation among homologous species (FIGS. 1A and 1B) but is believed to have common structural architecture with other members of the type I cytokine family (Boulay et al. 2003, Immunity. August; 19(2):159-632003; Dillon et al. 2004 Nat Immunol. July; 5(7):752-60). This up-down bundle topology is significant to the mode of receptor recognition shared by these cytokines (Dillon et al. supra, Cornelissen et al. 2012 Eur J Cell Biol. June-July; 91(6-7): 552-66). With variation in IL-31 protein sequence identities between different species, it is not possible to predict if antibodies raised against one species will cross-react with others given different epitope propensities and local amino acid compositions. As a consequence, multiple forms of IL-31 protein were considered for this work representing multiple species and expression systems. The canine IL-31 protein (cIL-31) was produced to use as an immunogen and a reagent to test affinity and potency of antibody hits. Recombinant cIL-31 was created in CHO cells using the CHROMOS ACE (Artificial Chromosome Expression) system (Chromos Molecular Systems, Inc., Burnaby, British Columbia) to generate the secreted canine IL-31 protein having the sequence of (SEQ ID NO: 155; Canine_IL31), the corresponding nucleotide sequence for which is (SEQ ID NO: 156; Canine_IL31). Conditioned medium from 400 ml of cell culture (CHO cell line) was obtained and dialyzed against 10 volumes of QA buffer (20 mM Tris pH 8.0, 20 mM NaCl) for 4.5 hours. Dialyzed medium was 0.2 μm filtered and loaded at 1 ml/min onto a SOURCE™ Q column (GE Healthcare, Uppsala, Sweden) pre-equilibrated with QA buffer. Protein was eluted using a multi-step linear gradient. The majority of cIL-31 remained in the flow through (FT) fraction, a small amount of cIL-31 eluted early in the gradient. Identity of the protein was previously confirmed by Western immunoblotting, and Mass-Spectrometry (MS) analysis of a tryptic digest. Protein in the FT fraction was concentrated 4-5 fold and dialyzed overnight against Phosphate Buffered Saline (PBS) at 4° C. Stability of the protein was checked following dialysis into PBS. No precipitation was observed, and no proteolysis was observed after several days at 4° C. De-glycosylation experiments using N-glycosidase F resulted in the protein condensing down to a single band of ~15 kDa on SDS-PAGE. Protein concentration was determined using a bicinchoninic assay (BCA assay) with Bovine Serum Albumin (BSA) as a standard (ThermoFisher Scientific, Inc., Rockford, Ill.). The protein solution was split into aliquots, snap frozen (liquid N2) and stored at −80° C.

1.2. Transient Expression of Wildtype and Mutant Feline Interleukin 31 (fIL-31) from CHO Cells To aid in the identification of antibodies with the appropriate epitope binding property, wildtype and mutant feline IL-31 proteins were expressed in a mammalian expression system for production, purification, and assessment in affinity and cell-based assays. The binding site of antibody 11E12 on IL-31 was described previously (U.S. Pat. No. 8,790,651 to Bammert, et al.). Characterization of the novel binding site on IL-31 recognized by antibody 15H05 is described herein. The wildtype designation is full length feline IL-31 protein with no changes to the native amino acid residues. Mutant proteins were designated by their corresponding antibodies name (11E12 and 15H05) referring to mutations in amino acids in the IL-31 protein that (when altered) affect the binding to each respective antibody. Identification of the appropriate mutations required for the feline IL-31 15H05 protein are described below in section 1.10. The objective was to change amino acids in the IL-31 epitope and observe a loss of binding phenotype to each respective antibody. A comparison can then be made during screening to see if new candidate antibodies bind to the wildtype protein and not to the mutant.

New antibody hits can then be binned according to binding to the same or similar epitope as antibody 11E12 or 15H05.

Expression constructs were codon optimized and synthesized for expression in Chinese Hamster Ovarian (CHO) cells. The synthesized genes were cloned into pD2529 (ATUM vector) for transient expression use. Wildtype feline IL-31 protein is represented by (SEQ ID NO: 157; Feline_IL31_wildtype), the corresponding nucleotide sequence for which is (SEQ ID NO: 158; Feline_IL31_wildtype). Mutant feline IL-31_11E12 protein is represented by (SEQ ID NO: 161; Feline_IL31_11E12 mutant), the corresponding nucleotide sequence for which is (SEQ ID NO: 162; Feline_IL31_11E12 mutant). Mutant feline IL-31 15H05 protein is represented by (SEQ ID NO: 163; Feline_IL31_15H05 mutant), the corresponding nucleotide sequence for which is (SEQ ID NO: 164; Feline_IL31_15H05 mutant). Recombinant feline IL-31 proteins were expressed in ExpiCHO-S™ cells (ThermoFisher Scientific, Inc., Rockford, Ill.) by following the manufacturer's maximum titer protocol for transient CHO expression. Twelve days post transfection the cells were centrifuged and filtered to capture the secreted protein in the conditioned media. For each construct (wild type and mutants), 120 mL of conditioned media (from CHO cell culture, 0.2 μm filtered) was adjusted to 30 mS/cm with the addition of NaCl, 5 mM imidazole, and pH 7.4. Each media sample was combined with 5 mL of HisPur Cobalt resin (ThermoFisher Scientific, Inc., Rockford, Ill.) which had been equilibrated with 5 mM imidazole, 20 mM sodium phosphate, 300 mM NaCl, pH 7.4. Each sample and resin was allowed to mix at 4° C., overnight. Resins were collected (and separated from the unbound fraction) by pouring through BioRad Econcolumns (Bio-Rad, Hercules, Calif.). Resins were washed with 5×5 mL of buffer (as above) and then eluted with 5×5 mL of 500 mM imidazole in the same buffer. Fractions were evaluated by SDS-PAGE. Concentration was measured by a BCA protein assay using standard methods.

1.3. Production of Feline Interleukin 31 (fIL-31) from *E. coli*

Recombinant feline IL-31 protein was generated in an *E. coli* expression host to use as an assay reagent and for in vivo challenge studies to induce a pruritic response in cats. The gene representing feline IL-31 was synthesized for optimal expression in *E. coli*. Expression constructs were created with the full length feline IL-31 gene containing an N-terminal 6-His tag for detection and purification. This feline IL-31 protein is represented by (SEQ ID NO: 159; Feline_IL-31_E_coli), the corresponding nucleotide sequence for which is (SEQ ID NO: 160; Feline_IL-31_E_coli). Sequence confirmed plasmids were used to transform *E. coli* BL21 DE3 (Invitrogen Corp., Carlsbad, Calif.) and subsequent protein expression carried out.

Cell paste (262.3 g) from *E. coli* was lysed as follows: The cell paste was resuspended in 500 mL of 50 mM Tris pH 8, filtered through a stainless mesh filter to remove particles, and then lysed via two passes through a microfluidizer at 1300 psi. The lysate (~1200 mL volume) was divided into four bottles, centrifuged at 12,000 g for 20 minutes at 10° C. The supernatant was decanted and discarded. Each pellet was washed by suspension in 300 mL of 5 mM EDTA, 0.5% Triton X-100, pH 9.0, and then centrifugation at 12,000 g, 50 minutes, at 10° C. The supernatant was decanted and discarded. The washed pellets were stored at −20° C. until folding and isolation.

Prior to isolation, one of the pellets was washed with water to remove the residual detergent, and then centrifuged at 10,000 g, 20 minutes, at 4° C. Again, the supernatant was decanted. Finally, the washed pellet was solubilized in 60 mL of 50 mM sodium phosphate, 300 mM NaCl, 6 M guanidine-HCl, 5 mM imidazole, pH 7.4. The pellet was allowed to mix at room temperature for approximately 25 minutes before centrifuging again at 10,000 g, 20 minutes, and 4° C. This time, the supernatant was decanted and kept for further processing. The pellet (resuspended in water to original volume) was set aside for SDS-PAGE only. Crude IMAC (immobilized metal affinity chromatography) was performed to increase purity prior to folding. In this case, 15 mL of Ni-NTA Superflow (Qiagen Inc, Germantown, Md., Cat #30450, pre-equilibrated in the same buffer) was added to the clarified supernatant and allowed to mix at room temperature for approximately 90 minutes. The unbound fraction was decanted and set aside for SDS-PAGE. The IMAC resin was washed with 5 mM imidazole, 50 mM sodium phosphate, 300 mM NaCl, 6 M guanidine-HCl, pH 7.4 (same as solubilization buffer). The resin was eluted with (first 7.5 mL and then multiples of 15 mL, monitoring protein elution by Bradford assay) 200 mM imidazole, 50 mM sodium phosphate, 300 mM NaCl, 6 M guanidine-HCl, pH 7.4. Elution fractions containing protein (as per Bradford) were pooled (125 mL) for further processing.

The IL-31 protein was folded as follows. The IL-31 was reduced by the addition of dithiothreitol to a final of 10 mM, and allowed to mix at room temperature for 2 hours. The diluted sample was then diluted drop-wise into 2500 mL (20× volume) of PBS+1 M NaCl with rapid stirring. The theoretical concentration of urea should have been approximately 0.4 M at this point. The remainder of the urea was removed slowly by dialysis against 3 exchanges (4 L each) of PBS, at 4° C. overnight. Following dialysis, the sample was 0.2 μm filtered to remove any unfolded/precipitated protein.

The sample was further purified by a second round of IMAC, this time with a linear gradient elution. Fifteen mL of Ni-NTA Superflow resin was added to the sample and allowed to bind batch-wise by stirring (with a suspended stir bar) overnight at 4° C. Again, the unbound fraction was decanted and set aside. The Ni-NTA Superflow resin was packed in an XK16 column (GE Healthcare Lifesciences, Marlborough, Mass.) and hooked up to an AKTA brand chromatography system (GE Healthcare Lifesciences, Marlborough, Mass.). The column was then washed with 50 mM Tris, 300 mM NaCl, pH 8.2 and the eluted via a 150 mL linear gradient from 0 to 500 mM imidazole, each in wash buffer. Fractions were analyzed by SDS-PAGE. Fractions having sufficient purity of IL-31 were pooled and buffer exchanged again by dialysis against 3 exchanges (2 L each) of PBS, at 4° C., overnight. Finally, the folded and purified sample was collected from dialysis, sterile filtered, concentration measured aliquoted, snap-froze in a dry-ice/isopropanol bath, and stored at −80° C.

1.4. Method to Determine Affinity of Anti-IL-31 Antibodies for IL-31 Using Surface Plasmon Resonance The affinity with which candidate mAbs bind canine and feline IL-31 was determined using surface plasmon resonance (SPR) on a Biacore system (Biocore Life Sciences (GE Healthcare), Uppsala, Sweden). To avoid affinity differences associated with differential surface preparation that can occur when immobilizing antibodies to surfaces; a strategy was employed where IL-31 was directly conjugated to the surface. Immobilization was obtained by amine coupling 5 μg/mL IL-31 using N-hydroxysuccinimide (NHS)/1-Ethyl-3-(3-dimethylaminopropyl) carbodiimide (EDC) chemistry. Chips were quenched with ethanolamine and the affinity with which all candidate mAbs bound to the immobilized IL-31 was evaluated. All curves were fit to a 1:1 model. Affinity constants (KD) less than $1\times10^{-11}$M (1E-11 M) are below the lower limit of quantitation of detection for the instrument. Results for affinity measurements are described herein.

1.5. Method to Determine Potency of Anti-IL-31 Antibodies Assessed by Inhibition of Canine and Feline IL-31 Induced pSTAT3 Signaling in Canine and Feline Macrophage Cells To identify candidates with inhibitory activity, antibodies were assessed for their ability to affect IL-31-mediated STAT3 phosphorylation in either a canine or feline cell-based assay. STAT3 phosphorylation was determined in canine DH-82 (ATCC® CRL-10389™) or feline FCWF4 macrophage-like cells (ATCC CRL-2787). DH82 and FCWF4 cells were primed with canine interferon gamma (R&D Systems, Minneapolis, Minn.) at 10 ng/mL for 24 hours or feline interferon gamma (R&D Systems, Minneapolis, Minn.) at 125 ng/mL for 96 hours, respectively, to increase receptor expression. Both cell types were serum starved for 2 hours prior to IL-31 and mAb treatment. Using two independent methods, all candidate mAbs were evaluated for their ability to inhibit either 1 μg/mL canine or 0.2 μg/mL feline IL-31 induced STAT3 phosphorylation. Assays were also run to demonstrate cross-reactivity of canine and feline cytokines and cross-functionality of the antibodies ability to inhibit signaling in both species. To ensure complex formation, a one hour co-incubation of mAb and IL-31 cytokine prior to cell stimulation was completed. IL-31 cell stimulation was carried out for five minutes. STAT3 phosphorylation was measured using AlphaLISA SureFire ULTRA™ technology (Perkin Elmer, Waltham, Mass.). In the case where antibody concentration and purity are unknown, hybridoma supernatants were qualitatively measured for their ability to inhibit STAT3 phosphorylation following a 1 hour co-incubation with 1 mg/ml canine or 0.2 mg/ml feline IL-31. The potency of individual monoclonal antibodies defined by their ability to inhibit IL-31 mediated STAT3 phosphorylation in these assays was considered the key selection criteria for further advancement of select antibodies. The term potency refers to the IC50 value calculated from these assays and is the concentration of the antibody where signaling induced by IL-31 is reduced to one half its maximal value. Increased potency described herein correlates to a lower IC50 value.

1.6. Identification of Mouse and Canine Monoclonal Antibodies Recognizing Canine and Feline Interleukin 31

Mice and dogs were immunized with recombinant canine IL-31 (SEQ ID No. 155) for the purpose of identifying antibodies. Serum antibody titers from immunized animals were determined using an enzyme linked immunosorbent assay (ELISA). Canine or feline IL-31 (50 ng/well) was immobilized to polystyrene microplates and used as a capture antigen. Serum from immunized animals was diluted in phosphate buffered saline with 0.05% tween-20 (PBST). The presence of anti-IL-31 antibodies was detected with an appropriate secondary HRP labeled antibody. Following addition of a chromogenic substrate (SureBlue Reserve TMB 1-Component Microwell Peroxidase Substrate, KPL, Inc., Gaithersburg, Md.) and a ten minute incubation at room temperature (RT) the reaction was stopped with the addition of 1004 of 0.1 N HCl. The absorbance of each well was determined at an optical density (OD) of 450 nm. Antibodies were selected for their ability to bind canine and feline IL-31 using an ELISA. In some cases, further characterization was performed at the time of selection using an ELISA with a mutant form of the feline IL-31 protein as a capture antigen. Cells producing antibodies with desired binding and inhibitory properties were chosen for sequence analysis of RNA transcripts representing the variable heavy (VH) and variable light (VL) IgG chains.

In the case of mouse antibodies, donor splenocytes from a single responsive CF-1 mouse were used for fusion and hybridoma supernatants were screened for antibodies that bind to either canine or feline IL-31 proteins by ELISA. This resulted in the identification of a single mouse antibody, Mu-15H05, having a sub-nanomolar affinity to both species of IL-31 (FIG. 2, Section A). Mouse anti IL-31 15H05 was further subcloned to generate a hybridoma producing homogeneous antibody and for sequencing of the variable heavy and light chains. The mouse anti IL-31 variable sequences determined for antibody 15H05 are as follows, 15H05 variable heavy chain (SEQ ID NO: 67; MU-15H05-VH), the corresponding nucleotide sequence for which is (SEQ ID NO: 68; MU-15H05-VH), 15H05 variable light chain (SEQ ID NO: 69; MU-15H05-VL), the corresponding nucleotide sequence for which is (SEQ ID NO: 70; MU-15H05-VL). In addition to mouse antibody 15H05, further consideration was given to mouse-derived antibody 11E12 that was previously described in U.S. Pat. No. 8,790,651 to Bammert, et al. Described herein are data showing the ability of antibody 11E12 to bind both canine and feline IL-31 proteins with high affinity. The ability of 11E12 to bind feline IL-31 made this antibody a suitable candidate for felinization and potential therapeutic use in cats. The mouse anti IL-31 variable sequences previously determined for antibody 11E12 are as follows, 11E12 variable heavy chain (SEQ ID NO: 71; MU-11E12-VH), the corresponding nucleotide sequence for which is (SEQ ID NO: 72; MU-11E12-VH), 11E12 variable light chain (SEQ ID NO: 73; MU-11E12-VL), the corresponding nucleotide sequence for which is (SEQ ID NO: 74; MU-11E12-VL).

Dogs having elevated anti IL-31 titers following vaccination were selected for analysis of B-cell populations producing antibodies with desired phenotypes. B-cells were derived from PBMCs, bone marrow, spleen, or lymph nodes for further analysis. Single B-cells were segregated into individual wells and assayed for presence of secreted IgGs capable of binding wildtype, 11E12 mutant, and 15H05 mutant forms of canine IL-31 (AbCellera, Vancouver, BC) using methods described in US2012/0009671A1, US2016/0252495A1, U.S. Pat. No. 9,188,593, WO 2015/176162 A9, and WO 2016/123692 A1.

This screening strategy is based on known regions of the IL-31 protein that are critical for binding and signal transduction through its co-receptor complex. Selection of these mutant proteins for screening is described in section 1.2 of this application. Sequencing of the variable heavy and light IgG domains was carried following an RT-PCR reaction from individual candidate B-cells. These screens resulted in the identification of nine canine antibodies selected for further evaluation. These canine anti IL-31 variable sequences are as follows, ZIL1 variable heavy chain (SEQ ID NO:75; CAN-ZIL1_VH), the corresponding nucleotide sequence for which is (SEQ ID NO: 76; CAN-ZIL1_VH), ZIL1 variable light chain (SEQ ID NO: 77; CAN-ZIL1_VL), the corresponding nucleotide sequence for which is (SEQ ID NO: 78; CAN-ZIL1_VL);

ZIL8 variable heavy chain (SEQ ID NO:79; CAN-ZIL8_VH), the corresponding nucleotide sequence for which is (SEQ ID NO: 80; CAN-ZIL8_VH), ZIL8 variable light chain (SEQ ID NO: 81; CAN-ZIL8_VL), the corresponding nucleotide sequence for which is (SEQ ID NO: 82; CAN-ZIL8_VL); ZIL9 variable heavy chain (SEQ ID NO:83; CAN-ZIL9_VH), the corresponding nucleotide sequence for which is (SEQ ID NO: 84; CAN-ZIL9_VH), ZIL9 variable light chain (SEQ ID NO: 85; CAN-ZIL9_VL), the corresponding nucleotide sequence for which is (SEQ ID NO: 86; CAN-ZIL9_VL); ZIL11 variable heavy chain (SEQ ID NO:87; CAN-ZIL11_VH), the corresponding nucleotide sequence for which is (SEQ ID NO: 88; CAN-ZIL11_VH), ZIL11 variable light chain (SEQ ID NO: 89; CAN-ZIL11_VL), the corresponding nucleotide sequence for which is (SEQ ID NO: 90; CAN-ZIL11_VL); ZIL69 variable heavy chain (SEQ ID NO:91; CAN-ZIL69_VH), the corresponding nucleotide sequence for which is (SEQ ID NO: 92; CAN-ZIL69_VH), ZIL69 variable light chain (SEQ ID NO: 93; CAN-ZIL69_VL), the corresponding nucleotide sequence for which is (SEQ ID NO: 94; CAN-ZIL69_VL); ZIL94 variable heavy chain (SEQ ID NO:95; CAN-ZIL94_VH), the corresponding nucleotide sequence for which is (SEQ ID NO: 96; CAN-ZIL94_VH), ZIL94 variable light chain (SEQ ID NO: 97; CAN-ZIL94_VL), the corresponding nucleotide sequence for which is (SEQ ID NO: 98; CAN-ZIL94_VL); ZIL154 variable heavy chain (SEQ ID NO:99; CAN-ZIL154_VH), the corresponding nucleotide sequence for which is (SEQ ID NO: 100; CAN-ZIL154_VH), ZIL154 variable light chain (SEQ ID NO: 101; CAN-ZIL154_VL), the corresponding nucleotide sequence for which is (SEQ ID NO: 102; CAN-ZIL154_VL); ZIL159 variable heavy chain (SEQ ID NO:103; CAN-ZIL159_VH), the corresponding nucleotide sequence for which is (SEQ ID NO: 104; CAN-ZIL159_VH), ZIL159 variable light chain (SEQ ID NO: 105; CAN-ZIL159_VL), the corresponding nucleotide sequence for which is (SEQ ID NO: 106; CAN-ZIL159_VL); ZIL171 variable heavy chain (SEQ ID NO:107; CAN-ZIL171_VH), the corresponding nucleotide sequence for which is (SEQ ID NO: 108; CAN-ZIL171_VH), ZIL171 variable light chain (SEQ ID NO: 109; CAN-ZIL171_VL), the corresponding nucleotide sequence for which is (SEQ ID NO: 110; CAN-ZIL171_VL).

The aforementioned nine monoclonal antibodies which were selected for further characterization may be referred to elsewhere in the specification, figures, or claims as ZIL1, ZIL8, ZIL8, ZIL11, ZIL69, ZIL94, ZIL154, ZIL159, and ZIL171.

1.7. Construction of Recombinant Chimeric and Fully Canine Antibodies

Antibody variable domains are responsible for antigen binding. Grafting of the full variable domain onto respective constant region is expected to have little or no impact on the antibody's ability to bind the IL-31 immunogen. To simultaneously confirm that the correct sequence of the heavy and light chain variable regions were identified and to produce homogenous material, expression vectors were designed to produce recombinant chimeric or fully canine antibodies in mammalian expression systems. Chimeric antibodies described here consist of the variable sequence (both CDR and framework) from the host species antibody grafted onto the respective heavy and light constant regions of a feline or canine IgG molecule (for example; mouse variable: canine constant is referred to as mouse:canine chimera). Fully canine antibodies described here consist of the variable sequence (both CDR and framework) from the host species antibody (canine) grafted on to the respective heavy and light chain constant regions of the canine IgG molecule. Synthetic DNA sequences were constructed for the variable heavy (VH) and variable light (VL) sequences of selected antibodies. These sequences contain unique restriction endonuclease sites, a Kozak consensus sequence and, an N-terminal secretion leader to facilitate expression and secretion of the recombinant antibody from a mammalian cell line.

For mouse: feline chimeras, each respective variable region was cloned into a mammalian expression plasmid containing either the feline IgG heavy (SEQ ID NO: 173; Feline_HC_AlleleA_1) the corresponding nucleotide sequence for which is (SEQ ID NO: 174; Feline_HC_AlleleA_1) or light chain (SEQ ID NO: 175; Feline_LC_Kappa_G_minus) the corresponding nucleotide sequence for which is (SEQ ID NO: 176; Feline_LC_Kappa_G_minus) constant regions. For mouse: canine chimeras or fully canine antibodies, each mouse or canine variable region was cloned into a mammalian expression plasmid containing either the canine IgG heavy (SEQ ID NO: 177; Canine_HC_65_1) the corresponding nucleotide sequence for which is (SEQ ID NO: 178; Canine_HC_65_1) or light chain (SEQ ID NO: 179; Canine_LC_Kappa) the corresponding nucleotide sequence for which is (SEQ ID NO: 180; Canine_LC_Kappa) constant regions. The plasmids encoding each heavy and light chain, under the control of the CMV promoter, were co-transfected into HEK 293 cells using standard methods. Following six days of expression, chimeric mAbs were purified from 50 ml of transiently transfected HEK293FS cell supernatants using MabSelect Sure protein A resin (GE Healthcare, Uppsala, Sweden) according to standard methods for protein purification. Eluted fractions were pooled, concentrated to ~500 μl using a 10,000 nominal MW cutoff Nanosep Omega centrifugal device (Pall Corp., Port Washington, N.Y.), dialyzed overnight at 4° C. in 1×PBS, pH7.2 and stored at 4° C. for further use. Affinity and cell based potency of select recombinant antibodies are described below.

FIG. 2 details the affinity of antibodies with CDRs derived from mouse origin using biacore. FIG. 2, Section A shows the affinity of mouse anti IL-31 antibodies 11 E12 and 15H05 and the corresponding affinities of the feline and canine chimeric forms to both feline and canine IL-31 surfaces. These observations confirm the correct sequence for both mouse antibodies and indicate conversion to the chimeric form results in antibodies with equivalent or higher affinity when compared to the mouse parent with the exception of the mouse:feline 15H05 chimera which lost some affinity to both IL-31 species as a result of its conversion to the chimeric form. Fully mouse and chimeric forms of antibodies 11E12 and 15H05 were also tested for activity in the canine and feline cellular assays described in section 1.5. FIG. 3 shows the results for these assays. Mouse antibodies 11 E12 and 15H05 were tested for activity against canine and feline cell types using both canine and feline IL-31 to stimulate signaling. The potency of both mouse antibodies was comparable against both canine and feline cells using the feline cytokine with the exception of 15H05 against feline IL-31 in feline FCWF4 cells that shows a slight increase in IC50. Mouse 15H05 was capable of blocking canine IL-31 signaling in both feline and canine cells with the potency in the canine assay being slightly higher. These results indicate that the respective epitopes recognized by these antibodies exists on both canine and feline IL-31 and binding of these antibodies is capable of neutralizing receptor-mediated cellular signaling in a relevant cell line from both species.

FIG. 3 also describes the potency of select chimeras in both cellular assays. Conversion of mouse antibodies to feline and canine chimeras had minimal impact on the potency against feline IL-31 in the feline potency assay (IC50 range 1.15-3.45 μg/ml). Similar results were observed when these chimeras were tested against feline IL-31 signaling on the canine DH82 cell line with a slight increase in potency (IC50=0.71 μg/ml) observed for the 15H05 mouse: canine chimera. In general there was an increase in IC50 values against canine IL-31 in both canine and feline cell types. The mouse: feline 15H05 chimera was slightly less potent in this assay format compared to the mouse: canine form (IC50 28.61 vs. 12.49 μg/ml). Consistent with observations for the mouse antibodies, conversion to canine and feline chimeric forms resulted in minimal changes in potency.

Antibodies described above that were identified from single B cells of immunized dogs were constructed as recombinant IgG proteins following identification of their variable domain sequences. Grafting of these variable domains onto the canine heavy chain Fc (65_1 isotype) resulted in the generation of recombinant fully canine antibodies. It was of interest to identify additional canine antibodies that bound wildtype feline IL-31 and who's binding was decreased to the feline IL-31 15H05 mutant (i.e. are directed at the 15H05 epitope). These antibodies obtained from this alternate source (canine vs. mouse) provide additional paratopes (the portion of the antibody which recognizes the IL-31 protein, includes CDRs) recognizing the 15H05 epitope thus increasing the diversity of antibodies with different physical properties to select from.

FIG. 4 shows the results obtained for binding of these recombinant canine antibodies to various proteins using both ELISA and Biacore methods. For the indirect ELISA method, antibody binding to wildtype and feline IL-31 15H05 mutant proteins was assessed. All nine canine monoclonal antibodies (ZIL1, ZIL8, ZIL8, ZIL11, ZIL69, ZIL94, ZIL154, ZIL159, and ZIL171) were capable of binding to wildtype feline IL-31 and binding was impacted by mutations in the mAb 15H05 epitope region confirming the correct binding phenotype determined during the initial screening used to identify them. In comparison, the 11E12 antibody bound to the wild-type feline IL-31 and its binding was not impacted by the mutations in the 15H05 epitope region as evidenced by the data in FIG. 4. To confirm binding, biacore analysis was performed using canine, feline, equine, human, feline 15H05 mutant, and feline 11E12 mutant IL-31 proteins as surfaces and a single test concentration of antibody. Similar to ELISA observations, all antibodies tested bound to wildtype feline IL-31. In agreement with the data described above in this section, mouse antibodies 11 E12 and 15H05 both bound to canine and feline IL-31 surfaces. Three additional antibodies where shown to have this dual binding property, ZIL69 (partial canine binding), ZIL94, and ZIL159. From this group of nine fully canine antibodies, only ZIL1 and ZIL9 cross-reacted with equine IL-31. Of note, antibody 15H05 was the only one of all assayed herein that bound to canine, feline, and equine IL-31 indicating some level of epitope conservation across the three species. In contrast, none of the antibodies described herein bound to human IL-31. Additional biacore surfaces were used to verify ELISA observations showing differential binding of antibodies to wildtype feline IL-31 and two proteins with mutations in the 15H05 (15H05 mutant) or 11 E12 (11E12 mutant) epitopes. As expected, control mouse antibody 11 E12 bound to the 15H05 IL-31 mutant and did not bind to the 11 E12 IL-31 mutant due to mutations in the epitope. Likewise mouse 15H05 did not bind to the 15H05 mutant and retained binding to the 11E12 IL-31 mutant further distinguishing the separate binding epitopes recognized by these two antibodies. In agreement with the ELISA results, all fully canine antibodies were impacted by the 15H05 mutation with the exception of ZIL94, ZIL154, and ZIL171 (partially affected). Differing results can be attributed to differences in the two assay methodologies. In addition, binding of three antibodies was also shown to be impacted by the 11 E12 mutation; ZIL1 (partially effected), ZIL8, and ZIL159. These results indicate the epitope recognized by these antibodies is impacted by changes in both regions of the IL-31 protein. Taken together these results support the characterization nine antibodies derived from canine B cells sharing binding to a region on the feline IL-31 protein that is recognized by antibody 15H05.

1.8. Felinization of the Murine 11 E12 and 15H05 Antibodies and Optimization of Binding Affinities The generation of anti-drug antibodies (ADAs) can been associated with loss of efficacy for any biotherapeutic protein including monoclonal antibodies. Comprehensive evaluation of the literature has shown that speciation of monoclonal antibodies can reduce the propensity for mAbs to be immunogenic although examples of immunogenic fully human mAbs and non-immunogenic chimeric mAbs can be found. To help mitigate risks associated with ADA formation for the anti-IL-31 monoclonal antibodies provided herein, a felinization strategy was employed. This felinization strategy is based on identifying the most appropriate feline germline antibody sequence for CDR grafting. Following extensive analysis of all available feline germline sequences for both the variable heavy and light chain, germline candidates were selected based on their homology to the mouse mAbs, and the CDRs from the mouse progenitor mAbs were used to replace native feline CDRs. The objective was to retain high affinity and cell-based activity using feline antibody frameworks to minimize the potential of immunogenicity in vivo. Felinized mAbs were expressed and characterized for their affinity to feline IL-31 and their potency in cell-based assays. In the event that a felinized antibody loses its ability to bind IL-31, a systematic dissection was undertaken to identify; 1) the chain responsible for the loss of function, 2) the framework responsible for the loss of function and 3) the amino acid(s) responsible for the loss function.

Synthetic nucleotide constructs representing the felinized variable heavy and light chains of mAbs 11E12 and 15H05 were made. Following subcloning of each variable chain into plasmids containing the respective feline heavy or kappa constant region, plasmids were co-transfected for antibody expression in HEK 293 cells. Initial attempts at felinization of antibody 11E12 focused on utilization of a single feline VH framework (SEQ ID NO: 111; FEL_11E12_VH1) the corresponding nucleotide sequence for which is (SEQ ID NO: 112; FEL_11E12_VH1) paired independently with VL frameworks (SEQ ID NO: 113; FEL_11E12_VL1) the corresponding nucleotide sequence for which is (SEQ ID NO: 114; FEL_11E12_VL1) and (SEQ ID NO: 115; FEL_11E12_VL2) the corresponding nucleotide sequence for which is (SEQ ID NO: 116; FEL_11E12_VL2) to form Feline 11 E12 1.1 and Feline 11 E12 1.2 respectively. This attempt at speciation resulted in a loss of affinity with Feline 11E12 1.1 to both the feline and canine IL-31 proteins and a total loss of binding with the Feline 11E12 1.2 mAb when compared to the mouse form of the antibody (FIG. 2, Section B). Potency of these speciated antibodies was tested in the canine DH82 and Feline FCWF4 cell assays using the feline IL-31 cytokine. Felinized 11E12 1.1 had approximately a two-fold decrease in potency against feline IL-31 in the feline FCWF assay when compared to the mouse version of the antibody. In agreement with the loss of affinity for felinized 11E12 1.2, a complete loss of cellular potency was observed for this antibody (FIG. 3). Based on previous experience during caninization of the mAb 11E12 ortholog, a similar strategy was undertaken in attempt to restore the affinity loss to felinization (U.S. Pat. No. 8,790,651 to Bammert, et al.). Substitution of the felinized framework 2 (FW2) region of Feline 11E12 VL1 with the mouse FW2 from (SEQ ID NO: 73; Mu_11E12_VL) the corresponding nucleotide sequence for which is (SEQ ID NO: 74; Mu_11E12_VL) was done to generate Feline 11E12 VL1 FW2. In addition, a single substitution at position 46 of the feline VL (K46Q) was performed to generate (SEQ ID NO: 119; FEL_11E12_VL1_K46Q) the corresponding nucleotide sequence for which is (SEQ ID NO: 120; FEL_11E12_VL1_K46Q).

Pairing of the above VLs with Fel_11E12_VH1 resulted in Feline 11E12 1.1 FW2 and Feline 11E12 1.1 K460 respectively. Changing FW2 resulted in a restoration of affinity for Feline 11E12 1.1 FW2 to the feline IL-31 protein resulting in a KD equivalent to that of the mouse and chimeric form (FIG. 2, Sections A and B). These changes however had a detrimental effect on Feline 11 E12 1.1 FW2s affinity to the canine IL-31 protein indicating a clear distinction in the nature of antibody 11E12s ability to bind this epitope on the feline and canine cytokine. The single amino acid substitution in Feline 11E12 1.1K460 was unable to influence affinity of this antibody. Increased affinity of antibody 11 E12 1.1 FW2 for the feline IL-31 protein resulted in increased potency against the feline cytokine in the canine DH82 assay (FIG. 3).

Felinization efforts with mouse antibody 15H05 focused on the combinations of three feline VH frameworks with three feline VL frameworks for a total of 9 felinized mAbs. FEL_15H05_VH1 (SEQ ID NO: 121; FEL_15H05_VH1) the corresponding nucleotide sequence for which is (SEQ ID NO: 122; FEL_15H05_VH1) was combined with (SEQ ID NO: 127; FEL_15H05_VL1) the corresponding nucleotide sequence for which is (SEQ ID NO: 128; FEL_15H05_VL1), (SEQ ID NO: 129; FEL_15H05_VL2) the corresponding nucleotide sequence for which is (SEQ ID NO: 130; FEL_15H05_VL2), and (SEQ ID NO: 131; FEL_15H05_VL3) the corresponding nucleotide sequence for which is (SEQ ID NO: 132; FEL_15H05_VL3) to create Feline 15H05 1.1, Feline 15H05 1.2, and Feline 15H05 1.3 respectively. FEL_15H05_VH2 (SEQ ID NO: 123; FEL_15H05_VH2) the corresponding nucleotide sequence for which is (SEQ ID NO: 124; FEL_15H05_VH2) was combined with (SEQ ID NO: 127; FEL_15H05_VL1) the corresponding nucleotide sequence for which is (SEQ ID NO: 128; FEL_15H05_VL1), (SEQ ID NO: 129; FEL_15H05_VL2) the corresponding nucleotide sequence for which is (SEQ ID NO: 130; FEL_15H05_VL2), and (SEQ ID NO: 131; FEL_15H05_VL3) the corresponding nucleotide sequence for which is (SEQ ID NO: 132; FEL_15H05_VL3) to create Feline 15H05 2.1, Feline 15H05 2.2, and Feline 15H05 2.3 respectively. FEL_15H05_VH3 (SEQ ID NO: 125; FEL_15H05_VH3) the corresponding nucleotide sequence for which is (SEQ ID NO: 126; FEL_15H05_VH3) was combined with (SEQ ID NO: 127; FEL_15H05_VL1) the corresponding nucleotide sequence for which is (SEQ ID NO: 128; FEL_15H05_VL1), (SEQ ID NO: 129; FEL_15H05_VL2) the corresponding nucleotide sequence for which is (SEQ ID NO: 130; FEL_15H05_VL2), and (SEQ ID NO: 131; FEL_15H05_VL3) the corresponding nucleotide sequence for which is (SEQ ID NO: 132; FEL_15H05_VL3) to create Feline 15H05 3.1, Feline 15H05 3.2, and Feline 15H05 3.3 respectively. Similar to observations with antibody 11E12, the first attempt at felinization of antibody 15H05 resulted in a loss of affinity to the feline IL-31 protein when compared to mouse 15H05 and a neutral affect when compared to the 15H05 mouse feline chimera (FIG. 2, Sections A and C). Similar to observations with felinized antibody 11E12 binding to canine IL-31, certain combinations of feline 15H05_VH and VL frameworks had a neutral to positive impact on affinity to canine IL-31 (See FIG. 2, Section C Feline 15H05 1.1, 2.2, and 3.2).

In an effort to restore the affinity of felinized antibody 15H05, each felinized 15H05_VH was paired with the mouse 15H05_VL to generate heterochimeric antibodies. FEL_15H05_VH1 (SEQ ID NO: 121; FEL_15H05_VH1) the corresponding nucleotide sequence for which is (SEQ ID NO: 122; FEL_15H05_VH1) was combined with MU_15H05_VL (SEQ ID NO: 69; MU_15H05_VL) the corresponding nucleotide sequence for which is (SEQ ID NO: 70; MU_15H05_VL) to generate Feline 15H05_VH1 mouse VL. FEL_15H05_VH2 (SEQ ID NO: 123; FEL_15H05_VH2) the corresponding nucleotide sequence for which is (SEQ ID NO: 124; FEL_15H05_VH2) was combined with MU_15H05_VL (SEQ ID NO: 69; MU_15H05_VL) the corresponding nucleotide sequence for which is (SEQ ID NO: 70; MU_15H05_VL) to generate Feline 15H05 VH2 mouse VL. FEL_15H05_VH3 (SEQ ID NO: 125; FEL_15H05_VH3) the corresponding nucleotide sequence for which is (SEQ ID NO: 126;

FEL_15H05_VH3) was combined with MU_15H05_VL (SEQ ID NO: 69; MU_15H05_VL) the corresponding nucleotide sequence for which is (SEQ ID NO: 70; MU_15H05_VL) to generate Feline 15H05_VH3 mouse VL. These felinized VH mouse VL heterochimeras were analyzed for their affinity to canine and feline IL-31. Pairing of felinized 15H05_VH1 and VH3 with mouse 15H05_VL restored the affinity to feline IL-31 to equivalent or better than the mouse and chimeric forms. This trend in improved affinity was also observed to the canine IL-31 protein (FIG. 2, Sections A and C).

To further dissect the positions in the 15H05 frameworks responsible for affinity loss, a single felinized VH of 15H05 (FEL_15H05_VH1) was used to pair with individual framework substitutions from mouse 15H05_VL. FEL_15H05_VH1 (SEQ ID NO: 122; FEL_15H05_VH1) the corresponding nucleotide sequence for which is (SEQ ID NO: 123; FEL_15H05_VH1) was combined independently with FEL_15H05_VL1_FW1 (SEQ ID NO: 133; FEL_15H05_VL1_FW1) the corresponding nucleotide sequence for which is (SEQ ID NO: 134; FEL_15H05_VL1_FW1), FEL_15H05_VL1_FW2 (SEQ ID NO: 135; FEL_15H05_VL1_FW2) the corresponding nucleotide sequence for which is (SEQ ID NO: 136; FEL_15H05_VL1_FW2), and FEL_15H05_VL1_FW3 (SEQ ID NO: 137; FEL_15H05_VL1_FW3) the corresponding nucleotide sequence for which is (SEQ ID NO: 138; FEL_15H05_VL1_FW3) to create Feline 15H05 1.1 FW1, Feline 15H05 1.1 FW2, and Feline 15H05 1.1 FW3 respectively. Substitution of mouse 15H05 FW1 onto Feline 15H05 1.1 was detrimental to the affinity to both feline and canine IL-31, however, when mouse FW2 or FW3 were substituted on Feline 15H05 1.1, excellent affinity was achieved to canine and feline IL-31 with the FW2 being superior for both species (FIG. 2, Section C). Additional pairwise framework substitutions were performed to determine the extent of affinity modulation by this approach. FEL_15H05_VH1 (SEQ ID NO: 121; FEL_15H05_VH1) the corresponding nucleotide sequence for which is (SEQ ID NO: 122; FEL_15H05_VH1) was combined independently with FEL_15H05_VL1_FW1_2 (SEQ ID NO: 139; FEL_15H05_VL1_FW1_FW2) the corresponding nucleotide sequence for which is (SEQ ID NO: 140; FEL_15H05_VL1_FW1_FW2), FEL_15H05_VL1_FW2_3 (SEQ ID NO: 143; FEL_15H05_VL1_FW2_FW3) the corresponding nucleotide sequence for which is (SEQ ID NO: 144; FEL_15H05_VL1_FW2_FW3), and FEL_15H05_VL1_FW1_3 (SEQ ID NO: 141; FEL_15H05_VL1_FW1_FW3) the corresponding nucleotide sequence for which is (SEQ ID NO: 142; FEL_15H05_VL1_FW1_FW3) to give Feline 15H05 1.1_FW1_2, Feline 15H05 1.1 FW2_3, and Feline 15H05 1.1 FW1_3 respectively. Interestingly, the substitution of mouse FW1 alone was detrimental to affinity while combinations of FW1 with FW2 or FW3 resulted in good affinity to both feline and canine IL-31 (FIG. 2, Section C).

Finally an attempt was made to minimize the number of backmutations in the feline frameworks beginning with the most promising combinations of felinized VH and VL sequences. For this, FEL_15H05_VH1 (SEQ ID NO: 121; FEL_15H05_VH1) the corresponding nucleotide sequence for which is (SEQ ID NO: 122; FEL_15H05_VH1) was combined independently with FEL_15H05_VL1_FW2_K42N (SEQ ID NO: 145; FEL_15H05_VL1_FW2_K42N) the corresponding nucleotide sequence for which is (SEQ ID NO: 146; FEL_15H05_VL1_FW2_K42N), FEL_15H05_VL1_FW2_V43I (SEQ ID NO: 147; FEL_15H05_VL1_FW2_V43I) the corresponding nucleotide sequence for which is (SEQ ID NO: 148; FEL_15H05_VL1_FW2_V43I), FEL_15H05_VL1_FW2_L46V (SEQ ID NO: 149; FEL_15H05_VL1_FW2_L46V) the corresponding nucleotide sequence for which is (SEQ ID NO: 150; FEL_15H05_VL1_FW2_L46V), FEL_15H05_VL1_FW2_Y49N (SEQ ID NO: 151; FEL_15H05_VL1_FW2_Y49N) the corresponding nucleotide sequence for which is (SEQ ID NO: 152; FEL_15H05_VL1_FW2_Y49N), and FEL_15H05_VL1_FW2_K42N_V43I (SEQ ID NO: 153; FEL_15H05_VL1_FW2_K42N_V43I) the corresponding nucleotide sequence for which is (SEQ ID NO: 154; FEL_15H05_VL1_FW2_K42N_V43I) to give Feline 15H05 1.1 K42N, Feline 15H05 1.1 V43I, Feline 15H05 1.1 L46V, Feline 15H05 1.1 Y49N, and Feline 15H05 1.1K42N_V43I respectively. While the substitution of the entire mouse FW2 framework onto Felinized 15H05_VL1 resulted in an antibody with excellent affinity to canine and feline IL-31 (FIG. 2, Section C, Feline 15H05 1.1 FW2), the individual backmutations of FW2 amino acid residues had a neutral or detrimental effect indicating all 4 substitutions are necessary to maintain the optimal tertiary structure for positioning of the CDRs on the IL-31 epitope. Increased affinity of felinized 15H05 1.1 FW2 to feline and canine IL-31 lead to the selection of this antibody for further work.

Figure 5B:
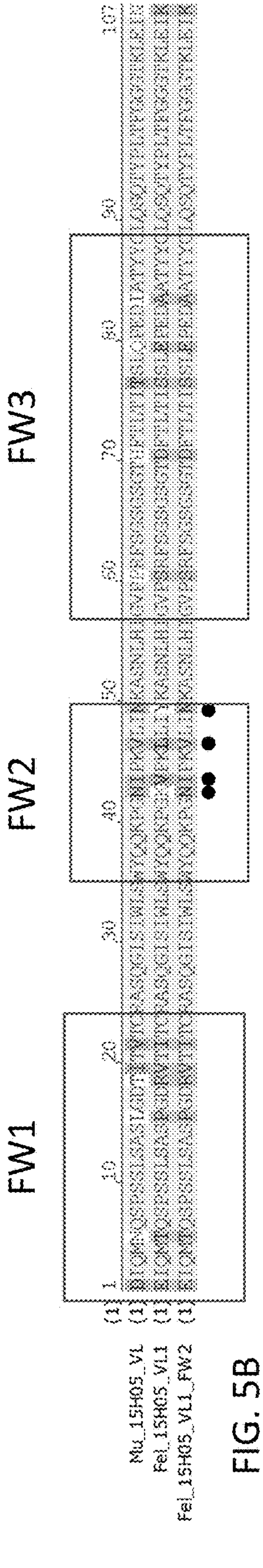
FIG. 5B shows an alignment of the mouse antibody 15H05 VL sequence designated herein as MU_15H05_VL (SEQ ID NO: 69) with the felinized 15H05 VL sequences designated herein as FEI_15H05_VL1 (SEQ ID NO: 127) and FEI_15H05_VL FW2 (SEQ ID NO: 135). The dots below the alignment in FIG. 5B indicate the necessary changes to the felinized 15H05_VL (Fel_15H05_VL1) that were required to not only restore, but improve, its affinity to canine and feline IL-31 when compared to the mouse and chimeric forms of this antibody.

FIG. 5A shows an alignment of mouse antibody 11 E1 2 VL sequence comparing previously referenced caninized 11E12 sequence to the felinized versions. Noted below the alignment are dots showing the positions of relevant changes to Fel_11E12_VL1 that were necessary to restore affinity of this antibody to the IL-31 protein. Likewise FIG. 5B shows the necessary changes to the felinized 15H05_VL (Fel_15H05_VL1) that were required to not only restore, but improve, its affinity to canine and feline IL-31 when compared to the mouse and chimeric forms of this antibody.

1.9. Generation of Cell Lines Expressing Felinized Anti IL-31 Antibodies from Glutamine Synthetase (GS) Plasmids Felinized 15H05 1.1 FW2 was chosen as a candidate for the generation of stable cell lines that will produce a homogenous supply of the antibody for further characterization. The genes encoding the felinized heavy and light chains for cell line production were cloned into GS plasmids pEE 6.4 and pEE 12.4 respectively (Lonza, Basel, Switzerland). The resulting plasmids were digested according to the manufacturer's protocol and ligated together to form a single mammalian expression plasmid. For ZTS-927, the heavy chain is (SEQ ID NO: 121; FEL_15H05_VH1) the corresponding nucleotide sequence for which is (SEQ ID NO: 122; FEL_15H05_VH1) combined with feline IgG heavy chain constant (SEQ ID NO: 171; Feline_HC_AlleleA_wt) the corresponding nucleotide sequence for which is (SEQ ID NO: 172; Feline_HC_AlleleA_wt). For ZTS-927, the light chain is (SEQ ID NO: 135; FEL-15H05-VL1_FW2) the corresponding nucleotide sequence for which is (SEQ ID NO: 136; FEL-15H05-VL1_FW2) combined with feline IgG light chain constant (SEQ ID NO: 175; Feline_LC_Kappa_G_minus) the corresponding nucleotide sequence for which is (SEQ ID NO: 176; Feline_LC_Kappa_G_minus). For ZTS-361, the heavy chain is (SEQ ID NO: 121; FEL_15H05_VH1) the corresponding nucleotide sequence for which is (SEQ ID NO: 122; FEL_15H05_VH1) combined with feline IgG heavy chain constant (SEQ ID NO: 173; Feline_HC_AlleleA_1) the corresponding nucleotide sequence for which is (SEQ ID NO: 174; Feline_HC_AlleleA_1). For ZTS-361, the light chain is (SEQ ID NO: 135; FEL-15H05-VL1_FW2) the corresponding nucleotide sequence for which is (SEQ ID NO: 136; FEL-15H05-VL1_FW2) combined with feline IgG light chain constant (SEQ ID NO: 175; Feline_LC_Kappa_G_minus) the corresponding nucleotide sequence for which is (SEQ ID NO: 176; Feline_LC_Kappa_G_minus).

To demonstrate transient production of antibody, each plasmid was used to transfect HEK 293 cells and expression was carried out in various size cultures. Protein was isolated from conditioned HEK medium using Protein A affinity chromatography according to standard protein purification methods. Medium was loaded onto chromatographic resin and eluted by pH shift. Eluted protein was pH adjusted, dialyzed, and sterile filtered prior to use. ZTS-361 was subsequently used for evaluation in the cat pruritus model to evaluate in vivo efficacy. Antibodies produced from a single GS plasmid, ZTS-927 and ZTS-361, were tested for affinity and potency. FIG. 2, Section D shows the results for the affinity assessment of these antibodies using biacore. The affinity of ZTS-927 and ZTS-361 to feline IL-31 is highly consistent with that of the mouse and chimeric form of the progenitor mouse mAb 15H05. The potency of these two antibodies was determined against canine and feline IL-31 using both canine and feline cell assays (FIG. 3). Consistent with previous observations the IC50 values were proportionally higher when using the canine form of IL-31 with both cell types. The IC50 values for ZTS-927 and ZTS-361 against feline IL-31 were also highly consistent with values derived from the chimeric and mouse form of the antibody indicating the final felinized version of mAb 15H05 produced form a single GS plasmid was suitable for cell line development.

For generation of a stable cell line producing candidate antibodies, the GS plasmid was linearized prior to transfection with the restriction enzyme, PvuI, which cuts at a single site in the plasmid backbone. GS-CHOK1SV (clone 144E12) cells were transfected with linearized plasmid DNA via electroporation. Following transfection, cells were plated in 48-well plates (48WP) in order to generate stable pools. When pools were at least 50% confluent in the 48 WPs, 100 μl of supernatant was analyzed for IgG expression using the ForteBio Octet and protein A biosensors (Pall ForteBio, Fremont, Calif.). The best expressing clones were scaled up into 6 well-plates (6 WP) and then into 125 mL shake flasks (SF). Once cells adapted to suspension culture in 125 mL flasks, 2 vials of each cell line pool were banked for LN storage. Since manufacturing cell lines must be clonal, the top 3 highest expressing pools were subcloned by limiting dilution in 96 well culture plates. In order to prove clonality and avoid a second round of limiting dilution, 96 well plates were imaged using Molecular Devices Clone-Select Imager (CSI) (Molecular Devices LLC, San Jose, Calif.) which captures images of single-cells and their subsequent growth. Clones were selected based on successful CSI images, growth and production in 96 WPs.

In order to assess cell culture growth and productivity, the top expressing pools were further evaluated in a 14-day fed batch in 125 mL SFs. Cells were seeded in platform media and feeds consisting of Life Technologies' CD CHO plus 4 amino acids, proprietary feed CDF v6.2, and 10% glucose. Following the 14-day Fed-Batch, pools were centrifuged and the CD CHO produced mAB was isolated by filtering the supernatant via a 0.20 μm Polyethersulfone (PES) membrane prior to purification.

A typical purification consists of two liters of conditioned medium (from CHO cell culture, 0.2 μm filtered) loaded onto a 235 mL column of MabSelect (GE healthcare, cat #17-5199-02). The column had been pre-equilibrated with PBS. The sample was loaded at a residence time of >2.5 minutes. Following load, the column was washed again with PBS, and then with 25 mM sodium acetate, pH neutral. The column was eluted with 25 mM acetic acid, pH 3.6, and then stripped with 250 mM acetic acid, 250 mM sodium chloride, pH ~2.2. Fractions (50 mL) were collected during the elution and strip steps. UV absorbance at A280 was monitored throughout. Peak fractions were pooled, pH adjusted to ~5.5 with the addition of 20 mM sodium acetate, and then dialyzed against three exchanges of buffer. The dialysate was collected, sterile filtered, and stored at 4° C.

1.10. Identification of the Epitope on IL-31 Recognized by Antibody 15H05

Knowledge of the epitope on IL-31 that is recognized by an antibody is critical to understanding the mechanism by which it neutralizes the cytokine from binding to the IL-31Ra: OSMR co-receptor. In addition, knowing the epitope enables (but is not limited to) optimization of antibody binding affinity and design of peptide epitope mimetics (mimotopes) which can have great utility as analytical capture reagents and as a subunit vaccines to elicit a relevant focused immune response. A multistep process using CLIPS (Chemical Linkage of Peptides onto Scaffolds) technology (Timmerman et al. J Mol Recognit. 2007; 20(5): 283-299) was used to identify and optimize a peptide capable of binding to the paratope of mAb 15H05 (Pepscan, Lelystad Netherlands). The affinity of mAb 15H05 to both canine and feline IL-31 proteins is high (FIG. 2, MU-15H05) so the primary sequence of both IL-31 species was considered relevant to this effort. A peptide microarray library representing the canine IL-31 protein was created and used to identify peptides capable of binding mAb 15H05 using an indirect ELISA. Following identification of peptides whose primary amino acid sequences represent the binding region of mAb 15H05 on IL-31, a focused full replacement analysis was performed using peptides representing a segment of IL-31 and replacing each of the 12 amino acids in this mAb 15H05 binding region with the 19 other possible amino acid residues at each position. This analysis was essential to identify the key amino acid residues on IL-31 involved with mAb 15H05 binding and also demonstrated where substitutions on the canine primary sequence lead to an enhancement of antibody binding.

The amino acids on the canine IL-31 protein that are recognized by antibody 11 E1.2 were described previously (U.S. Pat. No. 8,790,651 to Bammert, et al.). Therein were described the mutational analysis of the canine IL-31 protein showing positions on the canine IL-31 protein that affect binding of mAb 11 E1.2 when converted to alanine. Based on the full replacement analysis described for mAb 15H05 above and previous knowledge of the binding epitope of 11 E1.2, mutant forms of the feline IL-31 protein were created by substituting alanine for two key residues on the epitope recognized by each antibody (mutants described in section 1.2 above). Mutations for each epitope were named according to the antibody that recognizes the site of the mutation (mutant 11 E1.2 and 15H05 vs. the native wt protein sequence).

FIG. 6A shows the alignment of wildtype feline IL-31 (SEQ ID NO: 157) with mutants 15H05 (SEQ ID NO: 163) and 11E12 (SEQ ID NO: 161) highlighting the positions where the alanine substitutions occur. IL-31 belongs to the IL-6 family of cytokines with the four helical bundles possessing an up and down architecture (CATH database, Dawson et al. 2017 Nucleic Acids Res. 2017 Jan. 4; 45

Figure 6B:
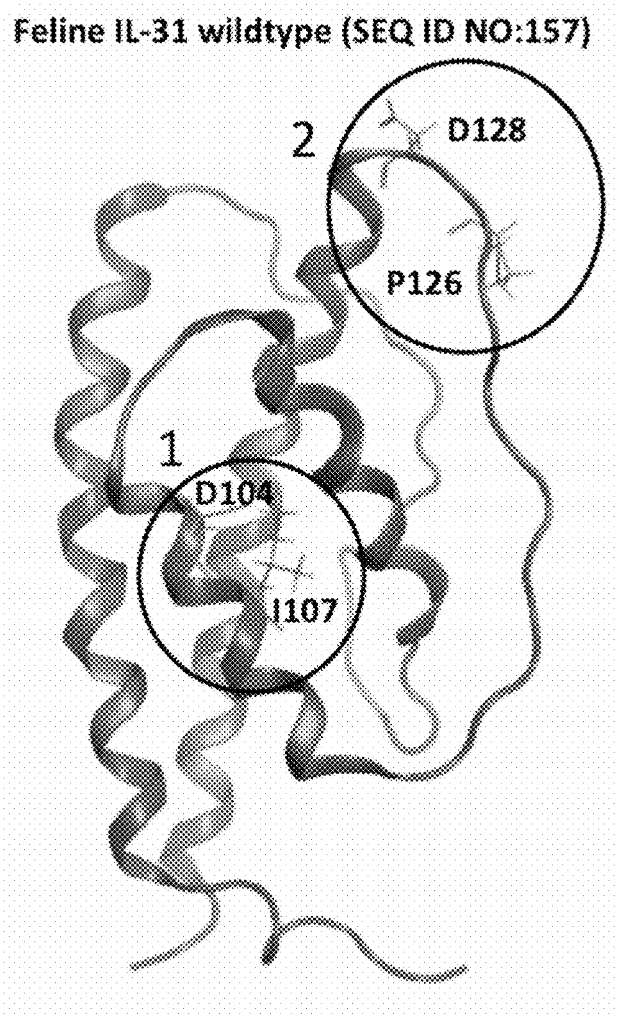
FIG. 6B shows the feline IL-31 homology model highlighting the positions of two amino acids involved with binding of antibodies 11E12 (site 1) and 15H05 (site 2).

(Database issue): D289-D295). A homology model was generated based on the human IL-6 structure 1 P9M (Boulanger et al. 2003 Science. Jun. 27; 300(5628):2101-4) using the MOE software (Chemical Computing Group, Montreal, QC, Canada). FIG. 6B shows the feline IL-31 homology model highlighting the positions of the amino acids involved with binding of antibodies 11 E1.2 (site 1) and 15H05 (site 2). The binding sites for each antibody appear to be located at separate positions on the IL-31 protein.

Figure 6C:
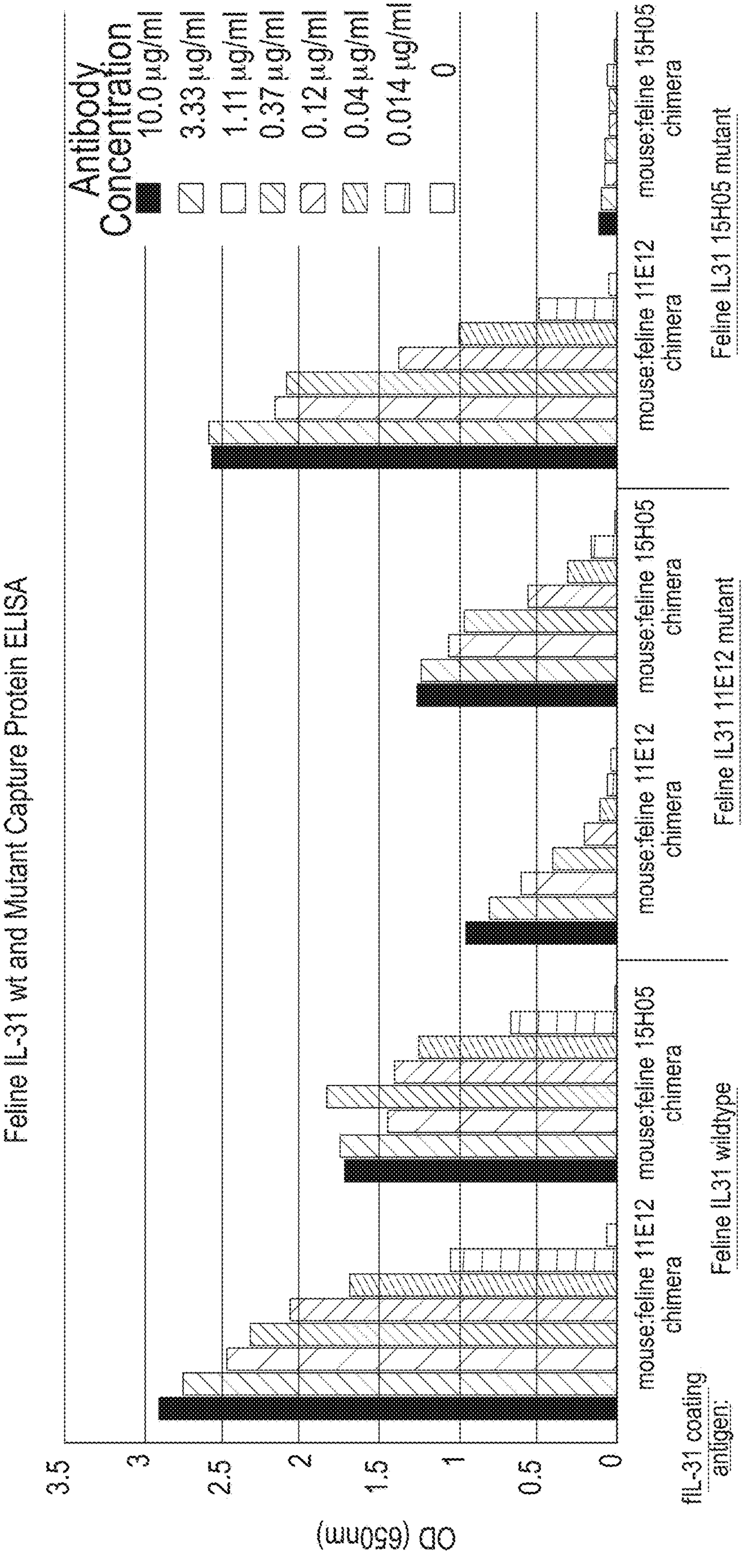
FIG. 6C is a graph showing the results obtained for binding of monoclonal antibodies 11E12 and 15H05 to wild-type feline IL-31 and to mutant IL-31 proteins 15H05 (SEQ ID NO: 163) and 11E12 (SEQ ID NO: 161) when the wild-type and these mutants are used as the coating antigens.

To determine the impact of mAbs 11E12 and 15H05 ability to bind these mutant forms of feline IL-31, an indirect ELISA was run using the mutants directly coated on to an immunoassay plate. FIG. 6C shows the results for this ELISA demonstrating that mAbs 11E1.2 and 15H05 are capable of binding to wildtype feline IL-31 in this assay format. When mutant 11E12 is used as a capture protein, binding of mAb 11E12 is highly attenuated and binding of mAb 15H05 is partially attenuated. Previous analysis of the 11 E12 epitope on canine IL-31 (described in U.S. Pat. No. 8,790,651 to Bammert et al.) indicated that 4 amino acid residues impact binding of the mAb when mutated to alanine so the mutation of 2 residues, in this case, may not be enough to completely eliminate the high affinity binding of mAb 11E12 using this ELISA format. The minor attenuation of mAb 15H05s binding to the 11E12 mutant is likely due to translational effects of the mutations from movement of the two front helices effecting the 15H05 binding site. The mutations designed to affect mAb 15H05s binding (mutant 15H05) show a complete loss of mAb 1505s ability to bind this IL-31 mutant by ELISA. Unlike the 11E12 mutant, the changes in the random coil recognized by mAb 15H05 (mutant 15H05) had no impact on mAb 11E12 binding further supporting the distinction between the two epitopes (FIG. 6C).

1.11. Competition Binding Assessment of mAbs 15H05 and 11E12 Using Biacore

Figure 7A:
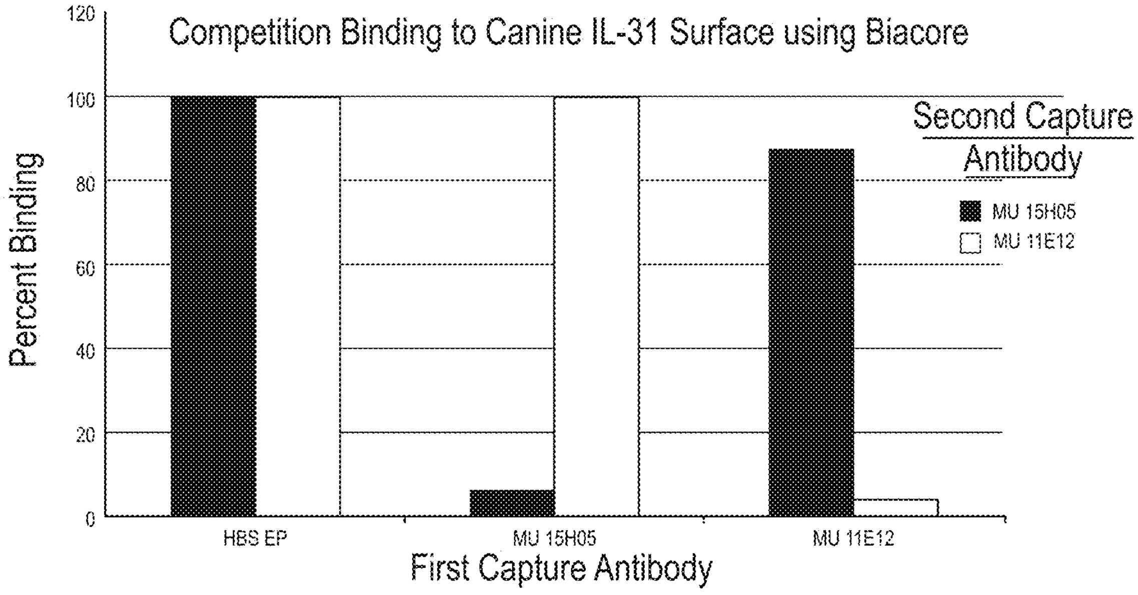
FIGS. 7A and 7B are of graphs showing competition binding assessments of mAbs 15H05 and 11E12 using Biacore.
Figure 7B:
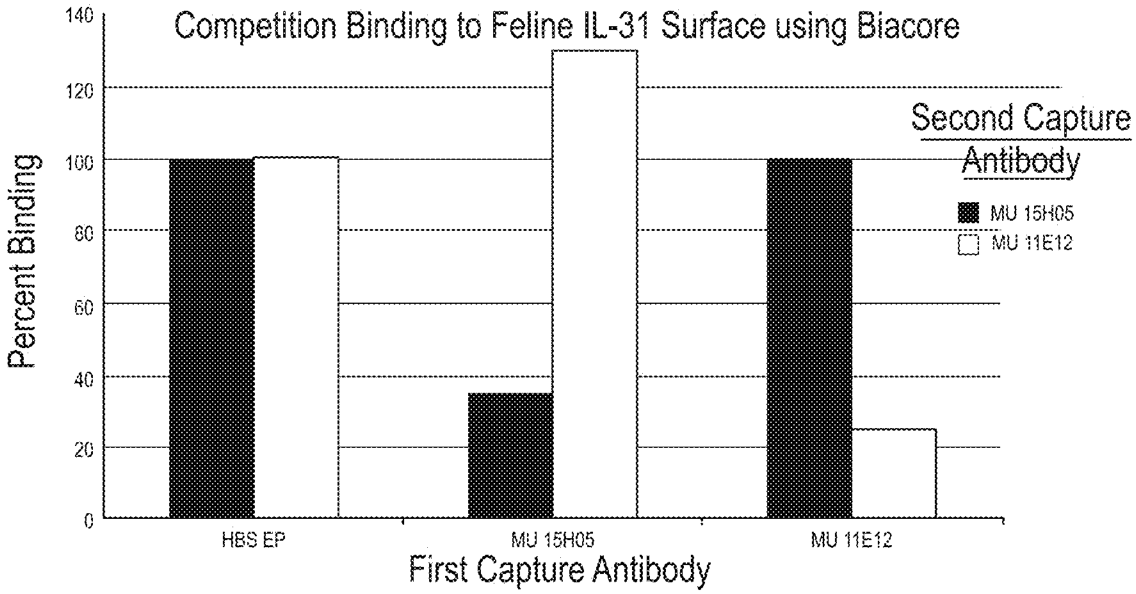

To further characterize the IL-31 epitopes bound by mAbs 15H05 and 11 E12, blocking experiments were performed using biacore where the surface containing the IL-31 protein was generated followed by sequential addition of antibodies. FIGS. 7A and 7B show the relative binding of each antibody to IL-31 following capture of 11E12 or 15H05. The columns labeled HBS-EP (assay buffer) indicate the maximum signal obtained from each antibody binding to the IL-31 surface alone without competition. FIG. 7A shows the competition binding data for mouse 15H05 and 11 E12 antibodies to canine IL-31. These results clearly indicate that antibodies 15H05 and 11E12 are capable of binding to canine IL-31 in the presence of one another indicating they recognized distinct epitopes on the protein. The sensograms related to FIG. 7A show the disassociation kinetics of both antibodies are very slow on this newly formed biacore surface therefore no additional occupation of binding sites can occur with addition of the same antibody (data not shown).

FIG. 7B shows the competition binding data for antibodies 15H05 and 11E12 on a feline IL-31 surface again showing no overlap in the epitope recognized. Binding of additional antibody in the presence of the same antibody is a result of the increased off rate due to the poorer quality of the surface used. Increased off rates can be seen and compared to the KD values from newly formed feline IL-31 surfaces in FIG. 2.

These results further support the epitope mapping data in section 1.10 indicating a distinct epitope is recognized by the CDRs contained in antibody MU-15H05 when compared to MU-11E12. The epitope recognized by antibody 15H05 is distinct from antibody 11E12 described in (U.S. Pat. No. 8,790,651 to Bammert, et al.) and is a novel target on the IL-31 protein for neutralization of this cytokines activity in multiple species. These findings highlight the distinct spatial relationship of binding sites described in the feline IL-31 homology model (FIG. 6B) and support the hypothesis that this face of the cytokine is critical for interaction with the IL-31 Ra:OSMR receptor complex.

1.12. Synthesis and Characterization of Soluble Feline IL-31 Co-Receptor (IL-31 RA and OSMR)

The human IL-31 heteromeric receptor co-complex, consisting of IL31Ra and OSMR subunits, was shown to be required for IL31-mediated intercellular activation of the JAK-STAT pathway and having involvement in atopic skin disease (Dillon et al. 2004 Nat Immunol. July; 5(7):752-60, Dreuw et al. 2004 J Biol Chem. 279:36112-36120; and Diveu et al. 2004 Eur Cytokine Netw. 15:291-302). The human IL-31Ra subunit was later described as the initial binding event that occurs when IL-31 is in contact with cell surface receptors and this event is a pre-requisite for the recruitment of OSMR with subsequent formation of a high affinity co-receptor complex (Le Saux et al. 2010 J Biol Chem. Jan. 29; 285(5):3470-7). We describe here evidence that the feline IL-31 protein is capable of binding to both OSMR and the IL-31Ra independently. This observation is novel and has important implications to understanding how the IL-31 protein interacts with the IL-31Ra:OSMR co-receptor and to the biological role of IL-31 as it interacts independently with individual subunits.

To enable understanding of how IL-31 binds to its co-receptor and to characterize the inhibitory properties of identified antibodies, two receptor forms were synthesized. The individual IL-31 receptor subunit IL-31Ra (SEQ ID NO: 169; Feline_IL31Ra_HIgG1_Fc_X1_Fn3) the corresponding nucleotide sequence for which is (SEQ ID NO: 170; Feline_IL31Ra_HIgG1_Fc_X1_Fn3), and OSMR-(SEQ ID NO: 167; Feline_OSMR_hIgG1_Fc) the corresponding nucleotide sequence for which is (SEQ ID NO: 168; Feline_OSMR_hIgG1_Fc) were both constructed as human IgG1 Fc fusions. By homology to the human homologs, the cytokine binding, fibronectin III, and Ig-like domains were identified. To evaluate the individual receptor subunits, the extracellular domains of OSMR and the IL-31Ra (with its expected N-terminal proximal fibronectin III domain) were generated as human IgG1 Fc fusions, both employing their native signal peptides. All synthetic cassettes were cloned into pcDNA3.1, expressed in the ExpiCHO system and purified as described above.

Figure 8:
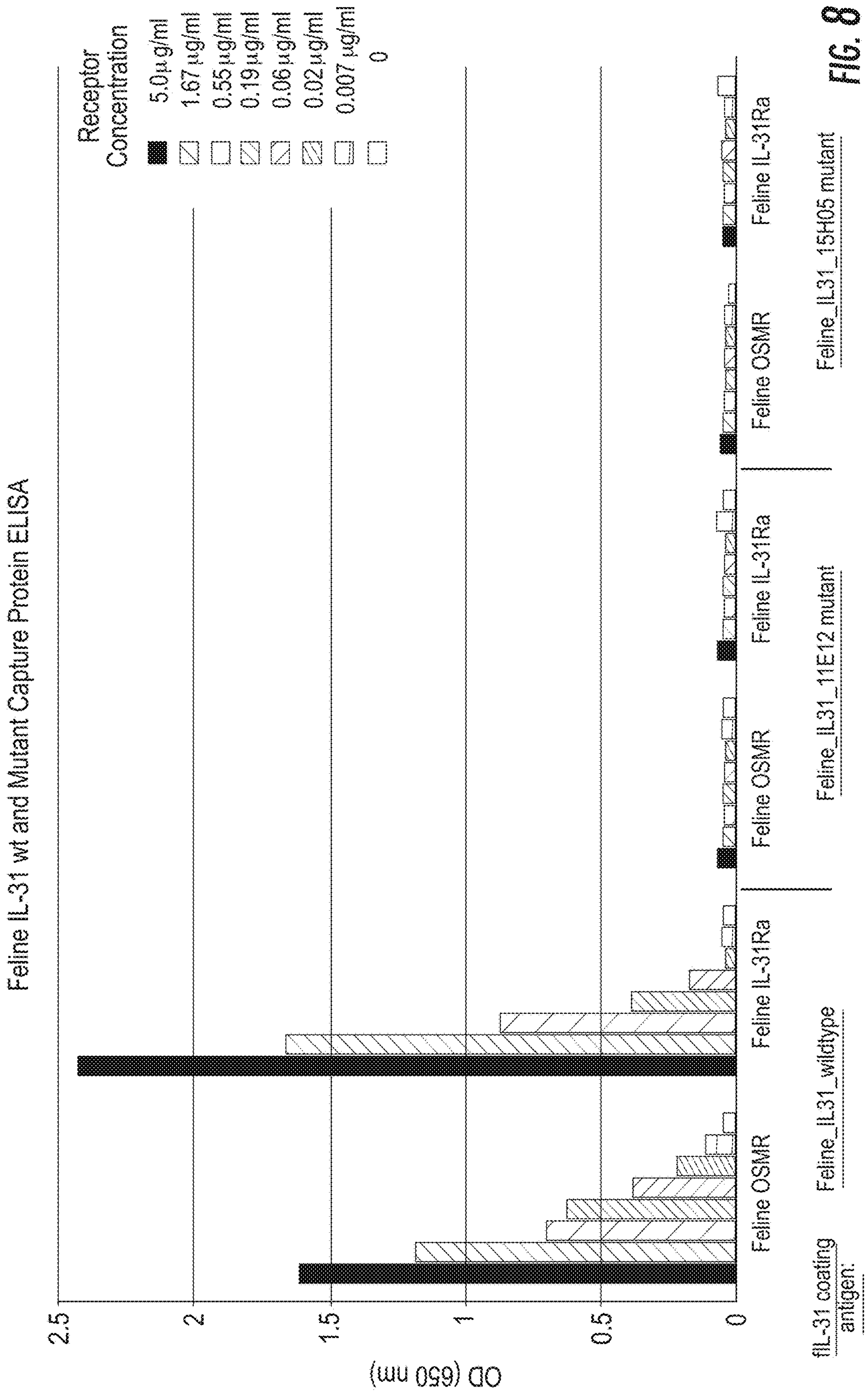
FIG. 8 is of a graph showing the results obtained for binding of the individual receptor subunits of OSMR and IL-31Ra to wild-type feline IL-31 and to mutant IL-31 proteins 15H05 (SEQ ID NO: 163) and 11E12 (SEQ ID NO: 161) when the wild-type and these mutants are used as the coating antigens.

To analyze the ability of these receptor forms to bind wildtype and mutant IL-31 proteins, and indirect ELISA was run by coating 100 ul of each respective protein on an immulon 2HB plate (1 μg/ml) overnight in carb/bicarb buffer (sigma C3041-100CAP) at 4 C. The ELISA plates were then blocked with 5% NFDM blocking buffer in PBST for 1 hour at room temperature followed by binding of multiple concentrations of each receptor construct at room for 1 hour. Following washing with PBST, the presence of the bound receptor (Fc fusion) was identified using mouse anti-human IgG1 (Lifetech A10684, 1:500 dilution) for 1 hour at room temperature. The wells were again washed with PBST and developed with KPL sureblue 3,3',5,5'-tetramethylbenzidine (TMB) microwell substrate. FIG. 8 shows the results for this indirect ELISA using wildtype and mutant forms of the feline IL-31 protein as a capture. These data demonstrate the ability of the wildtype feline IL-31 to independently bind to the IL-31Ra and OSMR receptor subunits. These observations are in contrast to previous reports indicating the IL-31 protein initially binds to the IL-31Ra subunit and further recruits OSMR to the site. As the biological role of IL-31 is still being determined, it is of great importance to understand the dynamics of receptor binding and the potential consequences to attenuation of its role in diseases such as atopic dermatitis. For this reason, consideration was further given to these observations when characterizing antibodies the bind to epitopes capable of disrupting the ability of IL-31 to recognize IL-31Ra and OSMR.

In section 1.2 we describe the attenuated binding of antibodies 11E12 and 15H05 to mutants with key amino acids in their binding sites converted to alanine (mutant 11E12 and 15H05 respectively). It was therefore of great interest to understand the impact of these mutations on the ability to bind to the individual IL-31Ra and OSMR receptor subunits. FIG. 8 shows that mutation in either the 11E12 or 15H05 binding site completely disrupts IL-31Ra and OSMRs ability to bind indicating both antibodies bind epitopes that are necessary for interaction of IL-31 with both receptor subunits. Lack of binding could also be due to changes in the confirmation of IL-31 resulting from mutation however these mutants are still capable of binding to antibody which suggests this is not the case. This key finding supports the ability of both antibodies 11E12 and 15H05 (and derivatives) recognizing epitopes on IL-31 that neutralize the cytokines ability to signal through its co-receptor and further block cell association of the cytokine to either receptor during this process. These data support the identification of antibodies that are capable of removing IL-31 from circulation and rendering it unable to bind to cell surface or soluble receptor forms.

1.13. In Vivo Evaluation of Chimeric Antibodies in a Feline IL-31 Pruritus Challenge Model The ability of an antibody to effectively neutralize its target can be assessed in vitro through examination of binding to a relevant epitope on the target protein with the appropriate affinity and potency in a cell based assays that allow extrapolation to in vivo potency. Described above are the steps taken to characterize two series of antibodies generated from the mouse progenitor mAbs 11E12 and 15H05. Section 1.7 describes the generation of mouse: feline chimeric forms of mAbs 11E12 and 15H05 with a resulting affinity to canine and feline IL-31 that are comparable to the original mouse monoclonal antibody (FIG. 2, Section A). The mouse: feline chimeric forms of 11 E12 and 15H05 also had comparable IC50 values showing inhibition of feline IL-31 induced pSTAT3 signaling in canine and feline macrophage cells (FIG. 3). During the felinization process in section 1.8, mouse mAb 11 E12 was converted to the felinized version (Feline 11E12 1.1) with subsequent loss of affinity to canine and feline IL-31 (FIG. 3) and loss of potency against feline IL-31 signaling in canine and feline cells (FIG. 3). Prior to optimization of the felinized 11 E12 and 15H05 antibodies described in section 1.8, it was of interest to understand the ability of these preliminary felinized and chimeric forms to neutralize the pruritic activity of feline IL-31 in a cat challenge model. Of interest was the pharmacodynamic effect of these different antibodies on neutralization of pruritus and to understand any correlation to affinity, cellular potency, or epitope recognition that may influence efficacy. Going forward a range of cellular potency that correlates to in vivo efficacy in the pruritus challenge model could be predictive of further optimization necessary using in vitro assays.

Figure 9:
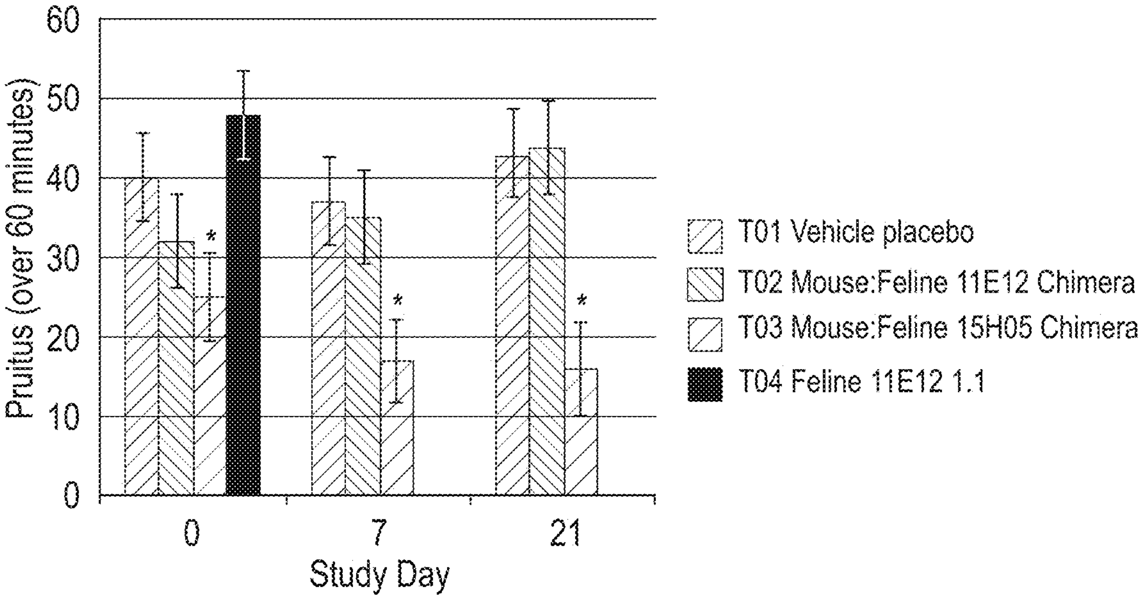
FIG. 9 is of a graph showing the preliminary efficacy of mouse: feline 11E12 chimera, mouse: feline 15H05 chimera, and felinized 11E12 (Feline 11E12 1.1) in an IL-31 induced pruritus model in cats.

To test the preliminary efficacy of mouse: feline 11E12 chimera, mouse: feline 15H05 chimera, and felinized 11 E12 (Feline 11E12 1.1), an IL-31 induced pruritus model in cats was developed. Following an intravenous dose of 0.5 μg/kg feline IL-31 (SEQ ID NO: 159; Feline_IL-31_E_coli), the corresponding nucleotide sequence for which is (SEQ ID NO: 160; Feline_IL-31_E_coli), cats will portray transient pruritic behavior that includes (but is not limited to) licking, chewing, scratching, and head or body shaking. Rubbing up against the cage was not considered a pruritic activity. Pruritic observations take place by a trained investigator for 30 minutes prior to administration of the IL-31 protein and for 1 hour following. For this study, a baseline challenge with feline IL-31 was performed up to 1 month prior to dosing with antibody. On day zero, a 0.5 mg/kg antibody dose was combined with 0.5 μg/kg of feline IL-31 at room temperature for 60 minutes prior to injecting the pre-bound complex into each animal. A "no mAb" control was included for a control. The dose of mAb represents a gross molar excess of antibody to cytokine. Pruritic activity was monitored as described on days 0, 7, and 21. Results in FIG. 9 show significant improvement ($p<0.05$) in pruritus scores with mAb mouse: feline 15H05 chimera at days 0, 7, and 21 when compared to the placebo control. Although the mouse: feline 11 E12 chimera showed an initial trend in efficacy at day zero, it did not achieve a significant reduction in pruritus at any timepoint when compared to vehicle placebo. Feline 11 E12 1.1 did not reduce pruritus at day zero and showed no trend in efficacy when compared to vehicle placebo so further IL-31 challenges on days 7 and 21 were not performed.

Taken together these results show a clear delineation between the activities of these antibodies with the lack of efficacy for feline 11 E1 2 1.1 at preventing pruritic behavior in the cat induced by IL-31. The loss of affinity and potency of feline 11E12 1.1 likely resulted in the lack of in vivo efficacy. When comparing the efficacy outcome of mouse: feline 11E12 chimera and mouse: feline 15H05 chimera the distinction is more subtle. The chimeric forms of both mAbs have a comparable KD value to their mouse progenitor with the affinity of mouse: feline 11E12 being slightly superior to both feline and canine IL-31 (FIG. 2, Section A). This increased affinity however does not translate directly to increased potency as the mouse: feline 15H05 chimera has an approximately 2-fold increased IC50 to that of mouse: feline 11E12 chimera against feline IL-31 induced pSTAT3 signaling in feline FCWF4 cells (FIG. 3). These data suggest that the manner in which antibody 15H05 CDRs recognize feline IL-31 is superior at neutralizing the cytokines ability to signal through its co-receptor in turn making it more effective at blocking pruritus in cats. The differences in IC50s observed in these cellular assays offers a promising means to predict in vivo potency and to discriminate subtle differences in epitope recognition both within and between series of antibodies.

1.14. In Vivo Evaluation of the Efficacy of Felinized 15H05 Anti IL-31 Antibodies in a Cat Pruritus Challenge Model Based on the positive efficacy outcome using the mouse: feline 15H05 chimera described above, further work was done to increase the affinity and potency of felinized 15H05 (described above in section 1.8). Systematic substitution of the variable light chain feline frameworks in antibody feline 15H05 1.1 lead to the identification of Feline 15H05 1.1 FW2 having increased affinity to both feline and canine IL-31 compared to mouse 15H05 (FIG. 2). Combination of the heavy and light chains of Feline 15H05 1.1 FW2 into a single plasmid lead to the formation of ZTS-927 and ZTS-361 antibodies following production from HEK and CHO expression systems. The affinity and potency of both antibodies resulting from expression from a single plasmid are also described in FIGS. 2 and 3 respectively.

Figure 10A:
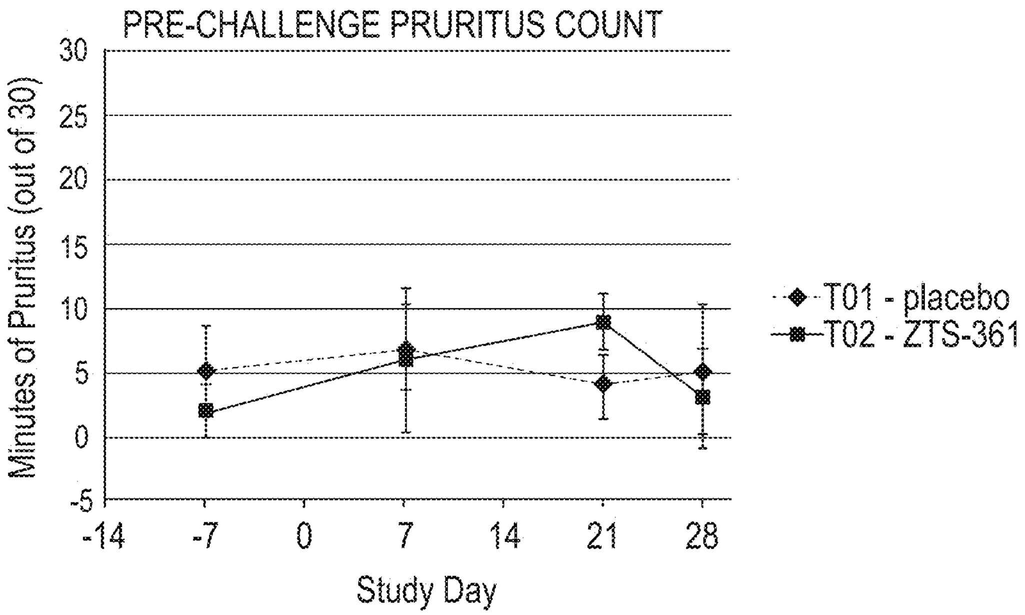
FIGS. 10A and 10B is of graphs showing the In vivo evaluation of the efficacy of a felinized15H05 anti IL-31 antibody termed ZTS-361 in a cat pruritus challenge model.

The efficacy of the fully felinized anti feline IL-31 mAb ZTS-361 was assessed for its ability to neutralize pruritic behavior in an IL-31 induced in vivo cat model. FIG. 10A shows the baseline pre-challenge pruritic behavior for the T01 vehicle placebo and T02 antibody ZTS-361 groups from day −7 through day 28 with day zero being the day of antibody administration to group T02. As shown in this graph, the variance of pruritic behavior scored for both T01 and T02 groups prior to IL-31 challenge varied little with the number of pruritic events observed between 0 and 10 within the 30 minute observation period. This study differed from the preliminary feline challenge model described above in section 1.13 in that on day zero cats were dosed with 4 mg/kg ZTS-361 subcutaneously without combination with feline IL-31 to generate a pre-bound complex. This represents a more rigorous assessment of efficacy as antibody ZTS-361 will be in circulation for seven days prior to the first IL-31 challenge requiring the antibody to have sufficient exposure to bind and neutralize circulating IL-31.

Figure 10B:
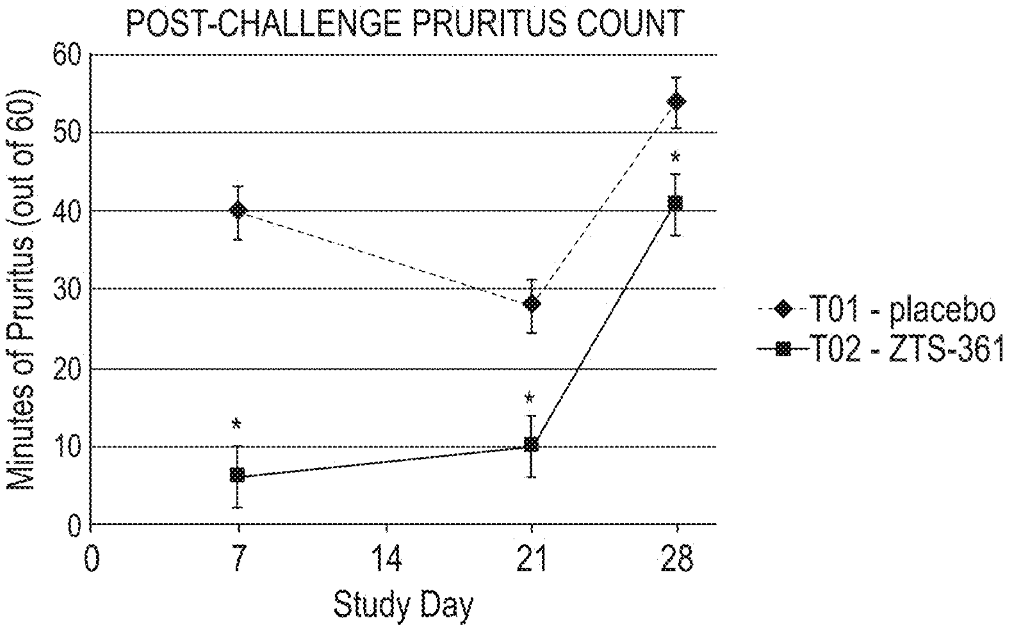

For this study, pruritic behavior was assessed on days 7, 21, and 28 for 1 hour following a 0.5 μg/kg intravenous challenge of the IL-31 protein. FIG. 10B shows the efficacy of antibody ZTS-361 demonstrating a significant reduction in pruritus observed on days 7 ($p<0.0001$), 21 ($p<0.0027$), and 28 ($p<0.0238$) following IL-31 challenge when compared to vehicle placebo control. Data from this challenge model support previous observations demonstrating the efficacy of mouse: feline 15H05 chimera and support the cell-based potency and relevance of the epitope on feline IL-31 recognized by the 15H05 CDRs. These data further support the ability of antibody ZTS-361 to neutralize pruritus induced by feline IL-31 in vivo and suggest this antibody may serve as a therapeutic in the treatment of IL-31 mediated disease in cats including atopic dermatitis.

Figure 11A:
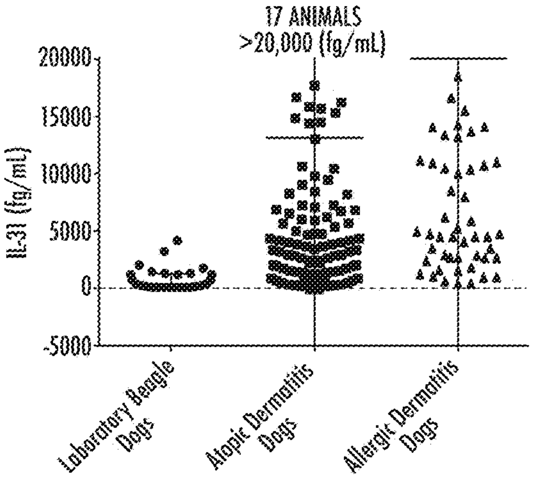
FIG. 11A is of a graph showing the plasma levels of IL-31 in client owned animals among dogs with atopic and allergic dermatitis compared to normal laboratory
Figure 11B:
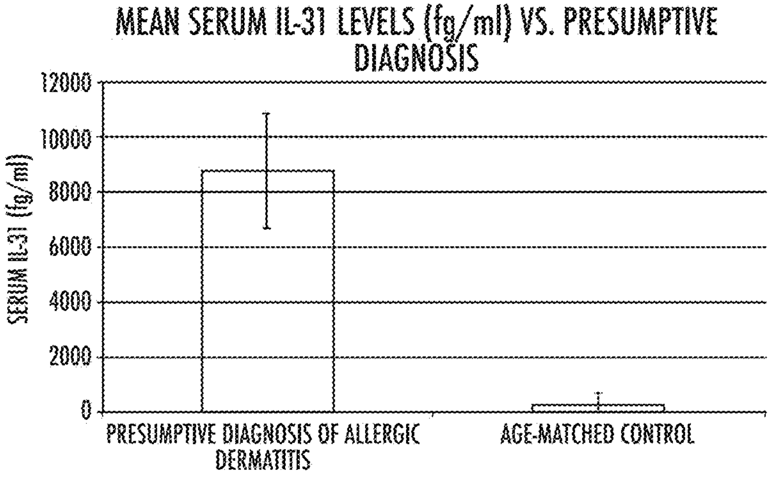
FIG. 11B is of a graph showing the results of a recent study to determine serum IL-31 levels in cats with a presumptive diagnosis of allergic dermatitis (AD) from several different geographic regions in the USA.
Figure 11C:
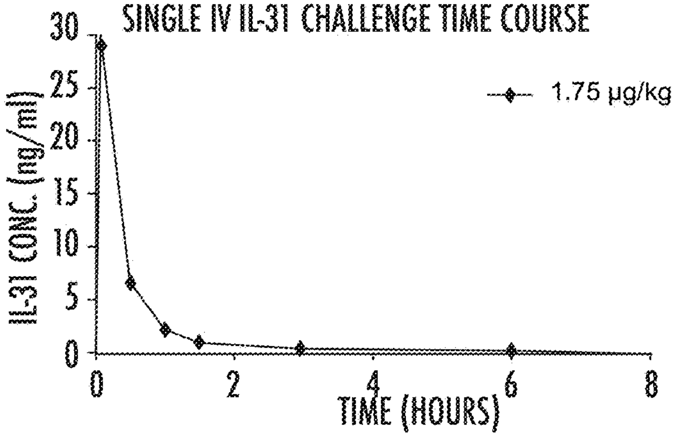

Recent data examining the plasma levels of IL-31 in client owned animals shows an increased amount of the cytokine in circulation among dogs with atopic and allergic dermatitis compared to normal laboratory beagles (FIG. 11A). A recent study was performed to determine serum IL-31 levels in cats with a presumptive diagnosis of allergic dermatitis (AD) from several different geographic regions in the USA. FIG. 11B shows the results from this assessment indicating that, like dogs with atopic and allergic dermatitis, 73 cats surveyed with this presumptive diagnosis had mean circulating IL-31 levels of 8799 fg/ml compared to 205 fg/ml in the 17 age-matched control cats. To understand the levels of canine IL-31 in a previous model development study, the pharmacokinetic profile of canine IL-31 was analyzed in dogs following administration of a subcutaneous dose of 1.75 μg/kg. FIG. 110 shows peak plasma levels within the first hour reaching a maximum of about 30 ng/ml and a maintained level of about 400 μg/ml at three hours. Based on these findings it is reasonable to believe that an intravenous dose of 0.5 μg/kg feline IL-31 used in this feline model will result in a circulating amount that is far excessive to that observed in the naturally occurring disease state for dogs and cats.

2. Example 2—Characterization and Use of IL-31 Mimotopes in Vaccines and in Diagnostics

2.1. Amino Acid Residues on Canine IL-31 that are Involved with Antibody 15H05 Binding As described in section 1.10 of this application, a full replacement scan of the canine IL-31 protein was performed encompassing the amino acids outlined in FIG. 12. Each position described within this section of IL-31 was individually replaced in the full length protein with one of the other possible 19 amino acids and binding of antibody 15H05 was assessed using an indirect ELISA. Those substitutions having no impact on binding resulted in an ELISA signal equivalent to (or higher) than the with IL-31 protein, while substitutions impacting antibody binding resulted in a lower (or no) signal from the assay. As detailed in FIG. 12, some positions on canine IL-31 were tolerant of certain substitutions of the amino acids indicated (SEQ ID NO: 155; positions 124, 125, 129, and 132-135) while others were not (SEQ ID NO: 155; positions 126, 127, 128, 130, and 131). For comparison, the corresponding region on feline (SEQ ID NO: 157), equine (SEQ ID NO: 165), and human IL-31 (SEQ ID NO: 181) are shown. One can extrapolate the mutational observations in canine IL-31 to the other species for design of homologous peptides. This fine positional mapping of the epitope region on canine IL-31 allowed for the design of both linear and constrained peptides that mimic the binding site on the IL-31 protein recognized by antibody 15H05. These results in conjunction with the feline IL-31 model described in section 1.10 (FIG. 6B) indicate the epitope recognized by mAb 15H05 is a consecutive region of amino acids that form the convergence of a random coil leading into the fourth helical domain of the cytokine. Presentation of this epitope allows binding of mAb 15H05 to both linear and constrained peptide representations with greater affinity associated with the constrained form. Mutational data described above (section 1.12) further emphasizes the important positioning of this epitope (and the 11E12 epitope previously described in U.S. Pat. No. 8,790,651 to Bammert et al.) on the face of the IL-31 protein with respect to binding to the co-receptor complex.

2.2. Characterization of Peptide Mimetics Representing the Epitope on IL-31 Recognized by Antibody 15H05

As mentioned previously, the design of peptide epitope mimetics (mimotopes) can have great utility as analytical capture reagents and as subunit vaccines to elicit a relevant focused immune response to generate antibodies in an animal directed at a neutralizing epitope on IL-31. Towards this goal, canine and feline peptides were designed and characterized for their affinity to antibody ZTS-927 and their ability to block antibody ZTS-361s ability to inhibit IL-31 mediated receptor signaling on feline FCFW4 cells. The construction of antibodies ZTS-927 and ZTS-361 (both containing CDRs from mouse antibody 15H05) are described above in section 1.9. Peptide ZTS-561 contains the amino acid sequence N-TEISVPADTFERKSFILT-C which corresponds to positions 121 through 138 of SEQ ID NO: 155 with the substitution of Arginine (R) for Cysteine (C) at position number 132. Peptide ZTS-561 also includes N and C terminal Cysteines to facilitate conjugation chemistry using the free thiol groups. Peptide ZTS-562 contains the amino acid sequence N-EISVPADTFERKSF-C which corresponds to positions 122 through 135 of SEQ ID NO: 155 with the substitution of Arginine (R) for Cysteine (C) at position number 132. Peptide ZTS-562 also includes N and C terminal Cysteines to facilitate conjugation chemistry using the free thiol groups. Peptide ZTS-563 contains the amino acid sequence N-AKVSMPADNFERKNFILT-C which corresponds to positions 121 through 138 of SEQ ID NO: 157 with the substitution of Threonine (T) for Alanine (A) at position number 138. Peptide ZTS-563 also includes N and C terminal Cysteines to facilitate conjugation chemistry using the free thiol groups. Peptide ZTS-564 contains the amino acid sequence N-TEISVPADTFERKSFILT-C which corresponds to positions 121 through 138 of SEQ ID NO: 155. Peptide ZTS-564 also includes N and C terminal Cysteines to facilitate conjugation chemistry using the free thiol groups. A multistep process using CLIPS technology (Timmerman et al. J Mol Recognit. 2007; 20(5): 283-299) was used to identify and optimize these four peptides capable of binding to the paratope of mAb 15H05 (Pepscan, Lelystad Netherlands). For the purpose of generating immunogens, these four peptides (depicted in FIG. 13A) were independently conjugated to a carrier protein which is an inactive mutant (non-toxic) form of diphtheria toxin (CRM197) using standard cross-linking chemistry. For affinity assessment, each peptide was independently immobilized to a biacore surface and the KD for the felinized anti IL-31 15H05 mAb (ZTS-927) was determined (FIG. 13B). All four peptides bound ZTS-927 with nanomolar affinity indicating they are close representations of the binding site on full length IL-31. To assess the potency of each peptide, a dose titration of conjugated or unconjugated peptides were co-incubated at 37° C. for 1 hour with 0.2 μM (6.5 μg/ml) of mAb ZTS-361 prior to addition of feline IL-31 on FCWF-4 (feline macrophage-like cells). IC50 values were calculated using increasing concentrations of peptide (x-axis) versus the percent effect (y-axis) defined as the ability of the peptide to bind and block mAb ZTS-361 inhibition of IL-31 protein mediated STAT3 phosphorylation in feline FCWF-4 macrophages. Peptide ZTS-564 had reduced solubility in solution which likely resulted in inefficient conjugation, low epitope density, and poor potency. Peptide ZTS-561 had poor potency in the conjugated form but maintained a good potency when unconjugated (1060-1.7 μg/ml). ZTS-562 and ZTS-563 both demonstrated excellent potency unconjugated with IC50s of 1.046 μg/ml and 1.742 μg/ml respectively. The potency declined approximately 3-fold following conjugation with IC50s for ZTS-562 and ZTS-563 of 3.024 μg/ml and 3.384 μg/ml respectively (FIG. 13B). The ability of these peptides to block the high affinity binding of mAb ZTS-361 to the IL-31 protein was highly promising and gave further evidence to support their utility as epitope mimetics (further referred to as IL-31 15H05 mimotopes) of a relevant epitope on IL-31. These IL-31_15H05 mimotopes were further explored for their utility as an immunogens to elicit an anti-IL-31 immune response.

Figure 14:
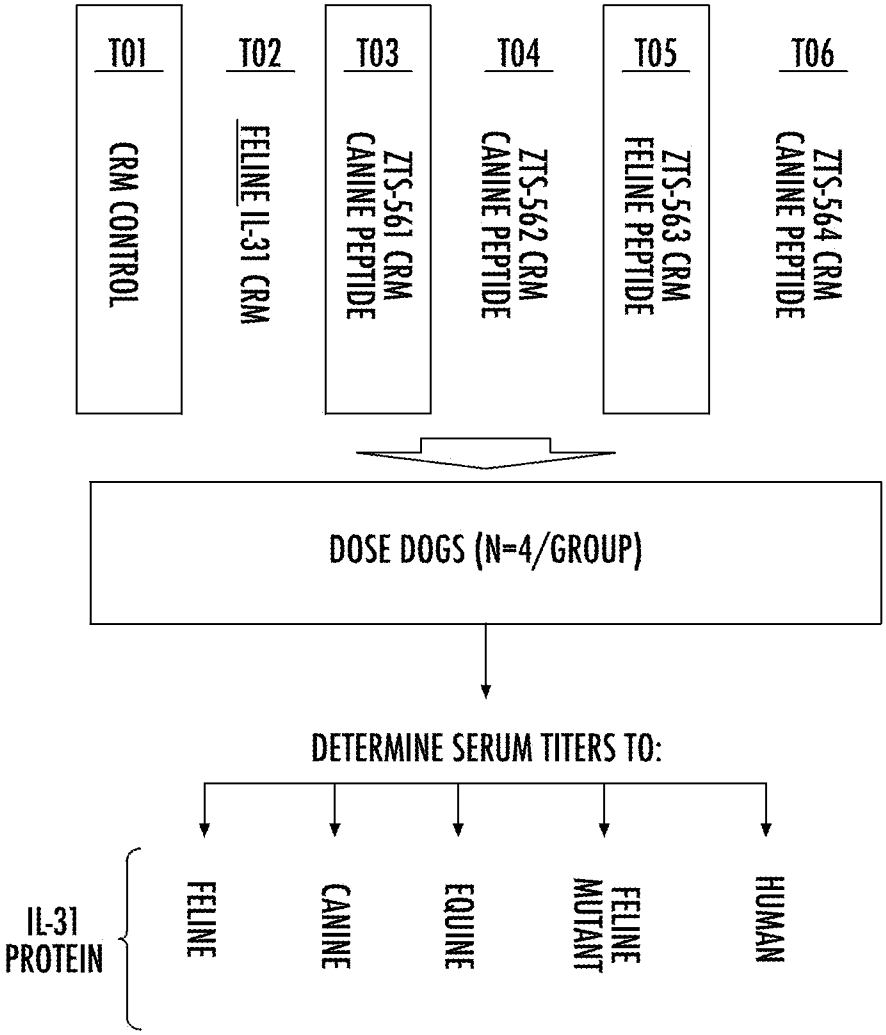
FIG. 14 depicts the study design for an immunogenicity study undertaken to assess the ability of CRM-197-conjugated IL-31 mimotopes to generate an epitope-specific immune response driven towards the relevant region on the IL-31 protein where antibody 15H05 and other anti-IL-31 antibodies disclosed herein bind.

2.3. Study Design for Generating Serum Titers to IL-31 Following Immunization of Beagle Dogs with IL-31 15H05 Canine and Feline Mimotopes and Full Length Feline IL-31 Protein An immunogenicity study was undertaken to assess the ability of CRM-197-conjugated IL-31 15H05 mimotopes to generate an epitope-specific immune response driven towards the relevant region on the IL-31 protein where antibody 15H05 binds and neutralizes the cytokines ability to activate the IL-31Ra:OSMR co-receptor. The study design is depicted in FIG. 14. Purebred male beagle dogs were subcutaneously administered the conjugated IL-31_15H05 mimotopes adjuvanted with ZA-01. The diagram below shows the experimental design by group. Control groups were included containing ZA-01 adjuvant CRM-197 alone (T01) and CRM-197 conjugated feline IL-31 (SEQ ID NO: 159; Feline_IL-31_E_coli), the corresponding nucleotide sequence for which is (SEQ ID NO: 160; Feline_IL-31_E_coli) in ZA-01 (T02). 10 μg/dose of each adjuvanted mimotope or control was administered subcutaneously on days 0, 28, and 56 (0.5 ml of a 20 μg/ml solution). Blood for serum was taken on day 0 (pre-dose), 7, 12, 28 (pre-dose) 35, 42, 49, 56 (pre-dose), 63, 70, 77, and 84. In addition, on days 35 and 84, approximately 40 mls of blood was collected from each animal into lithium heparin tubes and processed for PBMC isolation using a standard method. PBMCs were cryopreserved following isolation until further evaluation of antigen-specific B-cells.

2.4. Serum Titers Generated Following Vaccination of Dogs with IL-31 15H05 Canine and Feline mimotopes and full length feline IL-31 protein Serum titers from each study day indicated in section 2.3 above were assessed for each animal. Titers were determined using an indirect ELISA where a full length IL-31 protein was used as the capture material for each respective assay. Serum was assayed from each study group for binding to feline, feline 15H05 mutant, canine, equine, and human IL-31 proteins. The objective was to understand the immune response elicited by feline IL-31 protein (SEQ ID NO: 159; Feline_IL-31_E_coli), or 15H05 peptide mimotopes, against multiple species of IL-31 having a range of amino acid sequence identities to one other (FIG. 1A). Treatment group 2 (full-length Feline_IL-31 CRM) represents the adaptive immune response to multiple epitopes spanning the entire protein sequence. Using the full protein as an immunogen will generate antibodies that are both neutralizing and non-neutralizing to the bioactivity of IL-31. Previous work in mice describing identification of neutralizing antibodies to IL-31 signaling indicates that the percentage of these antibodies are small and therefore the majority of the polyclonal response to the full length protein will be that of a non-neutralizing type (U.S. Pat. No. 8,790,651 to Bammert, et al.). As a vaccine approach, generation of non-neutralizing antibodies to IL-31 may have adverse effects on safety and efficacy. Non-neutralizing antibodies may result in increased amounts of bioactive IL-31 in circulation resulting from bound antibody cytokine complexes. These complexes can allow monomeric or aggregated forms of IL-31 to exist in circulation allowing availability of the receptor binding portion of the IL-31 to interact with the IL-31:OSMR co-receptor. Increased pSTAT signaling resulting from increased IL-31 in circulation will exacerbate pruritic activity in a disease state like atopic dermatitis (Gonzales et al. Vet Dermatol. 2013 February; 24(1):48-53.e11-2).

FIGS. 15A-E show the average titer results to each respective IL-31 protein organized by treatment group showing the response at each day serum was taken. Serum titers were examined to IL-31 using multiple species of the protein to understand the extent of Cross-Reactive Antibody Response (CRAR) that may occur. The maximum dilution tested for each serum sample was 1:50,000 so when the titer exceeded this value it was designated as 50,000. For clarity, the following description of figures will proceed according to the individual treatment groups response to each IL-31 protein used for the capture ELISA.

Figure 15A:
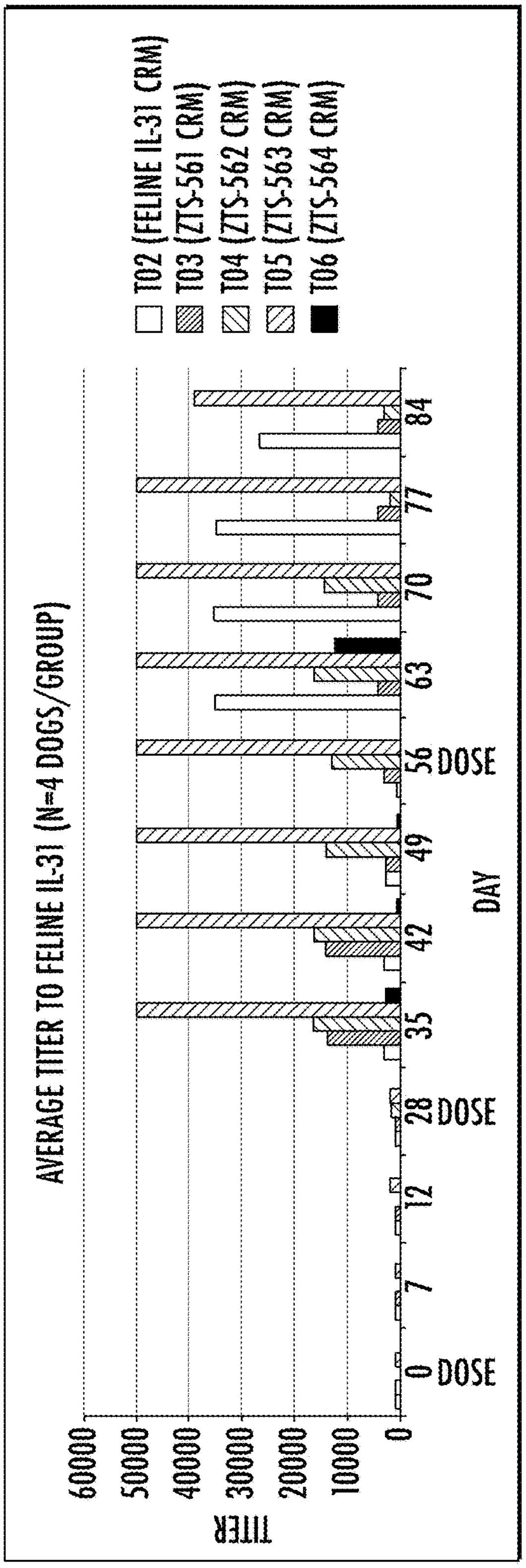
FIGS. 15A through 15E are of graphs showing serum titers generated following vaccination of dogs with IL-31 15H05 canine and feline mimotopes and full length feline IL-31 protein organized by treatment group showing the response at each day serum was taken.
Figure 15B:
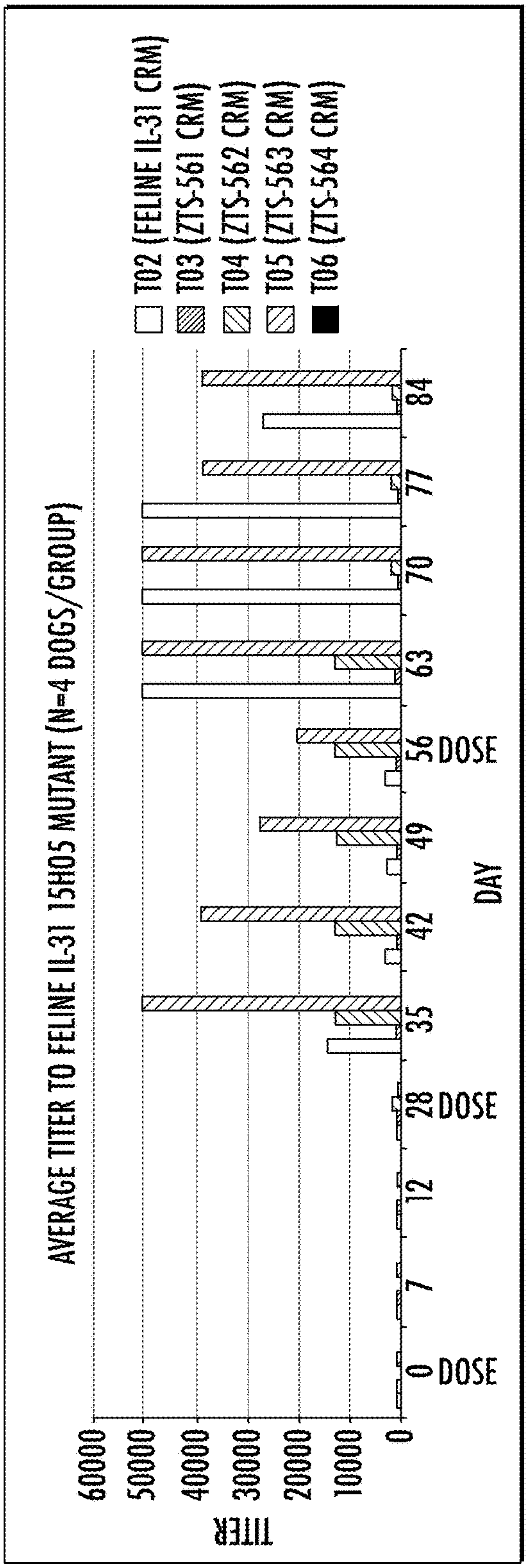
Figure 15C:
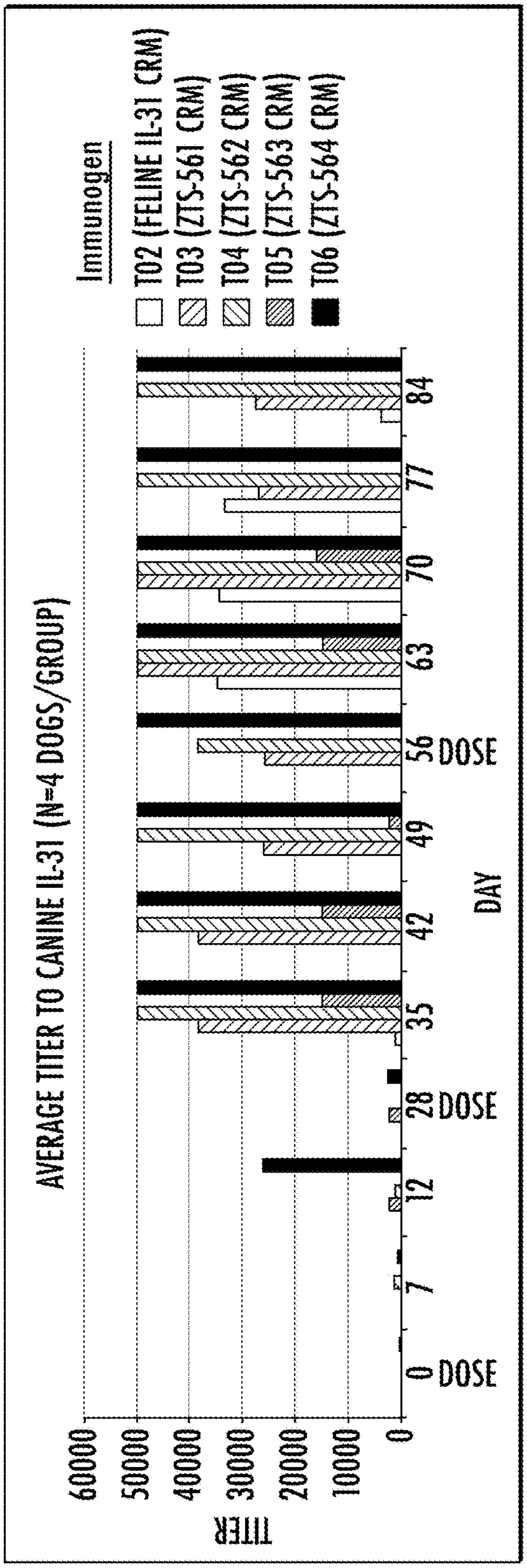
Figure 15D:
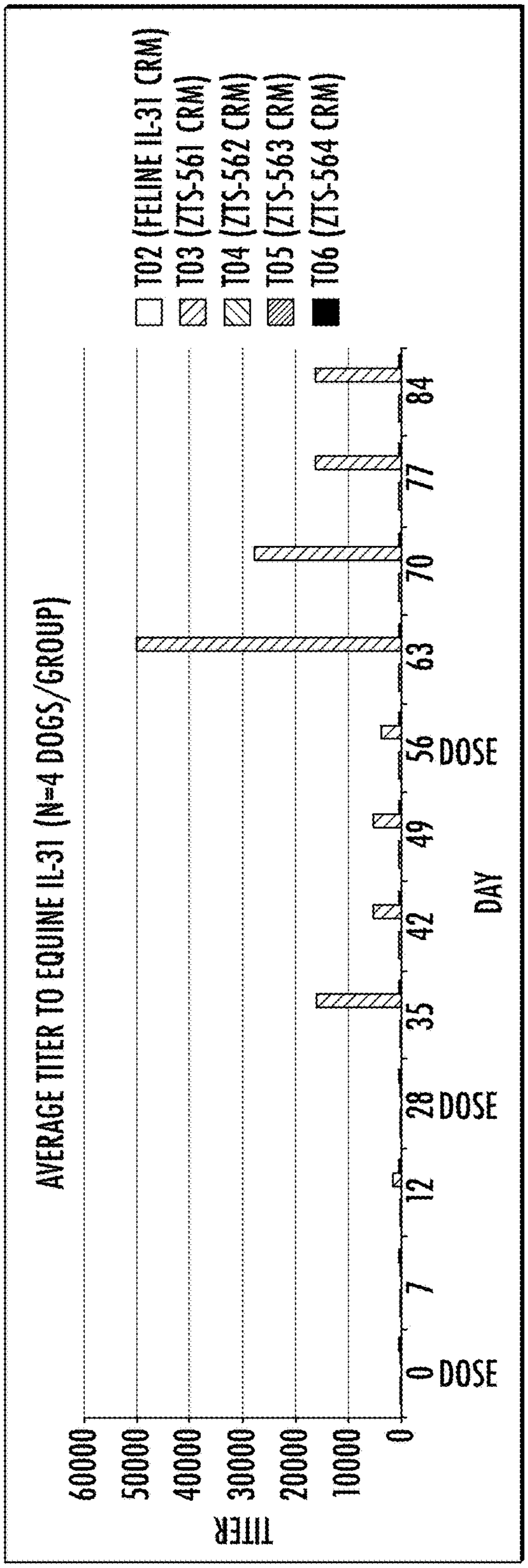
Figure 15E:
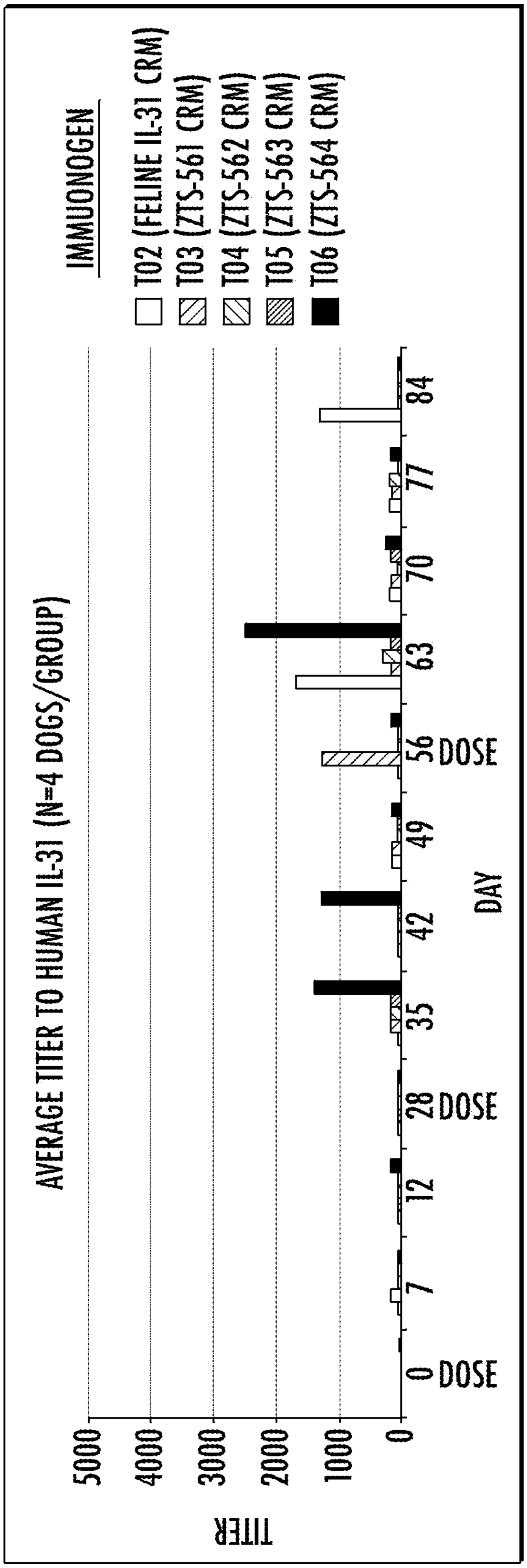

For dogs vaccinated with full-length feline IL-31 (T02), it was expected that the polyclonal serum generated would bind multiple species given the high percent identity between homologs. FIG. 15A shows the canine antibody titers generated that bind to feline IL-31. Analysis of the T02 group shows a moderate and sustained antibody response was generated to the full length feline IL-31 protein following the third dose which persisted to the termination of the study at day 84. When examining the T02 group response against the feline 15H05 mutant protein (SEQ ID NO: 163; Feline_IL31_15H05_mutant), a similar profile is seen with titers even further elevated on day 63, 70, and 77 (FIG. 15B). FIG. 15C shows the titers to canine IL-31. When looking at titers from the T02 group we examine the extent to which the vaccinated dogs mounted a CRAR to the canine IL-31 protein. No response was observed prior to the third dose of feline IL-31 CRM. Following dose 3 on day 56, a transient CRAR can be observed from days 63-77 returning to near baseline by day 84. The magnitude of the anti-canine response was similar to the anti-feline response however the duration of was shorter. Interestingly, the CRAR to horse and human IL-31 was negligible to minor respectively (FIGS. 15D and E, days 63 and 84 for human). In summary, the dog's immune response to feline IL-31 CRM was most robust and persistent against the feline IL-31 protein itself. Feline and canine IL-31 share a 76% amino acid identity to each other which appears to be a sufficiently high enough level for a CRAR to occur to the canine protein. Horse and human IL-31 have a 57 and 49% identity to feline respectively yielding only a minor CRAR in the case of human protein titers.

IL-31_15H05 mimotope ZTS-561 represents the binding site on canine IL-31 recognized by antibody 15H05. Antibody responses from dogs vaccinated with ZTS-561 CRM are described as T03 in FIGS. 15A-E. The objective here was to assess the antibody response to this specific region on IL-31 known to be involved with the cytokines interaction with its receptor. Focusing the immune response to a specific epitope will ensure antibodies are directed to an area on the protein that will result in neutralizing its biological activity. ZTS-561 CRM is a constrained 20-mer representing the portion of the canine IL-31 protein recognized by antibodies with identical CDRs to murine antibody 15H05 (SEQ ID NO: 67; MU_15H05_VH), the corresponding nucleotide sequence for which is (SEQ ID NO: 68; MU_15H05_VH) paired with VL (SEQ ID NO: 69; MU_15H05_VL), the corresponding nucleotide sequence for which is (SEQ ID NO: 70; MU_15H05_VL). Mimotope ZTS-561 failed to produce a strong anti-feline IL-31 response throughout the entire study (FIG. 15A) including to the feline IL-31 15H05 mutant (FIG. 15B). In contrast, the dogs immune response to ZTS-561 CRM against the canine IL-31 protein was very strong beginning at day 35 following the second injection and persisting through the termination of the study at day 84 (FIG. 15C). The CRAR elicited by ZTS-561 to equine IL-31 was negligible and to human only a small response was observed on day 56 of the study (FIGS. 15D and E). It is interesting to note that even though the feline and canine proteins share a high degree of identity in this region of the protein (FIG. 1), a species-specific immune response was directed toward the dog IL-31 protein following vaccination of dogs with the canine 15H05 mimotope.

ZTS-562 CRM is a constrained 16-mer truncated version of ZTS-561 again representing the portion of the canine IL-31 protein recognized by antibodies with identical CDRs to murine antibody 15H05 (SEQ ID NO: 67; MU_15H05_VH), the corresponding nucleotide sequence for which is (SEQ ID NO: 68; MU_15H05_VH) paired with VL (SEQ ID NO: 69; MU_15H05_VL), the corresponding nucleotide sequence for which is (SEQ ID NO: 70; MU_15H05_VL). Data for the dog's response to ZTS-562 are found as the T04 group in FIGS. 15A-E. Interesting the CRAR elicited by this shorter version was more pronounced resulting in modest anti-feline titers on days 35 through 70 (FIG. 15A). Some response was also observed to the mutant 15H05 IL-31 protein between days 35 and 63 (FIG. 15B). The anti-canine IL-31 response elicited by this mimotope was outstanding beginning on day 35 following the second dose and persisting through the termination of the study on day 84. Consistent with other results with canine peptide ZTS-561 CRM, ZTS-562 CRM had no CRAR with the equine and human proteins.

ZTS-563 CRM is a constrained 18-mer and is the only mimotope representing the portion of the feline IL-31 protein recognized by antibodies with identical CDRs to murine antibody 15H05 (SEQ ID NO: 67; MU_15H05_VH), the corresponding nucleotide sequence for which is (SEQ ID NO: 68; MU_15H05_VH) paired with VL (SEQ ID NO: 69; MU_15H05_VL), the corresponding nucleotide sequence for which is (SEQ ID NO: 70; MU_15H05_VL). Data for the dog's response to ZTS-563 are found as the T05 group in FIGS. 15A-E. Consistent with previous observations of a species-specific response to the canine mimotope, the cat mimotope (ZTS-563) elicited a feline-specific anti-IL31 response in the dog. FIG. 15A shows the anti-feline IL-31 titer response to vaccination with ZTS-563 reaching greater than 1:50,000 on day 35 and sustained at this level through day 77 falling modestly at day 84. Comparing the T05 (ZTS-563) treatment group between FIGS. 15A and 15B one can clearly see the difference in titer between feline IL-31 and the feline IL-31 15H05 mutant. The time dependent decrease in titer to the mutant protein (when compared to the wildtype protein) indicates that a significant portion of the immune response is directed to a very specific portion of the protein represented by mimotope ZTS-563. Remarkably, the anti-canine IL-31 response was modest to low, further supporting the species-specific response generated by the dogs immune system, to subtle differences in the amino acid sequences of the two species. Vaccination with ZTS-563 is the only mimotope that generated a CRAR in dog to the equine IL-31 protein. These observations demonstrate subtle changes in the mimotope sequence can lead to species specificity and may also impart a cross-species immunogenic response. Understanding these properties is beneficial to the design of an IL-31 directed vaccine for single or multi-species use using this technology.

Lastly is ZTS-564 CRM, a constrained 18-mer identical to ZTS-561 however utilizing an alternate linker, mT2b (FIG. 15A). ZTS-564 CRM represents the portion of the canine IL-31 protein recognized by antibodies with identical CDRs to murine antibody 15H05 (SEQ ID NO: 67; MU_15H05_VH), the corresponding nucleotide sequence for which is (SEQ ID NO: 68; MU_15H05_VH) paired with VL (SEQ ID NO: 69; MU_15H05_VL), the corresponding nucleotide sequence for which is (SEQ ID NO: 70; MU_15H05_VL). Data for the dog's response to ZTS-564 are found as the T06 group in FIGS. 15A-E. Consistent with other observations there is little to no dog anti-feline IL-31 response elicited by this mimotope (FIGS. 15A and 15B). The anti-canine IL-31 response generated by ZTS-564 was very robust. FIG. 15C shows of all the treatment groups in this study, T06 (ZTS-564) is the only one generating an immune response against canine IL-31 following a single dose. The anti-canine IL-31 titers generated following the second and third dose resulted in a maximal assay response (greater than 1:50000) at days 35 through the termination of the study at day 84. There was no CRAR to equine IL-31 observed however this mimotope produced the only consistent response to human IL-31 observed among the treatment groups. It is noteworthy that such subtle differences in the linker chemistry and perhaps the more defined constraints of the mT2b linker provide a more precise directed anti IL-31 response potentially alleviating the need for more frequent dosing.

Data from this study indicates that peptide mimetics representing the binding site of the neutralizing anti-IL-31 antibody 15H05 are capable of eliciting an immune response in an animal and this immune response is directed against the epitope recognized by the antibody 15H05 CDRs. It is conceived from these data that further characterization of this anti-serum using recombinant IL-31 co-receptors can be used to define the IL-31 neutralizing fraction generated during this polyclonal response. These results further suggest the utility of such an approach for use as a vaccine against an IL-31 mediated disorder like atopic dermatitis.

2.5. Identification of IL-31 Neutralizing Antibodies from Individual B-Cells Isolated from Plasma Cells of Beagle Dogs Immunized with IL-31 15H05 Mimotopes As described above, blood was harvested on days 35 and 84 of the study for the purpose of isolating PBMCs. PBMCs from a single T05 dog vaccinated with ZTS-563 CRM (the feline mimotope) were used for further evaluation of antibody positive B-cells due to the robust 15H05 epitope-directed response (FIGS. 15A and 15B). Activated memory B-cells were screened for those cells secreting antibodies using an anti-canine IgG Fc antibody coupled to a bead. Secreted IgGs were simultaneously assessed for their ability to bind wildtype feline IL-31 and bind to the feline IL-31 15H05 mutant. These primary screening results lead to the selection of 7 hits from this PBMC cell population. Of these 7 hits, 3 did not bind to the 15H05 mutant indicating these B-cells are making antibodies with the closest recognition of the 15H05 epitope as a result of immunization with the IL-31 15H05 mimotope ZTS-563 (data not shown). Following sequencing of the variable heavy and light chains for these 7 hits, recombinant fully canine versions were constructed, expressed in HEK cells, and purified as previously described herein. Re-screening of these 7 recombinant canine IgGs resulted in only a single hit (ZIL1) that retained binding to the feline IL-31 protein (FIG. 4). Furthermore, binding of ZIL1 to the IL-31 15H05 mutant is decreased, using ELISA and Biacore methods, indicating this antibody binds to a common epitope region as antibody 15H05. The additional hits derived directly from canine B-cells in section 1.6 and in FIG. 4 (ZIL8-ZIL171) were from dogs immunized with full length feline IL-31 and from other tissue sources previously described herein. Only the ZIL1 antibody was derived from PBMCs following vaccination with a peptide mimotope.

An important aspect of these findings is the ability to identify mAb 15H05 epitope-specific antibody secreting B-cells in the circulation of a dog following immunization with a peptide mimotope from the IL-31 protein. These results validate the use of a peptide mimicking the epitope region on IL-31 known to be relevant to the mode of inhibitory action of antibody 15H05. As antibodies with CDRs derived from mAb 15H05 are capable of preventing IL-31 mediated pruritus in vivo, these results further support the concept of immunization with such a mimetic designed to generate an epitope-focused immune response as a vaccine approach for the prevention of IL-31 mediated diseases such as atopic dermatitis.

2.6. Use of IL-31 15H05 Mimotope as a Capture Reagent to Measure the Identity and Potency of Antibody 15H05 and its Derivatives An IL-31 15H05 mimotope represents the binding site on the IL-31 protein that is recognized by the CDRs from the mouse progenator mAb 15H05. As mentioned previously it is desirable to have such a reagent to use in an ELISA (or other) assay format to monitor the antibody production process throughout manufacturing. It is conceived herein that such mimotopes described would have such utility where a production lot of an anti-IL-31 antibody is made and a peptide mimotope would be used for an analytical assay to verify the identity and quantity of antibody produced.

2.7. Use of IL-31 15H05 Mimotope as a Diagnostic to Measure Antibody Levels or to Determine IL-31 Levels in a Host Species It is further conceived herein the use of a peptide mimotope as described to be used as an analytical assay reagent to measure the amount of circulating antibody in a host following treatment of a therapeutic for an IL-31 mediated disorder such as atopic dermatitis. Body fluid from an animal is added directly to the mimotope which is bound to a solid surface and then appropriate secondary detection reagents are added to quantify the level of antibody. Additionally, an assay design is conceived here whereby a mimotope is used to capture an antibody that is labeled for detection in an assay. This captured antibody would have an affinity to the attached mimotope that is lower that the affinity of native circulating IL-31 in a host species. In this embodiment, incubation of the fluid derived from the host species is incubated with the labeled antibody: mimotope complex that is tethered to a solid surface. The presence of IL-31 in the test fluid derived from the host species will have a higher affinity to the antibody, thus liberating the labeled antibody from the solid surface where it can be removed during wash steps. The level of IL-31 in the test fluid can thus be correlated to the lack of signal that appears on the mimotope-bound surface. It is conceived that such an assay would have utility to measure IL-31 in a research or clinical setting for use as a diagnostic test.

2.8. Serum Titers to IL-31 Following Immunization of Beagle Dogs with IL-31 Mimotopes and Full Length Canine IL-31 Protein A second serology study was performed using purebred neutered male beagles like the study design described herein in section 2.3 however in this study different mimotopes were compared. Purebred male beagle dogs were subcutaneously administered the conjugated IL-31 mimotopes adjuvanted with ZA-01. A control group was included containing CRM-197 conjugated canine IL-31 (SEQ ID NO: 155; Canine_IL-31), the corresponding nucleotide sequence for which is (SEQ ID NO: 156; Canine_IL-31) in ZA-01 (T01). 10 μg/dose of each adjuvanted mimotope or control was administered subcutaneously on days 0, 28, and 56 (0.5 ml of a 20 μg/ml solution). Blood for serum was taken on day −1, 0 (pre-dose), 14, 28 (pre-dose), 42, 56 (pre-dose), 70, and 84. In addition, on days −1, 35 and 63, approximately 40 mls of blood was collected from each animal into lithium heparin tubes and processed for PBMC isolation using a standard method. PBMCs were cryopreserved following isolation until further evaluation of antigen-specific B-cells.

Treatment group 1 (full-length Canine_IL-31 CRM) represents the adaptive immune response to multiple epitopes spanning the entire protein sequence like the rationale described in section 2.4 using full length feline protein. FIG. 16A shows a table outlining the study treatment groups. In addition to the full-length protein described for T01, two mimotopes representing the 15H05 epitope on canine (T02, ZTS-420) and human (T03, ZTS-421) were used. ZTS-420 is like ZTS-561 described previously in the feline serology study however ZTS-420 is constrained by a disulphide bond formed by cysteines at the N and C terminus of the peptide compared to the mT2a linker found in ZTS-561. ZTS-421 is the homologous region on the human IL-31 protein (SEQ ID NO: 181; Human_IL-31) constrained by linking the N and C termini with the mT2b linker described in FIG. 13A. Reference to the key amino acid sequences involved with antibody 15H05 binding can be found in FIG. 12. A forth group was included to explore the immunogenic potential of a key antibody binding region on canine IL-31 previously described using two antibodies known to neutralize IL-31 mediated pSTAT signaling and IL-31 mediated pruritus in dogs (U.S. Pat. No. 8,790,651 to Bammert, et al.). This region on feline IL-31 is highlighted in the homology model shown in FIG. 6B. The accepted model of IL-31 is as a four-helical domain cytokine with the helices forming an alternating up and down topology. For further descriptions, the structure of the IL-31 protein will be described regarding these four helices on canine IL-31 (SEQ ID NO: 155; Canine_IL-31), the corresponding nucleotide sequence for which is (SEQ ID NO: 156; Canine_IL-31) with respect to the corresponding positions on homologous IL-31 proteins from other species (FIG. 1). Helix A is composed of the sequence from about amino acid 33 to 59, helix B is composed of the sequence from about amino acid 83 to 98, helix C is composed of the sequence from about amino acid 101 to 114, and helix D is composed of the sequence from about amino acid 129 to 156. A defined loop region exists between about amino acid 97 to 101. A loop following helix A exists from about amino acid 57 to 62 and a loop preceding helix D from about amino acid 126 to 129. Any intervening sequence lacking predicted secondary structure will be referred to as random coil. Treatment group 4 (ZTS-766) is a mimotope representing helices B and C of canine IL-31 and includes an N-terminal cysteine residue to facilitate coupling the CRM-197 carrier protein. The peptide sequence alignment of this region of the IL-31 protein is shown FIG. 16B comparing canine, feline, equine, and human proteins with the corresponding sequence reference number and amino acid position annotated.

Figure 17A:
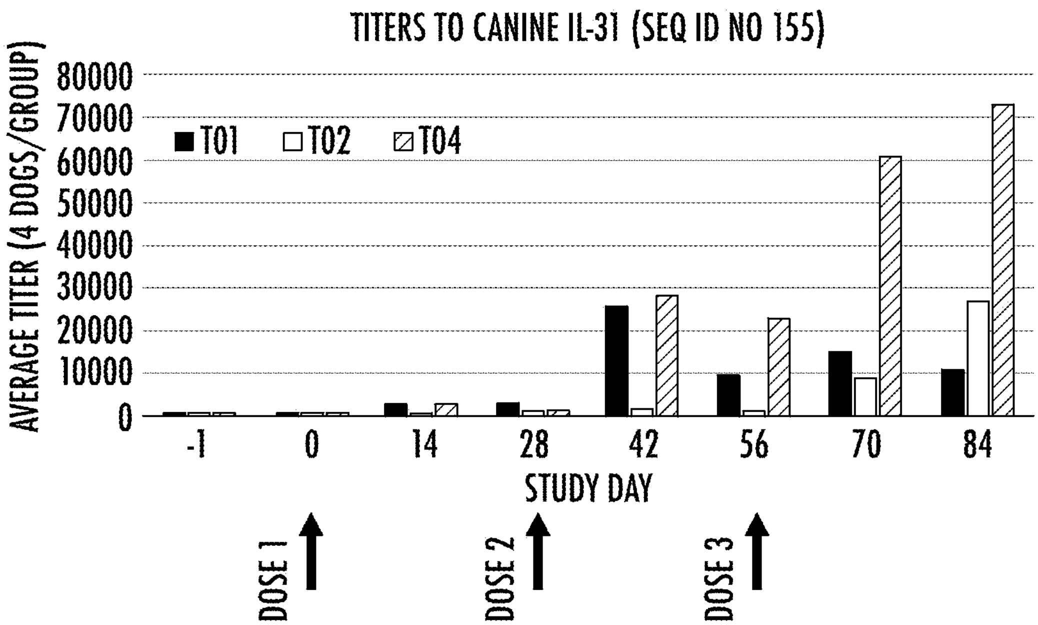
FIGS. 17A and 17B are of graphs showing serum titers generated following vaccination of dogs with IL-31 15H05 canine and human mimotopes, canine BC helix mimotope, and full length feline IL-31 protein organized by treatment group showing the response at each day serum was taken. Dogs were dosed on days 0, 28, and 56 indicated with arrows.
Figure 17B:
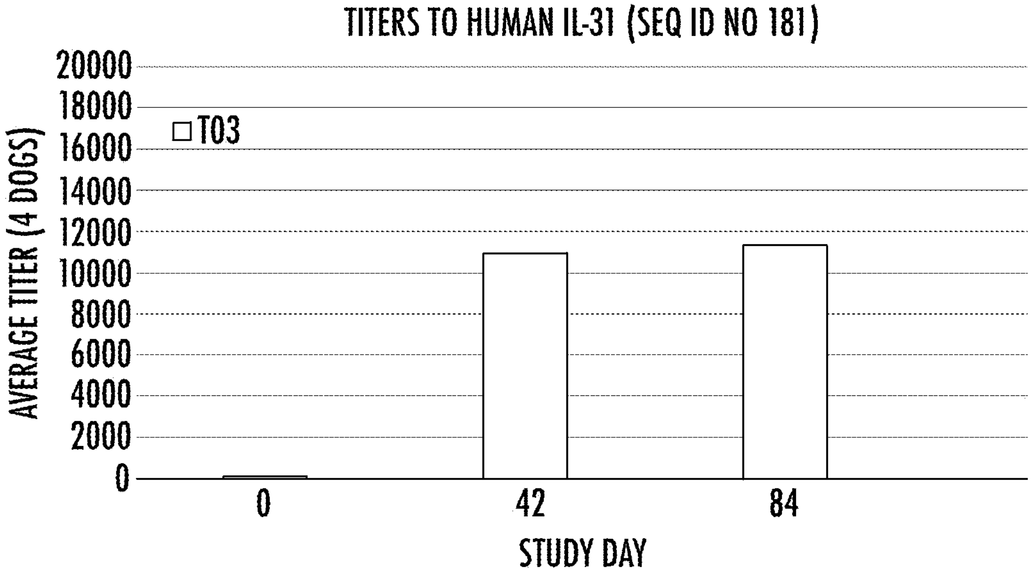

Titers were determined using an indirect ELISA where a full-length IL-31 protein was used as the capture material for each respective assay. Serum was assayed from each study group for binding to canine and human IL-31 proteins (FIGS. 17A and 17B respectively). Dogs vaccinated with CRM-197 conjugated full length canine IL-31 protein (T01) showed a modest increase in titer at day 42 following the second dose on day 28. This group showed a diminishing titer response for the duration of the study even after a third dose at day 56. Given the general response to all epitopes on the IL-31 protein (both neutralizing and non-neutralizing), coupled with the poor titers, it is unlikely that vaccination with a full-length IL-31 protein represents a viable candidate for vaccine development. Group 2 from this study (ZTS-420) is a canine 15H05 mimotope with like ZTS-561 described in section 2.4 however ZTS-420 is constrained by a disulphide bond between cysteines added at the N and C terminus of the peptide in contrast to the mT2a linker on ZTS-561. This mimotope failed to produce a robust immune response when compared to the mT2a constrained form (compare FIG. 17A to 15C). A modest increase in titer is observed on day 84 following the third dose on day 56. It is possible the disulphide cyclization is inadequate or modified during CRM-197 conjugation resulting in sub optimal presentation of the immunogen to the immune cells in dogs. Group 4 (ZTS-766) representing the helices B and C of canine IL-31 produced the most robust response with titers appearing following the second dose on day 28 and increasing out to day 84 at the completion of the study. Given the IL-31 neutralizing capacity of the antibodies recognizing this sequence previously described, this mimotope represents a promising vaccine candidate for prevention of IL-31 mediated disorders. Treatment group 3 (ZTS-421) is the 15H05 epitope using the human IL-31 sequence in this region of the mimotope. Interestingly, none of the dogs vaccinated with this mimotope generated a response against the canine IL-31 protein (data not shown) however an immune response was observed to the human IL-31 protein following the second and third doses (FIG. 17B). This is remarkable specificity of the dog anti human IL-31 response given the similarity in sequence between the core epitope region of the 15H05 mimotope (FIG. 12).

2.9. Serum titers to IL-31 following immunization of laboratory cats with IL-31 feline and equine mimotopes and full length feline IL-31 protein A serology study was performed using laboratory cats like the study design described herein in section 2.3 however in this study feline and equine mimotopes were compared. Laboratory cats were subcutaneously administered the conjugated IL-31 mimotopes adjuvanted with a mixture including the glycolipid adjuvant Bay R1005 (N-(2-Deoxy-2-L-leucylamino-β-D-glucopyranosyl)-N-octadecyldodecanoylamidehydroacetate) as well as CpG oligonucleotides. A control group was included containing CRM-197 conjugated feline IL-31 (SEQ ID NO: 157; Feline_IL31_wildtype), the corresponding nucleotide sequence for which is (SEQ ID NO: 158; Feline_IL-31_wildtype) in an adjuvant mixture including the glycolipid adjuvant Bay R1005 (N-(2-Deoxy-2-L-leucylamino-β-D-glucopyranosyl)-N-octadecyldodecanoylamidehydroacetate) as well as CpG oligonucleotides. (T01). 10 μg/dose of each adjuvanted mimotope or control was administered subcutaneously on days 0, 28, and 56 (0.5 ml of a 20 μg/ml solution). Blood for serum was taken on day −14, 0 (pre-dose), 28 (pre-dose), 42, 56 (pre-dose), 70, and 84. In addition, on days 35 and 63, approximately 40 mls of blood was collected from each animal into lithium heparin tubes and processed for PBMC isolation using a standard method. PBMCs were cryopreserved following isolation until further evaluation of antigen-specific B-cells. The study treatment groups are outlined in FIG. 18A. ZTS-563 (T02) is described herein in section 2.4 as an immunogen that was used in the previous dog serology study. ZTS-563 is an mT2a constrained 15H05 mimotope conjugated to CRM-197. T03 (ZTS-418) is a 15H05 mimotope with equine sequence (compare the homologous canine version ZTS-420 in FIG. 16A). Treatment group 4 is ZTS-423, a mimotope peptide representing the BC helix described in section 2.8 with feline IL-31 sequence. Treatment group 5 is ZTS-422, a feline 15H05 mimotope with an aminohexanoic acid (Ahx) mT2b linker. FIG. 18B shows the results for the serum antibody response of treatment groups T01, T02, T04 and T05 (T03 had no CRAR to feline IL-31 protein, data not shown) on days −14, 42, and 84 to full length feline IL-31 using an indirect ELISA. Once again, the conjugated form of the full length IL-31 protein (T01) showed the poorest antibody response in cats with titers to full length IL-31 never exceeding 1:20000 for the duration of the study. T02 (ZTS-563) had a modest response throughout the study with a dose-dependent increase out to day 84 indicating this presentation of the feline 15H05 epitope may be a suitable vaccine. The average titer in cats to full length feline IL-31 protein following three doses of ZTS-423 (T04) are dose-dependentally increased to greater than 1:100,000 following the second and third dose indicating an outstanding immune response to a highly relevant epitope region. ZTS-422 (T05) representing the 15H05 mimotope with the AhX mT2b linker shows also shows a robust immune response in cats with titers exceeding 1:100000 following the second and third dose. The 15H05 epitope in this form is clearly a relevant presentation of this region of the IL-31 protein and represents a promising vaccine mimotope to neutralize in vivo IL-31 activity.

2.10. Sequence and Structural Considerations for the Appropriate Design of Mimotopes for Use as Vaccines Described herein are several peptide representations of epitopes on the IL-31 protein (mimotopes) with unique sequences corresponding to the amino acids of their species of origin. The ultimate objective in vaccine design is the portrayal of epitopes whereby the immune system recognizes them and generates a robust and specific response. Vaccine design is facilitated by, but not limited to, the addition of carrier proteins like CRM-197 and formulation with adjuvants. Described herein are examples of epitopes that have been identified based on the properties of the antibodies they are bound by. Key epitopes are those areas on the IL-31 protein which, when bound by an antibody, are not able to further engage the IL-31 RA: OSMR receptor complex and therefore are not able to elicit a pSTAT signaling response in cell culture or in vivo. Blockade of IL-31 mediated receptor signaling is therefore an approach to prevent and/or treat IL-31 mediated disorders like atopic dermatitis.

Mapping of antibody binding sites on proteins using mutational techniques is an effective way to identify key residues involved with antibody: antigen recognition as was previously described for IL-31 in U.S. Pat. No. 8,790,651 to Bammert, et al. Building upon this knowledge enabled the design of canine and feline BC helix mimotopes which are described herein as effective immunogens eliciting robust anti IL-31 responses in dogs and cat. Another method using a GST canine IL-31 fusion protein was described recently to map the anti-canine IL-31 antibody M14 (WO 2018/156367 (Kindred Biosciences, Inc.). These authors sought to define a minimum epitope sequence recognized by the M14 antibody comprised of the amino acids PSD$X_1$ $X_2$KI (SEQ ID NO 155, amino acids 34-40) where X is any amino acid. Description of this sequence with comparison to homologous IL-31 species can be found in FIG. 19A. A further description, including the flanking sequence surrounding the above, is described FIG. 19B. Following identification of a minimum binding fragment indicated in FIG. 19B (grey shaded box around amino acids 34-42) the authors generated alanine substitutions at each position using a GST fusion of this peptide fragment. From these data, the above M14 minimum binding fragment was described. The fundamental flaw with this approach is that the nature of the described binding fragment is dependent upon its structure in the context of a GST fusion protein. While not being bound to a single theory, it is believed that the amino acid sequence recognized by the M14 antibody is part of an ordered alpha helical domain described herein as helix A. Alpha helices in peptides and proteins exist, but are not limited to, the coordination of hydrogen bonding patterns between the oxygen of carbonyl and nitrogen of amine backbone groups (Corey-Pauling rules, a dictionary of chemistry, 2008). The minimum binding fragment described for the M14 antibody is not believed to represent an adequate description of the epitope as no evidence is given to binding properties in the absence of a GST scaffold. Furthermore, the composition of the sequence surrounding, and including, the reported M14 epitope contains an abundance of nonpolar amino acids (I, L, V, P, G, A, M) (FIG. 19B). The physical properties of these amino acids in a peptide will result in aqueous insolubility and a disordered secondary structure in the absence of intervening polar or charged amino acids. It is therefore conceived herein that the minimum binding fragment for the M14 antibody described in WO 2018/156367 (Kindred Biosciences, Inc.) is dependent upon properties conferred by the GST fusion product and not inherent to the peptide itself.

Several peptide presentations of IL-31 epitopes are described herein whose properties exist as independent peptides in the absence of a fusion protein. This was exemplified in section 2.2 (FIG. 13B) showing the binding and inhibitory properties of the 15H05 class of mimotopes in both a conjugated and unconjugated form. In addition to secondary structural features of peptides, primary amino acid sequence represents another key aspect of vaccine design necessary for appropriate presentation on the surface a T-cells. The appropriate amino acids sequences, in conjunction with a carrier protein having B and T cell epitopes, will elicit an immune response direct to key areas on the IL-31 protein. Multiple areas on the IL-31 have been described herein as being suitable to elicit a directed immune response in dogs and cats. The success of vaccine mimotopes depends on the factors described herein and are ultimately determined in vivo by the effectiveness of the response. However, based on the learnings from several epitope regions on IL-31 described here, it is conceived that other such epitopes may exist which would make suitable vaccine mimotopes. Antibody 15H05 recognizes a loop preceding helix D illustrated as site 2 on FIG. 6B. It is conceived that other loops on the protein maybe represent epitopes accessible by antibodies. As an example, the loop formed by the convergence of helix A with the trailing random coil sequence shares such positional and structural attributes as the 15H05 loop. This AB loop is described in FIG. 20 with comparison of the primary amino acid sequences from multiple species. Not wishing to be limited to this as a single example, it is believed that other such regions on the protein may share immunogenic 2.11. Serum titers to equine IL-31 mimotopes following vaccination of mice with full length equine IL-31 protein Mice were immunized with full length equine IL-31 (SEQ ID NO: 165; Equine_IL-31), the corresponding nucleotide sequence for which is (SEQ ID NO: 166; Canine_IL-31) conjugated to CRM-197 like the method described in section 1.6 of this application. Biotin conjugated peptides representing three epitope regions described herein were designed for use with a bio-layer interferometry binding assay (Octet, ForteBio). Description of these peptides are described in FIG. 21A. Each peptide contains an N terminal biotin with a three-amino acid spacer sequence (GSG) annotated with bold underlined text in the figure. The corresponding amino acid sequence position number from SEQ ID NO 165 are also indicated in the figure. The 15H05 mimotope includes two terminal cysteine residues (also highlighted in bold and underlined) to facilitate cyclization by a disulphide bond. FIG. 21B shows the results for a biolayer interferometry where the peptides described in FIG. 21A are immobilized to streptavidin coated pins and then used to probe multiple dilutions of mouse anti equine IL-31 or control mouse serum. Control mouse serum was from a mouse vaccinated with an unrelated protein. The response, described here as the amplitude of the signal following 120 seconds of antiserum association, is represented on the y axis of the figure. From these data, the immune response resulting from presentation of epitopes on the full equine IL-31 protein can be assessed. In addition, the ability of these IL-31 mimotopes to be recognized by those immune responses can be assessed through binding. These data indicate that all three mimotope peptides described (15H05, BC helix, and A helix) are recognized as relevant immunogens from processing and presentation of the equine IL-31 protein in vivo. Minimal signal was observed with binding of the control serum to each mimotope except for the A helix which showed some dilution dependent signal. Like presentation of mimotopes described herein which elicit immune responses to full length protein, this experiment describes a reciprocal validation of these epitopes where the immune response is validated from the protein against the mimotope.

What is claimed is:

1. A vaccine composition for immunizing and/or protecting a mammal against an interleukin-31 (IL-31) mediated disorder, wherein said composition comprises:

a) the combination of a carrier polypeptide and at least one IL-31 mimotope, wherein said IL-31 mimotope is:

i) a parent equine IL-31 mimotope which is a peptide from about 5 to about 40 amino acid residues in length and is and/or comprises as part thereof an amino acid sequence selected from the group consisting of SMPTDNFERKRF (SEQ ID NO: 189), NSSAILPYFKAISPSLNNDKSL YIIEQLDKLNF (SEQ ID NO: 194), GPIYQLQPKEIQAIIVELQNLSKK (SEQ ID NO: 198), and KGVQKF (SEQ ID NO: 202); or ii) a variants IL-31 mimotope which is a peptide from about 5 to about 40 amino acid residues in length that has at least 50% amino acid sequence identity with said parent equine IL-31 mimotope and is and/or comprises the amino acid sequence of said parent equine IL-31 mimotope except for one or more amino acid substitutions within said amino acid sequence, wherein said variant IL-31 mimotope retains anti-IL-31 binding;

and b) an adjuvant.

2. The vaccine composition of claim 1, wherein the mimotope binds to an anti-IL31 antibody or antigen-binding portion thereof that specifically binds to a region on a mammalian IL-31 protein involved with interaction of the IL-31 protein with its co-receptor.

3. The vaccine composition of claim 2, wherein the binding of said antibody to said region is impacted by mutations in a 15H05 epitope binding region between about amino acid residues 118 and 129 of an equine IL-31 sequence represented by SEQ ID NO: 165 (Equine_IL31).

4. The vaccine composition of claim 2, wherein the mimotope binds to an anti-IL-31 antibody or antigen-binding portion thereof comprising at least one of the following combinations of complementary determining region (CDR) sequences:

1) antibody 15H05: variable heavy (VH)-CDR1 of SYTIH (SEQ ID NO: 1), VH-CDR2 of NINPTSGYTENNQRFKD (SEQ ID NO: 2), VH-CDR3 of WGFKYDGEWSFDV (SEQ ID NO: 3), variable light (VL)-CDR1 of RASQGISIWLS (SEQ ID NO: 4), VL-CDR2 of KASNLHI (SEQ ID NO: 5), and VL-CDR3 of LQSQTYPLT (SEQ ID NO: 6);

2) antibody ZIL1: variable heavy (VH)-CDR1 of SYGMS (SEQ ID NO: 13), VH-CDR2 of HINSGGSSTYYADAVKG (SEQ ID NO:14), VH-CDR3 of VYTTLAAFWTDNFDY (SEQ ID NO: 15), variable light (VL)-CDR1 of SGSTNNIGILAAT (SEQ ID NO: 16), VL-CDR2 of SDGNRPS (SEQ ID NO: 17, and VL-CDR3 of QSFDTTLDAYV (SEQ ID NO:18);

3) antibody ZIL8: VH-CDR1 of DYAMS (SEQ ID NO: 19), VH-CDR2 of GIDSVGSGTSYADAVKG (SEQ ID NO: 20), VH-CDR3 of GFPGSFEH (SEQ ID NO: 21), VL-CDR1 of TGSSSNIGSGYVG (SEQ ID NO: 22), VL-CDR2 of YNSDRPS (SEQ ID NO: 23), VL-CDR3 of SVYDRTFNAV (SEQ ID NO: 24);

4) antibody ZIL9: VH-CDR1 of SYDMT (SEQ ID NO: 25), VH-CDR2 of DVNSGGTGTAYAVAVKG (SEQ ID NO: 26), VH-CDR3 of LGVRDGLSV (SEQ ID NO: 27), VL-CDR1 of SGESLNEYYTQ (SEQ ID NO: 28), VL-CDR2 of RDTERPS (SEQ ID NO: 29), VL-CDR3 of ESAVDTGTLV (SEQ ID NO: 30);

5) antibody ZIL11: VH-CDR1 of TYVMN (SEQ ID NO: 31), VH-CDR2 of SINGGGSSPTYADAVRG (SEQ ID NO: 32), VH-CDR3 of SMVGPFDY (SEQ ID NO: 33), VL-CDR1 of SGESLSNYYAQ (SEQ ID NO: 34), VL-CDR2 of KDTERPS (SEQ ID NO: 35), VL-CDR3 of ESAVSSDTIV (SEQ ID NO: 36);

6) antibody ZIL69: VH-CDR1 of SYAMK (SEQ ID NO: 37), VH-CDR2 of TINNDGTRTGYADAVRG (SEQ ID NO: 38), VH-CDR3 of GNAESGCTGDHCPPY (SEQ ID NO: 39), VL-CDR1 of SGESLNKYYAQ (SEQ ID NO: 40), VL-CDR2 of KDTERPS (SEQ ID NO: 41), VL-CDR3 of ESAVSSETNV (SEQ ID NO: 42);

7) antibody ZIL94: VH-CDR1 of TYFMS (SEQ ID NO: 43), VH-CDR2 of LISSDGSGTYYADAVKG (SEQ ID NO: 44), VH-CDR3 of FWRAFND (SEQ ID NO: 45), VL-CDR1 of GLNSGSVSTSNYPG (SEQ ID NO: 46), VL-CDR2 of DTGSRPS (SEQ ID NO: 47), VL-CDR3 of SLYTDSDILV (SEQ ID NO: 48);

8) antibody ZIL154: VH-CDR1 of DRGMS (SEQ ID NO: 49), VH-CDR2 of YIRYDGSRTDYADAVEG (SEQ ID NO: 50), VH-CDR3 of WDGSSFDY (SEQ ID NO: 51), VL-CDR1 of KASQSLLHSDGNTYLD (SEQ ID NO: 52), VL-CDR2 of KVSNRDP (SEQ ID NO: 53), VL-CDR3 of MQAIHFPLT (SEQ ID NO: 54);

9) antibody ZIL159: VH-CDR1 of SYVMT (SEQ ID NO: 55), VH-CDR2 of GINSEGSRTAYADAVKG (SEQ ID NO: 56), VH-CDR3 of GDIVATGTSY (SEQ ID NO: 57), VL-CDR1 of SGETLNRFYTQ (SEQ ID NO: 58), VL-CDR2 of KDTERPS (SEQ ID NO: 59), VL-CDR3 of KSAVSIDVGV (SEQ ID NO: 60);

10) antibody ZIL171: VH-CDR1 of TYVMN (SEQ ID NO: 61), VH-CDR2 of SINGGGSSPTYADAVRG (SEQ ID NO: 62), VH-CDR3 of SMVGPFDY (SEQ ID NO: 63), VL-CDR1 of SGKSLSYYYAQ (SEQ ID NO: 64), VL-CDR2 of KDTERPS (SEQ ID NO: 65), VL-CDR3 of ESAVSSDTIV (SEQ ID NO: 66); or 11) a variant of 1) to 10) that differs from respective parent antibody 15H05, ZIL1, ZIL8, ZIL9, ZIL11, ZIL69, ZIL94, ZIL154, ZIL159, or ZIL171 by addition, deletion, and/or substitution of one or more amino acid residues in at least one of VH or VL CDR1, CDR2, or CDR3.

5. The vaccine composition of claim 1, wherein the mimotope is a constrained mimotope.

6. The vaccine composition of claim 5, wherein the constrained mimotope is a chemically-linked cyclic peptide.

7. The vaccine composition of claim 1, wherein the mimotope is chemically conjugated to the carrier polypeptide.

8. The vaccine composition of claim 1, wherein the carrier polypeptide and the mimotope are part of a recombinant fusion protein.

9. The vaccine composition of claim 1, wherein the carrier polypeptide comprises a bacterial toxoid or a derivative thereof, keyhole limpet hemocyanin (KLH), or a virus-like particle.

10. The vaccine composition of claim 9, wherein the bacterial toxoid or derivative is a tetanus toxoid, a diphtheria toxoid, a tetanus toxoid, the outer membrane protein complex from group B *N. meningitidis, Pseudomonas* exotoxin, or the nontoxic mutant of diphtheria toxin (CRM197).

11. The vaccine composition of claim 9, wherein the virus-like particle is HBsAg, HBcAg, *E. coli* bacteriophage Qbeta, Norwalk virus, canine distemper virus (CDV), or influenza HA.

12. The vaccine composition of claim 10, wherein the carrier polypeptide comprises or consists of CRM197.

13. The vaccine composition of claim 1, wherein the adjuvant is selected from the group consisting of an oil-in-water adjuvant, a polymer and water adjuvant, a water-in-oil adjuvant, an aluminum hydroxide adjuvant, a vitamin E adjuvant and combinations thereof.

14. The vaccine composition of claim 1, wherein the adjuvant is a formulation comprising a saponin, a sterol, a quaternary ammonium compound, and a polymer.

15. The vaccine composition of claim 14, wherein the saponin is Quil A or a purified fraction thereof, the sterol is cholesterol, the quaternary ammonium compound is dimethyl dioctadecyl ammonium bromide (DDA), and the polymer is polyacrylic acid.

16. The vaccine composition of claim 1, wherein the adjuvant comprises the combination of a sterol, a saponin, and one or more immunostimulatory oligonucleotides.

17. The vaccine composition of claim 16, wherein the one or more isolated immunostimulatory oligonucleotides comprises CpG, the sterol is cholesterol, and the saponin is Quil A or a purified fraction thereof.

18. A method of protecting a mammal against an IL-31 mediated disorder, the method comprising administering to the mammal a vaccine composition according to claim 1.

19. The method of claim 18, wherein the mammal is selected from the group consisting of a dog, a cat, a horse, and a human.

20. The method of claim 18, wherein the IL-31 mimotope contained in the vaccine composition is administered to the mammal at about 10 μg to about 100 μg per dose.

* * * * *